(12) United States Patent
Popovich et al.

(10) Patent No.: US 10,423,222 B2
(45) Date of Patent: Sep. 24, 2019

(54) HOLOGRAPHIC WAVEGUIDE OPTICAL TRACKER

(71) Applicant: DigiLens, Inc., Sunnyvale, CA (US)

(72) Inventors: Milan Momcilo Popovich, Leicester (GB); Jonathan David Waldern, Los Altos Hills, CA (US); Alastair John Grant, San Jose, CA (US); Kimberly Sun Lokovic, Sunnyvale, CA (US)

(73) Assignee: DigiLens Inc., Sunnyvale, CA (US)

( * ) Notice: Subject to any disclaimer, the term of this patent is extended or adjusted under 35 U.S.C. 154(b) by 0 days.

(21) Appl. No.: 15/513,288

(22) PCT Filed: Sep. 25, 2015

(86) PCT No.: PCT/GB2015/000274
§ 371 (c)(1),
(2) Date: Mar. 22, 2017

(87) PCT Pub. No.: WO2016/046514
PCT Pub. Date: Mar. 31, 2016

(65) Prior Publication Data
US 2018/0232048 A1 Aug. 16, 2018

Related U.S. Application Data

(60) Provisional application No. 62/071,534, filed on Sep. 26, 2014, provisional application No. 62/124,154, (Continued)

(51) Int. Cl.
*G06F 3/01* (2006.01)
*A61B 3/113* (2006.01)
(Continued)

(52) U.S. Cl.
CPC .............. *G06F 3/013* (2013.01); *A61B 3/113* (2013.01); *G02B 6/0016* (2013.01); *G02B 6/105* (2013.01);
(Continued)

(58) Field of Classification Search
CPC ..... G06F 3/013; G02B 27/0093; G02B 6/105; G02B 27/0172
See application file for complete search history.

(56) References Cited

U.S. PATENT DOCUMENTS

| 1,043,938 A | 11/1912 | Huttenlocher |
| 3,482,498 A | 12/1969 | Becker |

(Continued)

FOREIGN PATENT DOCUMENTS

| BR | PI0720469 A2 | 1/2014 |
| CA | 2889727 A1 | 6/2014 |

(Continued)

OTHER PUBLICATIONS

US 9,488,474 B2, 11/2016, Abovitz et al. (withdrawn)
(Continued)

*Primary Examiner* — Qian Yang
(74) *Attorney, Agent, or Firm* — KPPB LLP

(57) ABSTRACT

There is provided an object tracker having: a first waveguide; a source of illumination light; a detector optically coupled to the waveguide; and at least one grating lamina formed within the waveguide. Illumination light propagating along a first optical path from the source to an object in relative motion to the object tracker. Image light reflected from at least one surface of an object is deflected by the grating lamina into a second optical path towards the detector.

21 Claims, 55 Drawing Sheets

Related U.S. Application Data filed on Dec. 10, 2014, provisional application No. 62/125,454, filed on Jan. 22, 2015, provisional application No. 62/179,336, filed on May 5, 2015.

(51) Int. Cl.
  *G02F 1/295* (2006.01)
  *F21V 8/00* (2006.01)
  *G02B 27/01* (2006.01)
  *G02B 27/00* (2006.01)
  *G02B 6/10* (2006.01)

(52) U.S. Cl.
  CPC ....... *G02B 27/0093* (2013.01); *G02B 27/017* (2013.01); *G02B 27/0172* (2013.01); *G02F 1/2955* (2013.01); *G02F 2201/307* (2013.01)

(56) References Cited

U.S. PATENT DOCUMENTS

| | | |
|---|---|---|
| 3,741,716 A | 6/1973 | Johne et al. |
| 3,804,496 A | 4/1974 | Crane et al. |
| 3,843,231 A | 10/1974 | Borel et al. |
| 3,965,029 A | 6/1976 | Arora |
| 3,975,711 A | 8/1976 | McMahon |
| 4,028,725 A | 6/1977 | Lewis |
| 4,035,068 A | 7/1977 | Rawson |
| 4,066,334 A | 1/1978 | Fray et al. |
| 4,248,093 A | 2/1981 | Andersson et al. |
| 4,251,137 A | 2/1981 | Knop et al. |
| 4,322,163 A | 3/1982 | Schiller |
| 4,386,361 A | 5/1983 | Simmonds |
| 4,389,612 A | 6/1983 | Simmonds et al. |
| 4,403,189 A | 9/1983 | Simmonds |
| 4,418,993 A | 12/1983 | Lipton |
| 4,472,037 A | 9/1984 | Lipton |
| 4,523,226 A | 6/1985 | Lipton et al. |
| 4,544,267 A | 10/1985 | Schiller |
| 4,562,463 A | 12/1985 | Lipton |
| 4,566,758 A | 1/1986 | Bos et al. |
| 4,583,117 A | 4/1986 | Lipton et al. |
| 4,643,515 A | 2/1987 | Upatnieks |
| 4,688,900 A | 8/1987 | Doane et al. |
| 4,711,512 A | 12/1987 | Upatnieks |
| 4,728,547 A | 3/1988 | Vaz et al. |
| 4,729,640 A | 3/1988 | Sakata et al. |
| 4,765,703 A | 8/1988 | Suzuki et al. |
| 4,791,788 A | 12/1988 | Sager et al. |
| 4,792,850 A | 12/1988 | Liptoh et al. |
| 4,811,414 A | 3/1989 | Fishbine et al. |
| 4,848,093 A | 7/1989 | Simmonds et al. |
| 4,852,988 A | 8/1989 | Velez et al. |
| 4,884,876 A | 12/1989 | Lipton et al. |
| 4,890,902 A | 1/1990 | Doane et al. |
| 4,933,976 A | 6/1990 | Fishbine et al. |
| 4,938,568 A | 7/1990 | Margerum et al. |
| 4,960,311 A | 10/1990 | Moss et al. |
| 4,964,701 A | 10/1990 | Dorschner et al. |
| 4,967,268 A | 10/1990 | Lipton et al. |
| 4,970,129 A | 11/1990 | Ingwall et al. |
| 4,971,719 A | 11/1990 | Vaz et al. |
| 4,994,204 A | 2/1991 | West |
| 5,004,323 A | 4/1991 | West |
| 5,009,483 A | 4/1991 | Rockwell et al. |
| 5,033,814 A | 7/1991 | Brown et al. |
| 5,053,834 A | 10/1991 | Simmonds |
| 5,063,441 A | 11/1991 | Lipton et al. |
| 5,096,282 A | 3/1992 | Margerum et al. |
| 5,099,343 A | 3/1992 | Margerum et al. |
| 5,110,034 A | 5/1992 | Simmonds et al. |
| 5,117,302 A | 5/1992 | Lipton |
| 5,119,454 A | 6/1992 | McMahon et al. |
| 5,139,192 A | 8/1992 | Simmonds et al. |
| 5,142,357 A | 8/1992 | Lipton et al. |
| 5,142,644 A | 8/1992 | Vansteenkiste et al. |
| 5,148,302 A | 9/1992 | Nagano et al. |
| 5,181,133 A | 1/1993 | Lipton |
| 5,193,000 A | 3/1993 | Lipton et al. |
| 5,198,912 A | 3/1993 | Ingwall et al. |
| 5,200,861 A | 4/1993 | Moskovich et al. |
| 5,218,480 A | 6/1993 | Moskovich et al. |
| 5,224,198 A | 6/1993 | Jachimowicz et al. |
| 5,239,372 A | 8/1993 | Lipton |
| 5,240,636 A | 8/1993 | Doane et al. |
| 5,241,337 A | 8/1993 | Betensky et al. |
| 5,242,476 A | 9/1993 | Bartel et al. |
| 5,251,048 A | 10/1993 | Doane et al. |
| 5,264,950 A | 11/1993 | West et al. |
| 5,268,792 A | 12/1993 | Kreitzer et al. |
| 5,284,499 A | 2/1994 | Harvey et al. |
| 5,295,208 A | 3/1994 | Caulfield et al. |
| 5,296,967 A | 3/1994 | Moskovich et al. |
| 5,299,289 A | 3/1994 | Omae et al. |
| 5,309,283 A | 5/1994 | Kreitzer et al. |
| 5,313,330 A | 5/1994 | Betensky |
| 5,315,324 A | 5/1994 | Simmonds et al. |
| 5,315,419 A | 5/1994 | Saupe et al. |
| 5,315,440 A | 5/1994 | Betensky et al. |
| 5,327,269 A | 7/1994 | Tilton et al. |
| 5,329,363 A | 7/1994 | Moskovich et al. |
| 5,343,147 A | 8/1994 | Sager et al. |
| 5,368,770 A | 11/1994 | Saupe et al. |
| 5,371,626 A | 12/1994 | Betensky |
| 5,410,376 A | 4/1995 | Cornsweet et al. |
| 5,416,510 A | 5/1995 | Lipton et al. |
| 5,418,871 A | 5/1995 | Revelli et al. |
| 5,428,480 A | 6/1995 | Betensky et al. |
| 5,437,811 A | 8/1995 | Doane et al. |
| 5,452,385 A | 9/1995 | Izumi et al. |
| 5,453,863 A | 9/1995 | West et al. |
| 5,455,693 A | 10/1995 | Wreede et al. |
| 5,455,713 A | 10/1995 | Kreitzer et al. |
| 5,463,428 A | 10/1995 | Lipton et al. |
| 5,465,311 A | 11/1995 | Caulfield et al. |
| 5,476,611 A | 12/1995 | Nolan et al. |
| 5,481,321 A | 1/1996 | Lipton |
| 5,485,313 A | 1/1996 | Betensky |
| 5,493,430 A | 2/1996 | Lu et al. |
| 5,493,448 A | 2/1996 | Betensky et al. |
| 5,499,140 A | 3/1996 | Betensky |
| 5,500,769 A | 3/1996 | Betensky |
| 5,515,184 A | 5/1996 | Caulfield et al. |
| 5,516,455 A | 5/1996 | Rakas et al. |
| 5,530,566 A | 6/1996 | Kumar |
| 5,532,875 A | 7/1996 | Betemsky |
| RE35,310 E | 8/1996 | Moskovich |
| 5,543,950 A | 8/1996 | Lavrentovich et al. |
| 5,559,637 A | 9/1996 | Moskovich et al. |
| 5,572,250 A | 11/1996 | Lipton et al. |
| 5,576,888 A | 11/1996 | Betensky |
| 5,585,035 A | 12/1996 | Vesley et al. |
| 5,593,615 A | 1/1997 | Nerad et al. |
| 5,619,586 A | 4/1997 | Sibbald et al. |
| 5,621,529 A | 4/1997 | Gordon et al. |
| 5,621,552 A | 4/1997 | Coates et al. |
| 5,625,495 A | 4/1997 | Moskovich et al. |
| 5,668,614 A | 9/1997 | Chien et al. |
| 5,677,797 A | 10/1997 | Betensky et al. |
| 5,680,231 A | 10/1997 | Grinberg et al. |
| 5,682,255 A | 10/1997 | Friesem et al. |
| 5,686,931 A | 11/1997 | Fuenfschilling et al. |
| 5,686,975 A | 11/1997 | Lipton |
| 5,691,795 A | 11/1997 | Doane et al. |
| 5,695,682 A | 12/1997 | Doane et al. |
| 5,706,136 A | 1/1998 | Okuyama et al. |
| 5,710,645 A | 1/1998 | Phillips et al. |
| 5,745,266 A | 4/1998 | Smith et al. |
| 5,745,301 A | 4/1998 | Betensky et al. |
| 5,748,272 A | 5/1998 | Tanaka et al. |
| 5,748,277 A | 5/1998 | Huang et al. |
| 5,751,452 A | 5/1998 | Tanaka et al. |
| 5,757,546 A | 5/1998 | Lipton et al. |
| 5,790,314 A | 8/1998 | Duck et al. |
| 5,798,641 A | 8/1998 | Spagna et al. |

(56) References Cited

U.S. PATENT DOCUMENTS

| | | |
|---|---|---|
| 5,808,804 A | 9/1998 | Moskovich |
| 5,822,089 A | 10/1998 | Phillips et al. |
| 5,825,448 A | 10/1998 | Bos et al. |
| 5,831,700 A | 11/1998 | Li et al. |
| 5,835,661 A | 11/1998 | Tai et al. |
| 5,841,587 A | 11/1998 | Moskovich et al. |
| 5,856,842 A | 1/1999 | Tedesco |
| 5,867,238 A | 2/1999 | Miller et al. |
| 5,870,228 A | 2/1999 | Kreitzer et al. |
| 5,875,012 A | 2/1999 | Crawford et al. |
| 5,877,826 A | 3/1999 | Yang et al. |
| 5,892,599 A | 4/1999 | Bahuguna |
| 5,900,987 A | 5/1999 | Kreitzer et al. |
| 5,900,989 A | 5/1999 | Kreitzer |
| 5,929,960 A | 7/1999 | West et al. |
| 5,930,433 A | 7/1999 | Williamson et al. |
| 5,936,776 A | 8/1999 | Kreitzer |
| 5,937,115 A | 8/1999 | Domash |
| 5,942,157 A | 8/1999 | Sutherland et al. |
| 5,949,508 A | 9/1999 | Kumar et al. |
| 5,956,113 A | 9/1999 | Crawford |
| 5,963,375 A | 10/1999 | Kreitzer |
| 5,966,223 A | 10/1999 | Friesem et al. |
| 5,969,874 A | 10/1999 | Moskovich |
| 5,969,876 A | 10/1999 | Kreitzer et al. |
| 5,973,727 A | 10/1999 | McGrew et al. |
| 5,974,162 A | 10/1999 | Metz et al. |
| 5,986,746 A | 11/1999 | Metz et al. |
| 5,999,089 A | 12/1999 | Carlson et al. |
| 5,999,282 A | 12/1999 | Suzuki et al. |
| 6,014,187 A | 1/2000 | Okuda et al. |
| 6,023,375 A | 2/2000 | Kreitzer |
| 6,046,585 A | 4/2000 | Simmonds |
| 6,052,540 A | 4/2000 | Koyama |
| 6,061,107 A | 5/2000 | Yang |
| 6,061,463 A | 5/2000 | Metz et al. |
| 6,069,728 A | 5/2000 | Huignard et al. |
| 6,094,311 A | 7/2000 | Moskovich |
| 6,097,551 A | 8/2000 | Kreitzer |
| 6,104,448 A | 8/2000 | Doane et al. |
| 6,115,152 A | 9/2000 | Popovich et al. |
| 6,128,058 A | 10/2000 | Walton et al. |
| 6,133,971 A | 10/2000 | Silverstein et al. |
| 6,133,975 A | 10/2000 | Li et al. |
| 6,141,074 A | 10/2000 | Bos et al. |
| 6,141,154 A | 10/2000 | Kreitzer et al. |
| 6,151,142 A | 11/2000 | Phillips et al. |
| 6,154,190 A | 11/2000 | Yang et al. |
| 6,169,594 B1 | 1/2001 | Aye et al. |
| 6,169,613 B1 | 1/2001 | Amitai et al. |
| 6,169,636 B1 | 1/2001 | Kreitzer |
| 6,188,462 B1 | 2/2001 | Lavrentovich et al. |
| 6,191,887 B1 | 2/2001 | Michaloski et al. |
| 6,195,209 B1 | 2/2001 | Kreitzer et al. |
| 6,204,835 B1 | 3/2001 | Yang et al. |
| 6,211,976 B1 | 4/2001 | Popovich et al. |
| 6,268,839 B1 | 7/2001 | Yang et al. |
| 6,269,203 B1 | 7/2001 | Davies et al. |
| 6,275,031 B1 | 8/2001 | Simmonds et al. |
| 6,278,429 B1 | 8/2001 | Ruth et al. |
| 6,297,860 B1 | 10/2001 | Moskovich et al. |
| 6,301,056 B1 | 10/2001 | Kreitzer et al. |
| 6,301,057 B1 | 10/2001 | Kreitzer et al. |
| 6,317,228 B2 | 11/2001 | Popovich et al. |
| 6,320,563 B1 | 11/2001 | Yang et al. |
| 6,324,014 B1 | 11/2001 | Moskovich et al. |
| 6,330,109 B1 | 12/2001 | Ishii et al. |
| 6,351,273 B1 | 2/2002 | Lemelson et al. |
| 6,366,281 B1 | 4/2002 | Lipton et al. |
| 6,377,238 B1 | 4/2002 | McPheters |
| 6,377,321 B1 | 4/2002 | Khan et al. |
| 6,388,797 B1 | 5/2002 | Lipton et al. |
| 6,411,444 B1 | 6/2002 | Moskovich et al. |
| 6,414,760 B1 | 7/2002 | Lopez et al. |
| 6,417,971 B1 | 7/2002 | Moskovich et al. |
| 6,437,563 B1 | 8/2002 | Simmonds et al. |
| 6,445,512 B1 | 9/2002 | Moskovich et al. |
| 6,476,974 B1 | 11/2002 | Kreitzer et al. |
| 6,483,303 B2 | 11/2002 | Simmonds et al. |
| 6,504,629 B1 | 1/2003 | Popovich et al. |
| 6,509,937 B1 | 1/2003 | Moskovich et al. |
| 6,518,747 B2 | 2/2003 | Sager et al. |
| 6,519,088 B1 | 2/2003 | Lipton |
| 6,529,336 B1 | 3/2003 | Kreitzer et al. |
| 6,559,813 B1 | 5/2003 | DeLuca et al. |
| 6,563,648 B2 | 5/2003 | Gleckman et al. |
| 6,563,650 B2 | 5/2003 | Moskovich et al. |
| 6,567,573 B1 | 5/2003 | Domash et al. |
| 6,577,411 B1 | 6/2003 | David et al. |
| 6,577,429 B1 | 6/2003 | Kurtz et al. |
| 6,580,529 B1 | 6/2003 | Amitai et al. |
| 6,583,838 B1 | 6/2003 | Hoke et al. |
| 6,594,090 B2 | 7/2003 | Kruschwitz et al. |
| 6,597,176 B2 | 7/2003 | Simmonds et al. |
| 6,597,475 B1 | 7/2003 | Shirakura et al. |
| 6,600,590 B2 | 7/2003 | Roddy et al. |
| 6,618,104 B1 | 9/2003 | Date et al. |
| 6,625,381 B2 | 9/2003 | Roddy et al. |
| 6,646,772 B1 | 11/2003 | Popovich et al. |
| 6,667,134 B1 | 12/2003 | Sutherland et al. |
| 6,677,086 B1 | 1/2004 | Bunning et al. |
| 6,692,666 B2 | 2/2004 | Sutherland et al. |
| 6,699,407 B1 | 3/2004 | Bunning et al. |
| 6,706,086 B2 | 3/2004 | Emig et al. |
| 6,706,451 B1 | 3/2004 | Sutherland et al. |
| 6,730,442 B1 | 5/2004 | Sutherland et al. |
| 6,731,434 B1 | 5/2004 | Hua et al. |
| 6,738,105 B1 | 5/2004 | Hannah et al. |
| 6,747,781 B2 | 6/2004 | Trisnadi et al. |
| 6,791,629 B2 | 9/2004 | Moskovich et al. |
| 6,791,739 B2 | 9/2004 | Ramanujan et al. |
| 6,804,066 B1 | 10/2004 | Ha et al. |
| 6,805,490 B2 | 10/2004 | Levola |
| 6,821,457 B1 | 11/2004 | Sutherland et al. |
| 6,822,713 B1 | 11/2004 | Yaroshchuk et al. |
| 6,825,987 B2 | 11/2004 | Repetto et al. |
| 6,829,095 B2 | 12/2004 | Amitai |
| 6,830,789 B2 | 12/2004 | Doane et al. |
| 6,833,955 B2 | 12/2004 | Niv |
| 6,847,488 B2 | 1/2005 | Travis |
| 6,850,210 B1 | 2/2005 | Lipton et al. |
| 6,853,493 B2 | 2/2005 | Kreitzer et al. |
| 6,867,888 B2 | 3/2005 | Sutherland et al. |
| 6,878,494 B2 | 4/2005 | Bunning et al. |
| 6,927,570 B2 | 8/2005 | Simmonds et al. |
| 6,927,694 B1 | 8/2005 | Smith et al. |
| 6,950,173 B1 | 9/2005 | Sutherland et al. |
| 6,952,435 B2 | 10/2005 | Lai et al. |
| 6,958,868 B1 | 10/2005 | Pender |
| 6,963,454 B1 | 11/2005 | Martins et al. |
| 6,975,345 B1 | 12/2005 | Lipton et al. |
| 6,980,365 B2 | 12/2005 | Moskovich |
| 6,985,296 B2 | 1/2006 | Lipton et al. |
| 6,999,239 B1 | 2/2006 | Martins et al. |
| 7,002,618 B2 | 2/2006 | Lipton et al. |
| 7,002,753 B2 | 2/2006 | Moskovich et al. |
| 7,009,773 B2 | 3/2006 | Chaoulov et al. |
| 7,018,563 B1 | 3/2006 | Sutherland et al. |
| 7,018,686 B2 | 3/2006 | Bunning et al. |
| 7,019,793 B2 | 3/2006 | Moskovich et al. |
| 7,021,777 B2 | 4/2006 | Amitai |
| 7,026,892 B2 | 4/2006 | Kajiya |
| 7,054,045 B2 | 5/2006 | McPheters et al. |
| 7,068,405 B2 | 6/2006 | Sutherland et al. |
| 7,072,020 B1 | 7/2006 | Sutherland et al. |
| 7,075,273 B2 | 7/2006 | O'Gorman et al. |
| 7,077,984 B1 | 7/2006 | Natarajan et al. |
| 7,081,215 B2 | 7/2006 | Natarajan et al. |
| 7,088,457 B1 | 8/2006 | Zou et al. |
| 7,088,515 B2 | 8/2006 | Lipton |
| 7,099,080 B2 | 8/2006 | Lipton et al. |
| 7,108,383 B1 | 9/2006 | Mitchell et al. |
| 7,119,965 B1 | 10/2006 | Rolland et al. |
| 7,123,421 B1 | 10/2006 | Moskovich et al. |

(56) References Cited

U.S. PATENT DOCUMENTS

| | | |
|---|---|---|
| 7,133,084 B2 | 11/2006 | Moskovich et al. |
| 7,139,109 B2 | 11/2006 | Mukawa |
| RE39,424 E | 12/2006 | Moskovich |
| 7,145,729 B2 | 12/2006 | Kreitzer et al. |
| 7,149,385 B2 | 12/2006 | Parikka et al. |
| 7,167,286 B2 | 1/2007 | Anderson et al. |
| 7,175,780 B1 | 2/2007 | Sutherland et al. |
| 7,181,108 B2 | 2/2007 | Levola |
| 7,184,002 B2 | 2/2007 | Lipton et al. |
| 7,184,615 B2 | 2/2007 | Levola |
| 7,186,567 B1 | 3/2007 | Sutherland et al. |
| 7,198,737 B2 | 4/2007 | Natarajan et al. |
| 7,206,107 B2 | 4/2007 | Levola |
| 7,230,770 B2 | 6/2007 | Kreitzer et al. |
| 7,256,915 B2 | 8/2007 | Sutherland et al. |
| 7,265,882 B2 | 9/2007 | Sutherland et al. |
| 7,265,903 B2 | 9/2007 | Sutherland et al. |
| RE39,911 E | 11/2007 | Moskovich |
| 7,301,601 B2 | 11/2007 | Lin et al. |
| 7,312,906 B2 | 12/2007 | Sutherland et al. |
| 7,333,685 B2 | 2/2008 | Stone et al. |
| 7,375,886 B2 | 5/2008 | Lipton et al. |
| 7,391,573 B2 | 6/2008 | Amitai |
| 7,413,678 B1 | 8/2008 | Natarajan et al. |
| 7,413,679 B1 | 8/2008 | Sutherland et al. |
| 7,416,818 B2 | 8/2008 | Sutherland et al. |
| 7,418,170 B2 | 8/2008 | Mukawa et al. |
| 7,420,733 B1 | 9/2008 | Natarajan et al. |
| 7,453,612 B2 | 11/2008 | Mukawa |
| 7,454,103 B2 | 11/2008 | Parriaux |
| 7,457,040 B2 | 11/2008 | Amitai |
| 7,477,206 B2 | 1/2009 | Cowan et al. |
| 7,499,217 B2 | 3/2009 | Cakmakci et al. |
| 7,511,891 B2 | 3/2009 | Messerschmidt et al. |
| 7,522,344 B1 | 4/2009 | Curatu et al. |
| 7,542,210 B2 | 6/2009 | Chirieleison |
| 7,570,322 B1 | 8/2009 | Sutherland et al. |
| 7,570,405 B1 | 8/2009 | Sutherland et al. |
| 7,577,326 B2 | 8/2009 | Amitai |
| 7,583,423 B2 | 9/2009 | Sutherland et al. |
| 7,589,901 B2 | 9/2009 | DeJong et al. |
| 7,605,882 B1 | 10/2009 | Sutherland et al. |
| 7,619,739 B1 | 11/2009 | Sutherland et al. |
| 7,639,208 B1 | 12/2009 | Ha et al. |
| 7,643,214 B2 | 1/2010 | Amitai |
| 7,672,055 B2 | 3/2010 | Amitai |
| 7,672,549 B2 | 3/2010 | Schultz et al. |
| 7,710,622 B2 | 5/2010 | Takabayashi et al. |
| 7,724,443 B2 | 5/2010 | Amitai |
| 7,740,387 B2 | 6/2010 | Schultz et al. |
| 7,747,113 B2 | 6/2010 | Mukawa et al. |
| 7,751,122 B2 | 7/2010 | Amitai |
| 7,751,662 B2 | 7/2010 | Kleemann et al. |
| 7,764,413 B2 | 7/2010 | Levola |
| 7,777,819 B2 | 8/2010 | Simmonds |
| 7,843,642 B2 | 11/2010 | Shaoulov et al. |
| 7,866,869 B2 | 1/2011 | Karakawa |
| 7,872,707 B1 | 1/2011 | Sutherland et al. |
| 7,884,593 B2 | 2/2011 | Simmonds et al. |
| 7,884,985 B2 | 2/2011 | Amitai et al. |
| 7,907,342 B2 | 3/2011 | Simmonds et al. |
| 7,936,519 B2 | 5/2011 | Mukawa et al. |
| 7,944,616 B2 | 5/2011 | Mukawa |
| 7,949,214 B2 | 5/2011 | DeJong et al. |
| 7,969,657 B2 | 6/2011 | Cakmakci et al. |
| 8,000,020 B2 | 8/2011 | Amitai et al. |
| 8,014,050 B2 | 9/2011 | McGrew |
| 8,016,475 B2 | 9/2011 | Travis |
| 8,018,579 B1 | 9/2011 | Krah |
| 8,023,783 B2 | 9/2011 | Mukawa et al. |
| 8,073,296 B2 | 12/2011 | Mukawa et al. |
| 8,077,274 B2 | 12/2011 | Sutherland et al. |
| 8,093,451 B2 | 1/2012 | Simmonds et al. |
| 8,098,439 B2 | 1/2012 | Amitai et al. |
| 8,107,023 B2 | 1/2012 | Simmonds et al. |
| 8,107,780 B2 | 1/2012 | Simmonds |
| 8,132,948 B2 | 3/2012 | Owen et al. |
| 8,134,434 B2 | 3/2012 | Diederichs et al. |
| 8,142,016 B2 | 3/2012 | Legerton et al. |
| 8,155,489 B2 | 4/2012 | Saarikko et al. |
| 8,160,411 B2 | 4/2012 | Levola et al. |
| 8,167,173 B1 | 5/2012 | Simmonds et al. |
| 8,194,325 B2 | 6/2012 | Saarikko et al. |
| 8,213,065 B2 | 7/2012 | Mukawa |
| 8,213,755 B2 | 7/2012 | Mukawa et al. |
| 8,220,966 B2 | 7/2012 | Mukawa |
| 8,224,133 B2 | 7/2012 | Popovich et al. |
| 8,233,204 B1 | 7/2012 | Robbins et al. |
| 8,294,749 B2 | 10/2012 | Cable |
| 8,310,327 B2 | 11/2012 | Willers et al. |
| 8,314,993 B2 | 11/2012 | Levola et al. |
| 8,320,032 B2 | 11/2012 | Levola |
| 8,325,166 B2 | 12/2012 | Akutsu et al. |
| 8,329,773 B2 | 12/2012 | Fäcke et al. |
| 8,335,040 B2 | 12/2012 | Mukawa et al. |
| 8,351,744 B2 | 1/2013 | Travis et al. |
| 8,354,640 B2 | 1/2013 | Hamre et al. |
| 8,355,610 B2 | 1/2013 | Simmonds |
| 8,369,019 B2 | 2/2013 | Baker et al. |
| 8,376,548 B2 | 2/2013 | Schultz |
| 8,382,293 B2 | 2/2013 | Phillips, III et al. |
| 8,384,504 B2 | 2/2013 | Diederichs et al. |
| 8,396,339 B2 | 3/2013 | Mukawa et al. |
| 8,422,840 B2 | 4/2013 | Large |
| 8,432,614 B2 | 4/2013 | Amitai |
| 8,441,731 B2 | 5/2013 | Sprague |
| 8,466,953 B2 | 6/2013 | Levola et al. |
| 8,472,120 B2 | 6/2013 | Border et al. |
| 8,481,130 B2 | 7/2013 | Doornkamp et al. |
| 8,482,858 B2 | 7/2013 | Sprague |
| 8,488,246 B2 | 7/2013 | Border et al. |
| 8,491,136 B2 | 7/2013 | Travis et al. |
| 8,493,662 B2 | 7/2013 | Noui |
| 8,494,229 B2 | 7/2013 | Järvenpää et al. |
| 8,520,309 B2 | 8/2013 | Sprague |
| 8,547,638 B2 | 10/2013 | Levola |
| 8,548,290 B2 | 10/2013 | Travers et al. |
| 8,565,560 B2 | 10/2013 | Popovich et al. |
| 8,582,206 B2 | 11/2013 | Travis |
| 8,593,734 B2 | 11/2013 | Laakkonen |
| 8,611,014 B2 | 12/2013 | Valera et al. |
| 8,634,120 B2 | 1/2014 | Popovich et al. |
| 8,639,072 B2 | 1/2014 | Popovich et al. |
| 8,643,948 B2 | 2/2014 | Amitai et al. |
| 8,649,099 B2 | 2/2014 | Schultz et al. |
| 8,654,420 B2 | 2/2014 | Simmonds |
| 8,659,826 B1 | 2/2014 | Brown et al. |
| D701,206 S | 3/2014 | Luckey et al. |
| 8,698,705 B2 | 4/2014 | Burke et al. |
| 8,731,350 B1 | 5/2014 | Jacobs et al. |
| 8,736,963 B2 | 5/2014 | Robbins et al. |
| 8,746,008 B1 | 6/2014 | Simmonds et al. |
| 8,786,923 B2 | 7/2014 | Chuang et al. |
| 8,810,913 B2 | 8/2014 | Simmonds et al. |
| 8,810,914 B2 | 8/2014 | Amitai |
| 8,817,350 B1 | 8/2014 | Robbins et al. |
| 8,824,836 B2 | 9/2014 | Sugiyama et al. |
| 8,830,584 B2 | 9/2014 | Saarikko et al. |
| 8,842,368 B2 | 9/2014 | Simmonds et al. |
| 8,859,412 B2 | 10/2014 | Jain |
| 8,872,435 B2 | 10/2014 | Montgomery et al. |
| 8,873,149 B2 | 10/2014 | Bohn et al. |
| 8,873,150 B2 | 10/2014 | Amitai |
| 8,885,997 B2 | 11/2014 | Bohn et al. |
| 8,903,207 B1 | 12/2014 | Brown et al. |
| 8,906,088 B2 | 12/2014 | Flitsch et al. |
| 8,913,865 B2 | 12/2014 | Bennett |
| 8,917,453 B2 | 12/2014 | Bohn et al. |
| 8,929,589 B2 | 1/2015 | Publicover et al. |
| 8,937,771 B2 | 1/2015 | Robbins et al. |
| 8,950,867 B2 | 2/2015 | Macnamara |
| 8,964,298 B2 | 2/2015 | Haddick et al. |
| 8,965,152 B2 | 2/2015 | Simmonds |
| 8,985,803 B2 | 3/2015 | Bohn et al. |

(56) References Cited

U.S. PATENT DOCUMENTS

| | | |
|---|---|---|
| 8,989,535 B2 | 3/2015 | Robbins |
| 9,019,595 B2 | 4/2015 | Jain |
| 9,025,253 B2 | 5/2015 | Hadad et al. |
| 9,035,344 B2 | 5/2015 | Jain |
| 9,075,184 B2 | 7/2015 | Popovich et al. |
| 9,081,178 B2 | 7/2015 | Simmonds et al. |
| 9,128,226 B2 | 9/2015 | Fattal et al. |
| 9,129,295 B2 | 9/2015 | Border et al. |
| 9,164,290 B2 | 10/2015 | Robbins et al. |
| 9,201,270 B2 | 12/2015 | Fattal et al. |
| 9,215,293 B2 | 12/2015 | Miller |
| 9,269,854 B2 | 2/2016 | Jain |
| 9,274,338 B2 | 3/2016 | Bohn et al. |
| 9,310,566 B2 | 4/2016 | Valera et al. |
| 9,329,325 B2 | 5/2016 | Simmonds et al. |
| 9,341,846 B2 | 5/2016 | Popovich et al. |
| 9,354,366 B2 | 5/2016 | Jain |
| 9,366,862 B2 | 6/2016 | Osterhout et al. |
| 9,372,347 B1 | 6/2016 | Saarikko et al. |
| 9,377,623 B2 | 6/2016 | Robbins et al. |
| 9,389,415 B2 | 7/2016 | Fattal et al. |
| 9,400,395 B2 | 7/2016 | Travers et al. |
| 9,423,360 B1 | 8/2016 | Tervonen et al. |
| 9,431,794 B2 | 8/2016 | Jain |
| 9,456,744 B2 | 10/2016 | Popovich et al. |
| 9,459,451 B2 | 10/2016 | Saarikko et al. |
| 9,465,213 B2 | 10/2016 | Simmonds |
| 9,494,799 B2 | 11/2016 | Robbins et al. |
| 9,541,383 B2 | 1/2017 | Watson et al. |
| 9,547,174 B2 | 1/2017 | Gao et al. |
| 9,551,874 B2 | 1/2017 | Amitai et al. |
| 9,551,880 B2 | 1/2017 | Amitai et al. |
| 9,612,403 B2 | 4/2017 | Watson et al. |
| 9,651,368 B2 | 5/2017 | Watson et al. |
| 9,664,824 B2 | 5/2017 | Simmonds et al. |
| 9,664,910 B2 | 5/2017 | Mansharof et al. |
| 9,727,772 B2 | 8/2017 | Popovich et al. |
| 9,746,688 B2 | 8/2017 | Popovich et al. |
| 9,804,389 B2 | 10/2017 | Popovich et al. |
| 10,209,517 B2 | 2/2019 | Popovich et al. |
| 2001/0043163 A1 | 11/2001 | Waldern et al. |
| 2001/0050756 A1 | 12/2001 | Lipton et al. |
| 2002/0003509 A1 | 1/2002 | Lipton et al. |
| 2002/0009299 A1 | 1/2002 | Lipton |
| 2002/0011969 A1 | 1/2002 | Lipton et al. |
| 2002/0036825 A1 | 3/2002 | Lipton et al. |
| 2002/0047837 A1 | 4/2002 | Suyama et al. |
| 2002/0075240 A1 | 6/2002 | Lieberman et al. |
| 2002/0110077 A1 | 8/2002 | Drobot et al. |
| 2002/0126332 A1 | 9/2002 | Popovich |
| 2002/0167462 A1 | 11/2002 | Lewis et al. |
| 2002/0196332 A1 | 12/2002 | Lipton et al. |
| 2003/0007070 A1 | 1/2003 | Lipton et al. |
| 2003/0038912 A1 | 2/2003 | Broer et al. |
| 2003/0067685 A1 | 4/2003 | Niv |
| 2003/0086670 A1 | 5/2003 | Moridaira et al. |
| 2003/0107809 A1 | 6/2003 | Chen et al. |
| 2003/0197157 A1 | 10/2003 | Sutherland et al. |
| 2003/0202247 A1 | 10/2003 | Niv et al. |
| 2004/0004767 A1 | 1/2004 | Song |
| 2004/0089842 A1 | 5/2004 | Sutehrland et al. |
| 2004/0109234 A1 | 6/2004 | Levola |
| 2004/0112862 A1 | 6/2004 | Willson et al. |
| 2004/0141217 A1 | 7/2004 | Endo et al. |
| 2004/0175627 A1 | 9/2004 | Sutherland et al. |
| 2004/0179764 A1 | 9/2004 | Melikechi et al. |
| 2004/0263969 A1 | 12/2004 | Lipton et al. |
| 2004/0263971 A1 | 12/2004 | Lipton et al. |
| 2005/0018304 A1 | 1/2005 | Lipton et al. |
| 2005/0079663 A1 | 4/2005 | Masutani et al. |
| 2005/0105909 A1 | 5/2005 | Stone |
| 2005/0122395 A1 | 6/2005 | Lipton et al. |
| 2005/0134404 A1 | 6/2005 | Kajiya et al. |
| 2005/0141066 A1 | 6/2005 | Ouchi |
| 2005/0180687 A1 | 8/2005 | Amitai |
| 2005/0195276 A1 | 9/2005 | Lipton et al. |
| 2005/0232530 A1 | 10/2005 | Kekas et al. |
| 2005/0265585 A1 | 12/2005 | Rowe |
| 2005/0271258 A1 | 12/2005 | Rowe |
| 2005/0286133 A1 | 12/2005 | Lipton |
| 2006/0012878 A1 | 1/2006 | Lipton et al. |
| 2006/0043938 A1 | 3/2006 | O'Gorman et al. |
| 2006/0119837 A1 | 6/2006 | Raguin et al. |
| 2006/0132914 A1 | 6/2006 | Weiss et al. |
| 2006/0146422 A1 | 7/2006 | Koike |
| 2006/0171647 A1 | 8/2006 | Ye et al. |
| 2006/0191293 A1 | 8/2006 | Kuczma |
| 2006/0215244 A1 | 9/2006 | Yosha et al. |
| 2006/0221063 A1 | 10/2006 | Ishihara |
| 2006/0228073 A1 | 10/2006 | Mukawa et al. |
| 2006/0268104 A1 | 11/2006 | Cowan et al. |
| 2006/0268412 A1 | 11/2006 | Downing et al. |
| 2006/0284974 A1 | 12/2006 | Lipton et al. |
| 2006/0285205 A1 | 12/2006 | Lipton et al. |
| 2006/0291052 A1 | 12/2006 | Lipton et al. |
| 2007/0012777 A1 | 1/2007 | Tsikos et al. |
| 2007/0019152 A1 | 1/2007 | Caputo |
| 2007/0041684 A1 | 2/2007 | Popovich et al. |
| 2007/0070476 A1 | 3/2007 | Yamada et al. |
| 2007/0070504 A1 | 3/2007 | Akutsu et al. |
| 2007/0097502 A1 | 5/2007 | Lipton et al. |
| 2007/0109401 A1 | 5/2007 | Lipton et al. |
| 2007/0133089 A1 | 6/2007 | Lipton et al. |
| 2007/0154153 A1 | 7/2007 | Fomitchov et al. |
| 2007/0160325 A1 | 7/2007 | Son et al. |
| 2007/0177007 A1 | 8/2007 | Lipton et al. |
| 2007/0183650 A1 | 8/2007 | Lipton et al. |
| 2007/0188602 A1 | 8/2007 | Cowan et al. |
| 2007/0206155 A1 | 9/2007 | Lipton |
| 2007/0236560 A1 | 10/2007 | Lipton et al. |
| 2007/0237456 A1 | 10/2007 | Blauvelt et al. |
| 2007/0247687 A1 | 10/2007 | Handschy et al. |
| 2007/0258138 A1 | 11/2007 | Cowan et al. |
| 2007/0263169 A1 | 11/2007 | Lipton |
| 2008/0018851 A1 | 1/2008 | Lipton et al. |
| 2008/0024598 A1 | 1/2008 | Perlin et al. |
| 2008/0043334 A1 | 2/2008 | Itzkovitch et al. |
| 2008/0049100 A1 | 2/2008 | Lipton et al. |
| 2008/0062259 A1 | 3/2008 | Lipton et al. |
| 2008/0106775 A1 | 5/2008 | Amitai et al. |
| 2008/0106779 A1 | 5/2008 | Peterson et al. |
| 2008/0117289 A1 | 5/2008 | Schowengerdt et al. |
| 2008/0138013 A1 | 6/2008 | Parriaux |
| 2008/0143964 A1 | 6/2008 | Cowan et al. |
| 2008/0143965 A1 | 6/2008 | Cowan et al. |
| 2008/0149517 A1 | 6/2008 | Lipton et al. |
| 2008/0151370 A1 | 6/2008 | Cook et al. |
| 2008/0186573 A1 | 8/2008 | Lipton |
| 2008/0186574 A1 | 8/2008 | Robinson et al. |
| 2008/0198471 A1 | 8/2008 | Amitai |
| 2008/0226281 A1 | 9/2008 | Lipton |
| 2008/0239067 A1 | 10/2008 | Lipton |
| 2008/0239068 A1 | 10/2008 | Lipton |
| 2008/0273081 A1 | 11/2008 | Lipton |
| 2008/0285137 A1 | 11/2008 | Simmonds et al. |
| 2008/0297731 A1 | 12/2008 | Powell et al. |
| 2008/0298649 A1 | 12/2008 | Ennis et al. |
| 2008/0303895 A1 | 12/2008 | Akka et al. |
| 2008/0303896 A1 | 12/2008 | Lipton et al. |
| 2008/0304111 A1 | 12/2008 | Queenan et al. |
| 2008/0316303 A1 | 12/2008 | Chiu et al. |
| 2008/0316375 A1 | 12/2008 | Lipton et al. |
| 2009/0052047 A1 | 2/2009 | Amitai |
| 2009/0074356 A1 | 3/2009 | Sanchez et al. |
| 2009/0128495 A1 | 5/2009 | Kong et al. |
| 2009/0128911 A1 | 5/2009 | Itzkovitch et al. |
| 2009/0141324 A1 | 6/2009 | Mukawa |
| 2009/0190222 A1 | 7/2009 | Simmonds et al. |
| 2009/0242021 A1 | 10/2009 | Petkie et al. |
| 2009/0296218 A1 | 12/2009 | Ryytty |
| 2009/0303599 A1 | 12/2009 | Levola |
| 2010/0014312 A1 | 1/2010 | Travis et al. |
| 2010/0039796 A1 | 2/2010 | Mukawa |
| 2010/0053565 A1 | 3/2010 | Mizushima et al. |

(56) References Cited

U.S. PATENT DOCUMENTS

| | | |
|---|---|---|
| 2010/0079865 A1 | 4/2010 | Saarikko et al. |
| 2010/0086256 A1 | 4/2010 | Ben Bakir et al. |
| 2010/0097674 A1 | 4/2010 | Kasazumi et al. |
| 2010/0097820 A1 | 4/2010 | Owen et al. |
| 2010/0103078 A1 | 4/2010 | Mukawa et al. |
| 2010/0134534 A1 | 6/2010 | Seesselberg et al. |
| 2010/0149073 A1 | 6/2010 | Chaum et al. |
| 2010/0202725 A1 | 8/2010 | Popovich et al. |
| 2010/0220293 A1 | 9/2010 | Mizushima et al. |
| 2010/0231532 A1 | 9/2010 | Nho et al. |
| 2010/0246003 A1 | 9/2010 | Simmonds et al. |
| 2010/0246004 A1 | 9/2010 | Simmonds |
| 2010/0284085 A1 | 11/2010 | Laakkonen |
| 2010/0284090 A1 | 11/2010 | Simmonds et al. |
| 2010/0284180 A1 | 11/2010 | Popovich et al. |
| 2010/0321781 A1 | 12/2010 | Levola et al. |
| 2011/0019874 A1 | 1/2011 | Jarvenpaa et al. |
| 2011/0026128 A1 | 2/2011 | Baker et al. |
| 2011/0032602 A1 | 2/2011 | Rothenberg et al. |
| 2011/0032618 A1 | 2/2011 | Handerek et al. |
| 2011/0032706 A1 | 2/2011 | Mukawa |
| 2011/0063604 A1 | 3/2011 | Hamre et al. |
| 2011/0102711 A1 | 5/2011 | Sutherland et al. |
| 2011/0109880 A1 | 5/2011 | Nummela |
| 2011/0187293 A1 | 8/2011 | Travis et al. |
| 2011/0235179 A1 | 9/2011 | Simmonds |
| 2011/0236803 A1 | 9/2011 | Weiser et al. |
| 2011/0242661 A1 | 10/2011 | Simmonds |
| 2011/0242670 A1 | 10/2011 | Simmonds |
| 2011/0249309 A1 | 10/2011 | McPheters et al. |
| 2011/0274435 A1 | 11/2011 | Fini et al. |
| 2012/0033306 A1 | 2/2012 | Valera et al. |
| 2012/0044572 A1 | 2/2012 | Simmonds et al. |
| 2012/0044573 A1 | 2/2012 | Simmonds et al. |
| 2012/0062850 A1 | 3/2012 | Travis |
| 2012/0062998 A1 | 3/2012 | Schultz et al. |
| 2012/0075168 A1 | 3/2012 | Osterhout et al. |
| 2012/0081789 A1 | 4/2012 | Mukawa et al. |
| 2012/0092632 A1 | 4/2012 | McLeod et al. |
| 2012/0120493 A1 | 5/2012 | Simmonds et al. |
| 2012/0162549 A1 | 6/2012 | Gao et al. |
| 2012/0183888 A1 | 7/2012 | Oliveira et al. |
| 2012/0194420 A1 | 8/2012 | Osterhout et al. |
| 2012/0200532 A1 | 8/2012 | Powell et al. |
| 2012/0206811 A1 | 8/2012 | Mukawa et al. |
| 2012/0206937 A1 | 8/2012 | Travis et al. |
| 2012/0207432 A1 | 8/2012 | Travis et al. |
| 2012/0207434 A1 | 8/2012 | Large et al. |
| 2012/0214089 A1 | 8/2012 | Hönel et al. |
| 2012/0214090 A1 | 8/2012 | Weiser et al. |
| 2012/0235886 A1 | 9/2012 | Border et al. |
| 2012/0290973 A1 | 11/2012 | Robertson et al. |
| 2012/0300311 A1 | 11/2012 | Simmonds et al. |
| 2013/0016324 A1 | 1/2013 | Travis |
| 2013/0021392 A1 | 1/2013 | Travis |
| 2013/0021586 A1 | 1/2013 | Lippey |
| 2013/0033485 A1 | 2/2013 | Kollin et al. |
| 2013/0039619 A1 | 2/2013 | Laughlin et al. |
| 2013/0044376 A1 | 2/2013 | Valera et al. |
| 2013/0059233 A1 | 3/2013 | Askham |
| 2013/0069850 A1 | 3/2013 | Mukawa et al. |
| 2013/0077049 A1 | 3/2013 | Bohn |
| 2013/0117377 A1 | 5/2013 | Miller |
| 2013/0125027 A1 | 5/2013 | Abovitz et al. |
| 2013/0128230 A1 | 5/2013 | Macnamara |
| 2013/0143336 A1 | 6/2013 | Jain |
| 2013/0163089 A1 | 6/2013 | Bohn et al. |
| 2013/0176704 A1 | 7/2013 | Lanman et al. |
| 2013/0207887 A1 | 8/2013 | Raffle et al. |
| 2013/0224634 A1 | 8/2013 | Berneth et al. |
| 2013/0229717 A1 | 9/2013 | Amitai |
| 2013/0250207 A1 | 9/2013 | Bohn |
| 2013/0250430 A1 | 9/2013 | Robbins et al. |
| 2013/0250431 A1 | 9/2013 | Robbins et al. |
| 2013/0267309 A1 | 10/2013 | Robbins et al. |
| 2013/0271731 A1 | 10/2013 | Popovich et al. |
| 2013/0277890 A1 | 10/2013 | Bowman et al. |
| 2013/0322810 A1 | 12/2013 | Robbins |
| 2013/0342525 A1 | 12/2013 | Benko et al. |
| 2014/0003762 A1 | 1/2014 | Macnamara |
| 2014/0024159 A1 | 1/2014 | Jain |
| 2014/0055845 A1 | 2/2014 | Jain |
| 2014/0063055 A1 | 3/2014 | Osterhout et al. |
| 2014/0064655 A1 | 3/2014 | Bohn et al. |
| 2014/0071538 A1 | 3/2014 | Muller |
| 2014/0098010 A1 | 4/2014 | Travis |
| 2014/0104665 A1 | 4/2014 | Popovich et al. |
| 2014/0118647 A1 | 5/2014 | Momonoi et al. |
| 2014/0130132 A1 | 5/2014 | Cahill et al. |
| 2014/0140653 A1 | 5/2014 | Brown et al. |
| 2014/0140654 A1 | 5/2014 | Brown et al. |
| 2014/0146394 A1 | 5/2014 | Tout et al. |
| 2014/0160576 A1 | 6/2014 | Robbins et al. |
| 2014/0168735 A1 | 6/2014 | Yuan et al. |
| 2014/0168783 A1 | 6/2014 | Luebke et al. |
| 2014/0176528 A1 | 6/2014 | Robbins |
| 2014/0177023 A1 | 6/2014 | Gao et al. |
| 2014/0185286 A1 | 7/2014 | Popovich et al. |
| 2014/0198128 A1 | 7/2014 | Hong et al. |
| 2014/0198896 A1* | 7/2014 | Hemmendorff ........ A61B 6/4452 378/37 |
| 2014/0204455 A1 | 7/2014 | Popovich et al. |
| 2014/0211322 A1 | 7/2014 | Bohn et al. |
| 2014/0218468 A1 | 8/2014 | Gao et al. |
| 2014/0218801 A1 | 8/2014 | Simmonds et al. |
| 2014/0232759 A1 | 8/2014 | Simmonds et al. |
| 2014/0240834 A1 | 8/2014 | Mason et al. |
| 2014/0240842 A1 | 8/2014 | Nguyen et al. |
| 2014/0267420 A1 | 9/2014 | Schowengerdt et al. |
| 2014/0268353 A1* | 9/2014 | Fujimura ............ G02B 27/0101 359/630 |
| 2014/0300947 A1 | 10/2014 | Fattal et al. |
| 2014/0300960 A1 | 10/2014 | Santori et al. |
| 2014/0300966 A1 | 10/2014 | Travers et al. |
| 2014/0327970 A1 | 11/2014 | Bohn et al. |
| 2014/0330159 A1 | 11/2014 | Costa et al. |
| 2014/0367719 A1 | 12/2014 | Jain |
| 2014/0375542 A1 | 12/2014 | Robbins et al. |
| 2014/0375789 A1 | 12/2014 | Lou et al. |
| 2014/0375790 A1 | 12/2014 | Robbins et al. |
| 2015/0001677 A1 | 1/2015 | Venturato et al. |
| 2015/0003796 A1 | 1/2015 | Bennett |
| 2015/0010265 A1 | 1/2015 | Popovich et al. |
| 2015/0015946 A1 | 1/2015 | Muller |
| 2015/0016777 A1 | 1/2015 | Abovitz et al. |
| 2015/0035744 A1 | 2/2015 | Robbins et al. |
| 2015/0036068 A1 | 2/2015 | Fattal et al. |
| 2015/0058791 A1 | 2/2015 | Robertson et al. |
| 2015/0062675 A1 | 3/2015 | Ayres et al. |
| 2015/0062707 A1 | 3/2015 | Simmonds et al. |
| 2015/0086163 A1 | 3/2015 | Valera et al. |
| 2015/0125109 A1 | 5/2015 | Robbins et al. |
| 2015/0148728 A1 | 5/2015 | Sallum et al. |
| 2015/0185475 A1 | 7/2015 | Saarikko et al. |
| 2015/0235447 A1 | 8/2015 | Abovitz et al. |
| 2015/0235448 A1 | 8/2015 | Schowengerdt et al. |
| 2015/0260994 A1 | 9/2015 | Akutsu et al. |
| 2015/0268415 A1 | 9/2015 | Schowengerdt et al. |
| 2015/0277375 A1 | 10/2015 | Large et al. |
| 2015/0288129 A1 | 10/2015 | Jain |
| 2015/0289762 A1 | 10/2015 | Popovich et al. |
| 2015/0346490 A1 | 12/2015 | Klug et al. |
| 2015/0346495 A1 | 12/2015 | Cheng et al. |
| 2015/0355394 A1 | 12/2015 | Leighton et al. |
| 2016/0003847 A1 | 1/2016 | Ryan et al. |
| 2016/0004090 A1 | 1/2016 | Waldern et al. |
| 2016/0026253 A1 | 1/2016 | Bradski et al. |
| 2016/0033705 A1 | 2/2016 | Fattal |
| 2016/0033706 A1 | 2/2016 | Fattal et al. |
| 2016/0038992 A1 | 2/2016 | Arthur et al. |
| 2016/0041387 A1 | 2/2016 | Valera et al. |
| 2016/0077338 A1 | 3/2016 | Nguyen et al. |
| 2016/0085300 A1 | 3/2016 | Robbins et al. |
| 2016/0116739 A1 | 4/2016 | Schowengerdt et al. |

(56) References Cited

U.S. PATENT DOCUMENTS

| | | | |
|---|---|---|---|
| 2016/0124223 | A1 | 5/2016 | Shinbo et al. |
| 2016/0132025 | A1 | 5/2016 | Taff et al. |
| 2016/0195664 | A1 | 7/2016 | Fattal et al. |
| 2016/0209648 | A1 | 7/2016 | Haddick et al. |
| 2016/0209657 | A1 | 7/2016 | Popovich et al. |
| 2016/0231568 | A1 | 8/2016 | Saarikko et al. |
| 2016/0266398 | A1 | 9/2016 | Poon et al. |
| 2016/0274362 | A1 | 9/2016 | Tinch et al. |
| 2016/0299344 | A1 | 10/2016 | Dobschal et al. |
| 2016/0320536 | A1 | 11/2016 | Ferns et al. |
| 2016/0327705 | A1 | 11/2016 | Ferns et al. |
| 2016/0341964 | A1 | 11/2016 | Amitai et al. |
| 2017/0003505 | A1 | 1/2017 | Vallius et al. |
| 2017/0010488 | A1 | 1/2017 | Schowengerdt et al. |
| 2017/0030550 | A1 | 2/2017 | Popovich et al. |
| 2017/0031160 | A1 | 2/2017 | Popovich et al. |
| 2017/0031171 | A1 | 2/2017 | Vallius et al. |
| 2017/0034435 | A1 | 2/2017 | Vallius et al. |
| 2017/0038579 | A1 | 2/2017 | Schuelke et al. |
| 2017/0052376 | A1 | 2/2017 | Amitai et al. |
| 2017/0059759 | A1 | 3/2017 | Ayres et al. |
| 2017/0102543 | A1 | 4/2017 | Vallius et al. |
| 2017/0115487 | A1 | 4/2017 | Travis et al. |
| 2017/0123208 | A1 | 5/2017 | Vallius et al. |
| 2017/0131460 | A1 | 5/2017 | Lin et al. |
| 2017/0131546 | A1 | 5/2017 | Woltman et al. |
| 2017/0131551 | A1 | 5/2017 | Woltman et al. |
| 2017/0180404 | A1 | 6/2017 | Bersch et al. |
| 2017/0180408 | A1 | 6/2017 | Yu et al. |
| 2017/0219841 | A1 | 8/2017 | Popovich et al. |
| 2017/0299860 | A1 | 10/2017 | Juhola et al. |
| 2018/0113303 | A1 | 4/2018 | Popovich et al. |
| 2018/0275402 | A1 | 9/2018 | Popovich et al. |
| 2019/0041634 | A1 | 2/2019 | Popovich et al. |

FOREIGN PATENT DOCUMENTS

| | | |
|---|---|---|
| CN | 101103297 A | 1/2008 |
| CN | 100492099 C | 5/2009 |
| CN | 104204901 A | 12/2014 |
| CN | 104956252 A | 9/2015 |
| CN | 105074537 A | 11/2015 |
| CN | 105074539 A | 11/2015 |
| CN | 105190407 A | 12/2015 |
| CN | 105229514 A | 1/2016 |
| CN | 105393159 A | 3/2016 |
| CN | 105408801 A | 3/2016 |
| CN | 105408802 A | 3/2016 |
| CN | 105408803 A | 3/2016 |
| CN | 105531716 A | 4/2016 |
| CN | 105705981 A | 6/2016 |
| CN | 109073889 A | 12/2018 |
| DE | 19751190 A1 | 5/1999 |
| DE | 10221837 A1 | 12/2003 |
| DE | 102012108424 A1 | 3/2014 |
| EP | 0795775 A2 | 9/1997 |
| EP | 1347641 A1 | 9/2003 |
| EP | 1413972 A1 | 4/2004 |
| EP | 1526709 A2 | 4/2005 |
| EP | 1748305 A1 | 1/2007 |
| EP | 1413972 B1 | 10/2008 |
| EP | 2110701 A1 | 10/2009 |
| EP | 2244114 A1 | 10/2010 |
| EP | 2326983 A1 | 6/2011 |
| EP | 1828832 B1 | 5/2013 |
| EP | 2733517 A1 | 5/2014 |
| EP | 1573369 B1 | 7/2014 |
| EP | 2929378 A1 | 10/2015 |
| EP | 2748670 B1 | 11/2015 |
| EP | 2995986 A1 | 3/2016 |
| EP | 3198192 A1 | 8/2017 |
| EP | 3245444 A1 | 11/2017 |
| EP | 3245551 A2 | 11/2017 |
| GB | 2140935 A | 12/1984 |
| GB | 2508661 A | 6/2014 |
| GB | 2509536 A | 7/2014 |
| GB | 2512077 A | 9/2014 |
| GB | 2514658 A | 12/2014 |
| HK | 1204684 A1 | 11/2015 |
| HK | 1205563 A1 | 12/2015 |
| HK | 1205793 A1 | 12/2015 |
| HK | 1206101 A1 | 12/2015 |
| JP | 02186319 A | 7/1990 |
| JP | 03239384 A | 10/1991 |
| JP | 06294952 A | 10/1994 |
| JP | 07098439 A | 4/1995 |
| JP | 0990312 A | 4/1997 |
| JP | 11109320 A | 4/1999 |
| JP | 11142806 A | 5/1999 |
| JP | 2953444 B2 | 9/1999 |
| JP | 2000056259 A | 2/2000 |
| JP | 2000267042 A | 9/2000 |
| JP | 2001027739 A | 1/2001 |
| JP | 2001296503 A | 10/2001 |
| JP | 2002090858 A | 3/2002 |
| JP | 2002122906 A | 4/2002 |
| JP | 2002162598 A | 6/2002 |
| JP | 2002523802 A | 7/2002 |
| JP | 2003066428 A | 3/2003 |
| JP | 2003270419 A | 9/2003 |
| JP | 2008112187 A | 5/2008 |
| JP | 2009036955 | 2/2009 |
| JP | 2009211091 A | 9/2009 |
| JP | 4367775 B2 | 11/2009 |
| JP | 2012137616 A | 7/2012 |
| JP | 5303928 B2 | 10/2013 |
| KR | 20100092059 A | 8/2010 |
| KR | 20140140063 A | 12/2014 |
| KR | 20140142337 A | 12/2014 |
| TW | 200535633 A | 11/2005 |
| TW | 200801583 A | 1/2008 |
| TW | 201314263 A | 4/2013 |
| TW | 201600943 A | 1/2016 |
| TW | 201604601 A | 2/2016 |
| WO | 1997001133 A1 | 1/1997 |
| WO | 1997027519 A1 | 7/1997 |
| WO | 1998004650 A1 | 2/1998 |
| WO | 1999009440 A1 | 2/1999 |
| WO | 2000016136 A1 | 3/2000 |
| WO | 2000023830 | 4/2000 |
| WO | 2000023847 | 4/2000 |
| WO | 2000203832 A1 | 4/2000 |
| WO | 2001050200 A2 | 7/2001 |
| WO | 2001090822 A1 | 11/2001 |
| WO | 2002082168 A1 | 10/2002 |
| WO | 2003081320 A1 | 10/2003 |
| WO | 2005001753 A1 | 1/2005 |
| WO | 2005006065 A8 | 1/2005 |
| WO | 2005006065 A3 | 2/2005 |
| WO | 2005073798 A1 | 8/2005 |
| WO | 2006002870 | 1/2006 |
| WO | 2006064301 A1 | 6/2006 |
| WO | 2006064325 A1 | 6/2006 |
| WO | 2006064334 A1 | 6/2006 |
| WO | 2006102073 A2 | 9/2006 |
| WO | 2006132614 A1 | 12/2006 |
| WO | 2006102073 A3 | 1/2007 |
| WO | 2007015141 A2 | 2/2007 |
| WO | 2007029032 A1 | 3/2007 |
| WO | 2007085682 A1 | 8/2007 |
| WO | 2007130130 | 11/2007 |
| WO | 2007141587 A1 | 12/2007 |
| WO | 2007141589 A1 | 12/2007 |
| WO | 2008011066 A2 | 1/2008 |
| WO | 2008011066 A9 | 5/2008 |
| WO | 2008100545 A2 | 8/2008 |
| WO | 2008011066 A3 | 12/2008 |
| WO | 2009013597 A2 | 1/2009 |
| WO | 2009077802 A1 | 6/2009 |
| WO | 2009077803 A1 | 6/2009 |
| WO | 2009101238 A1 | 8/2009 |
| WO | 2007130130 A3 | 9/2009 |
| WO | 2009155437 A1 | 12/2009 |
| WO | 2009155437 A8 | 3/2010 |

(56) References Cited

FOREIGN PATENT DOCUMENTS

| | | |
|---|---|---|
| WO | 2010023444 A1 | 3/2010 |
| WO | 2010057219 A1 | 5/2010 |
| WO | 2010067114 A1 | 6/2010 |
| WO | 2010078856 A1 | 7/2010 |
| WO | 2010104692 A2 | 9/2010 |
| WO | 2010122330 A1 | 10/2010 |
| WO | 2010125337 A2 | 11/2010 |
| WO | 2011032005 A2 | 3/2011 |
| WO | 2011042711 A2 | 4/2011 |
| WO | 2011042711 A3 | 4/2011 |
| WO | 2011051660 A1 | 5/2011 |
| WO | 2011055109 A2 | 5/2011 |
| WO | 2011073673 A1 | 6/2011 |
| WO | 2011107831 A1 | 9/2011 |
| WO | 2011110821 A1 | 9/2011 |
| WO | 2011131978 A1 | 10/2011 |
| WO | 2012052352 A1 | 4/2012 |
| WO | 2012062658 A1 | 5/2012 |
| WO | 2012158950 A1 | 11/2012 |
| WO | 2012172295 A1 | 12/2012 |
| WO | 2013027004 | 2/2013 |
| WO | 2013027006 | 2/2013 |
| WO | 2013034879 A1 | 3/2013 |
| WO | 2013049012 A1 | 4/2013 |
| WO | 2013102759 | 7/2013 |
| WO | 2013163347 A1 | 10/2013 |
| WO | 2013167864 | 11/2013 |
| WO | 2014064427 A1 | 5/2014 |
| WO | 2014080155 A1 | 5/2014 |
| WO | 2014085734 A1 | 6/2014 |
| WO | 2014090379 A1 | 6/2014 |
| WO | 2014091200 A1 | 6/2014 |
| WO | 2014093601 A1 | 6/2014 |
| WO | 2014100182 A1 | 6/2014 |
| WO | 2014113506 A1 | 7/2014 |
| WO | 2014116615 A1 | 7/2014 |
| WO | 2014130383 A1 | 8/2014 |
| WO | 2014144526 A2 | 9/2014 |
| WO | 2014159621 A1 | 10/2014 |
| WO | 2014164901 A1 | 10/2014 |
| WO | 2014176695 A1 | 11/2014 |
| WO | 2014179632 A1 | 11/2014 |
| WO | 2014188149 A1 | 11/2014 |
| WO | 2014209733 A1 | 12/2014 |
| WO | 2014209819 A1 | 12/2014 |
| WO | 2014209820 A1 | 12/2014 |
| WO | 2014209821 A1 | 12/2014 |
| WO | 2014210349 A1 | 12/2014 |
| WO | 2015006784 A2 | 1/2015 |
| WO | 2015017291 A1 | 2/2015 |
| WO | 2015069553 A1 | 5/2015 |
| WO | 2015081313 A2 | 6/2015 |
| WO | 2015117039 A1 | 8/2015 |
| WO | 2015145119 A1 | 10/2015 |
| WO | 2016010289 A1 | 1/2016 |
| WO | 2016020643 A1 | 2/2016 |
| WO | 2016025350 A1 | 2/2016 |
| WO | 2016046514 A1 | 3/2016 |
| WO | 2016103263 A1 | 6/2016 |
| WO | 2016111706 A1 | 7/2016 |
| WO | 2016111707 A1 | 7/2016 |
| WO | 2016111708 A1 | 7/2016 |
| WO | 2016111709 A1 | 7/2016 |
| WO | 2016113533 A2 | 7/2016 |
| WO | 2016113534 A1 | 7/2016 |
| WO | 2016116733 A1 | 7/2016 |
| WO | 2016118107 A1 | 7/2016 |
| WO | 2016122679 A1 | 8/2016 |
| WO | 2016113533 A3 | 10/2016 |
| WO | 2017060665 A1 | 4/2017 |
| WO | 2017134412 A1 | 8/2017 |
| WO | 2017134412 A2 | 8/2017 |
| WO | 2017162999 A1 | 9/2017 |
| WO | 2017180403 A1 | 10/2017 |

OTHER PUBLICATIONS

Machine translation for JP 2009-036955, Takegawa et al., dated 2009.*
Stumpe et al., "New type of polymer-LC electrically switchable diffractive devices—POLIPHEM", May 19, 2015, p. 97.
Subbarayappa et al., "Bistable Nematic Liquid Crystal Device", Jul. 30, 2009, 14 pgs.
Sun et al., "Effects of multiwalled carbon nanotube on holographic polymer dispersed liquid crystal", Polymers Advanced Technologies, Feb. 19, 2010, DOI: 10.1002/pat. 1708, 8 pgs.
Sun et al., "Low-birefringence lens design for polarization sensitive optical systems", Proceedings of SPIE, 2006, vol. 6289, doi: 10.1117/12.679416, pp. 6289DH-1-6289DH-10.
Sutherland et al., "Bragg Gratings in an Acrylate Polymer Consisting of Periodic Polymer-Dispersed Liquid-Crystal Planes", Chem. Mater., 1993, vol. 5, pp. 1533-1538.
Sun et al., "Transflective multiplexing of holographic polymer dispersed liquid crystal using Si additives", eXPRESS Polymer Letters, 2011, vol. 5, No. 1, pp. 73-81.
Sutherland et al., "Electrically switchable volume gratings in polymer-dispersed liquid crystals", Applied Physics Letters, Feb. 28, 1994, vol. 64, No. 9, pp. 1071-1076.
Sutherland et al., "Enhancing the electro-optical properties of liquid crystal nanodroplets for switchable Bragg gratings", Proc. of SPIE, 2008, vol. 7050, pp. 705003-1-705003-9, doi: 10.1117/12.792629.
Sutherland et al., "Liquid crystal bragg gratings: dynamic optical elements for spatial light modulators", Hardened Materials Branch, Hardened Materials Branch, AFRL-L-WP-TP-2007-514, Jan. 2007, Wright-Patterson Air Force Base, OH, 18 pgs.
Sutherland et al., "The physics of photopolymer liquid crystal composite holographic gratings", presented at SPIE: Diffractive and Holographic Optics Technology San Jose, CA, 1996, SPIE, vol. 2689, pp. 158-169.
Sweatt, "Achromatic triplet using holographic optical elements", Applied Optics, May 1977, vol. 16, No. 5, pp. 1390-1391.
Talukdar, "Technology Forecast: Augmented reality", Changing the economics of Smartglasses, Issue 2, 2016, 5 pgs.
Tao et al., "TiO2 nanocomposites with high refractive index and transparency", J. Mater. Chem., Oct. 4, 2011, vol. 21, pp. 18623-18629.
Titus et al., "Efficient, Accurate Liquid Crystal Digital Light Deflector", Proc. SPIE 3633, Diffractive and Holographic Technologies, Systems, and Spatial Light Modulators VI, 1 Jun. 1, 1999, doi: 10.1117/12.349334, 10 pgs.
Tiziani, "Physical Properties of Speckles", Speckle Metrology, Chapter 2, Academic Press, Inc., 1978, pp. 5-9.
Tominaga et al., "Fabrication of holographic polymer dispersed liquid crystals doped with gold nanoparticles", 2010 Japanese Liquid Crystal Society Annual Meeting, 2 pgs.
Tomita, "Holographic assembly of nanoparticles in photopolymers for photonic applications", The International Society for Optical Engineering, SPIE Newsroom, 2006, 10.1117/2.1200612.0475, 3 pgs.
Trisnadi, "Hadamard Speckle Contrast Reduction", Optics Letters, Jan. 1, 2004, vol. 29, No. 1, pp. 11-13.
Trisnadi, "Speckle contrast reduction in laser projection displays", Proc. SPIE 4657, 2002, 7 pgs.
Tzeng et al., "Axially symmetric polarization converters based on photo-aligned liquid crystal films", Optics Express, Mar. 17, 2008, vol. 16, No. 6, pp. 3768-3775.
Upatnieks et al., "Color Holograms for white light reconstruction", Applied Physics Letters, Jun. 1, 1996, vol. 8, No. 11, pp. 286-287.
Ushenko, "The Vector Structure of Laser Biospeckle Fields and Polarization Diagnostics of Collagen Skin Structures", Laser Physics, 2000, vol. 10, No. 5, pp. 1143-1149.
Valoriani, "Mixed Reality: Dalle demo a un prodotto", Disruptive Technologies Conference, Sep. 23, 2016, 67 pgs.
Van Gerwen et al., "Nanoscaled interdigitated electrode arrays for biochemical sensors", Sensors and Actuators, Mar. 3, 1998, vol. B 49, pp. 73-80.

(56) References Cited

OTHER PUBLICATIONS

Vecchi, "Studi Esr Di Sistemi Complessi Basati Su Cristalli Liquidi", Thesis, University of Bologna, Department of Physical and Inorganic Chemistry, 2004-2006, 110 pgs.
Veltri et al., "Model for the photoinduced formation of diffraction gratings in liquid-crystalline composite materials", Applied Physics Letters, May 3, 2004, vol. 84, No. 18, pp. 3492-3494.
Vita, "Switchable Bragg Gratings", Thesis, Universita degli Studi di Napoli Federico II, Nov. 2005, 103 pgs.
Vuzix, "M3000 Smart Glasses, Advanced Waveguide Optics", brochure, Jan. 1, 2017, 2 pgs.
Wang et al., "Liquid-crystal blazed-grating beam deflector", Applied Optics, Dec. 10, 2000, vol. 39, No. 35, pp. 6545-6555.
Wang et al., "Optical Design of Waveguide Holographic Binocular Display for Machine Vision", Applied Mechanics and Materials, Sep. 27, 2013, vols. 427-429, pp. 763-769.
Wang et al., "Speckle reduction in laser projection systems by diffractive optical elements", Applied Optics, Apr. 1, 1998, vol. 37, No. 10, pp. 1770-1775.
Weber et al., "Giant Birefringent Optics in Multilayer Polymer Mirrors", Science, Mar. 31, 2000, vol. 287, pp. 2451-2456.
Wei, "Industrial Applications of Speckle Techniques", Doctoral Thesis, Royal Institute of Technology, Department of Production Engineering, Chair of Industrial Metrology & Optics, Stockholm, Sweden 2002, 76 pgs.
Welde et al., "Investigation of methods for speckle contrast reduction", Master of Science in Electronics, Jul. 2010, Norwegian University of Science and Technology, Department of Electronics and Telecommunications, 127 pgs.
White, "Influence of thiol-ene polymer evolution on the formation and performance of holographic polymer dispersed liquid crystals", The 232nd ACS National Meeting, San Francisco, CA, Sep. 10-14, 2006, 1 pg.
Wicht et al., "Nanoporous Films with Low Refractive Index for Large-Surface Broad-Band Anti-Reflection Coatings", Macromol. Mater. Eng., 2010, 295, DOI: 10.1002/mame.201000045, 9 pgs.
Wilderbeek et al., "Photoinitiated Bulk Polymerization of Liquid Crystalline Thiolene Monomers", Macromolecules, 2002, vol. 35, pp. 8962-8969.
Wilderbeek et al., "Photo-Initiated Polymerization of Liquid Crystalline Thiol-Ene Monomers in Isotropic and Anisotropic Solvents", J. Phys. Chem. B, 2002, vol. 106, No. 50, pp. 12874-12883.
Wofford et al., "Liquid crystal bragg gratings: dynamic optical elements for spatial light modulators", Hardened Materials Branch, Survivability and Sensor Materials Division, AFRL-ML-WP-TP-2007-551, Air Force Research Laboratory, Jan. 2007, Wright-Patterson Air Force Base, OH, 17 pgs.
Yaqoob et al., "High-speed two-dimensional laser scanner based on Bragg grating stored in photothermorefractive glass", Applied Optics, Sep. 10, 2003, vol. 42, No. 26, pp. 5251-5262.
Yaroshchuk et al., "Stabilization of liquid crystal photoaligning layers by reactive mesogens", Applied Physics Letters, Jul. 14, 2009, vol. 95, pp. 021902-1-021902-3.
Ye, "Three-dimensional Gradient Index Optics Fabricated in Diffusive Photopolymers", Thesis, Department of Electrical, Computer and Energy Engineering, University of Colorado, 2012, 224 pgs.
Yemtsova et al., "Determination of liquid crystal orientation in holographic polymer dispersed liquid crystals by linear and non-linear optics", Journal of Applied Physics, Oct. 13, 2008, vol. 104, pp. 073115-1-073115-4.
Yeralan et al., "Switchable Bragg grating devices for telecommunications applications", Opt. Eng., Aug. 2012, vol. 41, No. 8, pp. 1774-1779.
Yoshida et al., "Nanoparticle-Dispersed Liquid Crystals Fabricated by Sputter Doping", Adv. Mater. 2010, vol. 22, pp. 622-626.
Zhang et al., "Dynamic Holographic Gratings Recorded by Photopolymerisation of Liquid Crystalline Monomers", J. Am. Chem. Soc., 1994, vol. 116, pp. 7055-7063.
Zhang et al., "Switchable Liquid Crystalline Photopolymer Media for Holography", J. Am. Chem. Soc., 1992, vol. 114, pp. 1506-1507.
Zhao et al., "Designing Nanostructures by Glancing Angle Deposition", Proc. of SPIE, Oct. 27, 2003, vol. 5219, pp. 59-73.
Zlębacz, "Dynamics of nano and micro objects in complex liquids", Ph.D. dissertation, Institute of Physical Chemistry of the Polish Academy of Sciences, Warsaw 2011, 133 pgs.
Zou et al., "Functionalized nano interdigitated electrodes arrays on polymer with integrated microfluidics for direct bio-affinity sensing using impedimetric measurement", Sensors and Actuators A, Jan. 16, 2007, vol. 136, pp. 518-526.
Zyga, "Liquid crystals controlled by magnetic fields may lead to new optical applications", Nanotechnology, Nanophysics, Retrieved from http://phys.org/news/2014-07-liquid-crystals-magnetic-fields-optical.html, Jul. 9, 2014, 3 pgs.
International Preliminary Report on Patentability for International Application No. PCT/GB2012/000677, dated Feb. 25, 2014, dated Mar. 6, 2014, 5 pgs.
International Preliminary Report on Patentability for International Application No. PCT/GB2013/000005, dated Jul. 8, 2014, dated Jul. 17, 2014, 12 pgs.
International Preliminary Report on Patentability for International Application PCT/GB2013/000210, dated Nov. 11, 2014, dated Nov. 20, 2014, 6 pgs.
International Preliminary Report on Patentability for International Application PCT/GB2014/000197, dated Nov. 24, 2015, dated Dec. 3, 2015, 7 pgs.
International Preliminary Report on Patentability for International Application No. PCT/GB2014/000295, dated Feb. 2, 2016, dated Feb. 11, 2016, 4 pgs.
International Preliminary Report on Patentability for International Application PCT/GB2015/000225, dated Feb. 14, 2017, dated Feb. 23, 2017, 8 pgs.
International Preliminary Report on Patentability for International Application PCT/GB2015/000247, dated Mar. 28, 2017, 8 pgs.
International Preliminary Report on Patentability for International Application PCT/GB2016/000014, dated Jul. 25, 2017, dated Aug. 3, 2017, 7 pgs.
International Preliminary Report on Patentability for International Application PCT/US2014/011736, dated Jul. 21, 2015, dated Jul. 30, 2015, 9 pgs.
International Preliminary Report on Patentability for International Application PCT/US2016/017091, dated Aug. 15, 2017, dated Aug. 24, 2017, 5 pgs.
International Preliminary Report on Patentability for International Application PCT/GB2009/051676, dated Jun. 14, 2011, dated Jun. 23, 2011, 6 pgs.
International Preliminary Report on Patentability for International Application PCT/GB2011/000349, dated Sep. 18, 2012, dated Sep. 27, 2012, 10 pgs.
International Preliminary Report on Patentability for International Application PCT/GB2012/000331, dated Oct. 8, 2013, dated Oct. 17, 2013, 8 pgs.
International Preliminary Report on Patentability for International application PCT/GB2015/000274, dated Mar. 28, 2017, dated Apr. 6, 2017, 8 pgs.
International Preliminary Report on Patentability for International Application PCT/GB2016/000003, dated Jul. 18, 2017, dated Jul. 27, 2017, 11 pgs.
International Search Report and Written Opinion for International Application PCT/GB2009/051676, completed May 10, 2010, dated May 18, 2010, 7 pgs.
International Search Report and Written Opinion for International Application PCT/GB2016/000003, completed May 31, 2016, dated Aug 12, 2016, 16 pgs.
International Search Report and Written Opinion for International Application PCT/GB2017/000015, completed Apr. 25, 2017, dated May 8, 2017, 10 pgs.
International Search Report and Written Opinion for International Application. PCT/US2014/011736, completed Apr. 18, 2014, dated May 8, 2014, 10 pgs.
International Search Report and Written Opinion for International Application PCT/US2016/017091, by the European Patent Office dated Apr. 20, 2016, 7 pgs.

(56) References Cited

OTHER PUBLICATIONS

International Search Report for International Application No. PCT/GB2014/000295, completed Nov. 18, 2014, dated Jan. 5, 2015, 4 pgs.
International Search Report for International Application PCT/GB2017/000040, dated Jul. 18, 2017, completed Jul. 10, 2017, 3 pgs.
International Search Report for PCT/GB2011/000349, completed by the European Patent Office dated Aug. 17, 2011, 4 pgs.
International Search Report for PCT/GB2012/000331, completed by the European Patent Office dated Aug. 29, 2012, 4 pgs.
International Search Report for PCT/GB2012/000677, completed by the European Patent Office dated Dec. 10, 2012, 4 pgs.
International Search Report for PCT/GB2013/000005, completed by the European Patent Office dated Jul. 16, 2013, 3 pgs.
Marino et al., "Dynamical Behaviour of Policryps Gratings", Electronic-Liquid Crystal Communications, Feb. 5, 2004, 10 pgs.
Massenot et al., "Multiplexed holographic transmission gratings recorded in holographic polymer-dispersed liquid crystals: static and dynamic studies", Applied Optics, 2005, vol. 44, Issue 25, pp. 5273-5280.
Matay et al., "Planarization of Microelectronic Structures by Using Polyimides", Journal of Electrical Engineering, 2002,vol. 53, No. 3-4, pp. 86-90.
Mathews, "The LED FAQ Pages", Jan. 31, 2002, 23 pgs.
Matic, "Blazed phase liquid crystal beam steering", Proc. of the SPIE, 1994, vol. 2120, pp. 194-205.
McLeod, "Axicons and Their Uses", Journal of the Optical Society of America, Feb. 1960, vol. 50, No. 2, pp. 166-169.
McManamon et al., "A Review of Phased Array Steering for Narrow-Band Electrooptical Systems", Proceedings of the IEEE, Jun. 2009, vol. 97, No. 6, pp. 1078-1096.
McManamon et al., "Optical Phased Array Technology", Proceedings of the IEEE, Feb. 1996, vol. 84, Issue 2, pp. 268-298.
Miller, "Coupled Wave Theory and Waveguide Applications", The Bell System Technical Journal, Short Hills, NJ, Feb. 2, 1954, 166 pgs.
Nair et al., "Enhanced Two-Stage Reactive Polymer Network Forming Systems", Polymer (Guildf). May 25, 2012, vol. 53, No. 12, pp. 2429-2434, doi:10.1016/j.polymer.2012.04.007.
Nair et al., "Two-Stage Reactive Polymer Network Forming Systems", Advanced Functional Materials, 2012, pp. 1-9, DOI: 10.1002/adfm.201102742.
Naqvi et al., "Concentration-dependent toxicity of iron oxide nanoparticles mediated by increased oxidative stress", International Journal of Nanomedicine, Dovepress, Nov. 13, 2010, vol. 5, pp. 983-989.
Natarajan et al., "Holographic polymer dispersed liquid crystal reflection gratings formed by visible light initiated thiol-ene photopolymerization", Polymer vol. 47, May 8, 2006, pp. 4411-4420.
Natarajan et al., "Electro Optical Switching Characteristics of Volume Holograms in Polymer Dispersed Liquid Crystals", Journal of Nonlinear Optical Physics and Materials, 1997, vol. 5, No. 1, pp. 666-668.
Naydenova et al., "Low-scattering Volume Holographic Material", DIT PhD Project, http://www.dit.ie/ieo/, Oct. 2017, 2 pgs.
Neipp et al., "Non-local polymerization driven diffusion based model: general dependence of the polymerization rate to the exposure intensity", Optics Express, Aug. 11, 2003, vol. 11, No. 16, pp. 1876-1886.
Nishikawa et al., "Mechanically and Light Induced Anchoring of Liquid Crystal on Polyimide Film", Mol. Cryst. Liq. Cryst., Aug. 1999, vol. 329, 8 pgs.
Nishikawa et al., "Mechanism of Unidirectional Liquid-Crystal Alignment on Polyimides with Linearly Polarized Ultraviolet Light Exposure", Applied Physics Letters, May 11, 1998, vol. 72, No. 19, 4 pgs.
Oh et al., "Achromatic diffraction from polarization gratings with high efficiency", Optic Letters, Oct. 15, 2008, vol. 33, No. 20, pp. 2287-2289.
Olson et al., "Templating Nanoporous Polymers with Ordered Block Copolymers", Chemistry of Materials, Web publication Nov. 27, 2007, vol. 20, pp. 869-890.
Ondax, Inc., "Volume Holographic Gratings (VHG)", 2005, 7 pgs.
Orcutt, "Coming Soon: Smart Glasses That Look Like Regular Spectacles", Intelligent Machines, Jan. 9, 2014, 4 pgs.
Osredkar, "A study of the limits of spin-on-glass planarization process", Informacije MIDEM, 2001, vol. 31, 2, ISSN0352-9045, pp. 102-105.
Osredkar et al., "Planarization methods in IC fabrication technologies", Informacije MIDEM, 2002, vol. 32, 3, ISSN0352-9045, 5 pgs.
Ou et al., "A Simple LCOS Optical System (Late News)", Industrial Technology Research Institute/OES Lab. Q100/Q200, SID 2002, Boston, USA, 2 pgs.
Paolini et al., "High-Power LED Illuminators in Projection Displays", Lumileds, Aug. 7, 2001, 19 pgs.
Park et al., "Aligned Single-Wall Carbon Nanotube Polymer Composites Using an Electric Field", Journal of Polymer Science: Part B: Polymer Physics, Mar. 24, 2006, DOI 10.1002/polb.20823, pp. 1751-1762.
Park et al., "Fabrication of Reflective Holographic Gratings with Polyurethane Acrylates (PUA)", Current Applied Physics, Jun. 2002, vol. 2, pp. 249-252.
Plawsky et al., "Engineered nanoporous and nanostructured films", MaterialsToday, Jun. 2009, vol. 12, No. 6, pp. 36-45.
Potenza, "These smart glasses automatically focus on what you're looking at", The Verge, Voc Media, Inc., Jan. 29, 2017, https://www.theverge.com/2017/1/29/14403924/smart-glasses-automatic-focus-presbyopia-ces-2017, 6 pgs.
Presnyakov et al., "Electrically tunable polymer stabilized liquid-crystal lens", Journal of Applied Physics, Apr. 29, 2005, vol. 97, pp. 103101-1-103101-6.
Qi et al., "P-111: Reflective Display Based on Total Internal Reflection and Grating-Grating Coupling", Society for Information Display Digest, May 2003, pp. 648-651, DOI: 10.1889/1.1832359.
Ramón, "Formation of 3D micro- and nanostructures using liquid crystals as a template", Technische Universiteit Eindhoven, Apr. 17, 2008, Thesis, DOI:http://dx.doi.org/10.6100/IR634422, 117 pgs.
Ramsey, "Holographic Patterning of Polymer Dispersed Liquid Crystal Materials for Diffractive Optical Elements", Thesis, The University of Texas at Arlington, Dec. 2006, 166 pgs.
Ramsey et al., "Holographically recorded reverse-mode transmission gratings in polymer-dispersed liquid crystal cells", Applied Physics B: Laser and Optics, Sep. 10, 2008, vol. 93, Nos. 2-3, pp. 481-489.
Reid, "Thin film silica nanocomposites for anti-reflection coatings", Oxford Advance Surfaces, www.oxfordsurfaces.com, Oct. 18, 2012, 23 pgs.
Riechert, "Speckle Reduction in Projection Systems", Dissertation, University Karlsruhe, 2009, 178 pgs.
Rossi et al., "Diffractive Optical Elements for Passive Infrared Detectors", Submitted to OSA Topical Meeting "Diffractive Optics and Micro-Optics", Quebec, Jun. 18-22, 2000, 3 pgs.
Saleh et al., "Fourier Optics : 4.1 Propagation of light in free space, 4.2 Optical Fourier Transform, 4.3 Diffraction of Light, 4.4 Image Formation, 4.5 Holography", Fundamentals of Photonics 1991, Chapter 4, pp. 108-143.
Saraswat, "Deposition & Planarization", EE 311 Notes, Aug. 29, 2017, 28 pgs.
Schreiber et al., "Laser display with single-mirror MEMS scanner", Journal of the SID 17/7, 2009, pp. 591-595.
Seiberle et al., "Photo-aligned anisotropic optical thin films", Journal of the SID 12/1, 2004, 6 pgs.
Serebriakov et al., "Correction of the phase retardation caused by intrinsic birefringence in deep UV lithography", Proc. of SPIE, May 21, 2010, vol. 5754, pp. 1780-1791.
Shi et al., "Design considerations for high efficiency liquid crystal decentered microlens arrays for steering light", Applied Optics, vol. 49, No. 3, Jan. 20, 2010, pp. 409-421.

(56) References Cited

OTHER PUBLICATIONS

Shriyan et al., "Analysis of effects of oxidized multiwalled carbon nanotubes on electro-optic polymer/liquid crystal thin film gratings", Optics Express, Nov. 12, 2010, vol. 18, No. 24, pp. 24842-24852.
Simonite, "How Magic Leap's Augmented Reality Works", Intelligent Machines, Oct. 23, 2014, 7 pgs.
Smith et al., "RM-PLUS—Overview", Licrivue, Nov. 5, 2013, 16 pgs.
Sony Global, "Sony Releases the Transparent Lens Eyewear 'SmartEyeglass Developer Edition'", printed Oct. 19, 2017, Sony Global—News Releases, 5 pgs.
Steranka et al., "High-Power LEDs—Technology Status and Market Applications", Lumileds, Jul. 2002, 23 pgs.
Stumpe et al., "Active and Passive LC Based Polarization Elements", Mol. Cryst. Liq. Cryst., 2014, vol. 594: pp. 140-149.
International Search Report for PCT/GB2015/000274, Completed by the European Patent Office dated Jan. 7, 2016, 4 Pages.
Chigrinov et al., "Photo-aligning by azo-dyes: Physics and applications", Liquid Crystals Today, Sep. 6, 2006, http://www.tandfonline.com/action/journalInformation?journalCode=tlcy20, 16 pgs.
Cho et al., "Electro-optic Properties of $CO_2$ Fixed Polymer/Nematic LC Composite Films", Journal of Applied Polymer Science, Nov. 5, 2000, vol. 81, Issue 11, pp. 2744-2753.
Cho et al., "Fabrication of Reflective Holographic PDLC for Blue", Molecular Crystals and Liquid Crystals Science, 2001, vol. 368, pp. 3845-3853.
Cho et al., "Optimization of Holographic Polymer Dispersed Liquid Crystals for Ternary Monomers", Polymer International, Nov. 1999, vol. 48, pp. 1085-1090.
Colegrove et al., "P-59: Technology of Stacking HPDLC for Higher Reflectance", SID 00 Digest, May 2000, pp. 770-773.
Cruz-Arreola et al., "Diffraction of beams by infinite or finite amplitude-phase gratings", Investigacio' N Revista Mexicana De Fi'Sica, Feb. 2011, vol. 57, No. 1, pp. 6-16.
Dainty, "Some statistical properties of random speckle patterns in coherent and partially coherent illumination", Optica Acta, Mar. 12, 1970, vol. 17, No. 10, pp. 761-772.
Date, "Alignment Control in Holographic Polymer Dispersed Liquid Crystal", Journal of Photopolymer Science and Technology, Nov. 2, 2000, vol. 13, pp. 289-284.
Date et al., "52.3: Direct-viewing Display Using Alignment-controlled PDLC and Holographic PDLC", Society for Information Display Digest, May 2000, pp. 1184-1187, DOI: 10.1889/1.1832877.
Date et al., "Full-color reflective display device using holographically fabricated polymer-dispersed liquid crystal (HPDLC)", Journal of the SID, 1999, vol. 7, No. 1, pp. 17-22.
De Bitetto, "White light viewing of surface holograms by simple dispersion compensation", Applied Physics Letters, Dec. 15, 1966, vol. 9, No. 12, pp. 417-418.
Developer World, "Create customized augmented reality solutions", printed Oct. 19, 2017, LMX-001 holographic waveguide display, Sony Developer World, 3 pgs.
Dhar et al., "Recording media that exhibit high dynamic range for digital holographic data storage", Optics Letters, Apr. 1, 1999, vol. 24, No. 7, pp. 487-489.
Domash et al., "Applications of switchable Polaroid holograms", SPIE Proceedings, vol. 2152, Diffractive and Holographic Optics Technology, Jan. 23-29, 1994, Los Angeles, CA, pp. 127-138, ISBN: 0-8194-1447-6.
Drake et al., "Waveguide Hologram Fingerprint Entry Device", Optical Engineering, Sep. 1996, vol. 35, No. 9, pp. 2499-2505.
Drevensek-Olenik et al., "In-Plane Switching of Holographic Polymer-Dispersed Liquid Crystal Transmission Gratings", Mol. Cryst. Liq. Cryst., 2008, vol. 495, pp. 177/[529]-185/[537].
Drevensek-Olenik et al., "Optical diffraction gratings from polymer-dispersed liquid crystals switched by interdigitated electrodes", Journal of Applied Physics, Dec. 1, 2004, vol. 96, No. 11, pp. 6207-6212.
Ducharme, "Microlens diffusers for efficient laser speckle generation", Optics Express, Oct. 29, 2007, vol. 15, No. 22, pp. 14573-14579.
Duong et al., "Centrifugal Deposition of Iron Oxide Magnetic Nanorods for Hyperthermia Application", Journal of Thermal Engineering, Yildiz Technical University Press, Istanbul, Turkey, Apr. 2015, vol. 1, No. 2, pp. 99-103.
Fattal et al., "A multi directional backlight for a wide-angle glasses-free three-dimensional display", Nature, Mar. 21, 2012, vol. 495, 348-351.
Fontecchio et al., "Spatially Pixelated Reflective Arrays from Holographic Polymer Dispersed Liquid Crystals", SID 00 Digest, May 2000, pp. 774-776.
Forman et al., "Materials development for PhotoINhibited Super-Resolution (PINSR) lithography", Proc. of SPIE, 2012, vol. 8249, 824904, doi: 10.1117/12.908512, pp. 824904-1-824904-9.
Forman et al., "Radical diffusion limits to photoinhibited super-resolution lithography", Phys.Chem. Chem. Phys., May 31, 2013, vol. 15, pp. 14862-14867.
Friedrich-Schiller, "Spatial Noise and Speckle", Version 1.12.2011, Dec. 2011, Abbe School of Photonics, Jena, Germany, 27 pgs.
Fujii et al., "Nanoparticle-polymer-composite volume gratings incorporating chain-transfer agents for holography and slow-neutron optics", Optics Letters, Apr. 25, 2014, vol. 39, Issue 12, 5 pgs.
Funayama et al., "Proposal of a new type thin film light-waveguide display device using", The International Conference on Electrical Engineering, 2008, No. P-044, 5 pgs.
Gabor, "Laser Speckle and its Elimination", Eliminating Speckle Noise, Sep. 1970, pp. 509-514.
Gardiner et al., "Bistable liquid-crystals reduce power consumption for high-efficiency smart glazing", SPIE, 2009, 10.1117/2.1200904.1596, 2 pgs.
Giancola, "Holographic Diffuser, Makes Light Work of Screen Tests", Photonics Spectra, 1996, vol. 30, No. 8, p. 121.
Goodman, "Some fundamental properties of speckle", J. Opt. Soc. Am., Nov. 1976, vol. 66, No. 11, pp. 1145-1150.
Goodman, "Statistical Properties of Laser Speckle Patterns", Applied Physics, 1975, vol. 9, Chapter 2, Laser Speckle and Related Phenomena, pp. 9-75.
Goodman et al., "Speckle Reduction by a Moving Diffuser in Laser Projection Displays", The Optical Society of America, 2000, 15 pgs.
Guldin et al., "Self-Cleaning Antireflective Optical Coatings", Nano Letters, Oct. 14, 2013, vol. 13, pp. 5329-5335.
Guo et al., "Review Article: A Review of the Optimisation of Photopolymer Materials for Holographic Data Storage", Physics Research International, vol. 2012 (2012), Article ID 803439, Academic Editor: Sergi Gallego, 16 pages, http://dx.doi.org/10.1155/2012/803439, May 4, 2012.
Ha et al., "Optical Security Film Based on Photo-alignment Technology", Department of Electronic & Computer Engineering, May 9, 2016, 1 pg.
Han et al., "Study of Holographic Waveguide Display System", Advanced Photonics for Communications, 2014, 4 pgs.
Harbers et al., "I-15.3: LED Backlighting for LCD-HDTV", Journal of the Society for Information Display, 2002, vol. 10, No. 4, pp. 347-350.
Harbers et al., "Performance of High Power LED Illuminators in Color Sequential Projection Displays", Lumileds Lighting, 2007, 4 pgs.
Harbers et al., "Performance of High Power LED Illuminators in Color Sequential Projection Displays", Lumileds, Aug. 7, 2001, 11 pgs.
Harbers et al., "Performance of High-Power LED illuminators in Projection Displays", Proc. Int. Disp. Workshops, Japan. vol. 10, pp. 1585-1588, 2003.
Harding et al., "Reactive Liquid Crystal Materials for Optically Anisotropic Patterned Retarders", Merck, licrivue, 2008, ME-GR-RH-08-010, 20 pgs.
Harding et al., "Reactive Liquid Crystal Materials for Optically Anisotropic Patterned Retarders", SPIE Lithography Asia—Taiwan, 2008, Proceedings vol. 7140, Lithography Asia 2008; 71402J, doi: 10.1117/12.805378.

(56) References Cited

OTHER PUBLICATIONS

Hariharan, "Optical Holography: Principles, techniques and applications", Cambridge University Press, 1996, pp. 231, 233.
Harris, "Photonic Devices", EE 216 Principals and Models of Semiconductor Devices, Autumn 2002, 20 pgs.
Harrold et al., "3D Display Systems Hardware Research at Sharp Laboratories of Europe: an update", Sharp Laboratories of Europe, Ltd., received May 21, 1999, 7 pgs.
Harthong et al., "Speckle phase averaging in high-resolution color holography", J. Opt. Soc. Am. A, Feb. 1997, vol. 14, No. 2, pp. 405-409.
Hasan et al., "Tunable-focus lens for adaptive eyeglasses", Optics Express, Jan. 23, 2017, vol. 25, No. 2, 1221, 13 pgs.
Hasman et al., "Diffractive Optics: Design, Realization, and Applications", Fiber and Integrated Optics, 16:1-25, 1997.
Hata et al., "Holographic nanoparticle-polymer composites based on step-growth thiol-ene photopolymerization", Optical Materials Express, Jun. 1, 2011, vol. 1, No. 2, pp. 207-222.
He et al., "Properties of Volume Holograms Recording in Photopolymer Films with Various Pulse Exposures Repetition Frequencies", Proceedings of SPIE vol. 5636, Bellingham, WA, 2005, doi: 10.1117/12.580978, pp. 842-848.
"Technical Data Sheet LPR1", Luminus Devices, Inc., Luminus Projection Chipset, Release 1, Preliminary, Revision B, Sep. 21, 2004, 9 pgs.
"The Next Generation of TV", SID Information Display, Nov./Dec. 2014, vol. 30, No. 6, 56 pgs.
"Thermal Management Considerations for SuperFlux LEDs", Lumileds, application brief AB20-4, Sep. 2002, 14 pgs.
"UVTOP240", Roithner LaserTechnik GmbH, v 2.0, Jun. 24, 2013, 6 pgs.
"UVTOP310", Roithner LaserTechnik GmbH, v 2.0, Jun. 24, 2013, 6 pgs.
"Velodyne's HDL-64E: A High Definition Lidar Sensor for 3-D Applications", High Definition Lidar, white paper, Oct. 2007, 7 pgs.
"VerLASE Gets Patent for Breakthrough Color Conversion Technology That Enables Full Color MicroLED Arrays for Near Eye Displays", Cision PRweb, Apr. 28, 2015, Retrieved from the Internet http://www.prweb.com/releases/2015/04/prweb12681038.htm, 3 pgs.
"X-Cubes—Revisited for LCOS", BASID, RAF Electronics Corp. Rawson Optics, Inc., Oct. 24, 2002, 16 pgs.
Aachen, "Design of plastic optics for LED applications", Optics Colloquium 2009, Mar. 19, 2009, 30 pgs.
Abbate et al., "Characterization of LC-polymer composites for opto-electronic application", Proceedings of OPTOEL'03, Leganes-Madrid, Spain, Jul. 14-16, 2003, 4 pgs.
Al-Kalbani et al., "Ocular Microtremor laser speckle metrology", Proc. of SPIE, 2009, vol. 7176 717606-1, 12 pgs.
Almanza-Workman et al., "Planarization coating for polyimide substrates used in roll-to-roll fabrication of active matrix backplanes for flexible displays", HP Laboratories, HPL-2012-23, Feb. 6, 2012, 12 pgs.
Amundson et al., "Morphology and electro-optic properties of polymer-dispersed liquid-crystal films", Physical Review E, Feb. 1997, vol. 55. No. 2, pp. 1646-1654.
An et al., "Speckle suppression in laser display using several partially coherent beams", Optics Express, Jan. 5, 2009, vol. 17, No. 1, pp. 92-103.
Apter et al., "Electrooptical Wide-Angle Beam Deflector Based on Fringing-Field-Induced Refractive Inhomogeneity in a Liquid Crystal Layer", 23rd IEEE Convention of Electrical and Electronics Engineers in Israel, Sep. 6-7, 2004, pp. 240-243.
Arnold et al., "52.3: An Improved Polarizing Beamsplitter LCOS Projection Display Based on Wire-Grid Polarizers", Society for Information Display, Jun. 2001, pp. 1282-1285.
Ayras et al., "Exit pupil expander with a large field of view based on diffractive optics", Journal of the SID, May 18, 2009, 17/8, pp. 659-664.

Baets et al., "Resonant-Cavity Light-Emitting Diodes: a review", Proceedings of SPIE, 2003, vol. 4996, pp. 74-86.
Bayer et al., "Introduction to Helmet-Mounted Displays", 2016, pp. 47-108.
Beckel et al., "Electro-optic properties of thiol-ene polymer stabilized ferroelectric liquid crystals", Liquid Crystals, vol. 30, No. 11, Nov. 2003, pp. 1343-1350.
Bergkvist, "Biospeckle-based Study of the Line Profile of Light Scattered in Strawberries", Master Thesis, Lund Reports on Atomic Physics, LRAP-220, Lund 1997, pp. 1-62.
Bernards et al., "Nanoscale porosity in polymer films: fabrication and therapeutic applications", Soft Matter, Jan. 1, 2010, vol. 6, No. 8, pp. 1621-1631.
Bleha et al., "Binocular Holographic Waveguide Visor Display", SID Symposium Digest of Technical Papers, Holoeye Systems Inc., Jun. 2014, San Diego, CA, 4 pgs.
Bleha et al., "D-ILA Technology for High Resolution Projection Displays", Sep. 10, 2003, Proceedings, vol. 5080, doi:10.1117/12.497532, 11 pgs.
Bone, "Design Obstacles for LCOS Displays in Projection Applications "Optics architectures for LCOS are still evolving"", Aurora Systems Inc., Bay Area SID Seminar, Mar. 27, 2001, 22 pgs.
Born et al., "Optics of Crystals", Principles of Optics 5th Edition 1975, pp. 705-707.
Bourzac, "Magic Leap Needs to Engineer a Miracle", Intelligent Machines, Jun. 11, 2015, 7 pgs.
Bowen et al., "Optimisation of interdigitated electrodes for piezoelectric actuators and active fibre composites", J Electroceram, Jul. 2006, vol. 16, pp. 263-269, DOI 10.1007/s10832-006-9862-8.
Bowley et al., "Variable-wavelength switchable Bragg gratings formed in polymer-dispersed liquid crystals", Applied Physics Letters, Jul. 2, 2001, vol. 79, No. 1, pp. 9-11.
Bronnikov et al., "Polymer-Dispersed Liquid Crystals: Progress in Preparation, Investigation and Application", Journal of Macromolecular Science Part B, published online Sep. 30, 2013, vol. 52, pp. 1718-1738.
Brown, "Waveguide Displays", Rockwell Collins, 2015, 11 pgs.
Bruzzone et al., "Compact, high-brightness LED illumination for projection systems", Journal of the SID 17/12, Dec. 2009, pp. 1043-1049.
Buckley, "Colour holographic laser projection technology for heads-up and instrument cluster displays", Conference: Proc. SID Conference 14th Annual Symposium on Vehicle Displays, Jan. 2007, 5 pgs.
Buckley, "Pixtronix DMS technology for head-up displays", Pixtronix, Inc., Jan. 2011, 4 pgs.
Buckley et al., "Full colour holographic laser projector HUD", Light Blue Optics Ltd., Aug. 10, 2015, 5 pgs.
Buckley et al., "Rear-view virtual image displays", in Proc. SID Conference 16th Annual Symposium on Vehicle Displays, Jan. 2009, 5 pgs.
Bunning et al., "Effect of gel-point versus conversion on the real-time dynamics of holographic polymer-dispersed liquid crystal (HPDLC) formation", Proceedings of SPIE—vol. 5213, Liquid Crystals VII, Iam-Choon Khoo, Editor, Dec. 2003, pp. 123-129.
Bunning et al., "Electro-optical photonic crystals formed in H-PDLCs by thiol-ene photopolymerization", American Physical Society, Annual APS, Mar. 3-7, 2003, abstract #R1.135.
Bunning et al., "Holographic Polymer-Dispersed Liquid Crystals (H-PDLCs)1", Annu. Rev. Mater. Sci., 2000, vol. 30, pp. 83-115.
Bunning et al., "Morphology of Anisotropic Polymer Dispersed Liquid Crystals and the Effect of Monomer Functionality", Polymer Science: Part B: Polymer Physics, Jul. 30, 1997, vol. 35, pp. 2825-2833.
Busbee et al., "SiO2 Nanoparticle Sequestration via Reactive Functionalization in Holographic Polymer-Dispersed Liquid Crystals", Advanced Materials, Sep. 2009, vol. 21, pp. 3659-3662.
Butler et al., "Diffractive Properties of Highly Birefringent Volume Gratings: Investigation", Journal of Optical Society of America, Feb. 2002, vol. 19, No. 2, pp. 183-189.
Cai et al., "Recent advances in antireflective surfaces based on nanostructure arrays", Mater. Horiz., 2015, vol. 2, pp. 37-53.

(56) References Cited

OTHER PUBLICATIONS

Cameron, "Optical Waveguide Technology & Its Application in Head Mounted Displays", Proc. of SPIE, May 22, 2012, vol. 8383, pp. 83830E-1-83830E-11.
Caputo et al., "POLICRYPS Composite Materials: Features and Applications", Advances in Composite Materials—Analysis of Natural and Man-Made Materials, www.intechopen.com, Sep. 2011, pp. 93-118.
Caputo et al., "POLICRYPS Switchable Holographic Grating: A Promising Grating Electro-Optical Pixel for High Resolution Display Application", Journal of Display Technology, Mar. 2006, vol. 2, No. 1, pp. 38-51.
Carclo Optics, "Guide to choosing secondary optics", Carclo Optics, Dec. 15, 2014, www.carclo-optics.com, 48 pgs.
Chen et al, "Polarization rotators fabricated by thermally-switched liquid crystal alignments based on rubbed poly(N-vinyl carbazole) films", Optics Express, Apr. 11, 2011, vol. 19, No. 8, pp. 7553-7558.
Cheng et al., "Design of an ultra-thin near-eye display with geometrical waveguide and freeform optics", Optics Express, Aug. 2014, 16 pgs.
Chi et al., "Ultralow-refractive-index optical thin films through nanoscale etching of ordered mesoporous silica films", Optic Letters, May 1, 2012, vol. 37, No. 9, pp. 1406-1408.
He et al., "Dynamics of peristrophic multiplexing in holographic polymer-dispersed liquid crystal", Liquid Crystals, Mar. 26, 2014, vol. 41, No. 5, pp. 673-684.
He et al., "Holographic 3D display based on polymer-dispersed liquid-crystal thin films", Proceedings of China Display/Asia Display 2011, pp. 158-160.
Herman et al., "Production and Uses of Diffractionless Beams", J. Opt. Soc. Am. A., Jun. 1991, vol. 8, No. 6, pp. 932-942.
Hisano, "Alignment layer-free molecular ordering induced by masked photopolymerization with nonpolarized light", Appl. Phys. Express 9, Jun. 6, 2016, pp. 072601-1-072601-4.
Hoepfner et al., "LED Front Projection Goes Mainstream", Luminus Devices, Inc., Projection Summit, 2008, 18 pgs.
Holmes et al., "Controlling the anisotropy of holographic polymer-dispersed liquid-crystal gratings", Physical Review E, Jun. 11, 2002, vol. 65, 066603-1-066603-4.
Hoyle et al., "Advances in the Polymerization of Thiol-Ene Formulations", Heraeus Noblelight Fusion UV Inc, 2003 Conference, 6 pgs.
Hua et al., "A Closed Form Solution to Natural Image Matting", Illumination & Displays 3D Visualization and Imaging Systems Laboratory (3DVIS) College of Optical Sciences University of Arizona Tucson, 2014, 8 pgs.
Hua, "Sunglass-like displays become a reality with free-form optical technology", Illumination & Displays 3D Visualization and Imaging Systems Laboratory (3DVIS) College of Optical Sciences University of Arizona Tucson, AZ. 2014, 3 pgs.
Huang et al., "Theory and characteristics of holographic polymer dispersed liquid crystal transmission grating with scaffolding morphology", Applied Optics, Jun. 20, 2012, vol. 51, No. 18, pp. 4013-4020.
Huang et al., "Diffraction properties of substrate guided-wave holograms", Optical Engineering, Oct. 1995, vol. 34, No. 10, pp. 2891-2899.
Iannacchione et al., "Deuterium NMR and morphology study of copolymer-dispersed liquid-crystal Bragg gratings", Europhysics Letters, 1996, vol. 36, No. 6, pp. 425-430.
Jeng et al., "Aligning liquid crystal molecules", SPIE, 2012, 10.1117/2.1201203.004148, 2 pgs.
Jo et al., "Control of Liquid Crystal Pretilt Angle using Polymerization of Reactive Mesogen", IMID 2009 Digest, P1-25, 2009, pp. 604-606.
Juhl et al., "Holographically Directed Assembly of Polymer Nanocomposites", ACS Nano, Oct. 7, 2010, vol. 4, No. 10, pp. 5953-5961.
Juhl, "Interference Lithography for Optical Devices and Coatings", Dissertation, University of Illinois at Urbana-Champaign, 2010.

Jurbergs et al., "New recording materials for the holographic industry", Proc. of SPIE, 2009 vol. 7233, pp. 72330K-1-72330L-10, doi: 10.1117/12.809579.
Kahn et al., "Private Line Report on Large Area Display", Kahn International, Jan. 7, 2003, vol. 8, No. 10, 9 pgs.
Karasawa et al., "Effects of Material Systems on the Polarization Behavior of Holographic Polymer Dispersed Liquid Crystal Gratings", Japanese Journal of Applied Physics, vol. 36, pp. 6388-6392, 1997.
Karp et al., "Planar micro-optic solar concentration using multiple imaging lenses into a common slab waveguide", Proc. of SPIE vol. 7407, 2009 SPIE, CCC code: 0277-786X/09, doi: 10.1117/12.826531, pp. 74070D-1-74070D-11.
Karp et al., "Planar micro-optic solar concentrator", Optics Express, Jan. 18, 2010, vol. 18, No. 2, pp. 1122-1133.
Kato et al., "Alignment-Controlled Holographic Polymer Dispersed Liquid Crystal (HPDLC) for Reflective Display Devices", SPIE,1998, vol. 3297, pp. 52-57.
Kessler, "Optics of Near to Eye Displays (NEDs)", Oasis 2013, Tel Aviv, Feb. 19, 2013, 37 pgs.
Keuper et al., "26.1: RGB LED Illuminator for Pocket-Sized Projectors", SID 04 Digest, 2004, ISSN/0004-0966X/Apr. 3502, pp. 943-945.
Keuper et al., "P-126: Ultra-Compact LED based Image Projector for Portable Applications", SID 03 Digest, 2003, ISSN/0003-0966X/03/3401-0713, pp. 713-715.
Kim et al., "Enhancement of electro-optical properties in holographic polymer-dispersed liquid crystal films by incorporation of multiwalled carbon nanotubes into a polyurethane acrylate matrix", Polym. Int,, Jun. 16, 2010, vol. 59, pp. 1289-1295.
Kim et al., "Optimization of Holographic PDLC for Green", Mol. Cryst. Liq. Cryst., vol. 368, pp. 3855-3864, 2001.
Kim et al., "Effect of Polymer Structure on the Morphology and Electro optic Properties of UV Curable PNLCs", Polymer, Feb. 2000, vol. 41, pp. 1325-1335.
Klein, "Optical Efficiency for Different Liquid Crystal Colour Displays", Digital Media Department, HPL-2000-83, Jun. 29, 2000, 18 pgs.
Kogelnik, "Coupled Wave Theory for Thick Hologram Gratings", The Bell System Technical Journal, vol. 48, No. 9, pp. 2909-2945, Nov. 1969.
Kotakonda et al., "Electro-optical Switching of the Holographic Polymer-dispersed Liquid Crystal Diffraction Gratings", Journal of Optics A: Pure and Applied Optics, Jan. 1, 2009, vol. 11, No. 2, 11 pgs.
Kress et al., "Diffractive and Holographic Optics as Optical Combiners in Head Mounted Displays", UbiComp '13, Sep. 9-12, 2013, Session: Wearable Systems for Industrial Augmented Reality Applications, pp. 1479-1482.
Lauret et al., "Solving the Optics Equation for Effective LED Applications", Gaggione North America, LLFY System Design Workshop 2010, Oct. 28, 2010, 26 pgs.
Lee, "Patents Shows Widespread Augmented Reality Innovation", PatentVue, May 26, 2015, 5 pgs.
Levola, "Diffractive optics for virtual reality displays", Journal of the SID, 2006, 14/5, pp. 467-475.
Levola et al., "Near-to-eye display with diffractive exit pupil expander having chevron design", Journal of the SID, 2008, 16/8, pp. 857-862.
Li et al., "Design and Optimization of Tapered Light Pipes", Proceedings vol. 5529, Nonimaging Optics and Efficient Illumination Systems, Sep. 29, 2004, doi: 10.1117/12.559844, 10 pgs.
Li et al., "Dual Paraboloid Reflector and Polarization Recycling Systems for Projection Display", Proceedings vol. 5002, Projection Displays IX, Mar. 28, 2003, doi: 10.1117/12.479585, 12 pgs.
Li et al., "Light Pipe Based Optical Train and its Applications", Proceedings vol. 5524, Novel Optical Systems Design and Optimization VII, Oct. 24, 2004, doi: 10.1117/12.559833, 10 pgs.
Li et al., "Novel Projection Engine with Dual Paraboloid Reflector and Polarization Recovery Systems", Wavien Inc., SPIE EI 5289-38, Jan. 21, 2004, 49 pgs.

(56) References Cited

OTHER PUBLICATIONS

Li et al., "Polymer crystallization/melting induced thermal switching in a series of holographically patterned Bragg reflectors", Soft Matter, Jul. 11, 2005, 1, 238-242.
Lin et al., "Ionic Liquids in Photopolymerizable Holographic Materials", in book: Holograms—Recording Materials and Applications, Nov. 9, 2011, 21 pgs.
Liu et al., "Holographic Polymer-Dispersed Liquid Crystals: Materials, Formation, and Applications", Advances in OptoElectronics, Nov. 30, 2008, vol. 2008, Article ID 684349, 52 pgs.
Lorek, "Experts Say Mass Adoption of augmented and Virtual Reality is Many Years Away", Siliconhills, Sep. 9, 2017, 4 pgs.
Lowenthal et al., "Speckle Removal by a Slowly Moving Diffuser Associated with a Motionless Diffuser", Journal of the Optical Society of America, Jul. 1971, vol. 61, No. 7, pp. 847-851.
Lu et al., "Polarization switch using thick holographic polymer-dispersed liquid crystal grating", Journal of Applied Physics, Feb. 1, 2004, vol. 95, No. 3, pp. 810-815.
Lu et al., "The Mechanism of electric-field-induced segregation of additives in a liquid-crystal host", Phys Rev E Stat Nonlin Soft Matter Phys., Nov. 27, 2012, 14 pgs.
Ma et al., "Holographic Reversed-Mode Polymer-Stabilized Liquid Crystal Grating", Chinese Phys. Lett., 2005, vol. 22, No. 1, pp. 103-106.
Mach et al., "Switchable Bragg diffraction from liquid crystal in colloid-templated structures", Europhysics Letters, Jun. 1, 2002, vol. 58, No. 5, pp. 679-685.
Magarinos et al., "Wide Angle Color Holographic infinity optics display", Air Force Systems Command, Brooks Air Force Base, Texas, AFHRL-TR-80-53, Mar. 1981, 100 pgs.
International Search Report for PCT/GB2013/000210, completed by the European Patent Office dated Aug. 12, 2013, 3 pgs.
International Search Report for PCT/GB2014/000197, completed by the European Patent Office dated Jul. 31, 2014, 3 pgs.
International Search Report for PCT/GB2015/000203, completed by the European Patent Office dated Oct. 9, 2015, 4 pgs.
International Search Report for PCT/GB2015/000225, completed by the European Patent Office dated Nov. 10, 2015, dated Dec 2, 2016, 5 pgs.
International Search Report for PCT/GB2016/000005, completed by the European Patent Office dated May 27, 2016, 4 pgs.
International Search Report for PCT/GB2016/000014, completed by the European Patent Office dated Jun. 27, 2016, 4 pgs.
Written Opinion for International Application No. PCT/GB2011/000349, completed Aug. 17, 2011, dated Aug. 25, 2011, 9 pgs.
Written Opinion for International Application No. PCT/GB2012/000331, Search completed Aug. 29, 2012, dated Sep. 6, 2012, 7 pgs.
Written Opinion for International Application No. PCT/GB2012/000677, Completed Dec. 10, 2012, dated Dec. 17, 2012, 4 Pgs.
Written Opinion for International Application PCT/GB2013/000005, search completed Jul. 16, 2013, dated Jul. 24, 2013, 11 pgs.
Written Opinion for International Application No. PCT/GB2013/000210, completed Aug. 12, 2013, dated Aug. 20, 2013, 5 pgs.
Written Opinion for International Application No. PCT/GB2014/000197, search completed Jul. 31, 2014, dated Aug. 7, 2014, 6 pgs.
Written Opinion for International Application No. PCT/GB2014/000295, search completed Nov. 18, 2014, dated Jan. 5, 2015, 3 pgs.
Written Opinion for International Application No. PCT/GB2015/000225, search completed Nov. 10, 2015, dated Feb. 4, 2016, 7 pgs.
Written Opinion for International Application No. PCT/GB2015/000274, search completed Jan. 7, 2016, dated Jan. 19, 2016, 7 pgs.
Written Opinion for International Application No. PCT/GB2016/000014, search completed Jun. 27, 2016, dated Jul. 7, 2016, 6 pgs.
Written Opinion for International Application No. PCT/GB2017/000040, search completed Jul. 10, 2017, dated Jul. 18, 2017, 6 pgs.
"Agilent ADNS—2051 Optical Mouse Sensor: Data Sheet", Agilent Technologies, Jan. 9, 2002, 40 pgs.
"Application Note—MOXTEK ProFlux Polarizer use with LCOS displays", CRL Opto Limited, http://www.crlopto.com, 2003, 6 pgs.

"Application Note AN16: Optical Considerations for Bridgelux LED Arrays", BridgeLux, Jul. 31, 2010, 23 pgs.
"Application Note: Variable Attenuator for Lasers", Technology and Applications Center, Newport Corporation, www.newport.com, 2006, DS-08067, 6 pgs.
"Bae Systems to Unveil Q-Sight Family of Helmet-Mounted Display at AUSA Symposium", Released on Tuesday, Oct. 9, 2007, 1 pg.
"Beam Steering Using Liquid Crystals", Boulder Nonlinear Systems, Inc., info@bnonlinear.com, May 8, 2001, 4 pgs.
"BragGrate—Deflector: Transmitting Volume Bragg Grating for angular selection and magnification", 2015, www.OptiGrate.com.
"Cree XLamp XP-E LEDs", Cree, Inc., Retrieved from www.cree.com/Xlamp, CLD-DS18 Rev 17, 2013, 17 pgs.
"Desmodur N 3900", Bayer MaterialScience AG, Mar. 18, 2013, www.bayercoatings.com, 4 pgs.
"Digilens—Innovative Augmented Reality Display and Sensor Solutions for OEMs", Jun. 6, 2017, 31 pgs.
"Exotic Optical Components", Building Electro-Optical Systems, Making it All Work, Chapter 7, John Wley & Sons, Inc., pp. 233-261.
"FHS Lenses Series", Fraen Corporation, www.fraen.com, Jun. 16, 2003, 10 pgs.
"FLP Lens Series for LUXEONTM Rebel and Rebel ES LEDs", Fraen Corporation, www.fraensrl.com, Aug. 7, 2015, 8 pgs.
"Head-up Displays, See-through display for military aviation", BAE Systems, 2016, 3 pgs.
"Holder for LUXEON Rebel—Part No. 180", Polymer Optics Ltd., 2008, 12 pgs.
"LED 7—Segment Displays", Lumex, uk.digikey.com, 2003, UK031, 36 pgs.
"LED325W UVTOP UV LED with Window", Thorlabs, Specifications and Documentation, 21978-S01 Rev. A, Apr. 8, 2011, 5 pgs.
"Liquid Crystal Phases", Phases of Liquid Crystals, http://plc.cwru.edu/tutorial/enhanced/files/lc/phase, Retrieved on Sep. 21, 2004, 6 pgs.
"LiteHUD Head-up display", BAE Systems, 2016, 2 pgs.
"LiteHUD Head-up display infographic", BAE Systems, 2017, 2 pgs.
"Luxeon C: Power Light Source", Philips Lumileds, www.philipslumileds.com, 2012, 18 pgs.
"Luxeon Rebel ES: Leading efficacy and light output, maximum design flexibility", LUXEON Rebel ES Datasheet DS61 Feb. 21, 2013, www.philipslumileds.com, 2013, 33 pgs.
"Mobile Display Report", Insight Media, LLC, Apr. 2012, vol. 7, No. 4, 72 pgs.
"Molecular Imprints Imprio 55", Engineering at Illinois, Micro + Nanotechnology Lab, retrieved from https://mntl.illinois.edu/facilities/cleanrooms/equipment/Nano-Imprint.asp, Dec. 28, 2015, 2 pgs.
"Optical measurements of retinal flow", Industrial Research Limited, Feb. 2012, 18 pgs.
"Osterhout Design Group Develops Next-Generation, Fully-integrated Smart Glasses Using Qualcomm Technologies", ODG, www.osterhoutgroup.com, Sep. 18, 2014, 2 pgs.
"Range Finding Using Pulse Lasers", OSRAM, Opto Semiconductors, Sep. 10, 2004, 7 pgs.
"Response time in Liquid-Crystal Variable Retarders", Meadowlark Optics, Inc., 2005, 4 pgs.
"Secondary Optics Design Considerations for SuperFlux LEDs", Lumileds, application brief AB20-5, Sep. 2002, 23 pgs.
"Solid-State Optical Mouse Sensor with Quadrature Outputs", IC Datasheet, UniqueICs, Jul. 15, 2004, 11 pgs.
"SVGA TransparentVLSITM Microdisplay Evaluation Kit", Radiant Images, Inc, Product Data Sheet, 2003, 3 pgs.
International Preliminary Report on Patentability for International Application PCT/GB2017/000015, Report Completed Aug. 7, 2018, dated Aug. 16, 2018, 7 Pgs.
Written Opinion for International Application PCT/GB2016/000003, completed May 31, 2016, dated Aug. 12, 2016, 10 pgs.

(56) References Cited

OTHER PUBLICATIONS

Sagan et al., "Electrically Switchable Bragg Grating Technology for Projection Displays", Proc. SPIE. vol. 4294, Jan. 24, 2001, pp. 75-83.

* cited by examiner

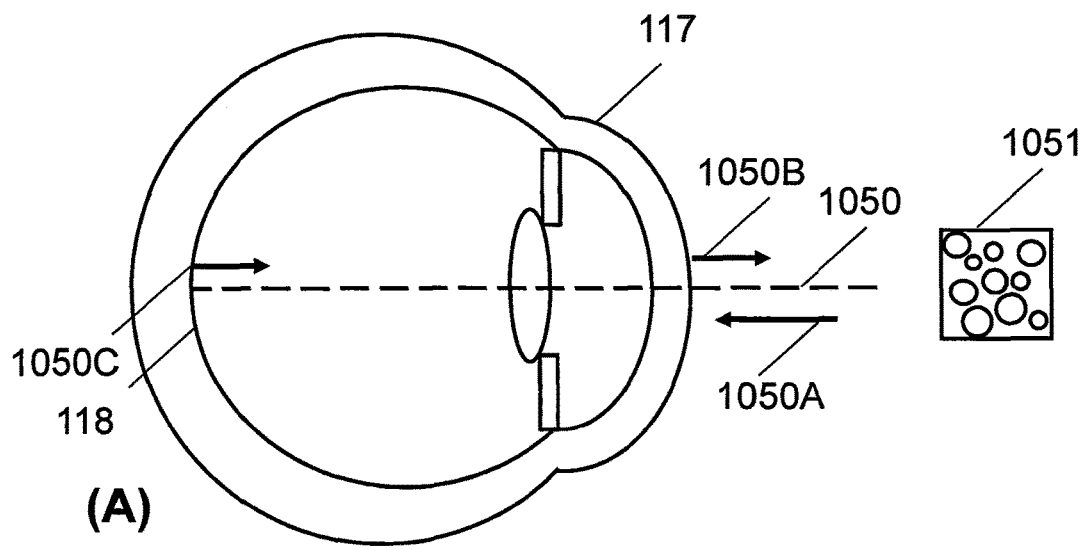
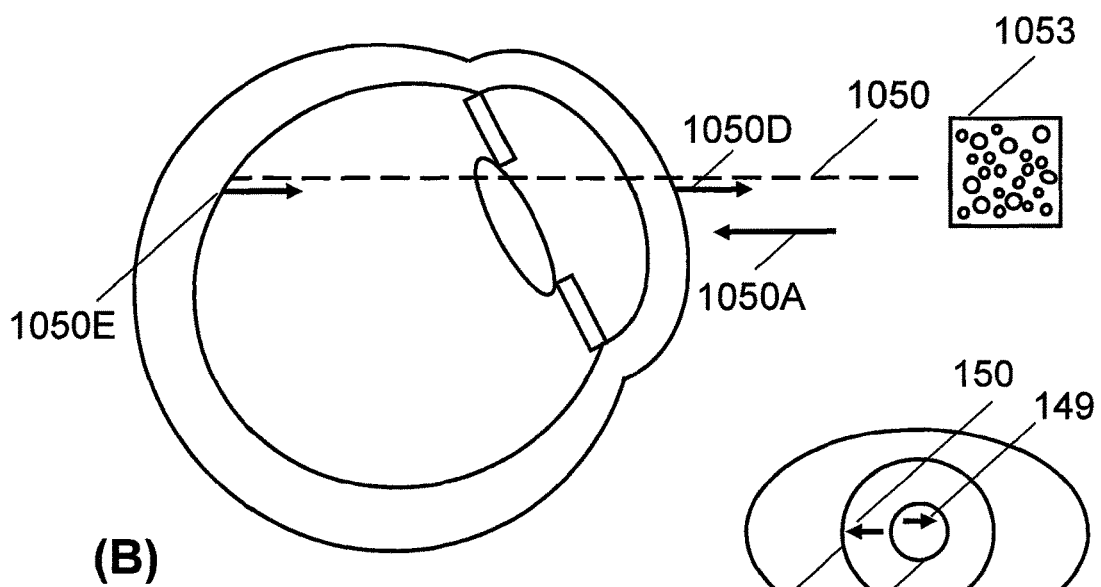
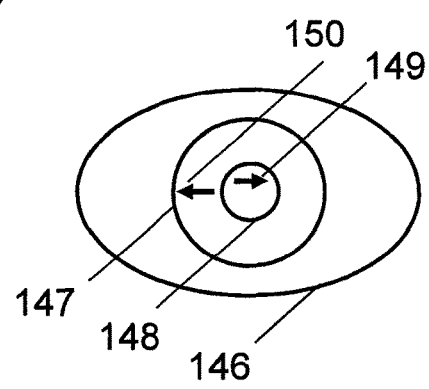
FIG. 13
FIG. 14

(A)

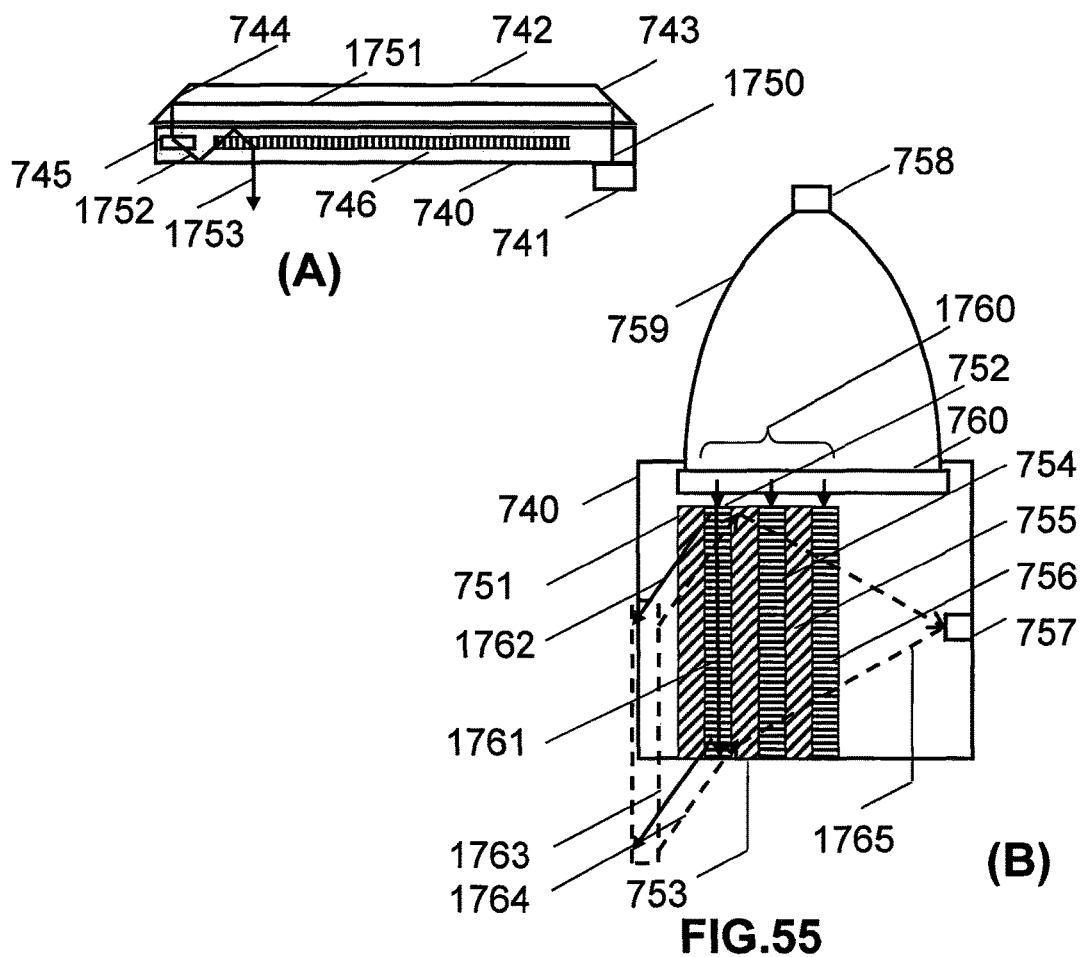
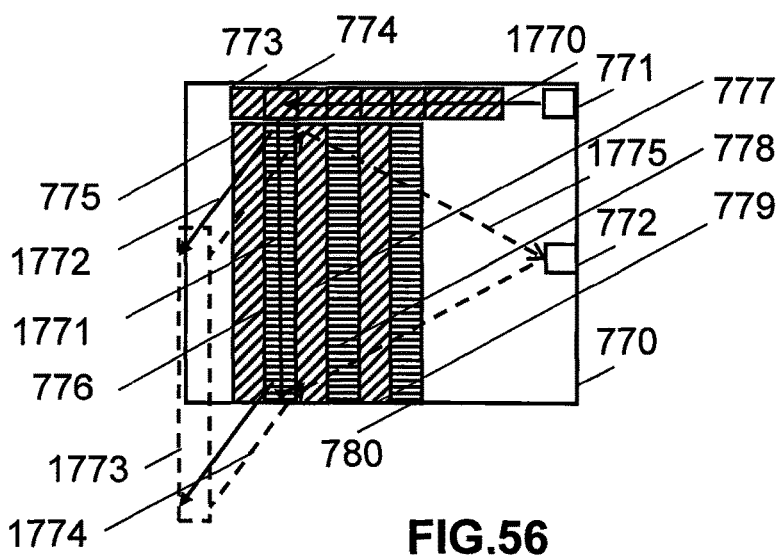
FIG.55
FIG.56

HOLOGRAPHIC WAVEGUIDE OPTICAL TRACKER

CROSS-REFERENCE TO PRIORITY APPLICATIONS

This application is a U.S. national phase of PCT Application No. PCT/GB2015/000274 filed on Sep. 25, 2015, which application claims the benefit of U.S. Provisional Patent Application No. 62/071,534 filed on Sep. 26, 2014, U.S. Provisional Patent Application No. 62/124,154 filed on Dec. 10, 2014, U.S. Provisional Patent Application No. 62/125,454 filed on Jan. 22, 2015, and U.S. Provisional Patent Application No. 62/179,336 filed on May 5, 2015, the disclosures of which are incorporated herein by reference in their entirety by reference herein.

BACKGROUND OF THE INVENTION

This invention relates to sensors, and more particularly to an object tracking device using waveguide display using electrically switchable gratings.

The tracking of objects is a key requirement in many fields including eye tracking (in augmented reality (AR), virtual reality (VR) and other display applications), robotics, collision avoidance systems and many others. Although the nature of the objects and their dynamics varies greatly there is a general requirement to track robustly, accurately and with minimal processing time lag (latency). Trackers are normally designed to operate in the infrared which offers the benefit of invisibility and can be made eye safe by operating at wavelengths around 1550 nm. Since the tracker will often be used with another device such as a display or some other type of sensor it is highly desirable that the tracker is transparent. The present application is motivated by the need for an improved eye tracker for use in HMDs and most of the embodiments to be disclosed will described in relation to eye tracking. The prerequisite for tracking an object is that it provides a detectable signature from one or more of its surfaces. The signature may be specular reflection, scatter, laser speckle or a combination of these. The object may contain multiple surfaces, for example, in the case of an eye the signature may be provided by surfaces of the cornea, lens and retina. In eye trackers the motion of the eye is detected relative to the sensor. In other tracking applications, such as robot vehicles, the detector may move relative to fixed. In high data content displays, such as those used in AR and VR, eye tracking is essential to reduce latency, the primary cause of motion sickness. Eye tracking enables foveated rendering, a process that limit the amount of image content to be computed and displayed at any time to that lying within the eye's foveal region. Eye tracking is also the key to solving the well-known vergence-accommodation problem that occurs in stereoscopic displays.

Eye tracking is important in Head Mounted Displays (HMDs) because it can extend the ability of the user to designate targets well beyond the head mobility limits. Eye tracking technology based on projecting IR light into the users eye and utilizing the primary Purkinje reflections (from the cornea and lens surfaces) and the pupil-masked retina reflection have been around since the 1980's. The general strategy is to track the relative motion of these images in order to establish a vector characterizing the point of regard. The cornea, which has an aspheric shape of smaller radius than the eye-ball, provides a reflection that tracks fairly well with angular motion until the reflected image falls off the edge of the cornea and onto the sclera. Most solutions rely on projecting IR light into the user's eye and tracking the reflections from the principal surfaces, that at least one surface of the lens, cornea and retina. The first practical challenge is how to introduce the image sensor and illuminator in such a way that both can work efficiently while avoiding obscuring the line of sight Most eye tracker implementations in HMDs have employed flat beam splitters in front of the users' eyes and relatively large optics to image the reflections onto an imaging sensor. Inevitably there are tradeoffs between exit pupil, field of view and ergonomics. The exit pupil is generally limited by either the beamsplitter size or the first lens of the imaging optics. In order to maximize the exit pupil, the imaging optics are positioned close to the beamsplitter, and represent a vision obscuration and a safety hazard. Another known limitation with eye trackers is the field of view, which is generally limited by the illumination scheme in combination with the geometry of the reflected images. The size of the corneal reflected angles would ordinarily require a large angular separation between the illumination and detection optical axes making using corneal reflections over large FOVs very difficult. Ideally, the eye tracker should minimise the angle between the illumination and reflection beams. The temporal resolution of an eye tracker should be at least 60 Hz. However, 90-120 Hz is preferred. Direct imaging by miniature cameras is becoming more attractive as camera get smaller and their resolution increases. However, the latency incurred by the need to recognize and track eye features remains a significant processing bottleneck. From the optical and ergonomic perspective providing a line-of-sight for a camera in a HMD is not trivial. Eye trackers are key components of AR and VR headsets. Desirable an eye tracker should enable the full range of benefits of augmented reality AR and VR displays, namely: a compact and lightweight form factor for encumbrance-free, see-through, mobile and extended use; wide field of view to allow meaningful connections between real world and computer generated images; and the capability of providing robust depth and occlusion cues. The latter are often one of the strongest depth cues. Although recent advances in displays have collectively spanned these requirements no one display technology possesses all of these characteristics.

The inventors have found that diffractive optical elements offer a route to providing compact, transparent, wide field of view eye trackers. One important class of diffractive optical elements is based on Switchable Bragg Gratings (SBGs). SBGs are fabricated by first placing a thin film of a mixture of photopolymerizable monomers and liquid crystal material between parallel glass plates. One or both glass plates support electrodes, typically transparent indium tin oxide films, for applying an electric field across the film. A volume phase grating is then recorded by illuminating the liquid material (often referred to as the syrup) with two mutually coherent laser beams, which interfere to form a slanted fringe grating structure. During the recording process, the monomers polymerize and the mixture undergoes a phase separation, creating regions densely populated by liquid crystal micro-droplets, interspersed with regions of clear polymer. The alternating liquid crystal-rich and liquid crystal-depleted regions form the fringe planes of the grating. The resulting volume phase grating can exhibit very high diffraction efficiency, which may be controlled by the magnitude of the electric field applied across the film. When an electric field is applied to the grating via transparent electrodes, the natural orientation of the LC droplets is changed causing the refractive index modulation of the fringes to reduce and the hologram diffraction efficiency to drop to very low levels. Note that the diffraction efficiency of the device can be adjusted, by means of the applied voltage, over a continuous range. The device exhibits near 100% efficiency with no voltage applied and essentially zero efficiency with a sufficiently high voltage applied. In certain types of HPDLC devices magnetic fields may be used to control the LC orientation. In certain types of HPDLC phase separation of the LC material from the polymer may be accomplished to such a degree that no discernible droplet structure results. SBGs may be used to provide transmission or reflection gratings for free space applications. SBGs may be implemented as waveguide devices in which the HPDLC forms either the waveguide core or an evanescently coupled layer in proximity to the waveguide. The parallel glass plates used to form the HPDLC cell provide a total internal reflection (TIR) light guiding structure. Light is "coupled" out of the SBG when the switchable grating diffracts the light at an angle beyond the TIR condition. Waveguides are currently of interest in a range of display and sensor applications. Although much of the earlier work on HPDLC has been directed at reflection holograms, transmission devices have proved to be much more versatile as optical system building blocks. Typically, the HPDLC used in SBGs comprise liquid crystal (LC), monomers, photoinitiator dyes, and coinitiators. The mixture frequently includes a surfactant. The patent and scientific literature contains many examples of material systems and processes that may be used to fabricate SBGs. Two fundamental patents are: U.S. Pat. No. 5,942,157 by Sutherland, and U.S. Pat. No. 5,751,452 by Tanaka et al. Both filings describe monomer and liquid crystal material combinations suitable for fabricating SBG devices. One of the known attributes of transmission SBGs is that the LC molecules tend to align normal to the grating fringe planes. The effect of the LC molecule alignment is that transmission SBGs efficiently diffract P polarized light (ie light with the polarization vector in the plane of incidence) but have nearly zero diffraction efficiency for S polarized light (ie light with the polarization vector normal to the plane of incidence. Transmission SBGs may not be used at near-grazing incidence as the diffraction efficiency of any grating for P polarization falls to zero when the included angle between the incident and reflected light is small.

There is a requirement for a compact, lightweight, transparent tracker with low latency and a wide field of view for tracking the relative motion of the tracker and one or more objects.

There is a requirement for a compact, lightweight, transparent tracker with low latency and a wide field of view for use in an eye-slaved display.

There is a requirement for a compact, lightweight, transparent tracker with low latency and a wide field of view for use in an eye-slaved display capable of delivering robust depth and occlusion visual cues.

There is a requirement for a compact, lightweight, transparent tracker with low latency and a wide field of view for use in a LIDAR system.

There is a requirement for a compact lightweight transparent display and a wide field of view that integrates a low latency eye tracker and a waveguide display

SUMMARY OF THE INVENTION

It is a first object of the invention to provide a compact, lightweight, transparent tracker with low latency and a wide field of view for tracking for tracking the relative motion of the tracker and one or more objects.

It is a second object of the invention to provide a compact, lightweight, transparent tracker with low latency and a wide field of view for use in an eye-slaved display.

It is a third object of the invention to provide a compact, lightweight, transparent tracker with low latency and a wide field of view for use in an eye-slaved display capable of delivering robust depth and occlusion visual cues.

It is a fourth object of the invention to provide a compact, lightweight, transparent tracker with low latency and a wide field of view for use in a LIDAR system.

It is a fifth object of the invention to provide compact lightweight transparent display with a wide field of view that integrates a low latency eye tracker and an image display.

The objects of the invention are achieved in one embodiment of the invention in which there is provided an object tracker for tracking at least one object comprising: a first waveguide; a source of illumination light; a detector optically coupled to said waveguide; and at least one grating lamina formed within said waveguide. The illumination light propagates along a first optical path from the source to an object. Image light reflected from at least one surface of an object is deflected by the grating lamina into a second optical path towards the detector. The object tracker and the object are in relative motion.

In one embodiment the first optical path includes a first waveguide path and the second optical path includes a second waveguide path, the grating lamina deflecting said illumination light out of the first waveguide path towards the object, and the second optical path is a second waveguide path.

In one embodiment at least one of the grating lamina comprises at least one switchable grating element having a diffracting state and a non-diffracting state.

In one embodiment the grating lamina comprises at least one switchable grating element having a diffracting state and a non-diffracting state. The grating element in its diffracting state deflects illumination light in the first waveguide path out of the first waveguide towards the object and deflects image light into the second waveguide path towards the detector.

In one embodiment the grating lamina comprises first and second switchable grating elements having a diffracting state and a non-diffracting state. The first grating element in its diffracting state deflects illumination light in the first waveguide path out of the first waveguide towards the object. The second grating element in its diffracting state deflects image light into the second waveguide path towards the detector.

In one embodiment the grating lamina comprises at least one elongate grating element with longer dimension aligned perpendicular to at least one of the first and second waveguide paths.

In one embodiment the first and second waveguide paths are parallel.

In some embodiments the grating lamina further comprises at least one of an input grating or prism for deflecting illumination light from the source into the first waveguide path and an output grating or prism for deflecting image light out of the second waveguide path towards the detector.

In one embodiment the grating lamina comprises at least one fold grating disposed along at least one of the first or second waveguide paths.

In one embodiment the first optical path traverses the reflecting surfaces of the waveguide.

In some embodiments at least one grating lamina is one of a switchable Bragg grating, a switchable grating recorded in a reverse mode holographic polymer dispersed liquid crystal, a switchable grating recorded in a reverse mode holographic polymer dispersed liquid crystal, a surface relief grating and a non-switching Bragg grating.

In one embodiment the grating lamina diffracts illumination light into output paths converging towards a center of rotation of the object.

In one embodiment the grating lamina diffracts illumination light into parallel output paths.

In some embodiments the image light is one of specular reflection, incoherent scatter, speckle formed by at least one surface of the object.

In some embodiments the object is an eye and the image light is a reflection off at least one of the cornea, lens, iris, sclera or retina.

In some embodiments the detector is one of a single element detector, a linear array or a two dimensional array and the source is one of a laser or a light emitting diode. In some embodiments the source and detector operate in the infrared In some embodiments the grating lamina encodes at least one of optical power or diffusing properties.

In one embodiment the detector is connected to an image processing apparatus for determining at least one spatio-temporal characteristic of an object movement.

In some embodiments the object tracker further comprises an image processing system which includes at least one of an edge finding algorithm, a centroid detection algorithm or a neural network.

In some embodiments the object tracker is implemented in an eye tracker, a LIDAR, an eye-slaved display, a display implementing foveated rendering or a display using gaze vector data to adjust a displayed image to provide vergence-accommodation related depth cues.

In one embodiment there is provided an eye-slaved waveguide display in which left and right eye trackers triangulate left and right eye gaze intersections to provide depth cues. The waveguide display overcome vergence-accommodation conflict by providing focal surfaces at different image depths with the display refocusing dynamically according to the depth data provided by the eye tracker. In embodiment the eye-slaved waveguide display also includes a dynamic occlusion mask based on a spatial light modulator.

A more complete understanding of the invention can be obtained by considering the following detailed description in conjunction with the accompanying drawings, wherein like index numerals indicate like parts. For purposes of clarity, details relating to technical material that is known in the technical fields related to the invention have not been described in detail.

BRIEF DESCRIPTION OF THE DRAWINGS

FIG. 13A is a schematic cross of the human eye in a first rotational state showing a typical speckle pattern formed by the cornea and retina.

FIG. 13B is a schematic cross of the human eye in a first rotational state showing a typical speckle pattern formed by the cornea and retina.

FIG. 14 is a schematic front elevation view of a human eye show showing the directions of motions of speckle patterns produced by the retina and cornea.

FIG. 55A is a schematic cross section of a detail of an object tracker in one embodiment.

FIG. 55B is schematic plan view of an object tracker in one embodiment.

FIG. 56 is schematic plan view of an object tracker in one embodiment.

DETAILED DESCRIPTION OF THE INVENTION

Figure 1:
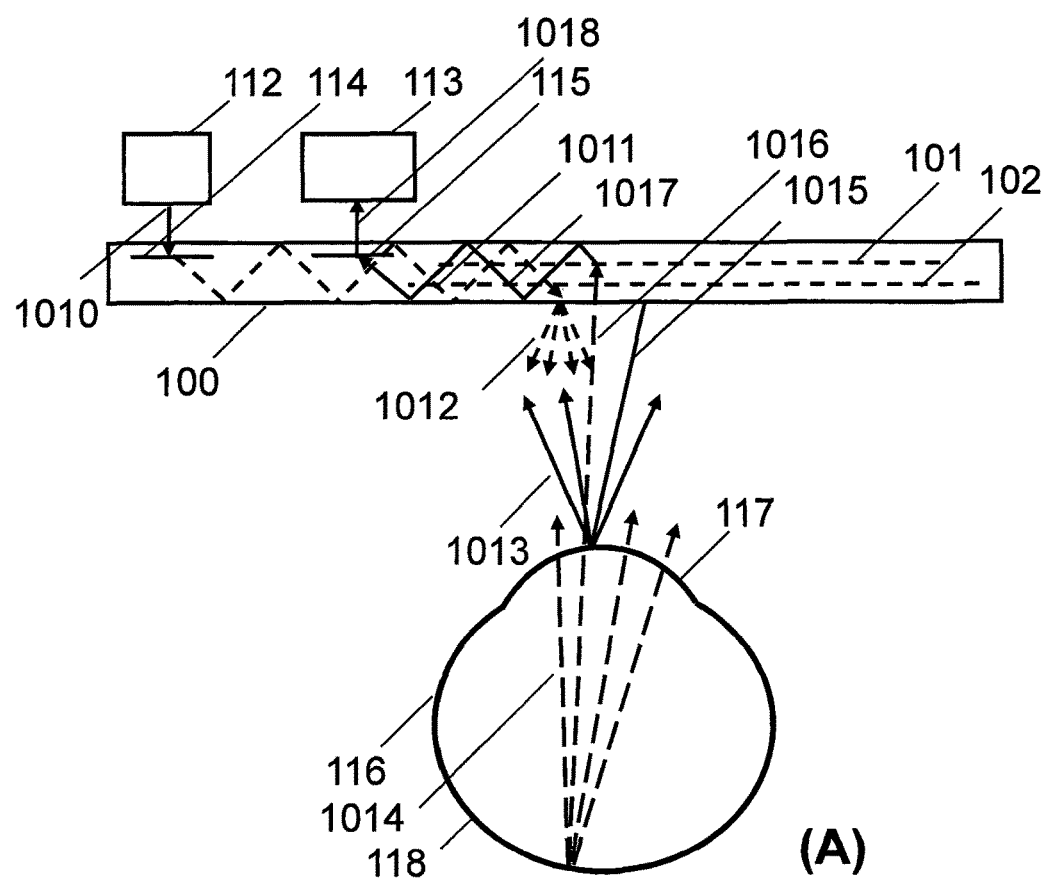
FIG. 1A is a schematic plan view of an eye tracker shown in relation to a human eye in one embodiment of the invention
FIG. 1B is a schematic front elevation view showing elongate grating elements used in the imaging grating in one embodiment of the invention.
FIG. 1C is a schematic front elevation view showing a two dimensional array of grating elements used in the imaging grating in one embodiment of the invention.
Figure 1:
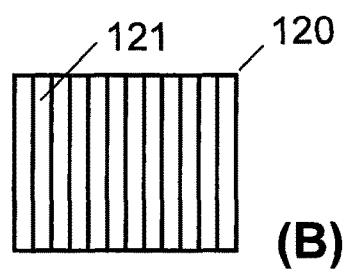
Figure 1:
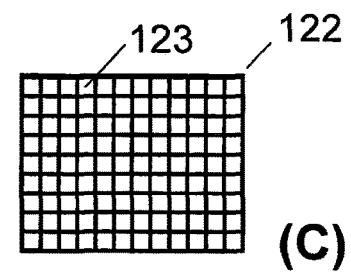

The invention will now be further described by way of example only with reference to the accompanying drawings. It should be apparent to those skilled in the art that the present invention may be practiced with some or all of the present invention as disclosed in the following description. For the purposes of explaining the invention well-known features of optical technology known to those skilled in the art of optical design and visual displays have been omitted or simplified in order not to obscure the basic principles of the invention. Unless otherwise stated the term "on-axis" in relation to a ray or a beam direction refers to propagation parallel to an axis normal to the surfaces of the optical components described in relation to the invention. In the following description the terms light, ray, beam and direction may be used interchangeably and in association with each other to indicate the direction of propagation of electromagnetic radiation along rectilinear trajectories. The term light and illumination may be used in relation to the visible and infrared bands of the electromagnetic spectrum. Parts of the following description will be presented using terminology commonly employed by those skilled in the art of optical design. It should also be noted that in the following description of the invention repeated usage of the phrase "in one embodiment" does not necessarily refer to the same embodiment.

The tracking of moving objects is a key requirement in many fields including eye tracking, augmented reality, virtual reality, robotics, collision avoidance systems and many others. Although the nature of the objects and their dynamics varies greatly there is a general requirement to track robustly, accurately and with minimal processing time lag (latency). The invention will be discussed in relation to eye tracking. However we would emphasize that the embodiments to be described in the following description are not limited to tracking an eye.

The ideal eye tracker should make minimum impact on the overall optical performance. The inventor believe that the following are realistic design goals: a field of view (FOV) of 60° horizontal×48° vertical; 17 mm eye relief; and eye motion box/exit pupil (20 mm.×10-15 mm). Moreover, the eye tracker must satisfy eye safety requirements for near-eye visual displays with regard to weight (minimal), center of gravity (ergonomic), and profile. Furthermore it should not compromise: pixel resolution, see-through (≥90%) and power consumption (minimal).

Eye Trackers based on classical Purkinje imaging methods suffer from high latency resulting mainly from the large delay incurred by feature recognition and tracking algorithms. The inventors are strongly motivated by a desire to develop an eye tracker that, firstly, simplifies the image processing problems of classical eye tracking that often result in unacceptably high latency and, secondly, can make use of relatively unsophisticated detector technology. The eye tracker embodiments to be described below avoid the cost and complexity of implementing classical Purkinje imaging methods by tracking eye signatures using low resolution high speed image sensors. In some embodiments of the invention a tracker may use detector technology equivalent in specification to that used in the infrared mouse a device which is now ubiquitous and, more importantly, capable of being manufactured using sub dollar components. In some embodiments a single element detector may be used. In eye tracking applications the signatures to be recorded do not need to be images of eye features such as pupil edges but can be random structures such as speckle patterns (including reflections from multiple surfaces and scatter from the optical media inside the eye). However, it is important that whatever signature is tracked has a strong spatio-temporal variation with gaze direction. The inventors believe that this approach offers significant advantages in terms of detector resolution, processing overhead and power consumption. Conventional iris image capture systems are an indicator the level of processing that will be required in an eye tracker. The iris image is typically acquired by a camera using infrared light in the 700 nm-900 nm band resolving in the region of 100-200 pixels along the iris diameter. The first step is usually to detect and remove stray light before proceeding to determine the boundaries of the iris. Typically the centers and radii of iris and pupil are approximated initially by applying a circular edge detector. High accuracy and rapid response times require high-performance and high-cost microprocessors that are beyond the scope of consumer products. Traditional image processing designs based on software are too slow. It is known that significant improvements may result from an an iris recognition algorithms based on a hardware-software co-design using low-cost FPGAs The system architecture consists of a 32-bit general purpose microprocessor and several dedicated hardware units. The microprocessor executes in software the less computationally intensive tasks, whereas the coprocessors speed-up the functions that have higher computational cost. Typically, depending on the function implemented, coprocessors speed-up the processing time by a factor greater than 10 compared to its software execution. However, the best latency achieved with hardware-software co-designs, is typically in the range 500-1000 ms. It should be noted that an eye tracker is a much more demanding proposition for an image processor. Detecting a clean iris image is only the first step. Applying the edge detection algorithms as the eye moves around the eye box will require several frames to be analysed adding to the overall latency.

An eye tracker according to the principles of the invention provides an infrared illumination optical channel for delivering infrared illumination to the eye and an imaging or detection optical channel for forming an image (or recording a signature) of the eye at a detector. In one embodiment of the invention illustrated in FIGS. 1-2, the eye tracker comprises a waveguide 100 for propagating illumination light towards an eye 116 and propagating image light reflected from at least one surface of an eye; a light source 112 optically coupled to the waveguide; and a detector 113 optically coupled to the waveguide. Disposed in the waveguide are: at least one input grating 114 for deflecting illumination light from the source into a first waveguide path; at least one illumination grating 102 for deflecting the illumination light towards the eye; at least one imaging grating 101 for deflecting the image light into a second waveguide path; and at least one output grating 115 for deflecting the image light towards the detector. The inventors also refer to the waveguide 100 as the DigiLens. The illumination and imaging gratings are arrays of switchable beam deflection grating elements with the preferred grating technology being a SBG as described above. In one embodiment of the invention shown in FIG. 1B the grating elements in the imaging grating 120 are elongate, as indicated by 121, with longer dimension orthogonal to the beam propagation direction. In one embodiment of the invention shown in FIG. 1C the imaging grating may comprise a two dimensional array 122 of SBG lens elements 123, each element having optical power in two orthogonal planes. Typically, the first and second waveguide paths, that is, the imaging and illumination paths in the waveguide are in opposing directions, as illustrated in FIG. 1A. The illumination light will, typically, be fully collimated while the image light will have some divergence of angle determined by the scattering properties of the tracked eye surfaces, the angular bandwidth of the gratings and the numerical aperture of the grating elements. As will be discussed later, in some embodiments the imaging and illumination gratings are provided by a single grating with the illumination and imaging ray paths counter-propagating in the same wave guiding structure. Where separate imaging and illumination gratings are used the two gratings may respond to different TIR angle ranges within the waveguide. This is advantageous in terms of avoiding the risk of cross-coupling of illumination light into the detector and image light into the light source.

In FIG. 1A the illumination light path is illustrated by the light 1010 from the source which is directed into a TIR path 1011 by the input grating and diffracted out of the waveguide as the light generally indicated by 1012. Typically, the eye tracker will have a pupil of size 20-30 mm. to allow capture of light reflected from the eye to continue should the waveguide change position relative to the eye. Since the eye tracker will usually be implemented as part of a HMD its pupil should desirably match that of the HMD. FIG. 1A shows return light 1013 reflected from the front surface of the cornea 117 and light 1014 reflected from the retina 118. The corneal and retinal image light enters the waveguide along tray paths such 1015, 1116 and is deflected into a TIR path such as 1017 by an active element of the imaging grating which is switched one element at a time. The light 1017 is deflected into a ray path 1018 toward the detector by the output grating. Advantageously, the detector reads out the image signal in synchronism with the switching of the SBG lens elements. The detector is connected to an image processing apparatus for determining at least one spatiotemporal characteristic of an eye movement. The image processor, which is not illustrated, detects pre-defined features of the backscattered signals from the cornea and retina. For example, the image processor may be used to determine the centroid of an eye feature such as the pupil. Other trackable features of the eye will be well known to those skilled in arts of eye tracker design and visual optics.

Advantageously, the light source is a laser emitting in the infrared band. The choice of wavelength will depend on laser efficiency, signal to noise and eye safety considerations. Light Emitting Diodes (LEDs) may also be used. In one embodiment of the invention the detector is a two dimensional array. However other types of detector may be used including linear arrays and analogue devices such as position sensing detectors. In the embodiment shown in FIG. 1 the illumination grating provides divergent light. In alternative embodiments of the invention the illumination grating provides collimated light.

Figure 2:
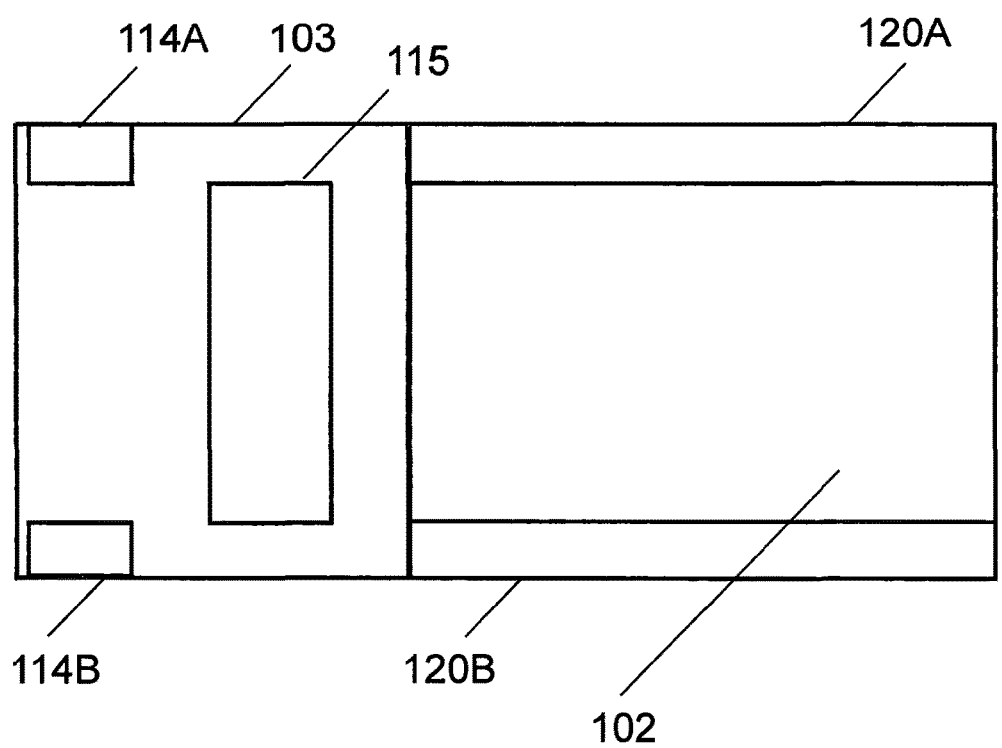
FIG. 2 is a schematic plan view of the eye tracker shown the imaging and illumination gratings and input and output gratings in one embodiment of the invention.

The gratings may be implemented as lamina within or adjacent an external surface of the waveguide. In other words the grating may be disposed adjacent an optical surface of the waveguide comprising at least one of an internal surface or an external surface of the waveguide. For the purposes of discussing the invention we will consider Bragg gratings disposed within the waveguide. Advantageously the gratings are switchable Bragg gratings (SBGs). In certain embodiments of the invention passive gratings may be used. However, passive gratings lack the advantage of being able to direct illumination and collect image light from precisely defined areas of the pupil. In one embodiment the gratings are reverse mode SBGs. Although the invention is discussed in relation to transmission gratings it should be apparent to those skilled in the art that equivalent embodiments using reflection gratings should be feasible in most cases. The gratings may be surface relief gratings. However, such gratings will be inferior to Bragg gratings in terms of their optical efficiency and angular/wavelength selectivity. The input and illumination gratings may be configured in many different ways. FIG. 2 is a schematic plan view showing one possible implementation for use with the embodiment of FIG. 1. Here the input grating comprises two grating elements 114A,114B and the illumination grating is also divided into the upper and lower gratings 120A,120B, each providing narrow beam deflecting grating strips above and below the imaging grating 102. The detector grating 115 is also indicated. Since the guided beams in the input and illumination grating are collimated, and likewise the guided beams in the imaging and detector gratings, there is no cross talk between the two regions of the waveguide.

Figure 3:
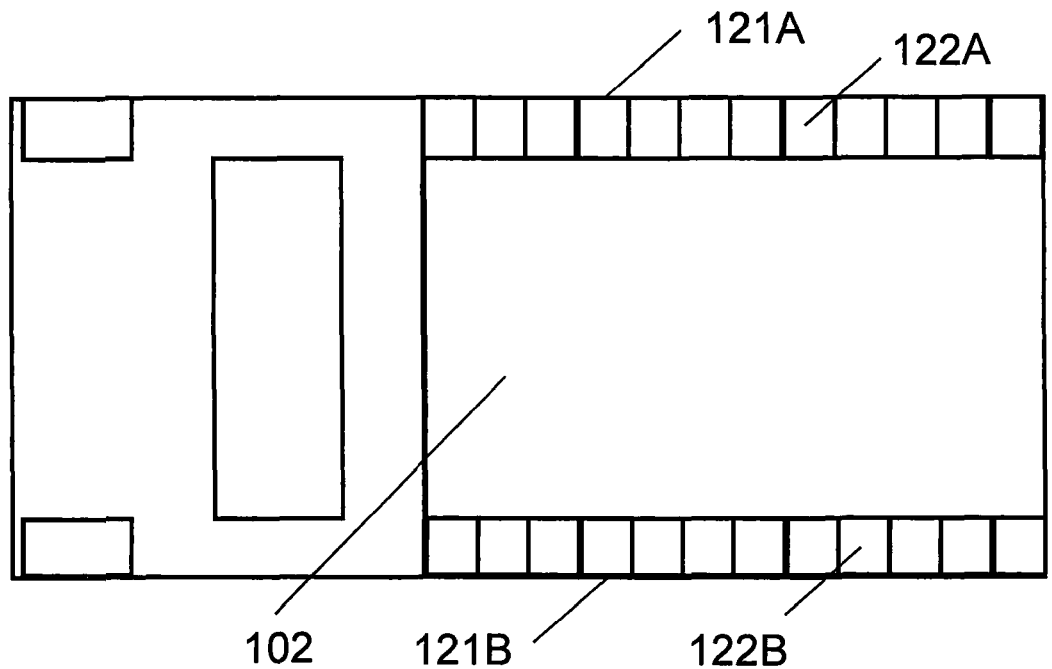
FIG. 3 is a schematic plan view of the eye tracker shown the imaging and illumination gratings and input and output gratings in one embodiment of the invention.
Figure 4:
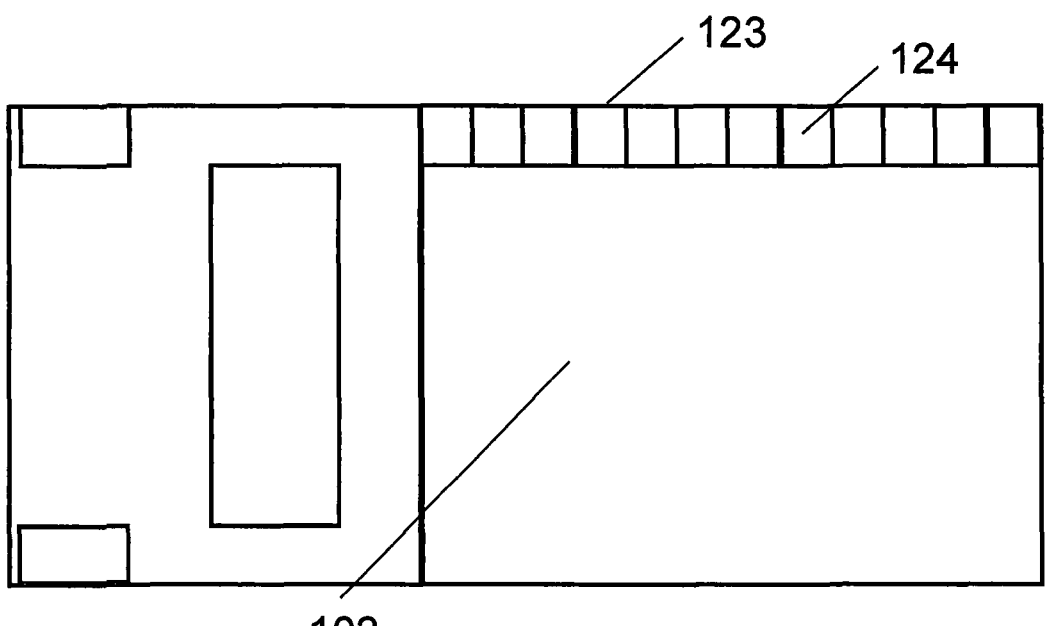
FIG. 4 is a plan view of the eye tracker shown the imaging and illumination gratings and input and output gratings in one embodiment of the invention.

In the embodiment of the invention shown in FIGS. 3-4, which is similar to the one of FIG. 2, the upper and lower illumination grating may be arrays of switchable grating elements 121A,121B comprising switchable grating elements such as 122A,122B. The SBG deflector arrays scroll illumination across the exit pupil in step with the activation of the imaging grating elements. Finally, in the embodiment of FIG. 4 the illumination grating comprises just one strip 123 containing elements 124 disposed along the top edge of the imaging grating.

The invention does not assume any particular configuration of the grating elements. It is important to note that the SBGs are formed as continuous lamina. Hence the illumination gratings elements may be considered to be part of the imaging grating. This is a significant advantage in terms of fabrication and overall form factor. In embodiments where the illumination grating is split into two elements as discussed above the input laser light may be provided by one laser with the upper and lower beam being provided by a beam splitting means. Alternatively, two separate laser modules may be used to provide light that is coupled into the waveguide via the input gratings 114A,114B are illustrated in FIGS. 3-4. The invention does not assume any particular method for providing the laser input illumination or coupling the laser light into the waveguide. Many alternative schemes should be apparent to those skilled in the art of optical design.

The illumination grating may provide illumination light of any beam geometry. For example, the light may be a parallel beam emitted normally to the surface of the eye tracker waveguide. The illuminator grating is illustrated in more detail in the schematic side elevation view of FIG. 5 in which the SBG linear array 130 is sandwiched between transparent substrates 130A,130B. Note that the substrate layers extend to cover the entire waveguide and therefore also act as the substrates for the imaging grating. Advantageously, the ITO layers are applied to the opposing surfaces of the substrates with at least one ITO layer being patterned such that SBG elements may be switched selectively. The substrates and SBG array together form a light guide. Each SBG array element has a unique optical prescription designed such that input light incident in a first direction is diffracted into output light propagating in a second direction.

Figure 5:
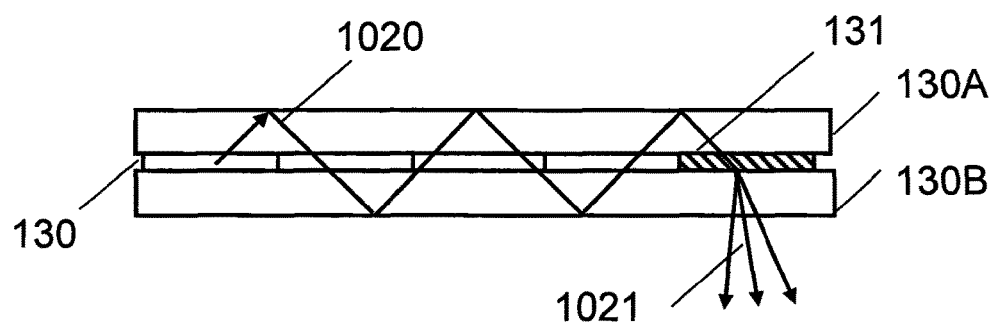
FIG. 5 is a schematic cross section view of an illumination grating used in one embodiment of the invention.

FIG. 5 shows TIR illumination beam 1020 being deflected by the active element 131 to provide divergent illumination light 1021.

Figure 6:
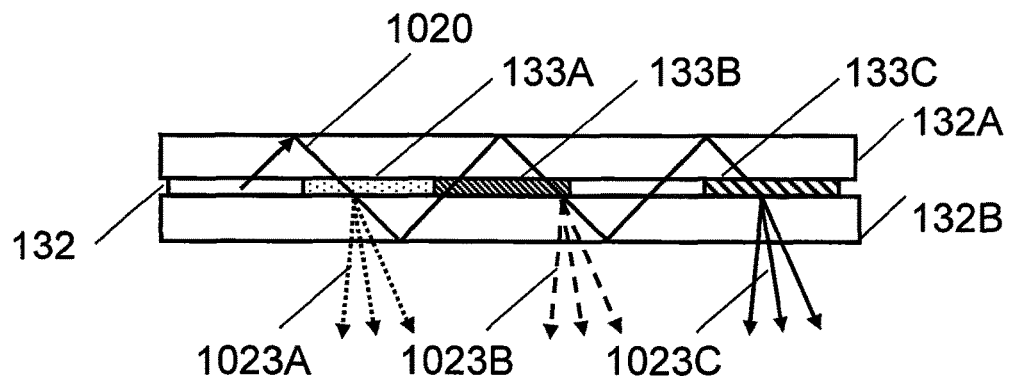
FIG. 6 is a schematic cross section view of an illumination grating used in one embodiment of the invention.
Figure 7:
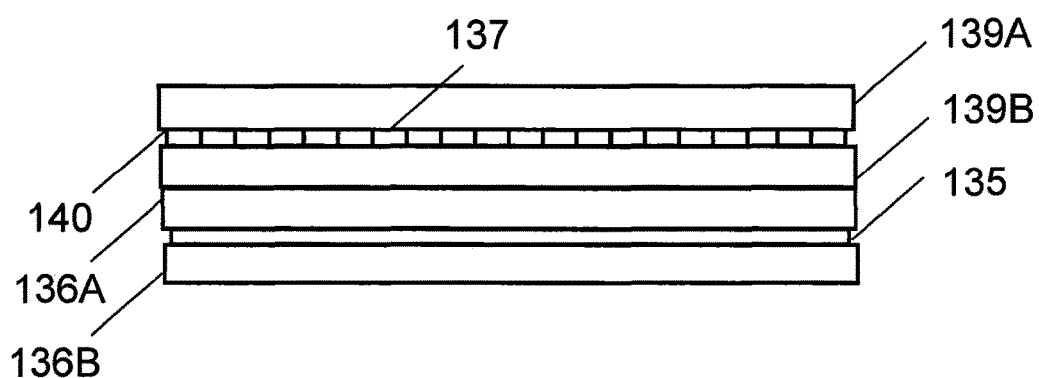
FIG. 7 is a schematic cross section view of a first aspect of an imaging grating used in one embodiment of the invention.

An alternative embodiment of the linear deflector array is shown in the schematic side elevation view of FIG. 6. In this cases the array 132 sandwiched by substrates 132A,132B is based on a lossy grating that diffracts incrementally increasing fractions of the guided beam out of the waveguide towards the eye. Beam portions 1023A-1023C diffracted by the grating elements 133A-133C are illustrated. Typically, the index modulation of the grating elements will be designed to provide uniform extraction along the array and hence uniform output illumination. Note that the geometrical optics of FIGS. 5-6 has been simplified for the sake of simplifying the description.

Advantageously, the illumination grating elements may encode optical power to provide sufficient beam spread to fill the exit pupil with light. A similar effect may be produce by encoding diffusion characteristics into the gratings. The apparatus may further comprise an array of passive holographic beam-shaping diffusers applied to the substrate, overlapping the linear SBG array, to enhance the diffusion. Methods for encoding beam deflection and diffusion into diffractive devices are well known to those skilled in the art of diffractive optics. Cross talk between the imaging and illumination channels is overcome by configuring the SBGs such that the illumination TIR path within the eye tracker lies outside the imaging TIR path.

Figure 8:
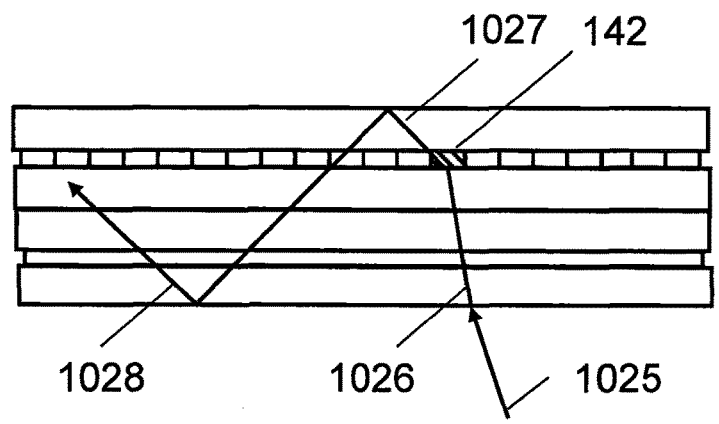
FIG. 8 is a schematic cross section view of a second aspect of an imaging grating used in one embodiment of the invention.
Figure 9:
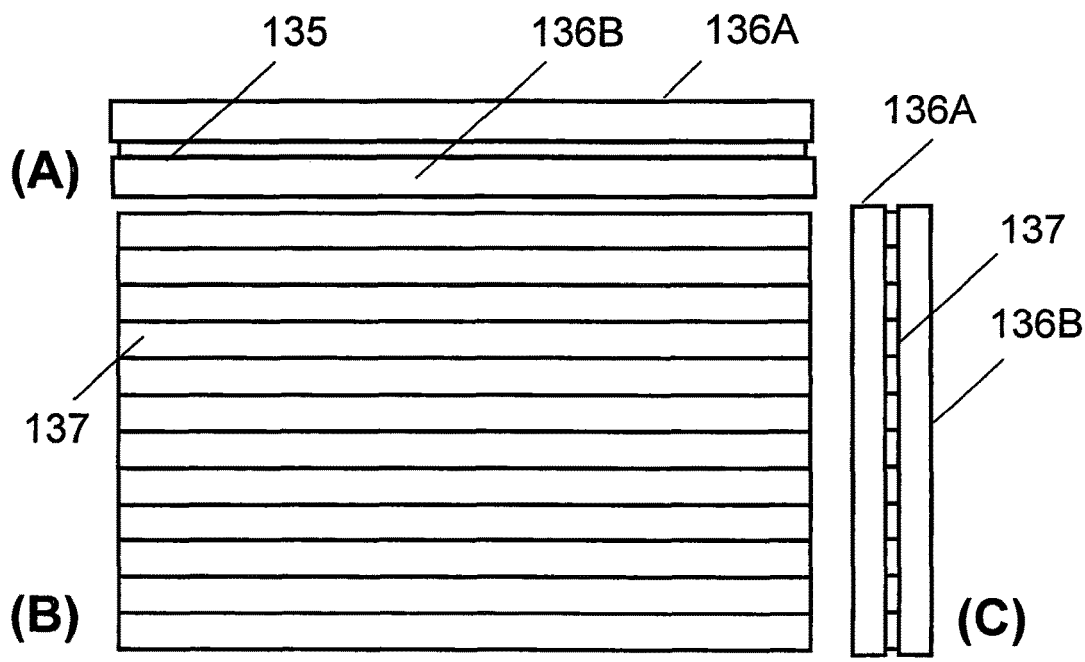
FIG. 9A is a schematic top elevation view of a first layer of a two layer imaging grating in one embodiment of the invention.
FIG. 9B is a schematic plan view of a first layer of a two layer imaging grating in one embodiment of the invention.
FIG. 9C is a schematic side elevation view of a first layer of a two layer imaging grating in one embodiment of the invention.
Figure 10:
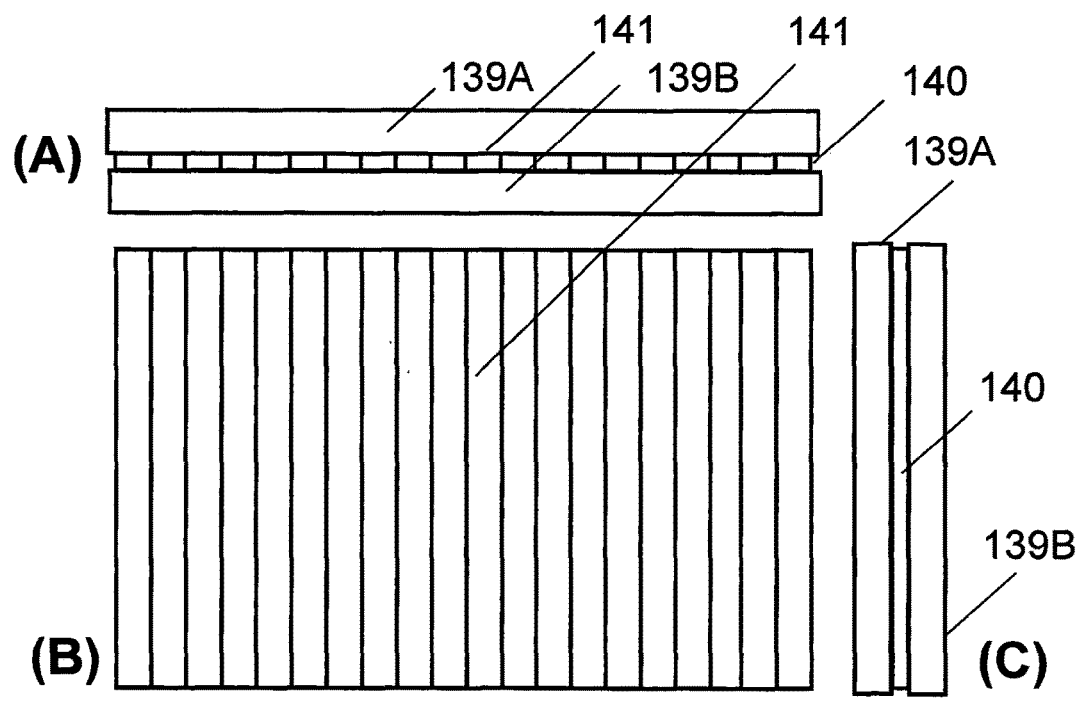
FIG. 10A is a schematic top elevation view of a second layer of a two layer imaging grating in one embodiment of the invention.
FIG. 10B is a schematic plan view of a second layer of a two layer imaging grating in one embodiment of the invention.
FIG. 10C is a schematic side elevation view of a second layer of a two layer imaging grating in one embodiment of the invention.
Figure 11:
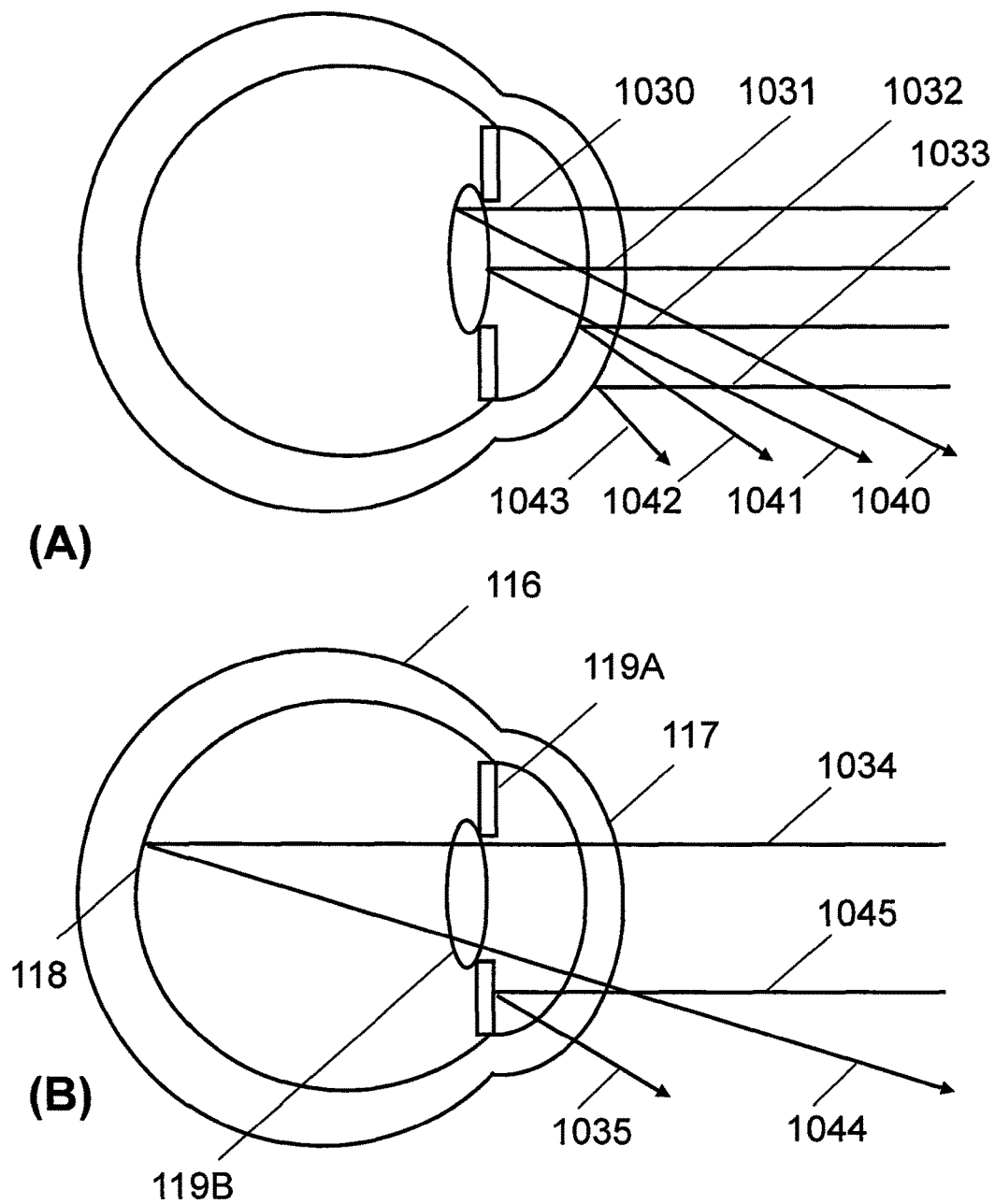
FIG. 11A is a schematic cross view of the human eye illustrating the the Purkinje images.
FIG. 11B is a schematic cross view of the human eye illustrating reflections off the retina and iris.
Figure 12:
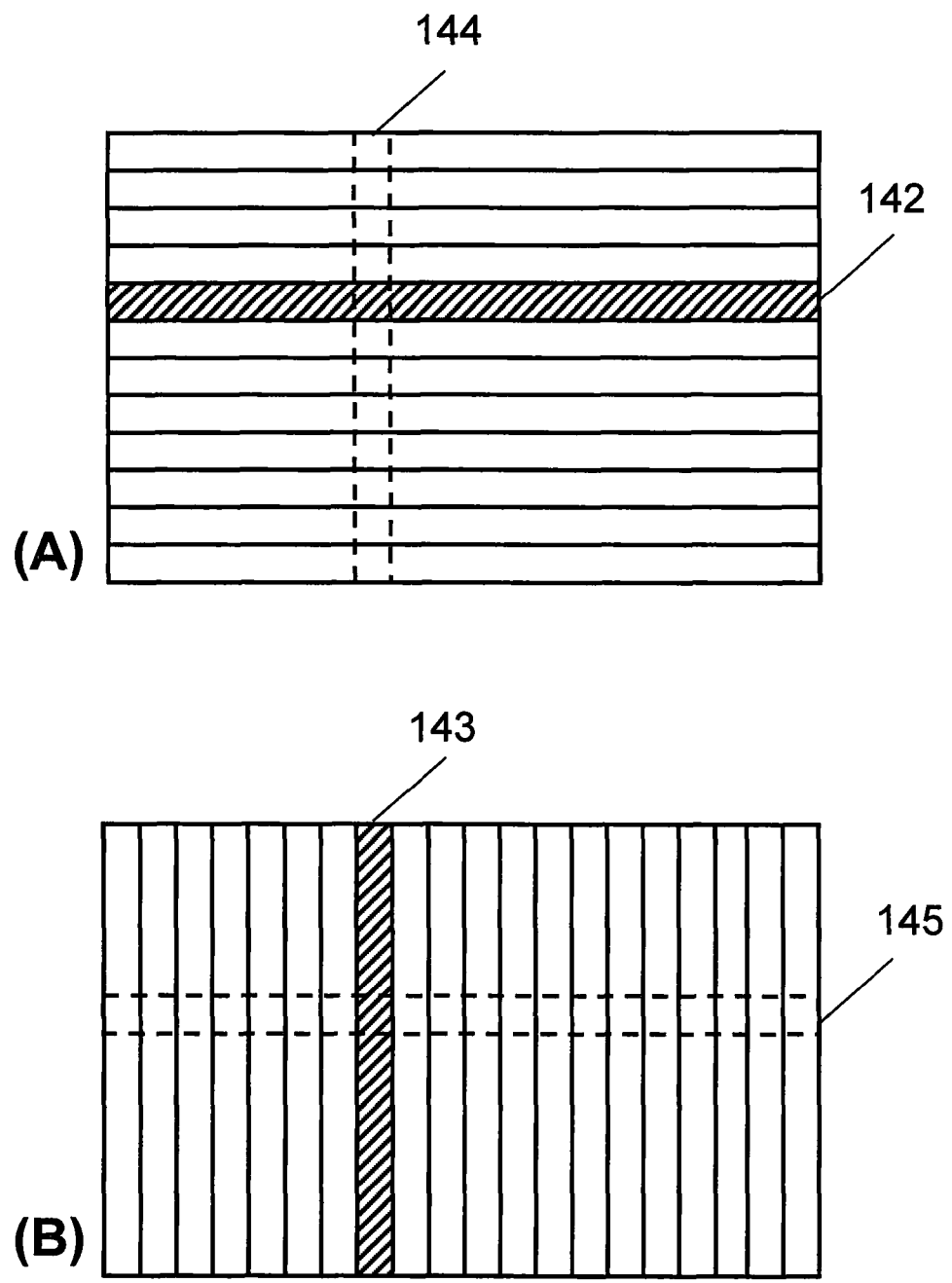
FIG. 12A is a a schematic plan view illustrating a first aspect of the localization of an eye feature by a two layer imaging grating each layer comprising elongate elements with the elements of the two gratings at right angle.
FIG. 12B is a a schematic plan view illustrating a second aspect of the localization of an eye feature by a two layer imaging grating each layer comprising elongate elements with the elements of the two gratings at right angle.

In one embodiment illustrated in FIGS. 7-10 there is proved a a eye tracker waveguide that includes a two layer SBG imaging grating with optical power. The arrays are shown in their stacked configuration in FIG. 7. The substrates 136A,136B and 139A,139B together provide the imaging waveguide as illustrated in FIG. 8 where the ray path from the eye into the waveguide via an activated SBG element 42 is represented by rays 1025-1028. The arrays are shown in front, plan and side elevation views in FIGS. 9-10. The arrays comprise linear arrays of column elements each having the optical characteristics of a cylindrical lens. The column vectors in the two arrays are orthogonal. The first array comprises the SBG array 135 sandwiched by the substrates 136A,136B with one particular element 137 being indicated. The second array comprises the SBG array 40 sandwiched by the substrates 139A,139B with one particular element 141 being indicated. FIG. 11A illustrates the principles of the formation of the first four Purkinje images corresponding to reflections off the front of the cornea 1033,1043; the back of the cornea 1032, 1042; the front of the eye lens 1031,1041; and the back of the eye lens 1030,1040. FIG. 11B illustrates the formation of images of the retina by rays 1034,1044 and the iris by rays 1035,1045. FIG. 12 shows how the first and second SBG lens arrays of FIGS. 7-10 may be used to localize an eye feature such as by scanning row and column SBG elements such as 142 and 143.

With regard to the use of speckle as an eye signature, FIG. 13 illustrates how the size of speckle feature as recorded in two captured speckle images may vary with the eye orientation and displacement with respect to the eye optical axis 1050. FIG. 13A illustrates speckle formed by illuminating the eye along the direction 1050A which is initially parallel to the eye optical axis. The components of the corneal and retinal speckle light parallel to the eye optical axis are indicated by 1050B,1050C. FIG. 14A shows the formation of speckle with the eye rotated in the plane of the drawing. The detected corneal and retinal speckle light 1050D,1050E parallel to the direction 1050 which is now no longer parallel to the eye optical axis is shown. As shown by the insets 1051,1053 the size and spatial distribution of the speckles changes as the eye rotates. Correlation of the two speckle patterns will provide a measure of the eye rotation. Note that, typically, the speckle patterns recorded at the detector will combine separate speckle patterns from the cornea and retina as well as other surfaces and biological media interacting with the illumination beam. In one embodiment of the invention the eye tracker processor compares the speckle images due to light being scattered from the retina and cornea. When the eye is panned horizontally or vertically the relative position of the speckle pattern from the cornea and retina change accordingly allowing the direction of gaze to be determined from the relative trajectories of the reflected light beams.

Figure 15:
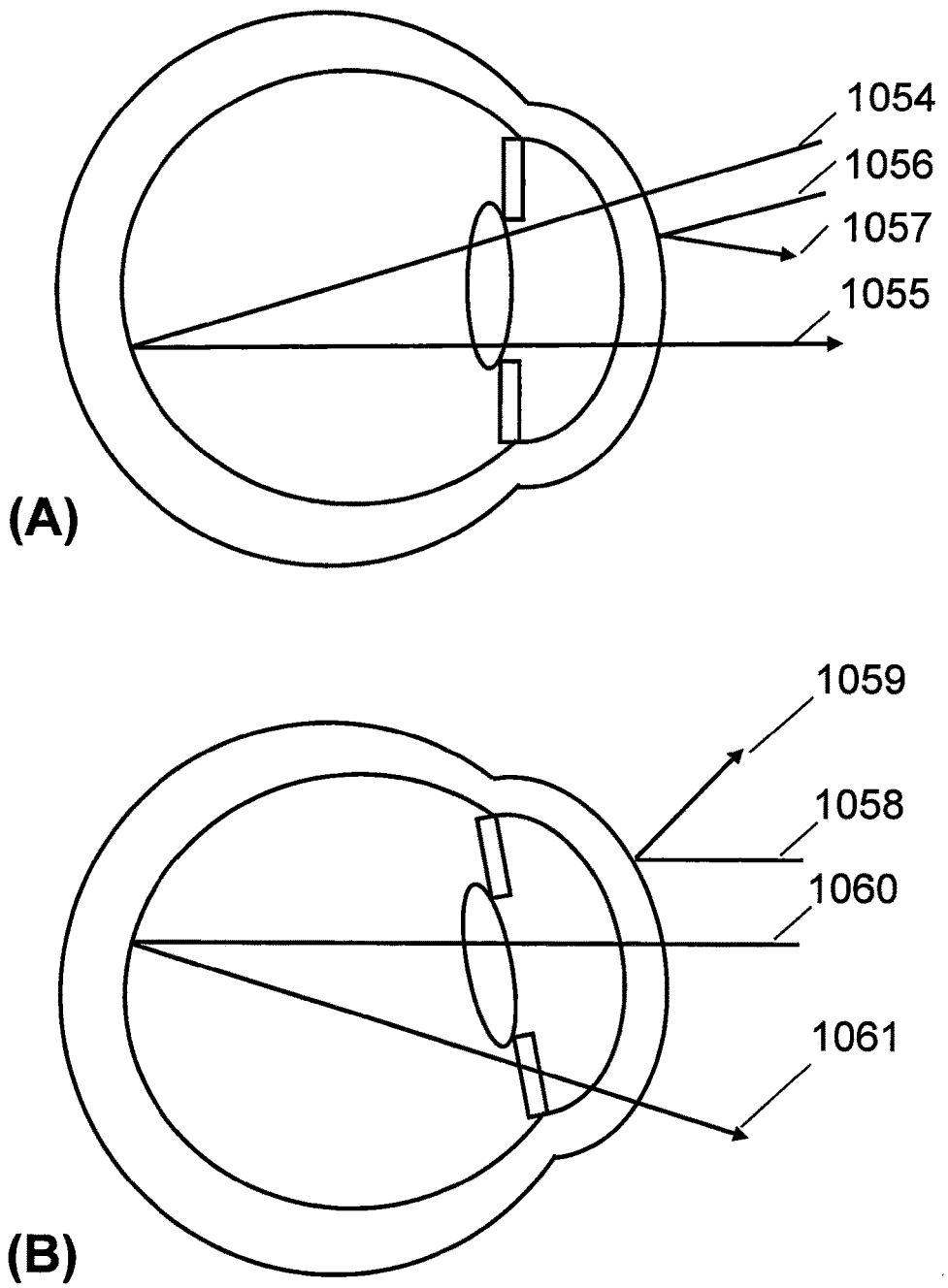
FIG. 15A is a schematic cross section view of a human eye in a first rotational state showing reflection from the retina and cornea.
FIG. 15B is a schematic cross section view of a human eye in a second rotational state showing reflection from the retina and cornea.

FIG. 14 which schematically illustrates the front of the eye 146, cornea 147 and illuminated region 148 of the retina shows the direction of movement of corneal and retinal speckle features as indicated by the vectors 149,150 corresponding to the ocular displacement illustrated in FIG. 15. In general, the ray reflection vector directions will be closely linked to eye rotation. FIG. 15A represents the reflection of rays from the cornea 1056,1057 and retina 1054,1055 for one eye position. FIG. 15B shows the reflection paths from the cornea 1058,1059 and the retina 1060,1061 after a horizontal (or vertical) eye rotation. Reflection from the cornea has a strong secular component. Retinal reflection is more diffuse. The size of the corneal reflected angles would ordinarily require a large angular separation between the illumination and detection optical axes. This would make eye tracking using corneal reflections over large fields of view very difficult. One way of avoiding the problem of imaging large reflection angles (and dealing with are lateral and vertical eye movements which can arise from slippage) that may applied using the invention is to configure the tracker to provide matched scrolling illumination and detection, which will be discussed in more detail later. Hence the reflection angle becomes relatively small and can be approximated to: $\Psi \sim 2[(D/r-1)\Phi + d/r]$ where r is the cornea radius $\Phi$ is the eye rotation and D is the distance of the eye centre from the displaced centre of curvature of the cornea and d is the lateral displacement of the eye centre.

Figure 16:
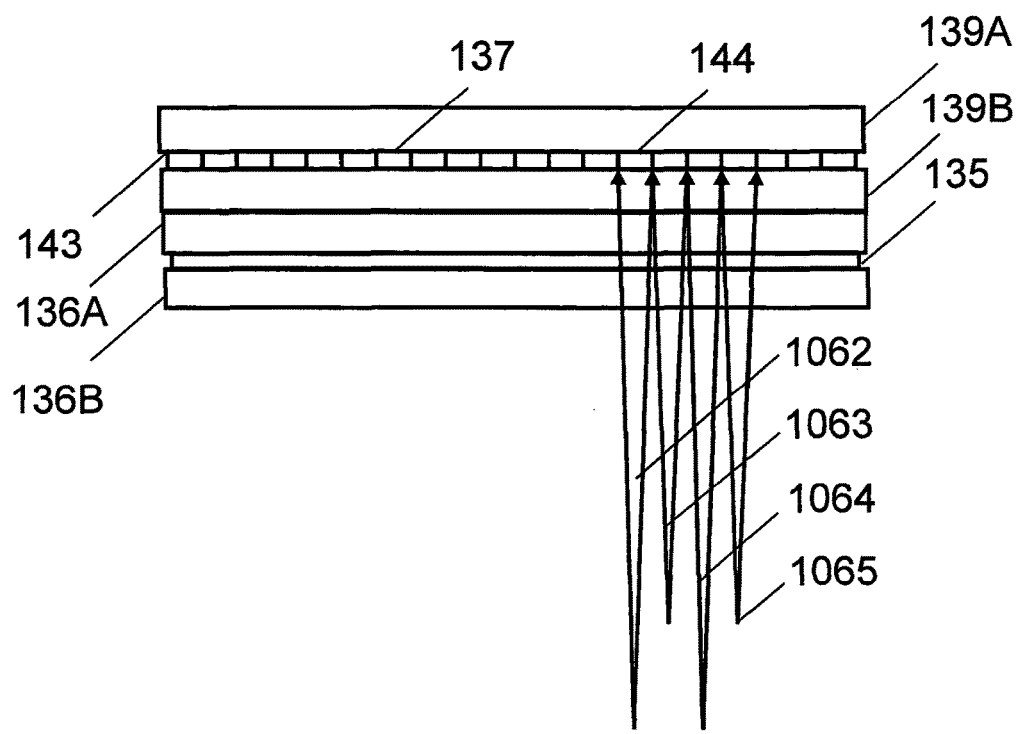
FIG. 16 is a schematic cross section view of an imaging grating comprising an array of SBG lens elements with focal length varying across the exit pupil in one embodiment of the invention.
Figure 17:
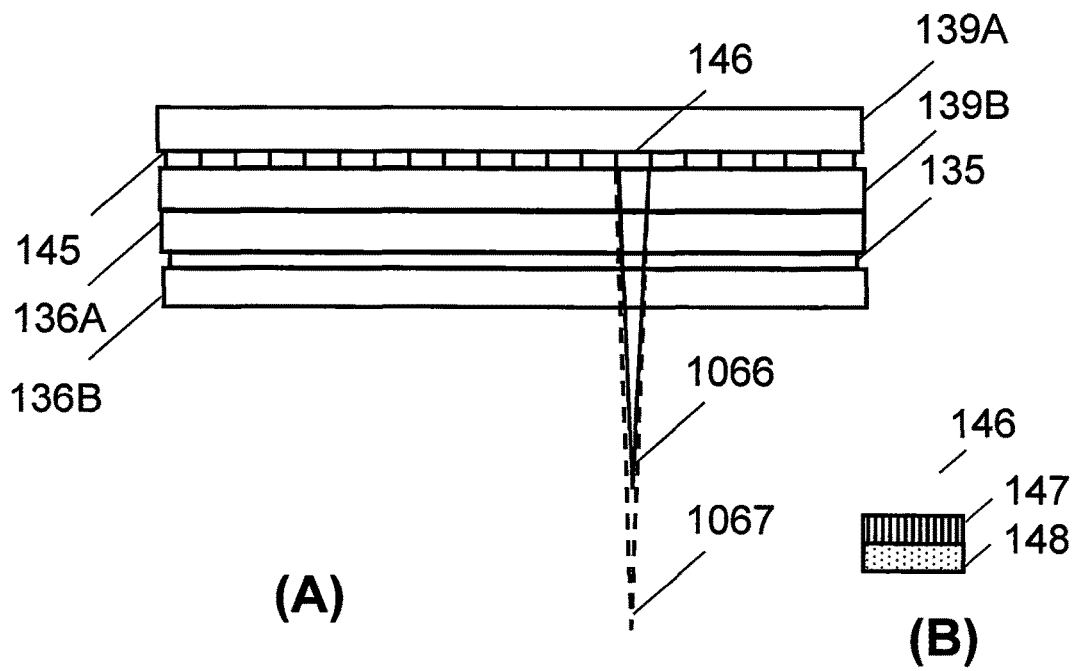
FIG. 17A is a schematic cross section view of an imaging grating comprising an array of variable power lenses in one embodiment of the invention.
FIG. 17B is a detail of FIG. 17A showing a variable power lens comprising a variable index layer and a diffractive element of fixed focal length.

In one embodiment of the invention based on the one illustrated in FIGS. 7-10 the imaging grating comprises an SBG array 143 in which the lens elements 144 have varying focal length across the exit pupil. In the embodiment of FIG. 16 grating elements of first and second focal length indicated by the divergent beams 1062,1064 and 1063,1065 are uniformly interspersed. In one embodiment illustrated in FIG. 17A the imaging waveguide comprises arrays 145 of variable power lens elements 146. As shown in the detail of FIG. 17B a variable power lens would be provided by combining a diffractive element 147 of fixed focal length with a variable index layer 148.

Figure 18:
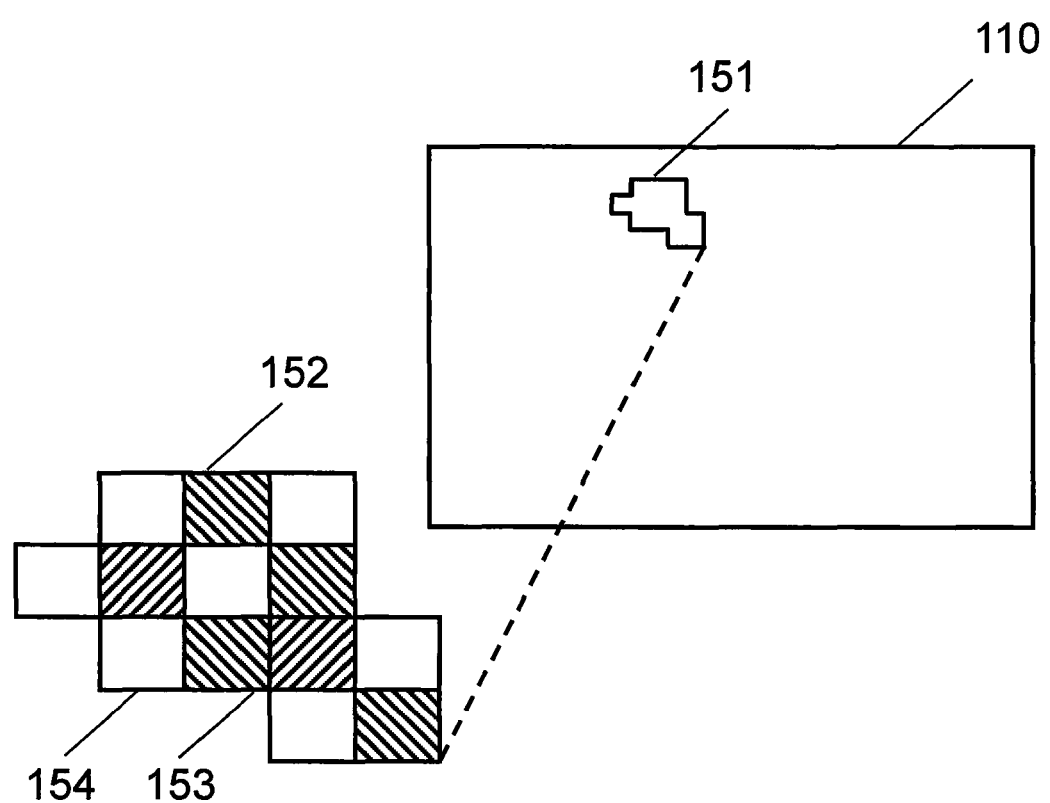
FIG. 18 is a schematic illustrate of an imaging grating in one embodiment of the invention in which the imaging grating comprises an array of interspersed grating elements having at least two different prescriptions.

In one embodiment of the invention shown in the schematic view of FIG. 18 the imaging grating comprises a single layer two dimensional SBG array. A group of elements labelled 152 which comprises interspersed elements such as 153,154. The group forms the image region 151 at the detector 110. Each SBG element is characterised by one from a set of at least two different prescriptions. FIG. 18 does not show the details of the waveguide and the illumination and input/output gratings. At least one of the SBG prescriptions corresponds to a lens for forming an image of the eye on the detector. At least one prescription is optimised for imaging a signature formed by a surface of the eye.

Hence the embodiment of FIG. 18 allows eye tracking to be performed using speckle patterns and conventional features such as Purkinje reflections.

Figure 19:
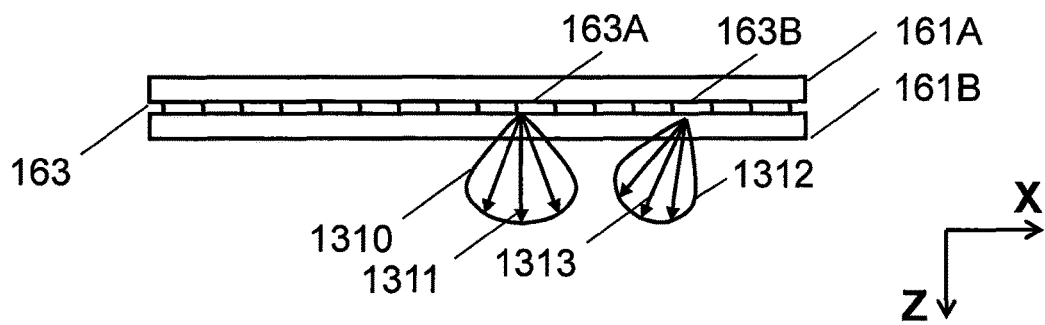
FIG. 19 is a schematic cross section view of the illumination grating of an eye tracker using separate illumination and imaging gratings in one embodiment of the invention.
Figure 20:
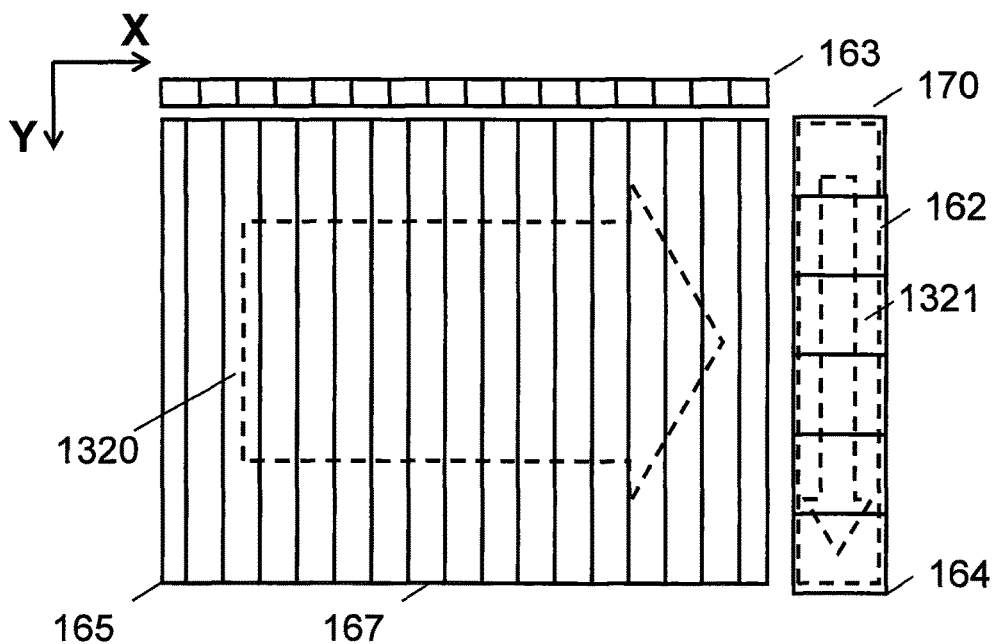
FIG. 20 is a schematic plan view the illumination grating of an eye tracker using separate illumination and imaging gratings in one embodiment of the invention.
Figure 21:
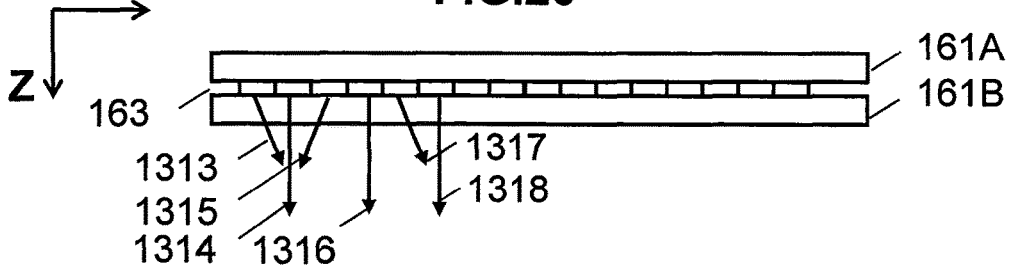
FIG. 21 is a schematic cross section view of an alternative illumination grating of an eye tracker using separate illumination and imaging gratings in one embodiment of the invention.
Figure 22:
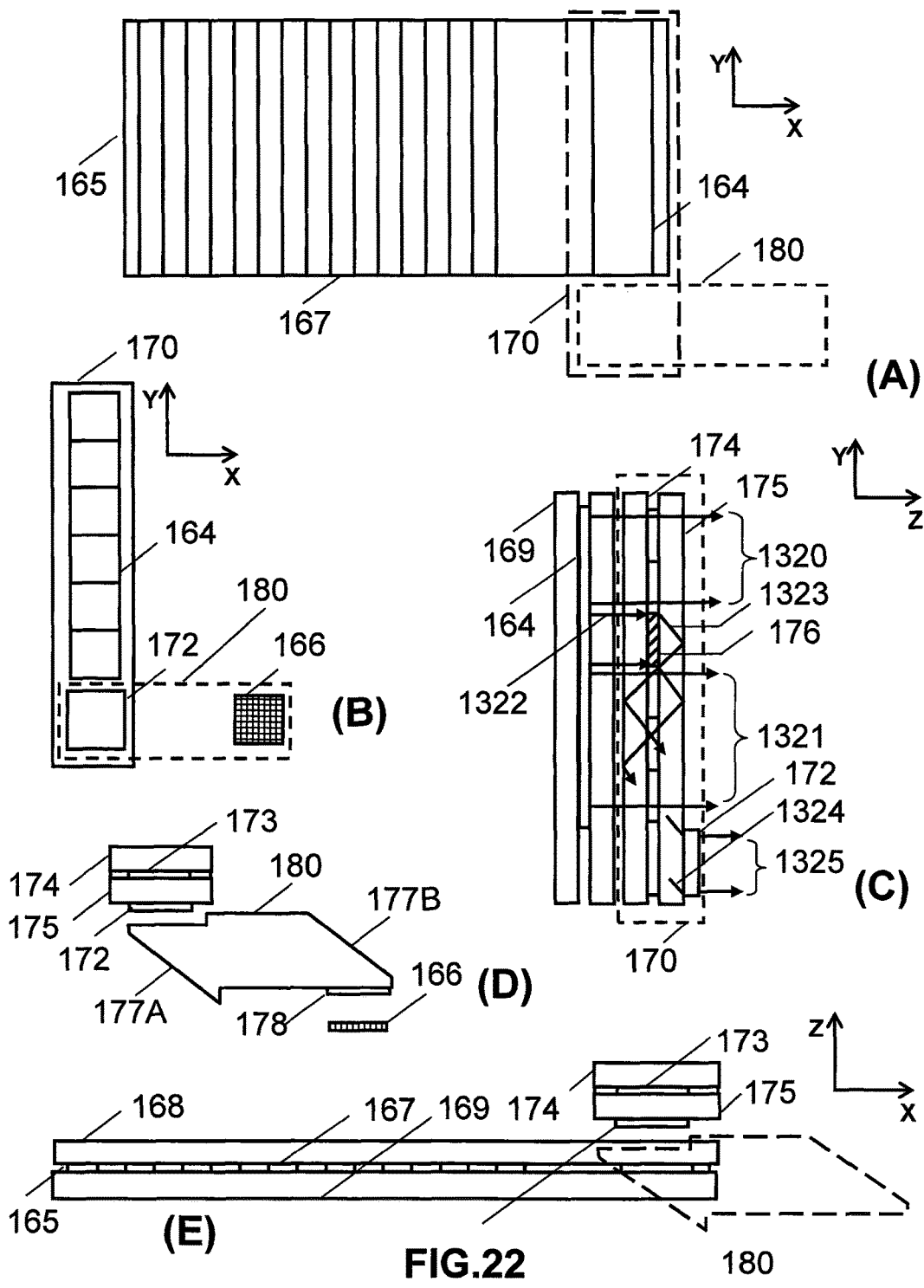
FIG. 22A is a schematic plan view of the imaging grating, the image sampling grating and the detector module of an eye tracker using separate illumination and imaging gratings in one embodiment of the invention.
FIG. 22B is a schematic plan view of image sampling grating and the detector module of an eye tracker using separate illumination and imaging gratings in one embodiment of the invention.
FIG. 22C is a schematic cross section view of the imaging grating and the image sampling grating of an eye tracker using separate illumination and imaging gratings in one embodiment of the invention.
FIG. 22D is a schematic cross section view of image sampling grating and the detector module of an eye tracker using separate illumination and imaging gratings in one embodiment of the invention.
FIG. 22E is a schematic cross section view of the imaging grating, the image sampling grating and the detector module of an eye tracker using separate illumination and imaging gratings in one embodiment of the invention.
Figure 23:
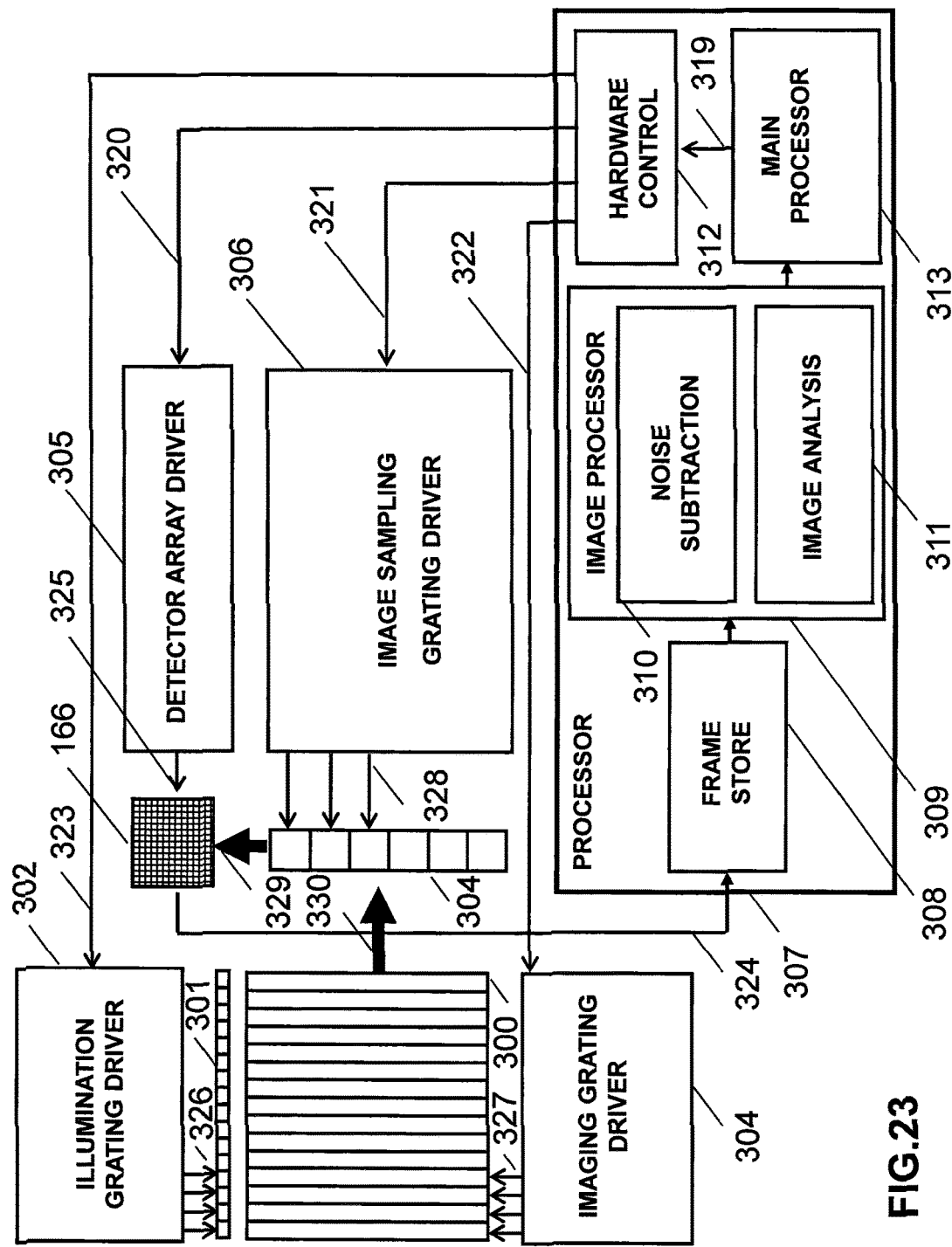
FIG. 23 is a block diagram showing the principal modules of an eye tracker system using separate illumination and imaging gratings in one embodiment of the invention.
Figure 24:
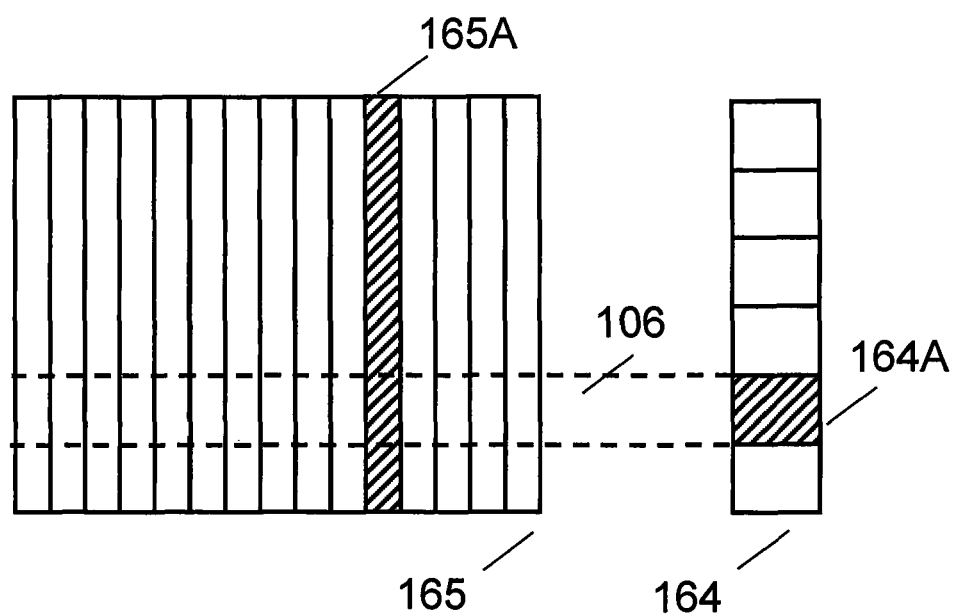
FIG. 24 is a schematic illustration of a grating element switching scheme provided by the imaging grating and image sampling grating in one embodiment of the invention.

FIGS. 19-24 provide schematic illustrations of aspects of an eye tracker based on the principles of FIGS. 1-6. In this embodiment of the invention the earlier described imaging, illumination, input and output gratings are augmented by an additional grating to be referred to as an image sampling grating which overlays the output grating. FIG. 19 shows a side elevation view of the illumination grating 163. FIG. 20 is a plan view showing the imaging grating 165, the illumination grating 163 and the image sampling grating 170 overlaid on the output grating 164. FIG. 21 is a side elevation view of an alternative embodiment of the illumination grating 163. FIG. 22A is a plan view of the imaging grating, the image sampling grating 14 and the detector module 180. FIG. 22B is a plan view of the image sampling grating and the detector module. FIG. 22C is a cross sectional view showing the imaging grating and the image sampling grating. FIG. 22D is a cross sectional view of the image sampling grating and the detector module. Finally, FIG. 22E is a cross sectional view of the imaging grating, the image sampling grating and the detector module. To assist the reader the projection plane of each illustration is referred to a Cartesian XYZ reference frame. The imaging grating 165 comprises an array of column-shaped SBG elements, such as the one labelled 167, sandwiched by substrates 168,169. Column elements of the imaging grating 165 are switched on and off in scrolling fashion backwards and forward along the direction indicated by the block arrow 1320 in FIG. 20 such that only one SBG column is in its diffractive state at any time. The illuminator array 163 is shown in detail in FIG. 19 comprises substrates 161A,161B sandwiching an array of SBG rectangular elements such as 163A,163B. The SBG elements may have identical diffracting characteristics or, as shown in FIG. 19, may have characteristics that vary with position along the array. For example, the element 163A provides a diffusion distribution 1310 centred on a vector at ninety degrees to the array containing rays such as 1311. However, the element 63B provides an angled distribution 1312 containing rays such as 1313. In an alternative embodiment shown in FIG. 21 the diffusion polar distributions may have central ray directions that varying in a cyclic fashion across the array as indicated by the rays 1313-1318. The image sampling grating 170, comprising an array of rectangular SBG beam deflecting elements 173 such as 176 (shown in its diffracting state in FIG. 22C) sandwiched by substrates 174,175. The waveguide containing the imaging grating 165, illumination grating 163 and the output grating 164 is separated from the image sampling grating 170 by a medium (not illustrated) which may be air or a low refractive index transparent material such as a nanoporous material. Infrared light from a surface of the eye is coupled into the waveguide by an active imaging grating element, that is, by a diffracting SBG column. The guided beam undergoes TIR in the waveguide up to the output grating. As shown in FIG. 22C the output grating 164 deflects the beam through ninety degrees into the direction 1322 towards the image sampling grating 170. As shown in FIG. 22C a portion of the beam 1322 is deflected into the image sampling grating by an active SBG element 176 where it undergoes TIR in the direction indicated by the ray 1323 (and also by block arrow 1321 in FIG. 20). The light that is not sampled by the image sampling grating indicated by 1320 1321 is trapped by a suitable absorbing material, which is not illustrated. The TIR beam is deflected in the detector module 180 by a first holographic lens 172 to provide out image light 1325. Turning now to FIG. 22D we see that the detector module contains mirror surfaces 177A,177B and a further holographic lens 178 which forms an image of the eye features or speckle pattern that is being tracked on the detector array 166. Note the holographic lens 172,178 may be replaced by equivalent diffractive elements based on Bragg or surfaces relief gratings. Conventional refractive lens elements may also be used where size constraints permit. FIG. 23 is a system block diagram of the eye tracker of FIGS. 19-22. The system modules comprise the imaging grating 300, illumination grating 301, illumination grating driver 302, illumination sampling grating 303, imaging grating driver 304, detector driver 30, image-sampling array driver 306, detector 166 and processor 307. The apparatus also comprises a laser driver which is not illustrated. The optical links from the image grating to the image sampling array and the image sampling array to the detector are indicated by the block arrows 329,330. The processor 307 comprises a frame store 308 or other image memory device for the storage of captured eye image or speckle pattern frames and an image processor 309 further comprising hardware or software modules for noise subtraction 310 and image analysis 311. The processor further comprises hardware control module 312 for controlling the illumination, imaging and image sampling grating drivers, all said modules operating under the control of a main processor 313. Data and control links between components of the system are indicated by 319-325. In particular, each driver module contains switching circuitry schematically indicated by 326-328 for switching the SBG elements in the imaging grating, illumination grating array, and image sampling grating. FIG. 24 illustrates the switching scheme used in the imaging grating and image sampling grating. The illumination grating elements are switched in phase with the imaging grating columns. Column element 165A of the imaging grating array 165 and element 170A of the readout array 170 are in their diffracting states. The projection (indicated by 170B) of element 170A on the column 65A defines an active detection aperture. Using such as scheme it is possible to track features of the eye using a X,Y localisation algorithm aided by predictions obtained from analysis of displacement vectors determined from successive frames. Methods for implementing such search schemes will be known to those skilled in the art. The invention does not rely on any particular algorithm or processing platform.

Figure 25:
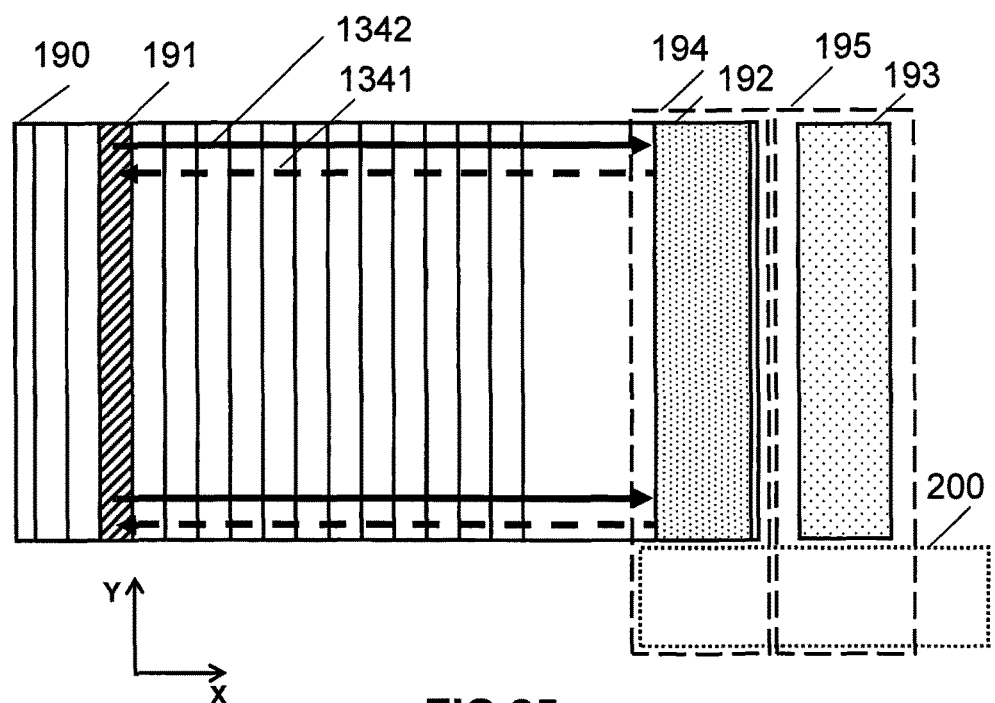
FIG. 25 is a schematic plan view of an eye tracker using common illumination and imaging gratings in one embodiment of the invention.
Figure 26:
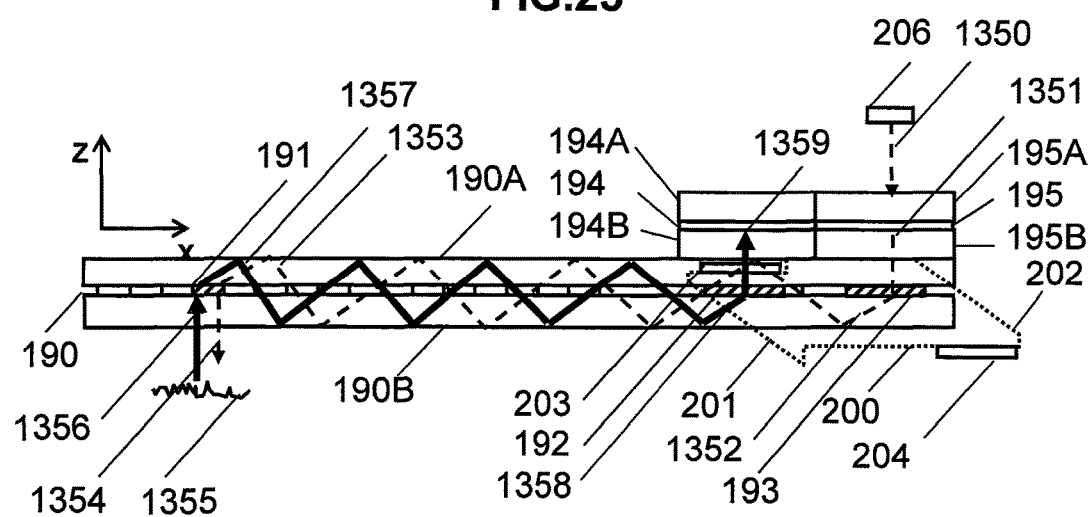
FIG. 26 is a schematic cross section view showing the imaging and illumination grating and the input, output, image sampling and detector sampling gratings of an eye tracker using common illumination and imaging gratings in one embodiment of the invention.
Figure 27:
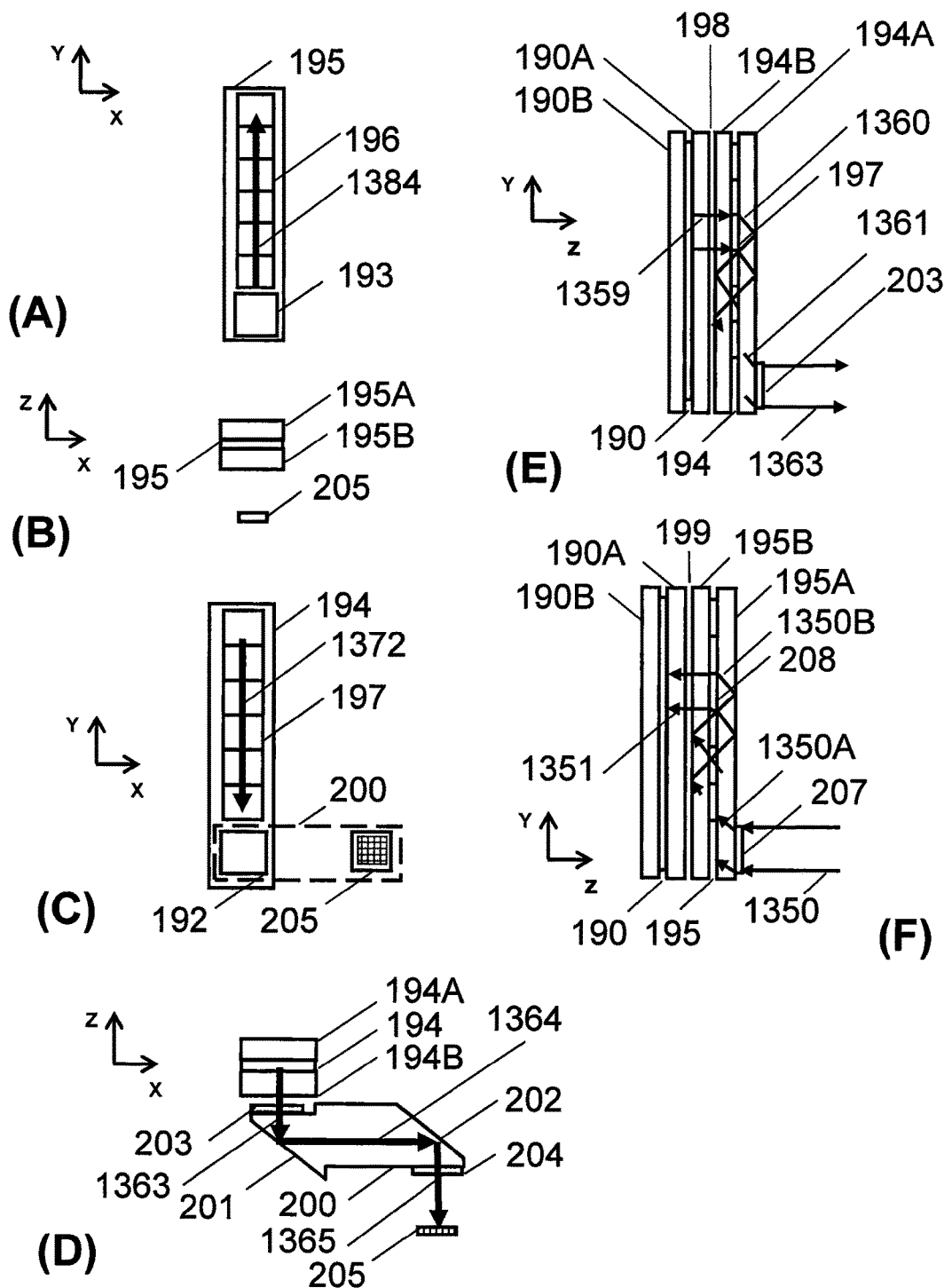
FIG. 27A is a schematic plan view of the image sampling grating of an eye tracker using common illumination and imaging gratings in one embodiment of the invention.
FIG. 27B is a schematic cross section view of the illumination sampling grating, the input grating and laser of an eye tracker using common illumination and imaging gratings in one embodiment.
FIG. 27C is a schematic plan view image sampling grating and the detector module with detector overlaid of an eye tracker using common illumination and imaging gratings in one embodiment.
FIG. 27D is a schematic plan side elevation view showing the image sampling grating and detector of an eye tracker using common illumination and imaging gratings in one embodiment.
FIG. 27E is a schematic cross section view of the output grating and the image sampling grating an eye tracker using common illumination and imaging gratings in one embodiment.
FIG. 27F is a schematic cross section view of the input grating and the illumination sampling of an eye tracker using common illumination and imaging gratings in one embodiment.

FIGS. 25-27 provide schematic illustrations of aspects of an eye tracker that extends the embodiment of FIGS. 19-24 by introducing a further grating component to be referred to as an illumination sampling grating which overlays the input grating. The other feature of this embodiment is that the illumination grating is no longer separate from the imaging gratings. Instead the two are combined in a bi-directional waveguide in which a common switchable column grating is used to illuminate and image the eye with the illumination and image wave-guided light propagating in opposing directions. The combined gratings will be referred to as the illumination and imaging grating. As will be explained below the function of the illumination sampling grating, which is similar in structure to the image sampling grating, is to concentrate the available illumination into region of the eye selected by the image sampling grating. This confers the dual benefits of light efficiency and avoidance of stray light from regions of the eye that are not being tracked. Turning now to the drawings, FIG. 25 is a plan view showing the imaging and illumination grating 190, the image sampling grating 194, illumination sampling grating 195 the input grating 193 and output grating 192 and the detector module 200. Column elements of the illumination and imaging grating are switched on and off in scrolling fashion backwards and forward such that only one SBG column is in its diffractive state at any time. The counter propagating beam paths are indicated by 1341,1342. FIG. 26 shows the components of FIG. 25 in a side elevation view. FIG. 27A is a plan view of the illumination sampling grating. FIG. 27B is a cross sectional view of the illumination sampling grating 195 including the input grating 193 and the laser 205. FIG. 27C is a plan view of the image sampling grating 194 showing the detector module 200 and detector 205 overlaid.

FIG. 27D is a side elevation view showing detector module 200 in more detail. The detector 205 and a cross section of the image sampling grating 194 are included. FIG. 27E is a cross sectional view of the output grating 192 and the image sampling grating 194. FIG. 27F is a cross section view of the input grating 193 and the illumination sampling grating 194. To assist the reader the projection plane of each illustration is referred to a Cartesian XYZ reference frame. The illumination and imaging grating comprises the array 190 of column-shaped SBG elements, such as the one labelled 191 sandwiched by the transparent substrates 190A, 190B. The input and output grating which are disposed in the same layer are labelled by 193,192 respectively. The detector module 200 is delineated by a dotted line in FIGS. 25-26 and in more detail in FIG. 27D. The image sampling grating 194, comprises an array of rectangular SBG beam deflecting elements (such as 197) sandwiched by substrates 194A, 194B. Typically the imaging grating and image sampling grating are separated by a medium 198 which may be air or a low refractive index transparent material such as a nanoporous material. The illumination sampling grating 195 which is has a very similar architecture to the image sampling grating comprises an array of rectangular SBG beam deflecting elements (such as 196) sandwiched by substrates 195A,195B. Typically the imaging grating and image sampling grating are separated by a medium 199 which may be air or a low refractive index transparent material such as a nanoporous material.

Referring to FIG. 26 and FIG. 27F illumination light 1350 from the laser is directed into the illumination sampling grating by a coupling grating 207. The light then proceeds along a TIR path as indicated by 1350A, 1350B up to an active element 208 where it is diffracted into the direction 1351 towards the input grating. Not that the image sampling grating directs all of the illumination light through the active element of the illumination sampling grating the elements of which are switched in synchronism with the elements of the image sampling grating to ensure that at any time the only the region of the that is being imaged receives illumination. The illumination path in the waveguide is indicated by 1352-1354. Infrared light 1356 (also illustrated as the signature 1355) from one or more surfaces of the eye is coupled into the waveguide by a diffracting SBG column such as 191. The guided beam indicated by 1357,1358 undergoes TIR in the waveguide up to the output grating 192. The output grating deflects the beam through ninety degree into the direction 1359 towards the image sampling grating. As shown in FIG. 27E the beam in direction 1359 is deflected into the image sampling grating by an active SBG element 197 where it undergoes TIR along the ray path indicated by 1360, 1361. The TIR beam is deflected into the detector module 200 as light 1363 by a first holographic lens 203. Any light that is not sampled by the image sampling grating is trapped by a suitable absorbing material, which is not illustrated. The absorbing material may be a prism, prism array, an infrared absorbing coating or some other means known to those skilled in the art.

The detector module contains mirror surfaces 201,202 and a further holographic lens 204 which forms an image of the eye signature that is being tracked on the detector array 205. The ray path from the image sampling grating to the detector is indicated by the rays 1363-1365. Advantageously, the mirror surfaces are coatings applied to opposing faces of a prismatic element. However, the invention does not rely on any particular scheme for steering the image light towards the detector array. Note that the holographic lens 203,204 may be replaced by equivalent diffractive elements based on Bragg or surfaces relief gratings. Conventional refractive lens elements may also be used where size constraints permit.

Figure 28:
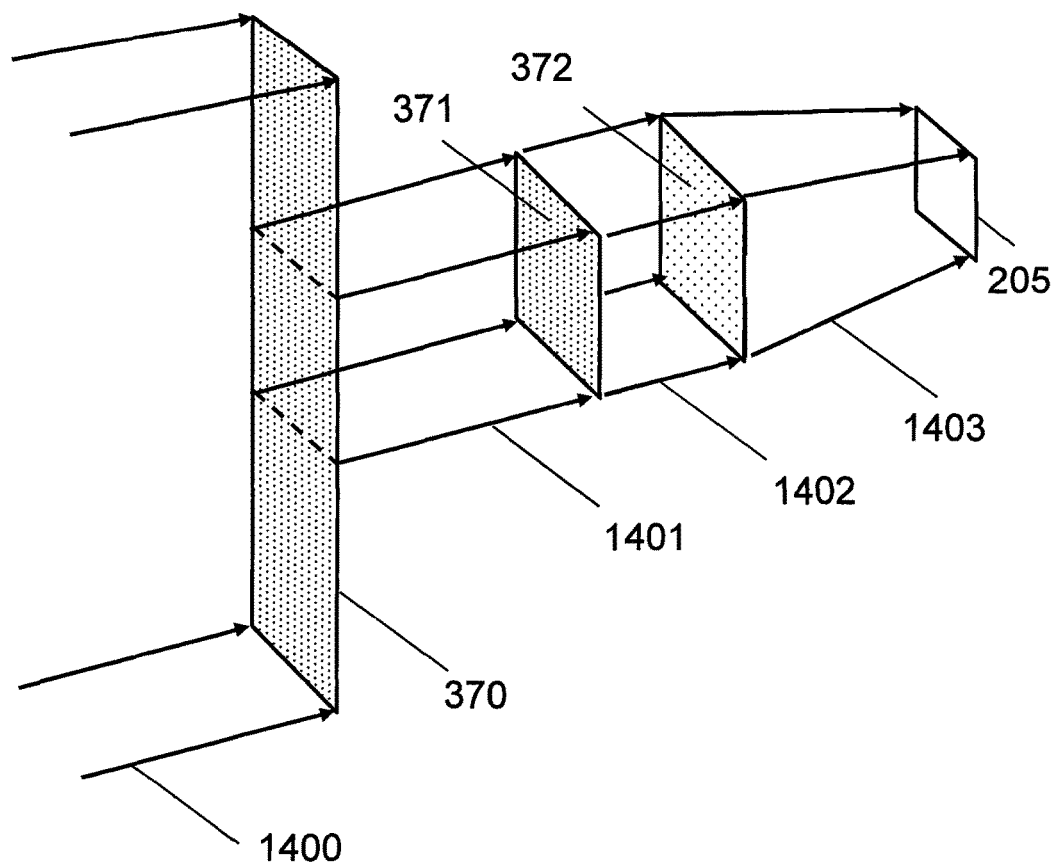
FIG. 28 is a simplified representation of the imaging process an eye tracker using common illumination and imaging gratings in one embodiment of the invention.

In one embodiment of the invention illumination light from laser module is converted into S-polarized light which is coupled into the eye tracker waveguide by the input grating. This light is then converted into circularly polarized light using a quarter wave plate. An active SBG column will then diffract the P-component of the circularly polarized wave guided light towards the eye, the remaining P-polarized light being collected in a light trap. The P-polarized light reflected back from the eye (which will be substantially P-polarized) is then diffracted into a return TIR path by the active SBG column and proceeds to the detector module as described above. This scheme ensures that image and illumination light is not inadvertently coupled into the input and output gratings respectively. In other embodiments of the invention the unwanted coupling of the image and illumination light may be overcome by optimizing the TIR angles, the angular bandwidths of the imaging and illumination gratings, the spacings along the waveguide of the input and output gratings, and the illumination and imaging beam cross sections. In one embodiment the illumination light which will typically in most embodiments of the invention be collimated may be angled such that the waveguide propagation angle of the illumination beam differs from the waveguide angles of the image light. FIG. 28 is a simplified representation of the detection path starting with the collimated rays 1400 from an active column element 370 of the imaging array. The rays 1400 are sampled by an element 371 of the detector grating to provide the rays 1402 which are imaged by the holographic lens 372 to provide the rays 1403 incident on the detector 205.

An important feature of the above embodiment is that elements of the illumination sampling grating are switched to allow illumination to be localized to a small region within the active column of the DigiLens ensuring that the illumination is concentrated exactly where it is needed. This also avoids stray light reflections a problem which can consume significant image processing resources in conventional eye tracker designs. Since the illumination is scrolled the cornea and retina are not exposed to continuous IR exposure allowing higher exposures levels to be used leading to higher SNR. A safety interlock which is not illustrated may be included to switch off the laser when no tracking activity has been detected for a predefined time. The proposed scheme for switching the columns and readout elements in the embodiments of FIGS. 25-27 is based on tracking the movement of the pupil using a X,Y localisation algorithm similar to the one illustrated in FIG. 24 which shows the how the ith activated column of DigiLens and jth activated element of the readout array are used to select the speckle pattern region (X,Y).

Figure 29:
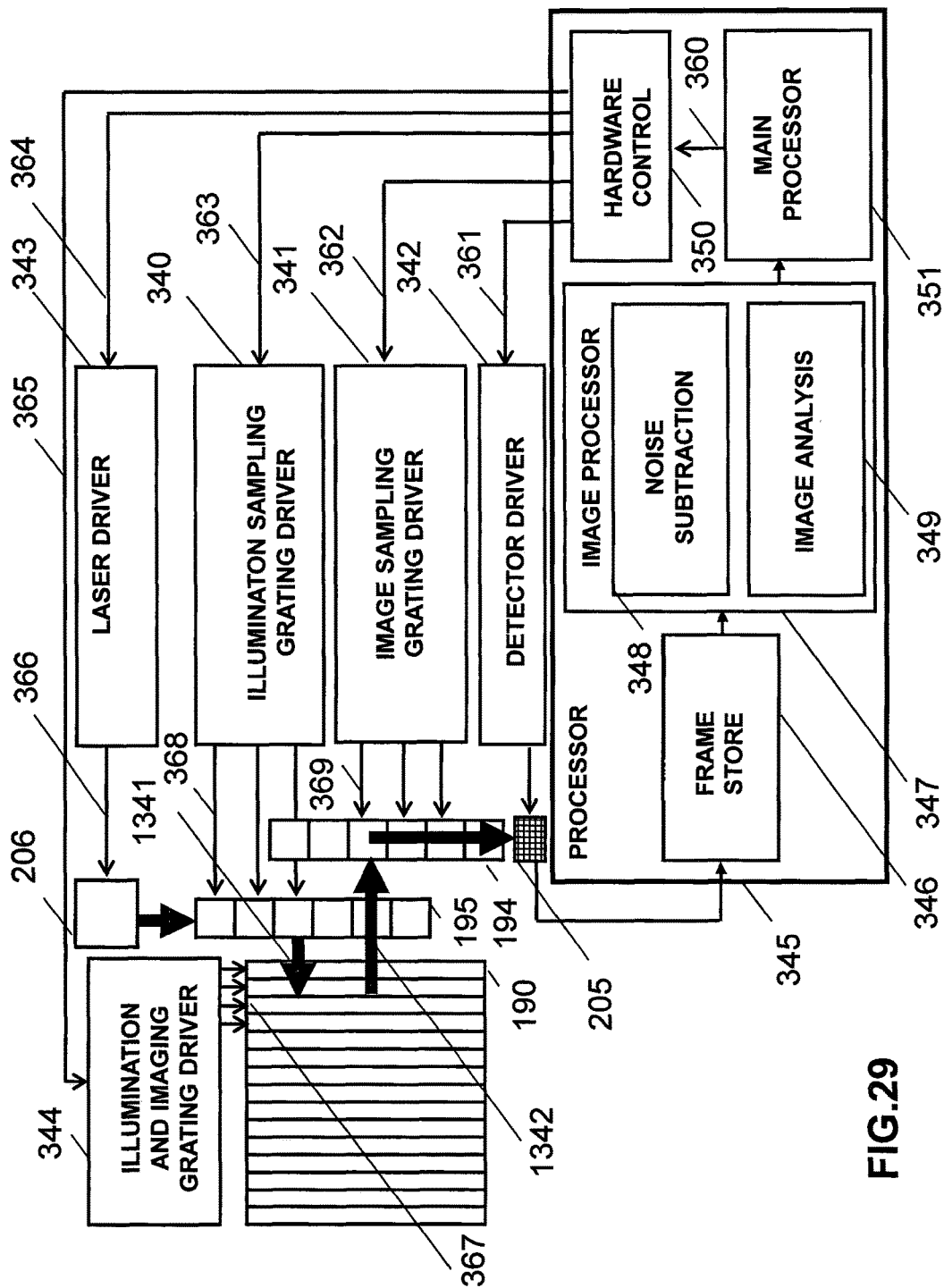
FIG. 29 provides a system block diagram showing the key modules of an eye tracker using common illumination and imaging gratings in one embodiment of the invention.

FIG. 29 is a system block diagram of the eye tracker of FIGS. 26-27. The system modules comprise the illumination and imaging grating 190, image sampling grating 194, illumination sampling grating 195, detector 205, laser 206, illumination sampling array driver 340, image sampling array driver 341, detector driver 342, laser driver 343, illumination and imaging grating driver 344 and processor 345. The processor 345 comprises a frame store or other image storage media 346 for the storage of captured eye image or speckle pattern frames and an image processor 347 further comprising hardware or software modules for noise subtraction 348 and image analysis 349. The processor further comprises hardware control module 350 for controlling the illumination, imaging and image sampling grating drivers, all said modules operating under the control of a main processor 351. The above described modules are connected by communication and control links schematically indicated by 360-369 include control lines for switching the SBG elements in the imaging grating, illumination sampling grating array, and image sampling grating 367-369.

In one embodiment of the invention the detector array is a detector array of resolution 16×16 with a framing rate of 2300 fps of the type commonly used in infrared mouse equipment. In alternative embodies similar sensor technology of resolution 64×64 operating at 670 fps may be used. The selection of a particular sensor will depend on factors such as the required tracking resolution and accuracy and the update rate of the eye tracker. Exemplary sensors are manufactured by Pixart Inc. The detector optical prescription will be determined by a detailed ray-tracing analysis and will require trade-offs of speckle size, F-number and DigiLens column width. In the case of speckle tracking the detector lens aperture defines the limiting speckle size. The detector field of view is determined by the detector size and the detector lens focal length. However, the invention could be applied with any currently available imaging sensor technology. In one embodiment the DigiLens provides 25 SBG scrolling columns×17 SBG readout elements. The Agilent device can be programmed to switch 2300 fps So a complete scan of the FOV will take (25×17)/2300 s.=185 ms. However, in practice the eye tracker will use a more sophisticated X-Y search process that localises the pupil using column and readout element coordinates. It is anticipated that on average around 10 search steps may be needed to converge on the pupil position resulting in a latency of 4.3 ms. On this basis the latency of the tracker is potentially ×100 lower than that of comparable image processing-based Purkinje-type eye trackers. It is also anticipated that the correlation process will be implemented in hardware resulting in a relatively modest data processing latency. The detected eye signature is stored and compared with other saved patterns to determine the eye gaze trajectory and to make absolute determinations of the gaze direction (bore sighting). Initial calibration (that is, building up the database of saved patterns) is carried out by directing the user to look at test targets at predefined points in the field of view (FOV) over which the eye gaze is to be tracked. Since the frames are of low resolution large numbers of samples may be collected without significant computational overhead.

Although the invention may be used to detect any type of eye signature, speckle is attractive because it avoids the image analysis problems of identifying and tracking recognisable features of the eye that are encountered in Purkinje imaging schemes. Prerequisites for measuring eye displacement vectors (rotational and/or translational) include achieving an adequate level of speckle contrast (after detector noise and ambient light have been subtracted from the detected signal) and being able to resolve individual speckle grains. A high signal to noise ratio (SNR) is essential for detecting variations in speckle properties at required angular resolution. The SNR depends on the speckle contrast, which is defined as the ratio of the root mean square (rms) variation of the speckle intensity to the mean intensity. The speckle contrast lies between 0-1 assuming Gaussian statistics. The detector should have low noise and a short integration time. If the motion of the eye is appreciably faster than the exposure time of the CCD camera rapid intensity fluctuations of the speckle pattern will occur, the average of the detected patterns resulting in a blurred image with reduced speckle contrast. The smallest speckle size is set by the diffraction limit. Applying the well known formula from diffraction theory: $w=\sim 2.44\ D/a$ (assuming: a detector lens to detector distance $D\sim 70$ mm; IR wavelength $\lambda=785$ nm; and detector lens aperture $a \sim 3$ mm.) we obtain a diffraction limited speckle diameter w at the detector of ~64 microns. The resolution of a typical mouse sensor is around 400-800 counts per inch (cpi), with rates of motion up to 14 inches per second (fps). Hence the limiting speckle size is equivalent to one count per 64 micron at 400 cpi which is roughly compatible with the expected speckle size.

The strategy for processing speckle data captured by the eye tracker is based on a number of assumptions. Firstly, speckle patterns provide unique "fingerprints" of regions of the cornea and retina. Secondly, unlike speckle interferometry which requires that the speckle motion is less than speckle size, speckle imaging using a detector array requires that the speckle displacement from frame to frame is greater than the speckle size. Thirdly, the speckle contrast and speckle size at the detector are compatible with the detector resolution and SNR. In many cases it is reasonable to assume that a displacement of the cornea and retina relative to the detector will result in a shift of the speckle pattern by the same amount and that shifts of the corneal and retinal speckle patterns will be in opposite directions. With regard to computing eye movement it is assumed that the motion of the speckles can be determined from the correlation of two consecutive frame speckle patterns. This information together with the relative motion of the corneal and retinal speckle patterns can be used to determine eye displacement vectors. The correlation and image analysis processes may take advantage standard techniques already developed in applications such as radar, biological imaging etc. The following characteristics of the speckle image may also be used to assist the tracking of the eye use speckle: speckle grain size; speckle brightness (either individual or collective brightness); speckle shape; rate of change of any of the preceding characteristics with ocular movement; and relative directions of corneal and retinal beam displacements. Each of these aspects of the speckle image will be dependent on the illumination beam direction (scanning or static); the detection optics and the focal length of the imaging optics. The rate of change of the corneal versus retinal speckles will depend on the focal length.

Figure 30:
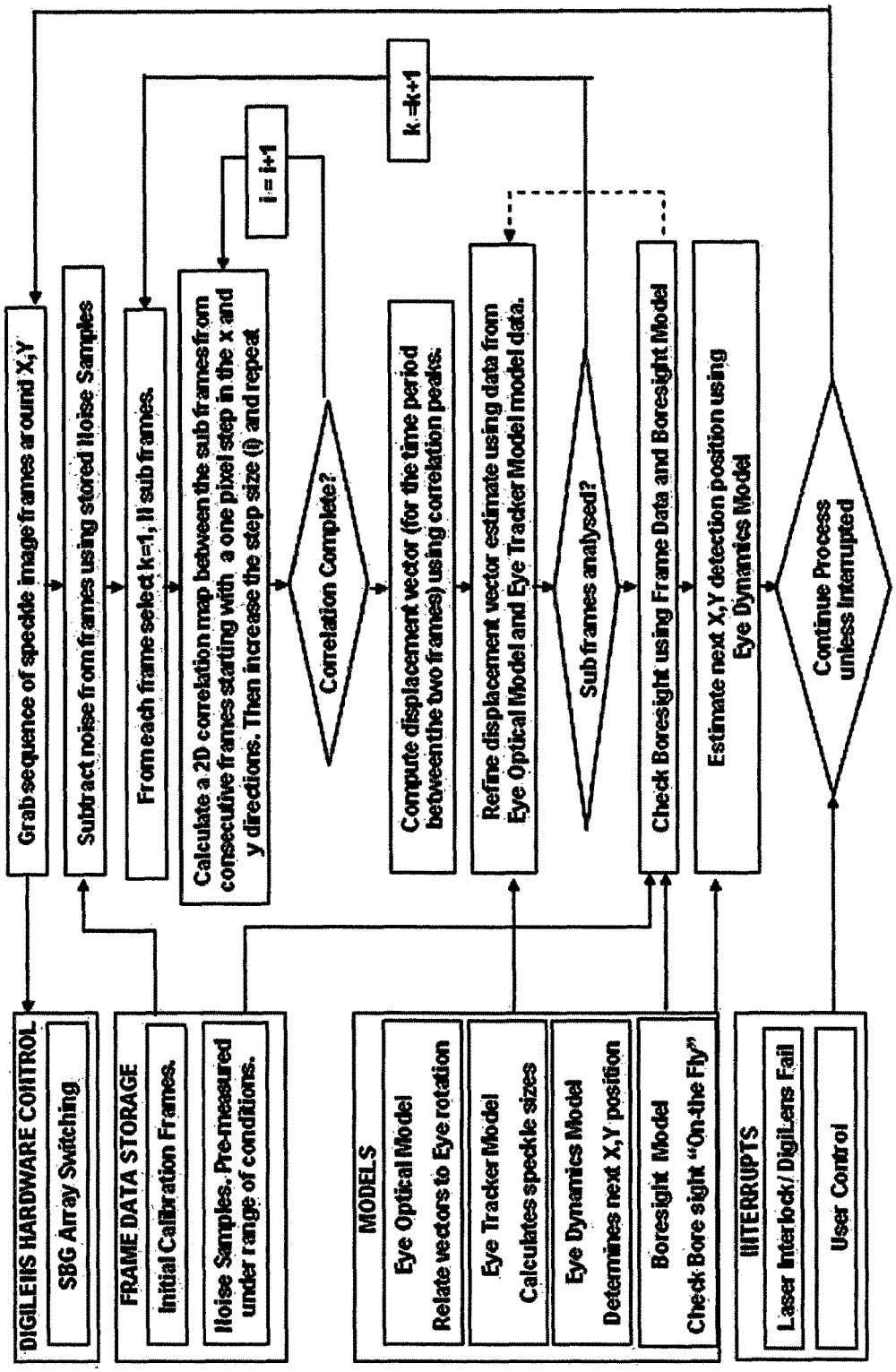
FIG. 30 is a flow chart showing the process for determining eye displacement vectors from the recorded speckle data.

The flow chart in FIG. 30 summarizes the process for determining eye displacement vectors from the recorded speckle data. The process relies on a database of frame data collected during initial calibration and noise characteristics. The calculation of the displacement vectors uses inputs from a suite of mathematical models that simulate the first order eye optics, the eye tracker optics and the eye dynamics. The process may be interrupted by the user or automatically when a switchable grating failure occurs. The process also includes grating hardware control to enable X,Y addressing of switchable grating columns and readout elements. The correlation process for obtaining the eye displacement vector from two detected frames in one embodiment may be summarized as follows. Each frame is subdivided into small sub frames. The sub-frame coordinates may be predefined or alternatively may be determined by an interactive scheme using the output from an Eye Dynamics Model. A 2D correlation map between the sub images from the two frames is calculated starting with a one pixel step in the x and y directions and repeat the calculation increasing the step size by one pixel at a time. Other statistical metrics may also be computed at this stage to assist in refining the calculation. We then repeat the correlation process for another selected frame region. A displacement vector is then computed using (for the time period between the two analysed frames) using the peaks of the correlation maps. Ideally the sub frames should be entirely within the corneal or retinal fields, the two being distinguished by their opposing directions. Data which does not yield clear separation of the two will be rejected) at this stage. The calculation is refined using data from an Eye Optical Model which models of the eye dynamics and an Eye Tracker Model which models the optical system. The verified displacement vector is used to determined the next search X,Y coordinates (ie SBG column, row) for the tracker using predicted gaze trajectory calculated using a Eye Dynamics Model. The basic ray optics used in the Eye Model in particular the relationship of the first order corneal and retinal reflection paths of the eye may be modelled using ray-tracing programs such as ZEMAX. Standard eye models well known to those skilled in the art will be adequate for this purpose. Further models may be used to simulate speckle from the retina and the cornea. The Eye Dynamics Model carries out a statistical analysis of the displacement vectors from previous frames to determine the most optical next X,Y search location (ie the columns and readout elements to be activated.

Initial calibration is carried out by directing the user to look at test targets at predefined points in the FOV. The bore-sighting process is illustrated in FIG. 32 which shows a flowchart (FIG. 32A) and a schematic illustrates of the initial calibration procedure (FIG. 32B). According to FIG. 31A the bore sighting procedure 400 comprises the following steps:

At step 401 present targets to the eye at location j;
At step 402 capture a series of frames at location j;
At step 403 store the capture frames;
At step 404 move to the next target position in the field of view (FOV).
At step 405 repeat the process while j is less than a predefined integer N; otherwise end the process (at step 406).

Figure 31:
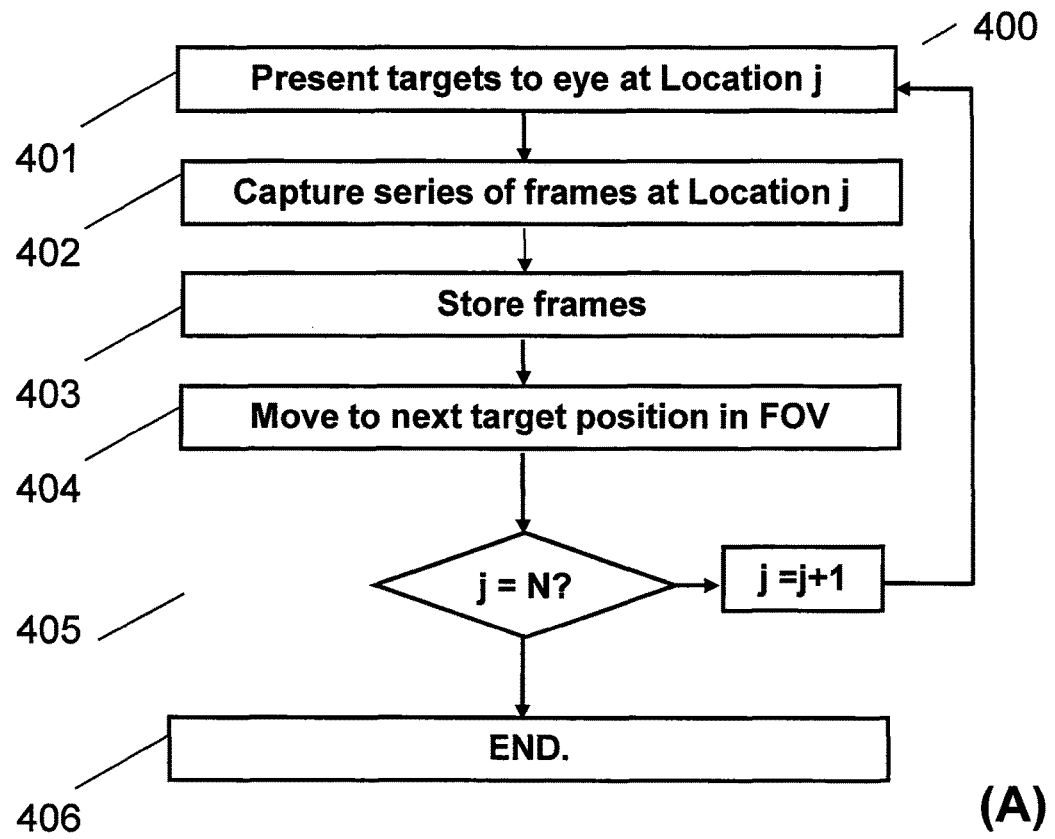
FIG. 31A is a flowchart for a calibration process for an eye tracker using common illumination and imaging gratings in one embodiment of the invention.
FIG. 31B is a schematic illustration of the initial calibration procedure used for an eye tracker in one embodiment of the invention.
Figure 31:
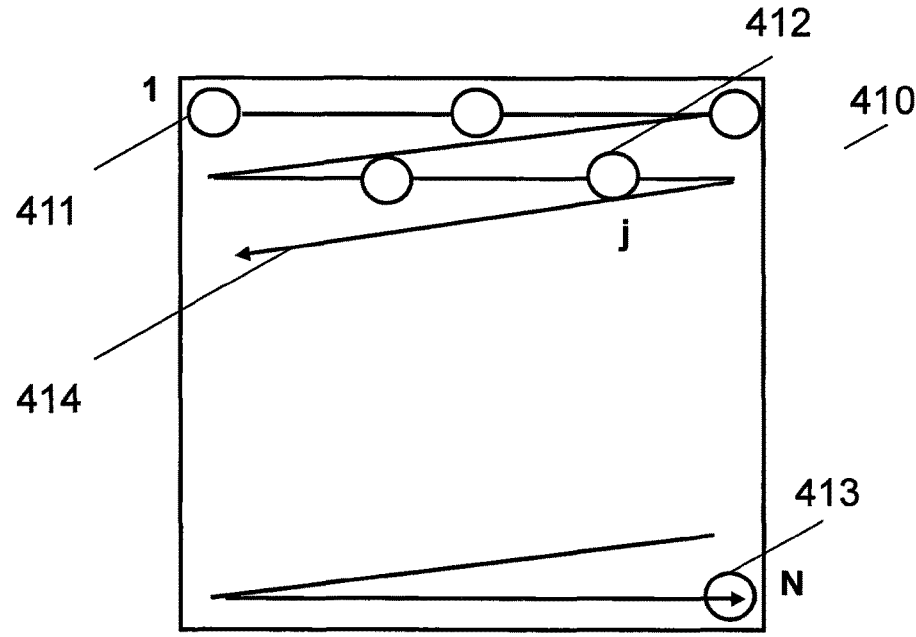
Figure 32:
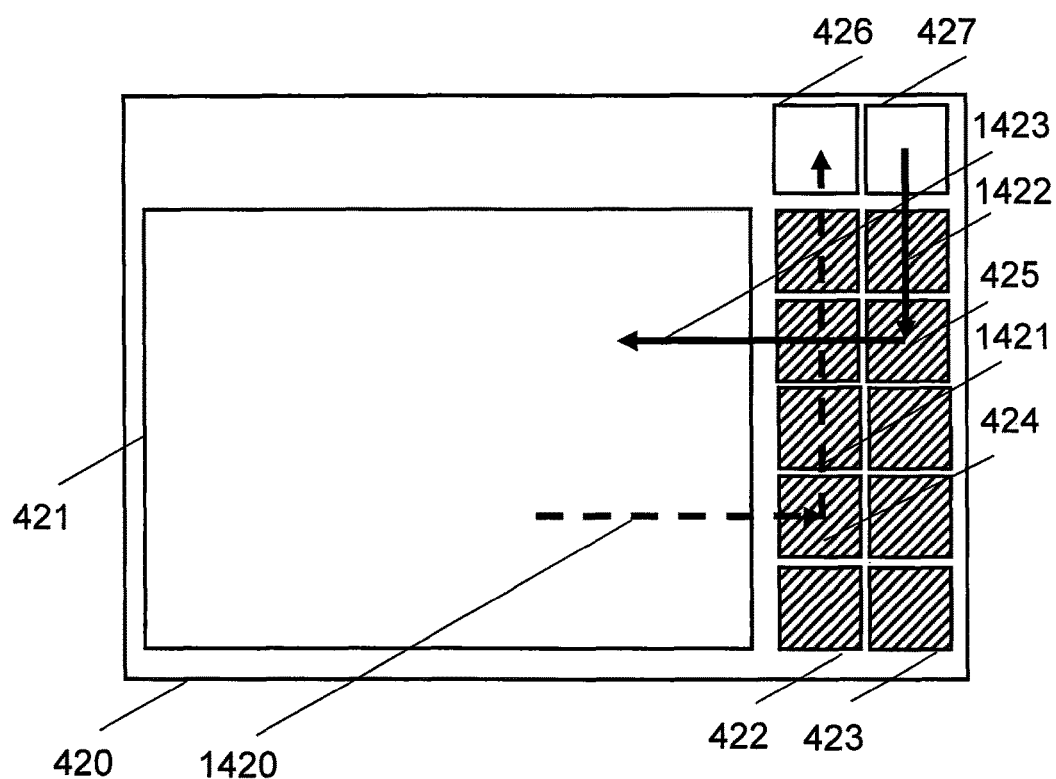
FIG. 32 is a schematic plan view of an eye tracker including an illumination sampling grating and an image sampling grating each based on gratings with grating vectors substantially aligned parallel to the waveguide plane in one embodiment of the invention.

Referring to FIG. 31B we see that initial calibration will be carried by presenting targets (typically lights sources, resolution targets etc) to the viewer at different points $1 \leq j \leq N$ in the field of view 410 (the point also being labelled as 411-413) and capturing and storing frames of signature images at each location. The targets may be presented sequentially along the sweep path labelled by 414. However, other presentation schemes may be used. The stored frames will be processed to enhance SNR and extract statistical metrics (such as histograms, probability density functions for speckle size etc) for subsequent "on-the-fly" frame comparison. Each frame provides a "fingerprint" for the region of the FOV concerned. The signatures will vary in: relative positions of the corneal and retinal reflections, or where speckle patterns are used: speckle contrast; and speckle size distribution (which is linked to optical magnification).

In relation to the embodiment of FIG. 25 we have described the use of an image sampling grating overlaying the output grating. The image sampling grating comprises a linear array of switchable grating elements, each element when in its diffracting state sampling a portion of the light in the waveguide and deflecting it along the image sampling grating towards said detector. In a similar fashion an illumination sampling grating overlays the input grating. The illumination sampling grating is optically coupled to the light source and comprises a linear array of switchable grating elements. Each element when in its diffracting state deflects light from the illumination sampling grating into the waveguide. Turning to FIG. 32 we next consider an embodiment that implements image and illuminations sampling grating using a single grating layer. The eye tracker 420 comprises a waveguide 420 (containing a grating array), image sampling gating 422 illumination sampling grating 423 containing elements such as 424 and 425 respectively. Output and input gratings 426,427 link the sampling gratings to the detector and light sources respectively. As indicated by the shading pattern of the grating elements each element comprising a switchable grating with Bragg fringes slanted at 45 degrees with grating vectors in the plane of the drawing; that is, in a plane parallel to the waveguiding surfaces. The inventors refer to these gratings as turning gratings. Hence illumination ray 1422 undergoing TIR in the waveguide is deflected through an angle of ninety degrees by the active element 425 into the ray direction 1423. Similarly the image ray 1420 is deflected through an angle of ninety degrees in the direction 1421 by the active element 424. It should also be apparent from consideration of the drawing that all of the gratings may be formed in a single layer in a single waveguide (with the appropriate electrode patterning of the sandwiching substrates. It should also be apparent that the turning grating principle may be applied in any of the above described embodiments including those in which the waveguide comprises separated overlapping illumination and imaging gratings. The sampling gratings may overlap. The design of the turning gratings may be based on the teachings of U.S. Pat. No. 8,233,204 entitled OPTICAL DISPLAYS which is incorporated herein by reference in its entirety.

Figure 33:
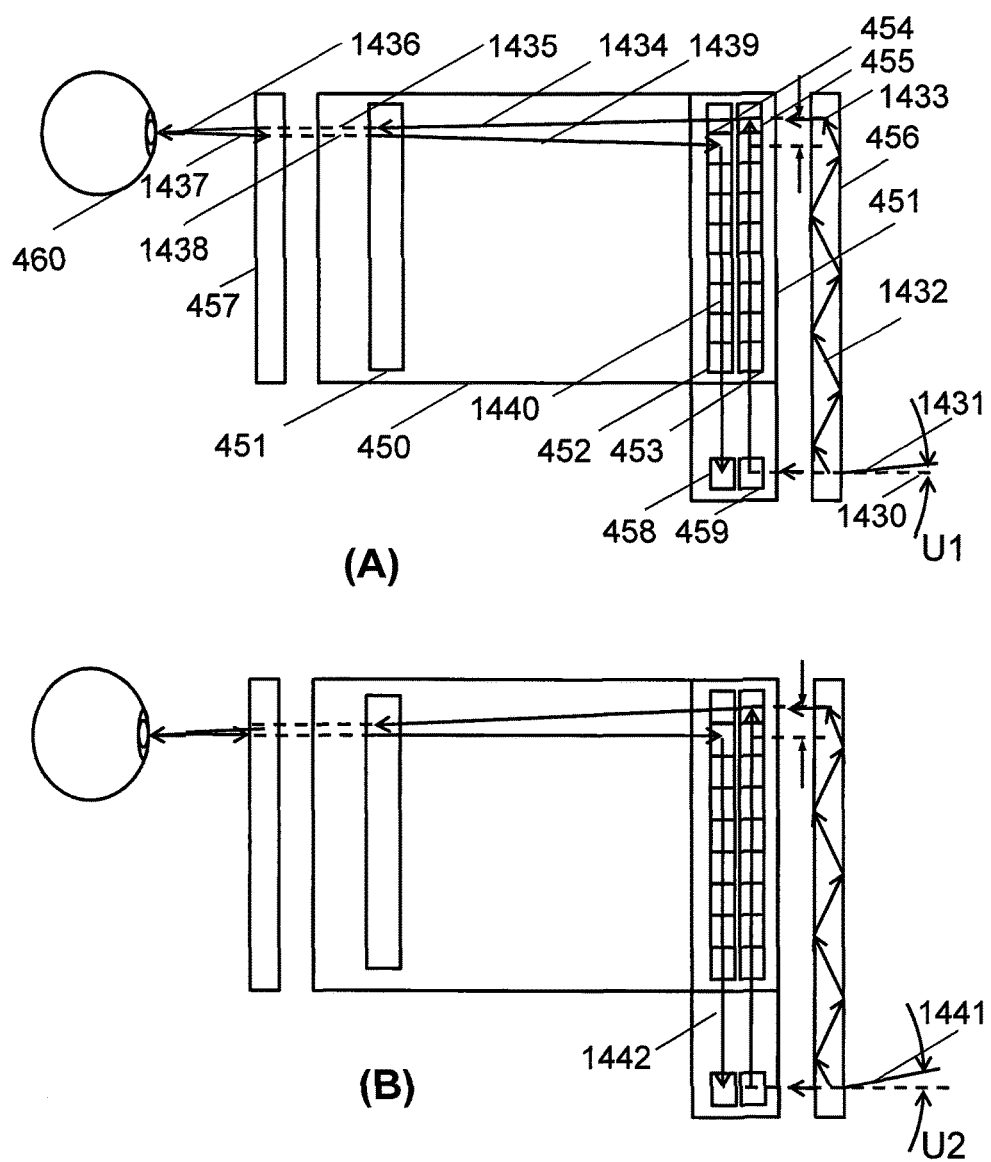
FIG. 33A is a schematic plan view illustrating a first aspect of an eye tracker including an illumination sampling grating and an image sampling grating in which the illumination light is angularly offset from the image light.
FIG. 33B is a schematic plan view illustrating a second aspect of an eye tracker including an illumination sampling grating and an image sampling grating in which the illumination light is angularly offset from the image light.

A challenge in a single layer eye tracker design of the type described above is to provide adequate eye illumination without compromising the ability of the waveguide to collected scattered light from the eye. Most attempts to use gratings for light management in bi-directional waveguides fail because of the fundamental principle of grating reciprocity. In practical terms this means that some of the image light almost always ends up getting coupled into the illumination path to the source by the input grating. In the reciprocal process some of the illumination light is diffracted into the imaging path to the detector by the output grating. The amount of this cross coupling will depend on the beam divergence and waveguide dimensions. The proposed solution which is illustrated in FIG. 33 assumes the common illumination and imaging waveguide architecture discussed above and, in particular, the one illustrated in FIG. 25. The apparatus comprises the waveguide 450 which comprises an array of SBG columns such as 451 and a waveguide component 451 comprising the illumination sampling and imaging sampling gratings 452,453 and containing grating elements (which we may refer to as pixels) such as 454,455. A cross section of the illumination sampling grating is provided by 456. The cross section of the waveguide is also shown and is indicated by 458. Gratings for coupling the image and illumination light to the detector and laser are indicated by 458,459. Finally, an eye is represented by 460. The input and output gratings, which will typically overlap the sampling gratings as discussed earlier, are not illustrated. We next consider the ray paths, first defining a normal to the illumination waveguide as indicated by 1430. The path of an incident beam at an angle U1 up the eye is indicated by the rays 1431-1436 comprising the TIR path 1432, coupling into the waveguide via the active element 455 as indicated by the ray 1433, propagating up to the active column element 451 as indicated by ray 1434, diffraction towards the eye along 1435, and light 1436 striking a surface of the eye. The reflection light path from the eye to the detector is indicated by the rays 1437-1440 with scattered light from the eye indicated by 1437 entering the waveguide as 1438 and propagating along the path 1439 before being diffracted into the image sampling grating via the element 454 and proceeding along the path 1440 leading the detector. FIG. 33B shows the corresponding ray paths 1441,1442 for an incident ray 1441 launched at the angle U2 (greater than U1) which terminates at the detector, the ray paths following the logic of FIG. 33A. In one embodiment of the invention the method illustrated in FIG. 33 eliminates unwanted light coupling by applying a small tilt to the input beam angle by an amount equivalent to at least 1 pixel of the eye tracker imaging matrix, for a specular beam. In other embodiments larger pixel offsets may be useful for better discrimination. A similar tilt is required in the case of diffuse beams. Gratings are currently the preferred option for producing the tilt. However, alternative methods based on prisms may be used. In one embodiment the method illustrated in FIG. 33 is used to provide different grating tilts for the upper and lower halves of the waveguide, thereby preventing over sizing of the lower portion of the waveguide.

Figure 34:
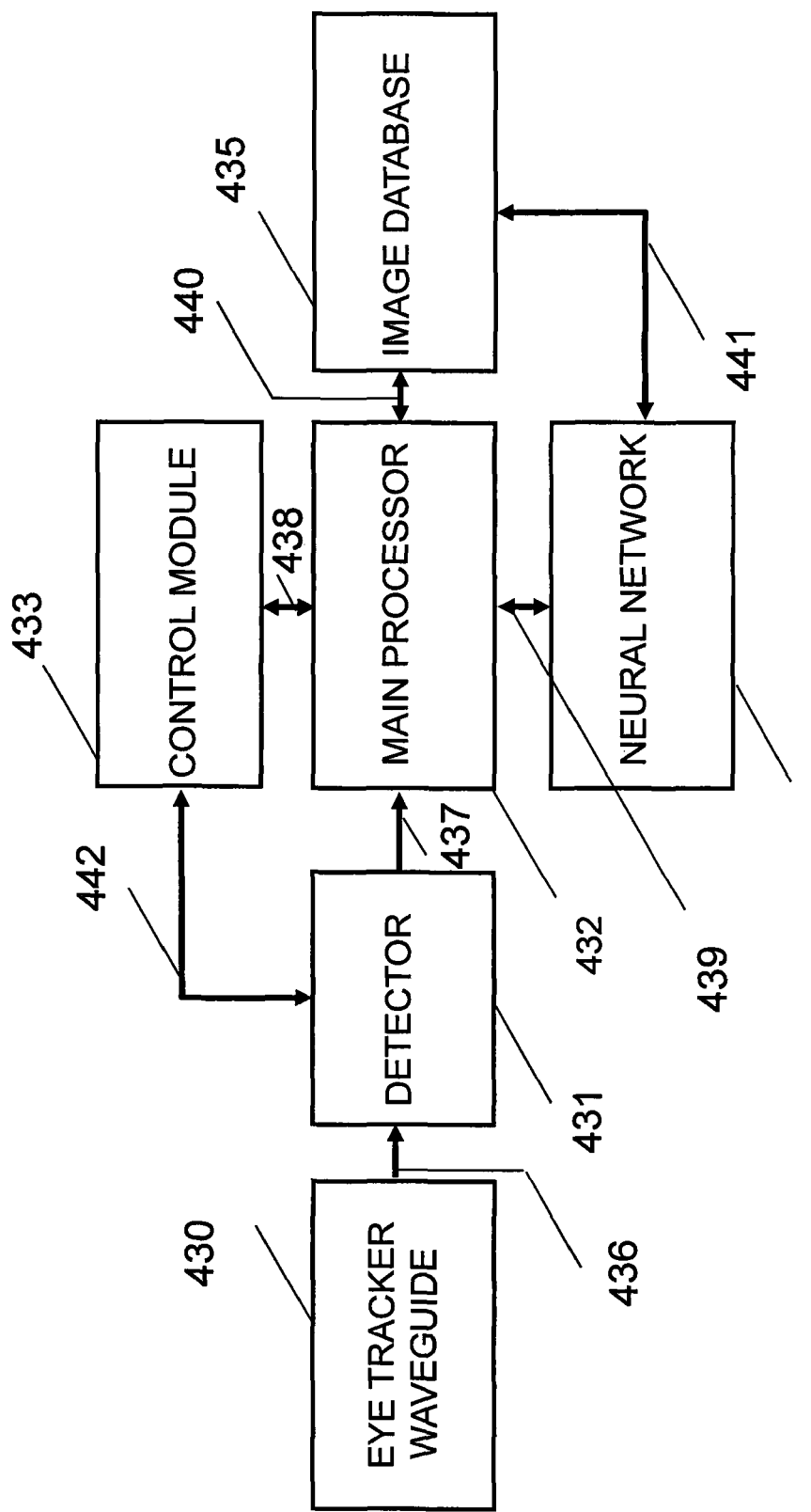
FIG. 34 is a block diagram showing the principal modules of an eye tracker system including a neural network in one embodiment of the invention.
Figure 35:
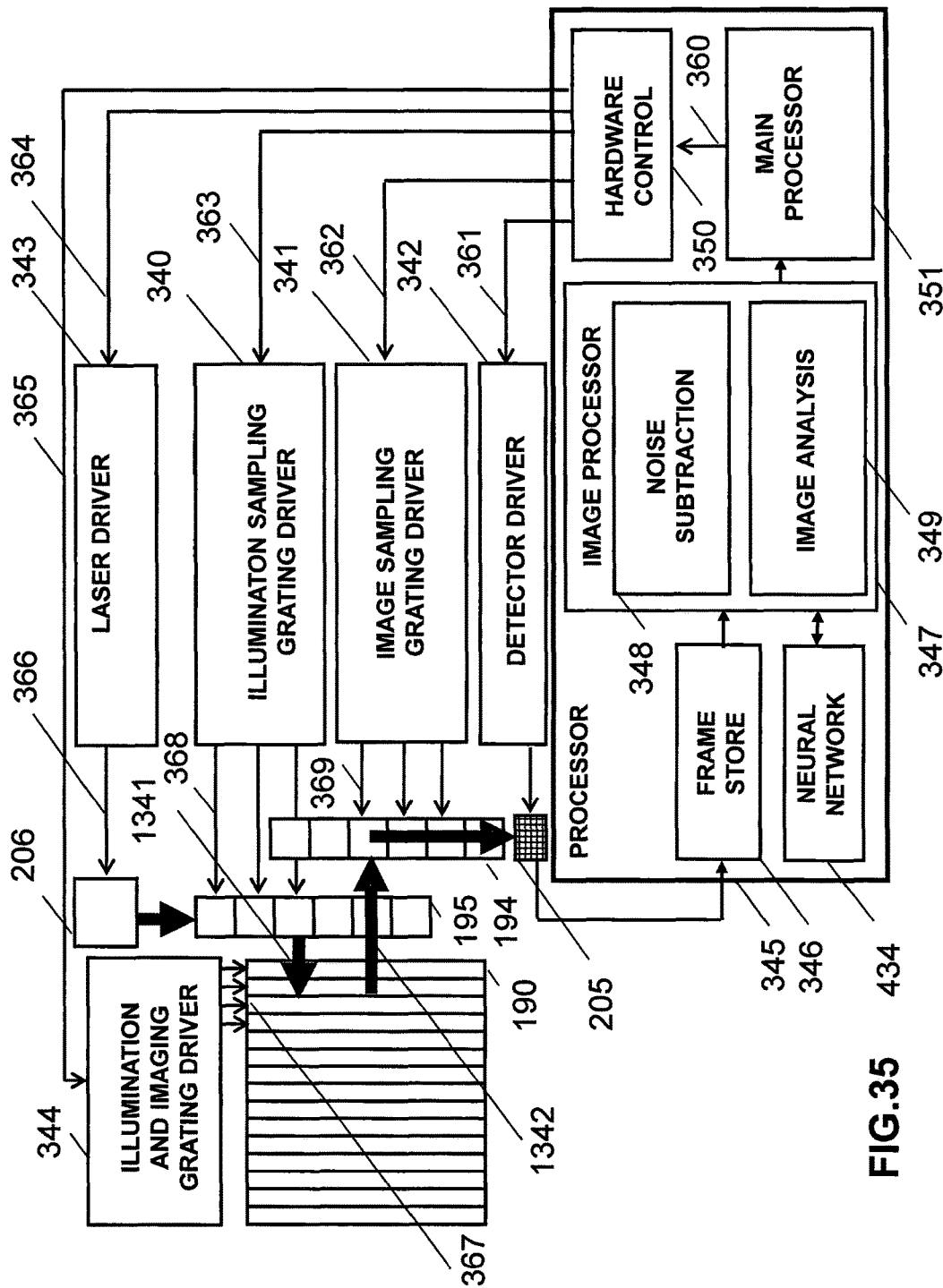
FIG. 35 is a block diagram showing the principal modules of an eye tracker system based common illumination and imaging grating in which the processing system includes a neural network in one embodiment of the invention.

In the description of the eye tracker data processing architecture we have discussed how initial calibration will be carried by presenting targets (typically lights sources, resolution targets etc) to the viewer at different points in the field of view and capturing and storing frames of speckle pattern images at each location. These images are used aid the processing of live data when the eye tracker is normal use. It is proposed that the process could be aided by incorporating an artificial neural network within the processor. The bore sighting process would correspond to training the networks. The network could be used to compensate at least part of any systematic measurements errors occurring in the processing. In one embodiment of the invention shown in the block diagram of FIG. 34 the eye tracker system comprises the eye tracker waveguide 430, detector 431, processor comprising: main processor 432, waveguide SBG control module 433, neural network 434 and image database 435. The system modules are connected by communication and control links referenced by numerals 436-442. A more detailed architecture incorporating a neural network is shown in FIG. 35 This is architecture is intended for use with a common illumination and imaging grating eye tracker designs such as the one of FIG. 25.

As already stated a major application of the invention is VR. VR is synonymous with extremely large FOV, with 100°-110° being seen as the baseline for the next generation of headsets. However, this is only part of the challenge faced by the developer. Meeting the immersion standards of VR poses other challenges that will require significant innovation in display and processing technologies. The current industry view is that the highest priority is overcoming motion sickness. The next two priorities are achieving the level of image detail needed for virtual world rendition and the focus/convergence accuracy needed for simulating visual depth. The VR user expects to simulate real world movements flawlessly. If the interval between the movement and corresponding update of the VR image, referred to as the latency, is too long motion sickness will result. This latency essentially arises from the time lag incurred by the computation of the VR image and the lag incurred by the sensors used for tracking head movement and gaze direction. Motion sickness is not fully understood and can vary significantly from user-to-user with younger subjects often being found to be more tolerant. Although many users seem to acclimatize to motion sickness over time this cannot be assumed in all cases. The problem is being tackled firstly by addressing content design and secondly by removing bottlenecks in the sensor data transfer and image processing pipeline. The root of the latency problem is that current computer-generated imagery (CGI) practice attempts to render a high-resolution image over the whole display. This is tremendously wasteful of power and computing resources and only exacerbates latency. Now, the challenge of reducing the image generation burden is being addressed by the recently rediscovered approach of concentrating image detail into an eye-tracked high-resolution insert merged into a low-resolution background image. This technique is currently referred to as foveated rendering. The rationale is that the human eye sees 135° vertically and 160° horizontally, but senses fine detail only within a 5° central circle called the fovea. By tracking eye gaze and adapting image resolution to eccentricity, we can omit unperceived detail and draw far fewer pixels and triangles. The result looks like a full-resolution image but reduces the number of pixels shaded by a factor of 10-15 with a dramatic impact on the data throughput. To give another example, we can accelerate graphics computation by a factor of 5-6 in a HD (1920× 1080) display. The prerequisite for foveated rendering is a low latency eye tracker. The traditional approach to eye tracking relies on a camera backed up by image processing algorithms for edge and shape finding. This works well in many applications but in VR it immediately poses a new problem: as the eye slews towards the extremities of its field the captured signature rapidly gets more distorted; the image processing problem escalates in proportion. In image processing parlance the signal to noise ratio of the detected signature diminishes. Obscuration by the camera and spurious reflections from the eye only make things worse. This is a major obstacle to VR implementation of foveated rendering, for which a prerequisite is high tracking SNR everywhere in the field. Solutions to this image possessing problem can be partially addressed by more sophisticated algorithms but only at the expense of latency. Hence a conventional camera-based eye tracker is not a viable solution for the foveated rendering of very large fields of view.

Figure 36:
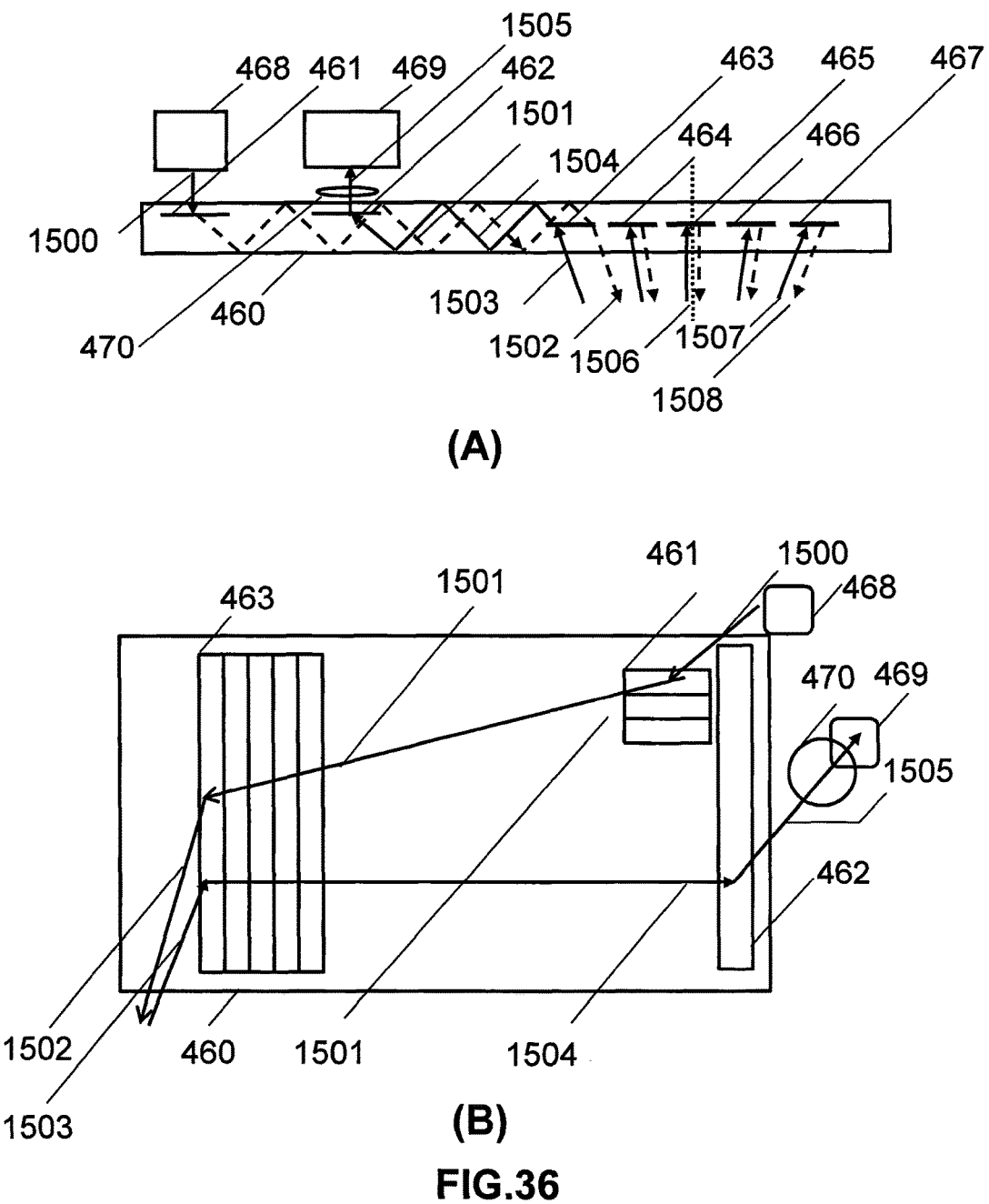
FIG. 36A is a cross section view of a bidirectional waveguide eye tracker in one embodiment.
FIG. 36B is a plan view of a bidirectional waveguide eye tracker in one embodiment.

What is required is to engineer more than one viewpoint to ensure that SNR is high for any gaze direction over the eyes FOV; but attempting to this with multiple cameras introduces integration problems, added imager processing burden and extra cost. The present invention provides more elegant solution both computationally and in terms of the optical implementation. FIG. 36 shows an embodiment of the invention that may be used provide an eye tracker for illuminating an eye and detecting backscattered light from one or more surfaces of the eye from a multiplicity of different directions corresponding to different viewpoints. FIG. 36A shows a cross section view. FIG. 36B shows a plan view. The eye tracker comprises a single SBG layer bidirectional waveguide 460 into which are recorded an input coupling grating 461, an output coupling grating 462 and an array of SBG columns 463-467. The input gratings couples light 1500 from an infrared source 468 into a TIR path 1501 in the waveguide. The light is diffracting out of the waveguide by an active SBG element 463 into a direction 1502. Light 1503 backscattered from a surface of the eye incoupled by the active grating 463 follows a reverse TIR path in the waveguide 1504 and is diffracted towards the image sensor 469 in the direction 1505. A lens 470 is used to focus the image of a surface of the eye onto the image sensor. The surface of the eye may be a surface of the cornea, lens or retina, for example. In one embodiment the surface may be some arbitrary virtual surface either within or external to the eye. In one embodiment the column SBG elements have k-vectors disposed in different directions. In the embodiment of FIG. 36 the k-vectors are symmetrical with respect to the normal to the waveguide indicated by 1506. Advantageously, the normal coincides with the centres of rotation of the eye. Each k-vector determines the diffraction angle from each column. Hence as shown in FIG. 36A the output ray directions are also symmetrical around the normal 1509. The output rays 1502,1506 have opposing angles and the backscatter ray paths 1503,1507 are likewise symmetrical. For the purposes of explaining the invention each column in FIG. 36A is shown in its diffracting state. Normally, only one column will be in a diffracting state at any time. However, in certain embodiments of the invention more than one column may be active at any time. Note that although the illumination light from the waveguides will be substantially collimated the backscattered light from the eye that is coupled into the waveguide by an SBG element will have an angular range determined by the diffraction efficiency angular bandwidth of the SBG. The angular range of the rays reaching the image sensor will also depend on the optical prescription of the image sensor lens. FIG. 36B shows the arrangement of the gratings elements in more detail. The imaging sensors and image lens and the infrared sources are illustrated schematically. The TIR paths of the illumination and imaging light are also shown schematically using the rays 1500-1505.

The invention allows several different configurations of the input coupling and output coupling. In FIG. 36B the input coupling grating comprises three SBG elements arrange in rows. Each element has a different grating prescription allowing a diversity of path direction to the SBG columns 463-465 to be provided by selective switching of the SBG elements 462. The output grating is a passive column shaped element. The output grating may be a conventional passive Bragg grating or a SBG configure as a non switching element. At any time one column element and one row element from each of the column and row SBG arrays are switched into a diffracting state. The columns are used for tracking horizontal eye rotation and the rows for expanding the vertical tracking range. The columns are scanned initially to determine the best eye location and as the eye rotates horizontally, the signal will transition from one column to an adjacent column (left or right) when the signal on a given column reduces to a predefined signal-to-noise ratio minimum, the active column can be moved to the adjacent column. Typically the columns have a large vertical gaze tracking range. The inventors have found that the eye rotation can be tracked over ±15° without the need to select a new row. However, the rows allow the system to be tailored to provide a larger eye box, to accommodate eye positional changes with respect to the center of the nominal eye box resulting from tracker slippage relative to the eye.

Figure 37:
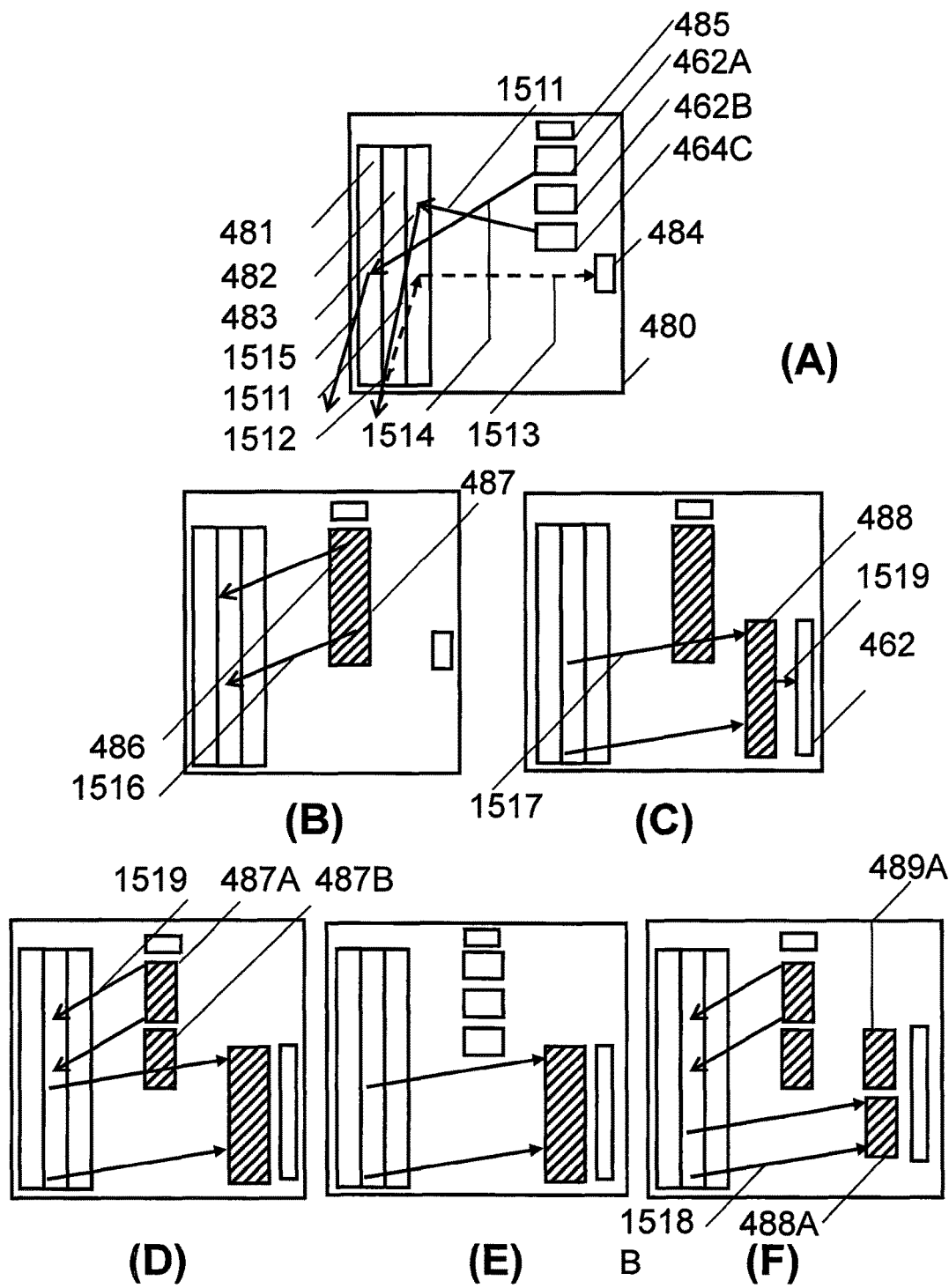
FIG. 37A is a plan view of a waveguide illustrating a grating architecture used in one embodiment of the invention
FIG. 37B is a plan view of a waveguide illustrating a grating architecture used in one embodiment of the invention
FIG. 37C is a plan view of a waveguide illustrating a grating architecture used in one embodiment of the invention
FIG. 37D is a plan view of a waveguide illustrating a grating architecture used in one embodiment of the invention
FIG. 37E is a plan view of a waveguide illustrating a grating architecture used in one embodiment
FIG. 37F is a plan view of a waveguide illustrating a grating architecture used in one embodiment
Figure 38:
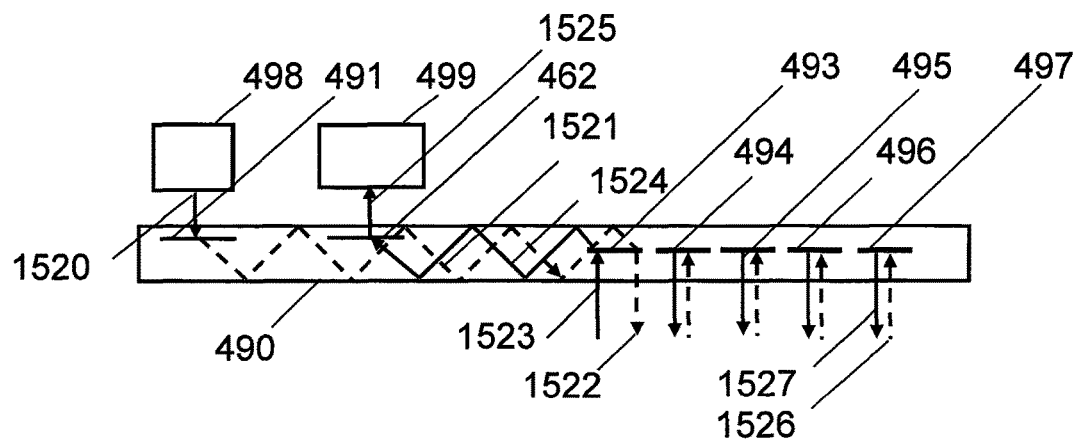
FIG. 38 is a cross section view of a bidirectional waveguide eye tracker in one embodiment.

FIG. 37 shows examples of waveguide grating configurations that may be used in some embodiments of the invention. In each case the waveguide, column gratings, input and output gratings are illustrated. In the embodiment of FIG. 37A the waveguide 480 contains column SBGs 481-483, input grating 485 steering gratings 462A-462C and a output coupling grating 484. The output grating is smaller than the one used in the embodiment of FIG. 36. TIR paths from the elements 462A to 481 and from 462C to 483 are indicated and image light path from 482 to the element 484 are indicated by the rays labelled 1510-1513. The column elements and the input coupling gratings are all switching gratings. In the embodiment of FIG. 37B the waveguide comprises input and output gratings, column gratings and a fold or turning grating 486. A fold grating is one that deflect light in the plane of the waveguide; conventional waveguide gratings diffract light in a plane normal to the plane of the waveguide. Used in combination with conventional gratings fold gratings can greatly enhance the design space for holographic waveguide optics, allowing beam expansion and beam steering to be accomplished with the minimum number of waveguiding layers. A further advantage is that the pupil-expanding property of fold gratings as indicated by the rays 1517 eliminates the need for large aperture lenses thus enabling a very compact eye tracker. Fold gratings may be passive or switching. However, switchable fold gratings tend to have higher diffraction efficiencies which are needed for high detection efficiency. FIG. 37C introduces a fold grating 488 into the imaging channel with output coupling grating comprising a column-shaped element 462 of FIG. 36. The expanded collection aperture resulting from the fold gratings is indicated by the rays 1518. In the embodiment of FIG. 37D the fold grating 487 of FIG. 37C is divided into the two elements 487A, 487B. Advantageously, these two elements are switching elements. In the embodiment of FIG. 37E the output coupling element 484 of FIG. 37A is replaced by the fold grating 488 and the output coupling column grating 462. Finally in the embodiment of FIG. 37F the imaging path fold grating 488 of FIG. 37D is replace by the two switching fold gratings 489A,489B. It should be apparent from consideration of the above description and the drawings that that many other combinations of gratings, fold gratings, switching gratings may be used in to apply the invention. It should also be apparent that in the cases where a fold grating has been dived into two switching elements as in FIG. 37D and FIG. 37F the grating could be divided into more elements to meet a specific beam management requirement. The number of elements of a given type and their prescription and relative position will be determined by the required eye tracker angular range, the size of the eye box and the practicalities of routing illumination light from the source to the eye and routing illumination light from the eye to the image sensors Although it is desirable to provide different eye perspectives as shown in FIG. 36A the output light may simply comprise parallel beams as shown in FIG. 38. The eye tracker comprises a single SBG layer bidirectional waveguide 490 into which are recorded an input coupling grating 491, an output coupling grating 492 and an array of SBG columns 493-497. The input grating couples light 1520 from an infrared source 498 into a TIR path 1521 in the waveguide. The light is diffracting out of the waveguide by an active SBG element 463 into a direction 1522. Light 1503 backscattered from a surface of the eye in is coupled by the active grating 493 follows a reverse TIR path in the waveguide 1524 and is diffracted towers the image sensor 499 in the direction 1525. A lens (not shown) is used to focus the image of a surface of the eye onto the image sensor.

Figure 39:
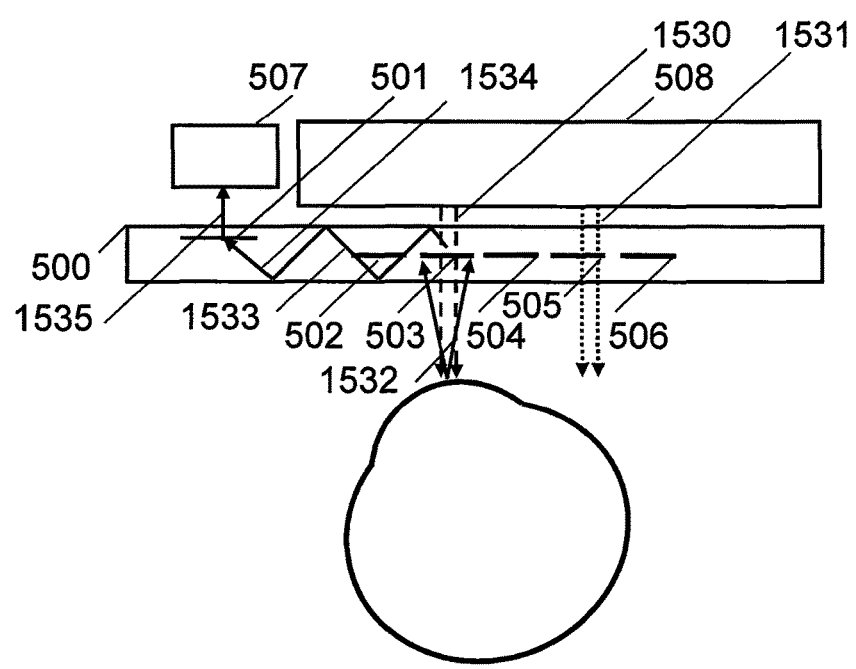
FIG. 39 is a cross section view of a bidirectional waveguide eye tracker using a separate illumination backlight in one embodiment of the invention

In one embodiment shown in FIG. 39 the eye illumination is provided by a separate backlight. The eye tracker comprises the waveguide 500 comprising an output coupling grating 500 an imaging sensor and an array of SBG columns 502-506. A backlight 508 is an Electrooptical device that illuminates the eye by scanning a sheet of light across the eye box. The illumination light is represented at one scan position by the rays 1530 and at a second scan position by the rays 1531. Since the waveguide is transparent there is little disturbance of the light. When the rays 1530 illuminate a surface of the eye backscatter de light 1532 is coupled into the waveguide by the SBG element 503 a follows the TIR path 1533-1534 until it is diffracted by the output coupling grating into an output path 1535 to the imaging sensor. In one embodiment the backlight is similar in concept to the ones disclose in PCT Application No.: PCT/GB2013/000005 entitled CONTACT IMAGE SENSOR USING SWITCHABLE BRAGG GRATINGS. In one embodiment the backlight may be provided by a computer screen with individual light sheets being provided by setting columns of pixels in the display to peak brightness and dimming the remaining pixels.

Figure 40:
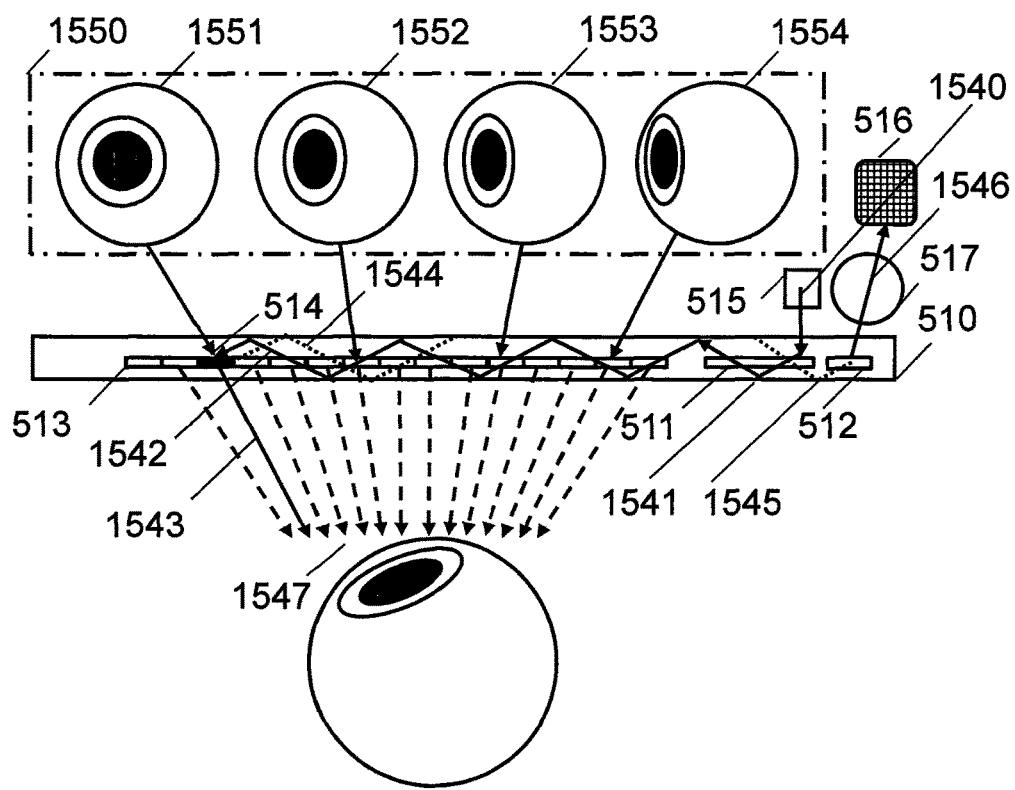
FIG. 40 is schematic illustration of an aspect of the operation of the embodiment of FIG. 36A

The embodiment of FIG. 39 is illustrated in more detail in FIG. 40 which illustrates the use of different eye viewing perspectives. The eye tracker comprises a single SBG layer bidirectional waveguide 510 into which are recorded an input coupling grating 511, an output coupling grating 512 and an array of SBG columns generally indicated by 513. The input gratings couples light 1500 from an infrared source 515 into a TIR path 1541-1542 in the waveguide. The light is diffracting out of the waveguide by an active SBG element 514 into a direction 1543. Light backscattered from a surface of the eye in is coupled by the active grating 463 follows a reverse TIR path in the waveguide 1544-1545 and is diffracted towards the image sensor 516 in the direction 1546. A lens 517 is used to focus the image of a surface of the eye onto the image sensor. The range of viewing perspective directions provided by the column elements is generally indicated by 1547. The inset 1550 shows a set of eye perspective views 1551-1554 correspond to four of the perspective directions.

Figure 41:
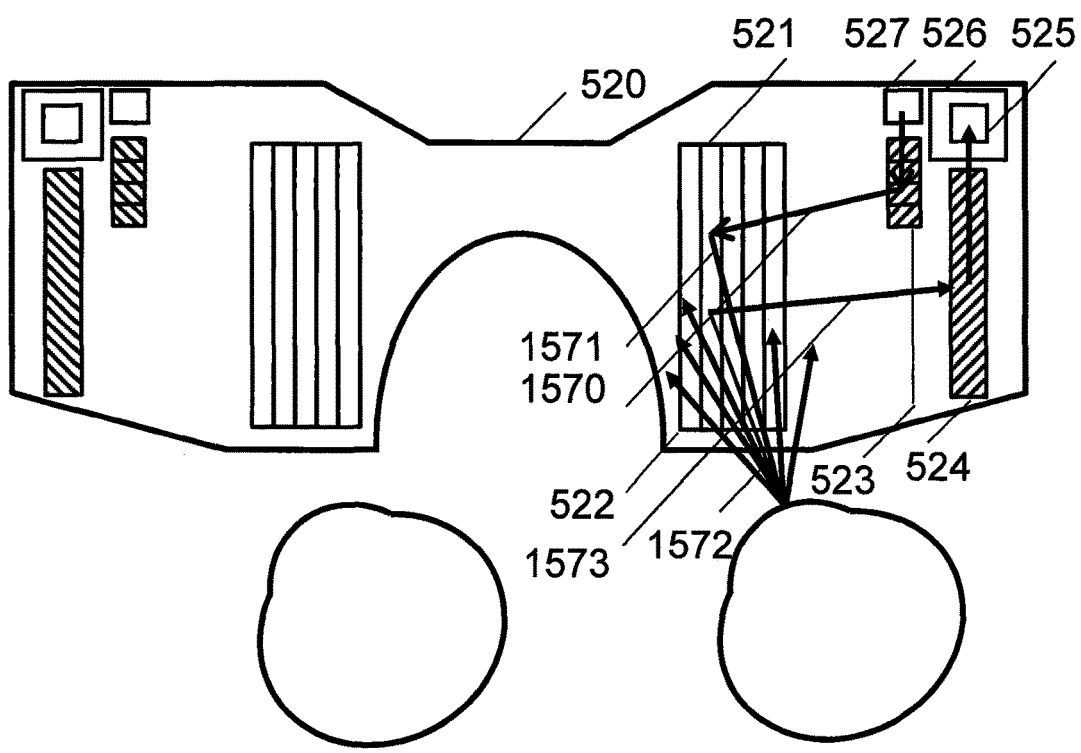
FIG. 41 is a schematic front elevation view of an eye tracker waveguide for used in a head mounted display in one embodiment of the invention.
Figure 42:
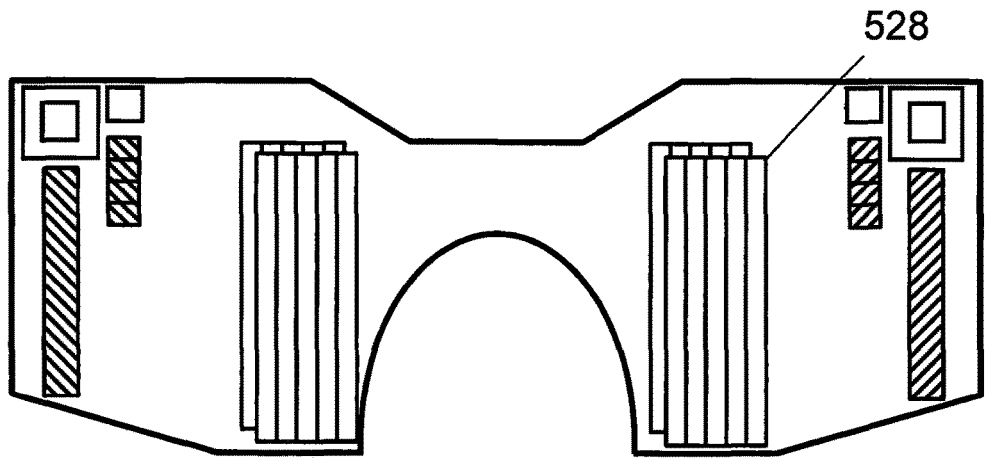
FIG. 42 is a schematic front elevation view of an eye tracker waveguide for used in a head mounted display in one embodiment of the invention.
Figure 43:
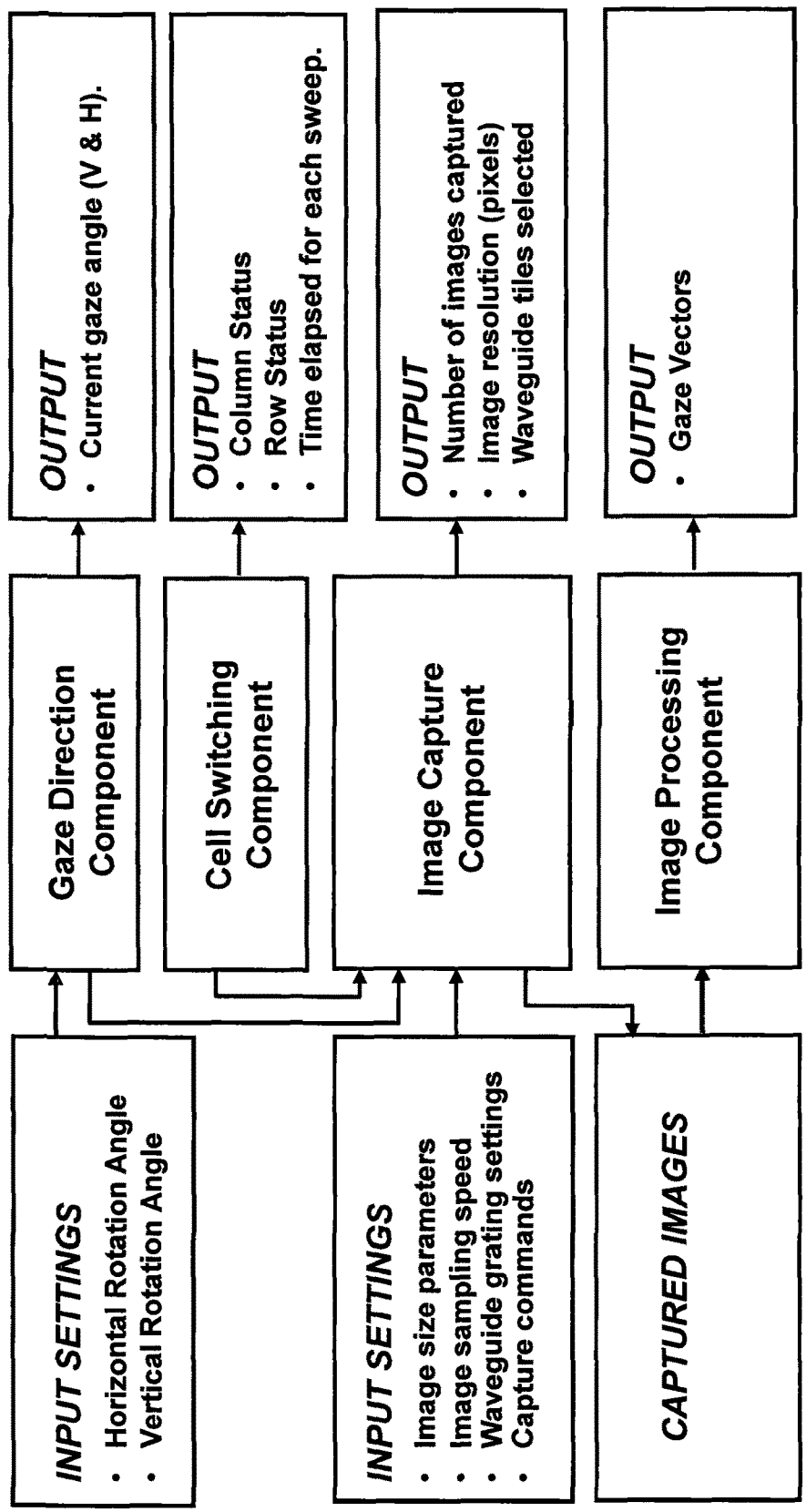
FIG. 43 is a flow diagram showing an image processing procedure for use with an eye tracker in one embodiment of the invention.

FIGS. 41-42 shows two embodiments of the invention that address the requirements of eye tracking in HMDs. The grating architecture comprising an array 521 of SBG columns containing elements such as 522 an arrays of input SBG fold gratings 523 and output fold grating 525 an output coupling grating 525 for directing image light to the detector array and detector lens indicated by 526 and an input infrared source 521. The beam path from the source to the eye is indicated by the rays 1570,1571. The beam path from the eye the imaging sensors is indicated by the rays 1572, 1573. The embodiments of FIGS. 42-43 are intended for integration with a HMD comprising an input image panel and binocular collimation lens. An exemplary HMD in this case is the Oculus Rift headset manufactured by Oculus Inc. The waveguide layer may be disposed between the collimating lenses and the eyes or between the input image panel and the lenses. In the latter case there is likely to be some distortion of the eye tracking imaging beam by the collimating lenses. In the embodiment of FIG. 43 the distortion is corrected by an array of column shaped diffractive lens overlaying the region of the waveguide containing the SBG column array. In an alternative embodiment the correction phase functions provide by the lens array elements could be holographically encoded into the SBG columns.

Figure 44:
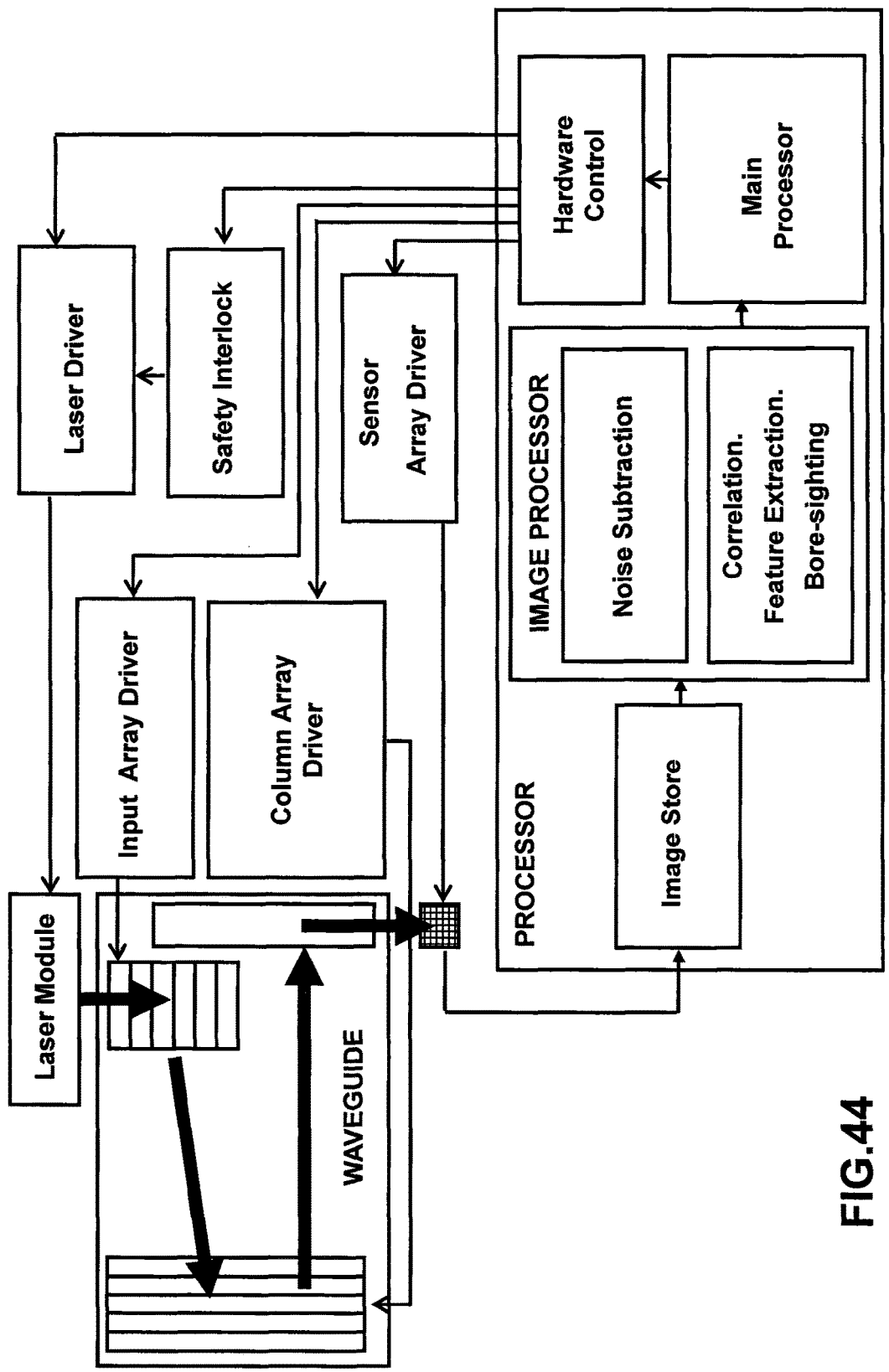
FIG. 44 is a flow diagram showing a system architecture for use with an eye tracker in one embodiment of the invention.

FIG. 43 is a block diagram illustrating a system architecture for controlling an eye tracker according to the principles of the invention. FIG. 44 is a block diagram illustrating an eye tracker system architecture based on the embodiments of FIG. 36-40.

Figure 45:
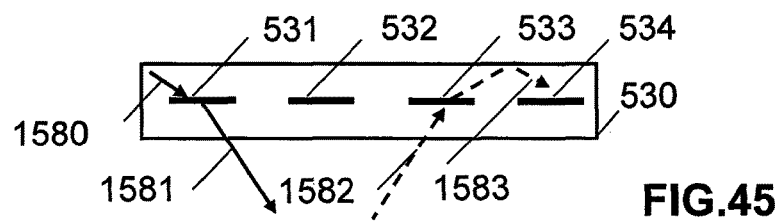
FIG. 45 is a schematic side view of a portion of a waveguide in which different elements of an SBG array are used for illumination and imaging of the eye.

In one embodiment based on the embodiment of FIG. 36 two of the elements of the SBG column array may be activated at any instant such that one is used to deflect illumination light towards the eye along a first direction and the second element is used to collect scattered from the eye along a second direction. The general principle is illustrated in FIG. 45 which shows a portion of a waveguide 530 containing output SBG array elements 531-532. The TIR illumination light 1580 is deflected out of the waveguide by the active SBG element 531 in the direction 1581 towards the eye. Simultaneously, the backscatter light in the direction 1582 is coupled into the waveguide via the SBG element 533 and waveguides as the TIR beam 1583.

Although the description of some embodiments of the invention has emphasised the detection of speckle patterns it should be apparent from consideration of the description and drawings that the same optical architecture and indeed many features of the processing architecture may be used to perform eye tracking using other optical signatures from the eye. For example features such as bright or dark pupils and glint may provide suitable signatures. The blurring of the eye feature being tracked does not present an impediment providing that the detected image contains enough content for correlations to be made between captured frames and stored images capture in the bore sighting (or neural network training) stage.

The optical design requires careful balancing of the high source flux needed to overcome throughput inefficiencies arising from the small collection angles, low transmission thorough the waveguide and the low reflectivity of the eye (~2.5% at the surface of the cornea) with the requirement for eye-safe IR illumination levels. Typically, for applications in which the eye tracker is used for hours at a time under continuous IR exposure the eye irradiance should not exceed around 1 mW/cm2. The appropriate standards for eye safe infrared irradiance are well known to those skilled in the art. Since the proposed eye tracker scrolls the illumination across the eye the cornea and retina are not exposed to continuous IR exposure allowing higher exposures levels to be used leading to higher speckle contrast level and therefore higher SNR at the detector. In a switchable grating based design there is the risk of a switching malfunction causing the laser beam scanning to freeze resulting in all of the available output laser power being concentrated into a small area of the eye.

An eye tracker according to the principles of the invention offers many advantages over competitor technology. Most importantly the eye tracker disclosed in the present application has intrinsically low latency owing to its use of multiple viewpoints and low resolution detectors and low resolution detectors to capture high SNR signatures in any gaze direction. In contrast camera-based eye trackers have a single fixed viewpoint. SNR diminishes with eye rotation incurring progressively increasing lag. Camera-based eye trackers have a high latency owing to imaging of more complex eye signatures requiring high resolution detectors and sophisticated image processing and tracking algorithms. The inventors anticipate that following full development the eye tracker will delivers update rates of at least 300 Hz; and tracking accuracy of ±0.5 degrees. The invention provides a thin, transparent, switchable holographic waveguide. The design eliminates refractive optics and provides a monolithic, planar architecture that can be manufactured cost-effectively and reliably using a holographic printing process.

The present invention overcomes the line-of-sight obscuration problem of camera-based eye trackers. The eye tracker is effectively invisible presenting only a highly transparent window to light from the displays/external scene. The bidirectional switchable holographic waveguide architecture allows efficient illumination of the eye, using a narrow angle or collimated IR beam to provide illumination exactly where it is needed: that is, on the eye surface to be tracked, and in line with the detection optical path. Since the IR irradiance at the eye is temporally modulated by the switched SBG elements the invention may use relatively high IR irradiance levels while remaining well below eye safe MPE thresholds. The eye box can be tailored to suit the application. In the case of HMDs the eye tracker pupil (currently around 10 mm. vertical) is more than adequate for VR HMDs. The eye tracker can track gaze direction over at least 50°. The inventors are confident that the existing design can be scaled-up to much larger angles, up to the 110° fields demanded by VR HMDs. As a thin highly transparent element the eye tracker is compatible with glasses and contact lenses. As a holographic waveguide technology the eye tracker will integrate seamlessly with HMDs based on the same technology.

Figure 46:
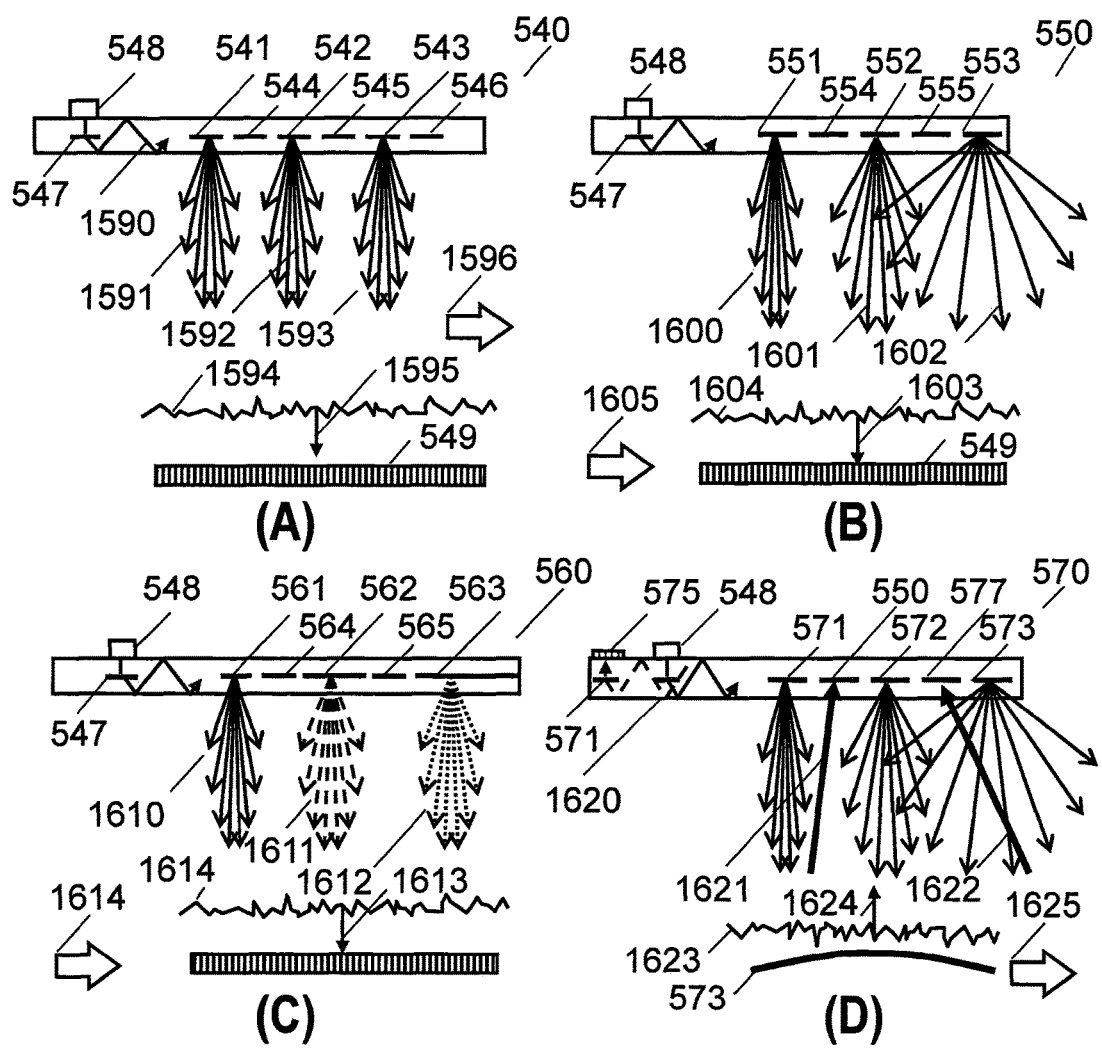
FIG. 46A is a schematic side elevation view of an apparatus for tracking an object using structured light in one embodiment of the invention.
FIG. 46B is a schematic side elevation view of an apparatus for tracking an object using structured light in one embodiment of the invention.
FIG. 46C is a schematic side elevation view of an apparatus for tracking an object using structured light in one embodiment of the invention.
FIG. 46D is a schematic side elevation view of an apparatus for tracking an object using structured light in one embodiment of the invention.

The invention also provides a means for tracking objects in 3D using structured light. Head tracking and hand gesture tracking are of particular interest in the context of VR and AR. Current tracker technology uses fixed cameras and requires that the subject to be tracked has reflective targets or light sources attached to its surface. This is not always practical. Moreover camera tracking systems suffer from the problems of obscuration and spatially varying SNR. The proposed approach is to track structured light, such as speckle, using holographic waveguide containing SBG elements for controlling the beam angle, diffusion angle, phase characteristic and speckle contrast. The embodiments to be discussed are based on the holographic waveguide embodiments and general teachings disclosed in U.S. patent application Ser. No. 13/506,389 entitled COMPACT EDGE ILLUMINATED DIFFRACTIVE DISPLAY, U.S. Pat. Nos. 8,224,133 and 8,565,560 both entitled LASER ILLUMINATION DEVICE and PCT/GB2013/000210 entitled APPARATUS FOR EYE TRACKING. U.S. patent application Ser. No. 13/506,389 discloses a holographic waveguide containing SBGs for projected structured IR light onto a surface received and sensors for detecting the return light. In one embodiment the waveguide provides structured light illumination for tracking objects in 3D. The waveguide may also be configured to provide a display allowing a virtual keyboard to be projected on a nearby surfaces. U.S. Pat. Nos. 8,224,133 and 8,565,560 both disclose waveguides containing SBGs for modifying the speckle (and other) characteristics of illumination light. The SBGs can be configured to control output beam direction, diffusion, optical power, phase and speckle contrast. PCT/GB2013/000210 APPARATUS FOR EYE TRACKING discloses a bidirectional waveguide containing SBGs for illuminating and detecting IR signatures (including speckle) from eye surfaces. The tracker uses multiple viewing/illumination perspectives to provide high SNR signatures everywhere in the FOV. The high SNR images enable the use of fast low resolution detectors resulting in very low latency. Although PCT/GB2013/000210 addresses eye tracking the invention is equally applicable to tracking other objects that provide a detectable signature. FIG. 46 shows a set of exemplary embodiments directed at object tracking using structured light. In the embodiment of FIG. 46A there is provide a waveguide 540 containing SBG elements 541-543 for deflecting TIR light out of the waveguide into output beams 1591-1593. The illumination light from the source 548 is coupled into the waveguide via the input grating 547. Each beam 1591-1593 provides structured light characterised by at least one of beam intensity profile, speckle contrast, phase distribution, or beam direction resulting in a structured illumination pattern generally indicated by 1594 in the beam direction 1595. The illumination is detected directly by the image detector array 549. Note that in the embodiment illustrated no lens is required. However, in other embodiments the illumination may be focused on the detector surface using a lens. The waveguide and the detector are in relative motion as indicated by the block arrow 1596. Either the waveguide or detector may be fixed in 3Dspace. Alternatively, the waveguide or detector may both be in motion relative to some fixed reference frame in the 3D space. Consecutively recorded frames from the image detector array may be correlated to determine movement vectors. In one embodiment the relative motion of the detector and waveguide may be in any direction within a plane parallel to the detector plane. In one embodiment either or both of the detector or waveguide may move along a curvilinear path in 3D space. In the embodiment of FIG. 46A the beams have similar optical characteristics. In the embodiment of FIG. 46B a waveguide 550 contains SBGs 551-555 which diffract light into beams having different divergences as illustrated by the beams 1600-1602. The broader beam divergences are useful for detecting objects at short range while the narrower divergence are more advantageous for longer ranges The resulting illumination patter 1604 in the direction 1603 is illustrated. It should be noted that in the above embodiments the illumination directions at the detector may result from the light deflected by one SBG element only. Alternatively, the illumination distribution may result from the integration of the illumination distributions from more than one of the SBG elements within the detector integration time. In the embodiment of FIG. 46C a waveguide 560 contains SBGs 561-565 which diffract light into beams having different speckle contrasts as illustrated by the beams 1610-1612. The embodiment of FIG. 46C also uses different sized SBG element to control the speckle grain size which is inversely proportion to the diffracting element dimension. This allows the speckle grain to be matched to the detector array pixel size at different ranges. The resulting illumination pattern 1614 in the direction 1613 is illustrated. In the embodiment of FIG. 46D which is similar to the one of FIG. 46B a waveguide 560 contains SBGs 571-572 which diffract light into beams having different divergence. The resulting illumination pattern 1614 in the direction 1613 is illustrated. The detector of FIG. 46 is replaced by the reflective surface 573 which reflects the illumination 1623 in the direction 1624. The reflected illumination is coupled into a TIR path 1620 within the waveguide by the SBG element 576 which couples-in reflected light incident in the direction 1621 and the SBG element 577 which couples-in reflected light incident in the different direction 1622. Finally, the detected light 1620 is diffracted out of the waveguide by the grating 574 towards an imaging detector 575. The detector is typically a fast low resolution device of the type used in computer mouse technology. It should be apparent to those skilled in the art that the detection directions 1621,1622 provide viewing perspectives by means of which the location of the reflective surface (or a portion thereof) may be determined using triangulation. Multiple perspectives allow a bigger FOV and high SNR everywhere in the tracking space. Camera systems have fixed perspective resulting in spatially varying SNR. By processing successive frames of image data the direction of motion of the reflective surface may be determined using image processing. In one particular embodiment the structured light is speckle and position and velocity vectors are determined from successive frames using correlation method as described earlier.

In one embodiment there is provided a waveguide device that incorporates an eye tracker and holographic elements for gesture detection. As an example the embodiment illustrated in FIGS. 47-48 combines the features of the eye tracker of FIG. 36 and the object tracker of FIG. 46D. The numerals used in FIG. 36 are again used to label the key components of the eye tracker The eye tracker waveguide of FIGS. 47-48 now includes the SBG elements contains SBGs 581-583 which diffract light into beams having different divergence angle as illustrated by the beams 1633-1635. Referring to the cross section view of FIG. 47, the reflected illumination from an external surface (not illustrated is coupled into a TIR path 1620 within the waveguide by the elements 584-586 which couple-in reflected light incident in the directions 1636-1638 respectively. Detected light 1640 is diffracted out of the waveguide by the grating 589 towards an imaging detector 590 coupled to an image processor 592 by a data link 600. Image light 1639 from the eye tracker is coupled out of the waveguide by the grating 462 towards the imaging detector 469 which is coupled to the image processor 591 by an electronic data link 601. The eye tracker illumination light is provided by the laser module 468 which is coupled to the waveguide by the grating 461 the illumination path being indicated by the ray 1630. The gesture tracker illumination light is provided by the laser module 588 which is coupled to the waveguide by the grating 587 the illumination path being indicated by the ray 1632. The eye tracker SBGs are indicated in simplified form in the FIG. 47 and in more detail in FIG. 48. The eye tracker output illumination path to the eye 593 is indicated by the ray 1631. Turning to the plan view of FIG. 48 the illumination path for the gesture tracker from the laser module 588 through the input grating 587 to the hand is indicated by the rays 1651,1652 with the speckle pattern associated with the illumination beam indicated by 1653. The path of the reflected light from the hand to the output coupling grating 589 to the detector array 590 is indicated by the ray 1654 with the speckle pattern associated with the reflected light being indicated by 1655. In all other respects FIG. 48 is identical to FIG. 36B.

Figure 47:
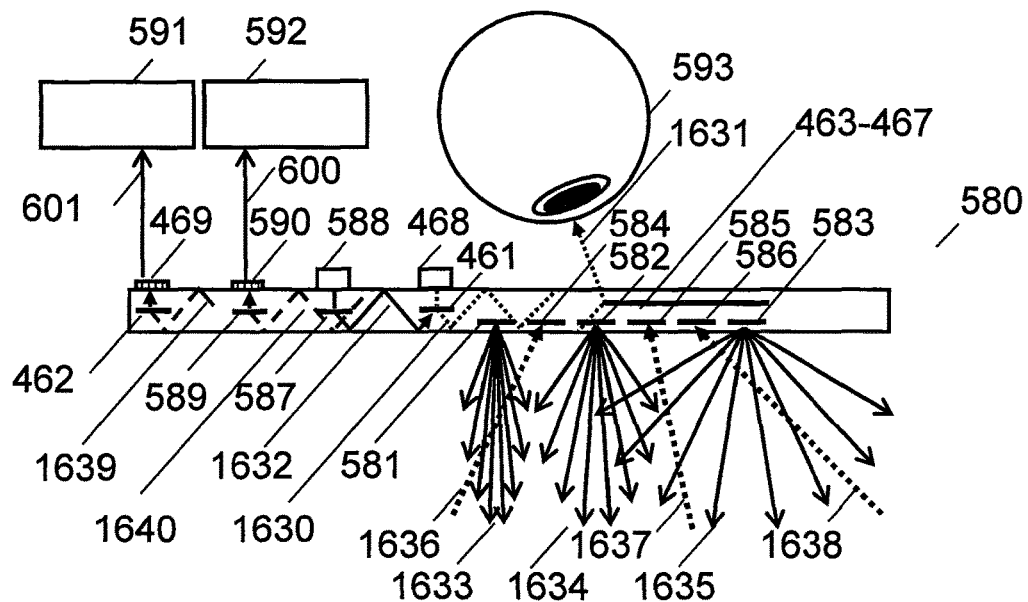
FIG. 47 is a schematic side elevation view of an apparatus for tracking an object using structured light in one embodiment of the invention based on the embodiment of FIG. 36.
Figure 48:
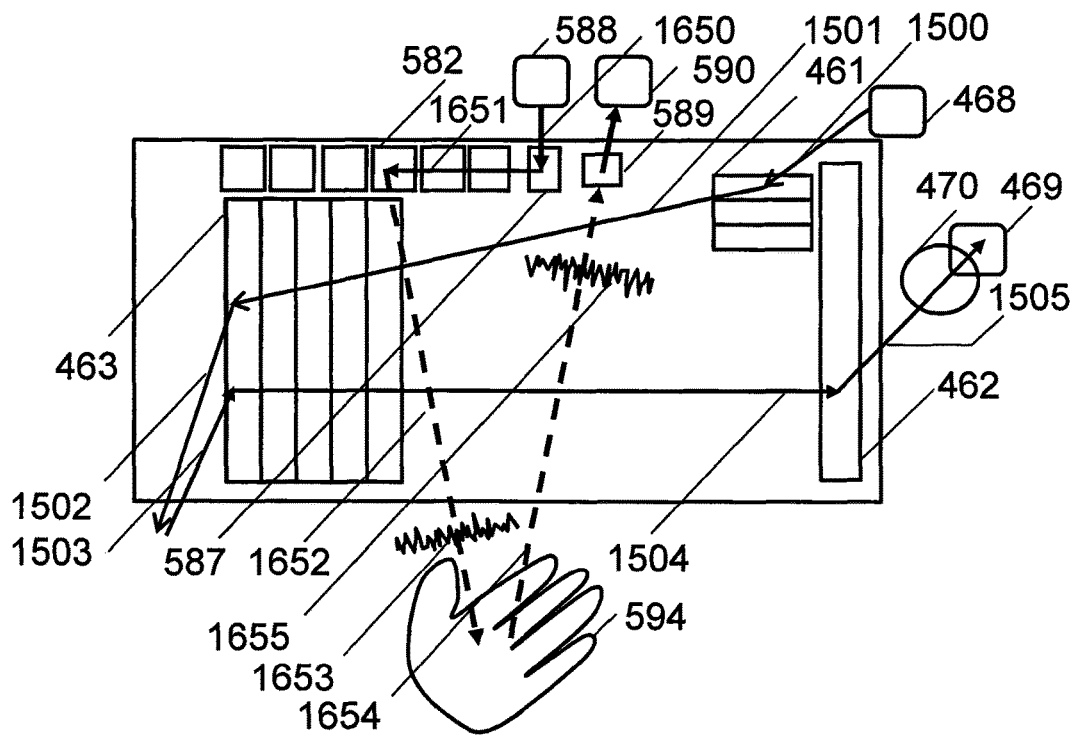
FIG. 48 is a schematic plan view of an apparatus for tracking an object using structured light in one embodiment of the invention based on the embodiment of FIG. 36.
Figure 49:
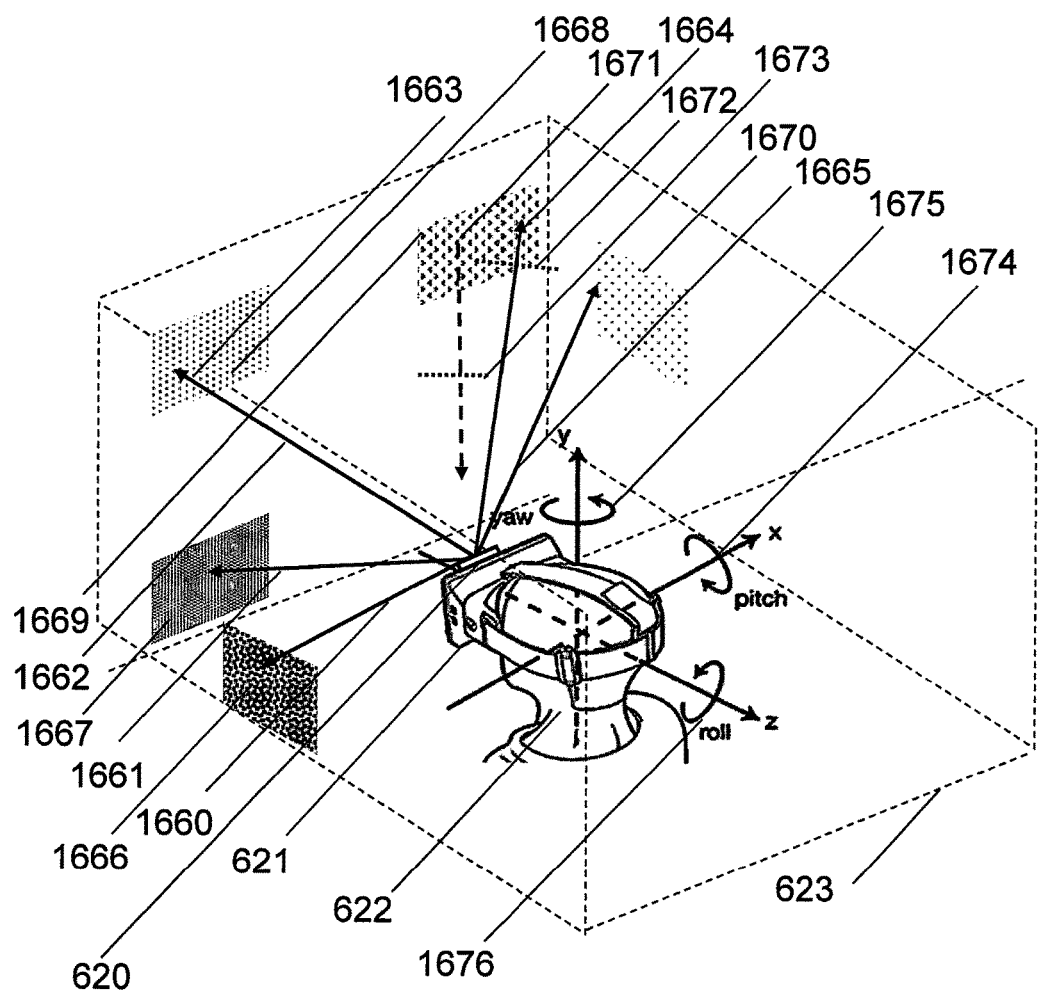
FIG. 49 is a schematic illustrated of a head tracker in one embodiment of the invention.

In one embodiment illustrated in FIG. 49 there is provided a head tracker 620 based on the principles of the holographic waveguide device of FIGS. 47-48. The head tracker, which is attached to a wearable display 621 mounted on the head 622, emits structured light beams in a set of different directions 1660-1665 and receives light from reflecting surfaces 1666-1669 within a tracking volume 623. In a preferred embodiment the structured light comprises speckle. Each surface is associated with a unique set of speckle patterns. For example the beam direction 1664, which has a speckle characteristic 1672, is reflected into the direction 1671 with a speckle characteristic 1673 which is detected by the head tracker waveguide. The characteristics of the speckle pattern seen by the detector will depend on the speckle characteristic of the output beam from the waveguide and the reflective or scattering properties of the surface. Sequences of images from the reflecting surfaces are correlated to determine vectors which are used to calculate the position of the head relative to a coordinate system defined with respect to the tracking volume. The same data may be used to calculate the yaw pitch and roll angles of the head.

Figure 50:
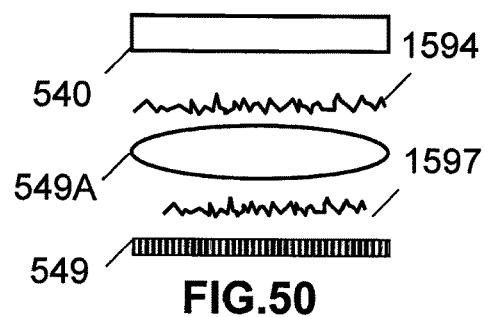
FIG. 50 is a schematic side elevation view of an apparatus for tracking an object using structured light and a detector lens in an embodiment of the invention based on the embodiment of FIG. 45A

FIG. 50 shows an embodiment related to the one of FIG. 46A in which a lens 549A located between the waveguide device 540 and the detector array 549 is used to image the speckle 1594 in the illumination beam in a second speckle pattern 1597 in proximity to the detector array.

Figure 51:
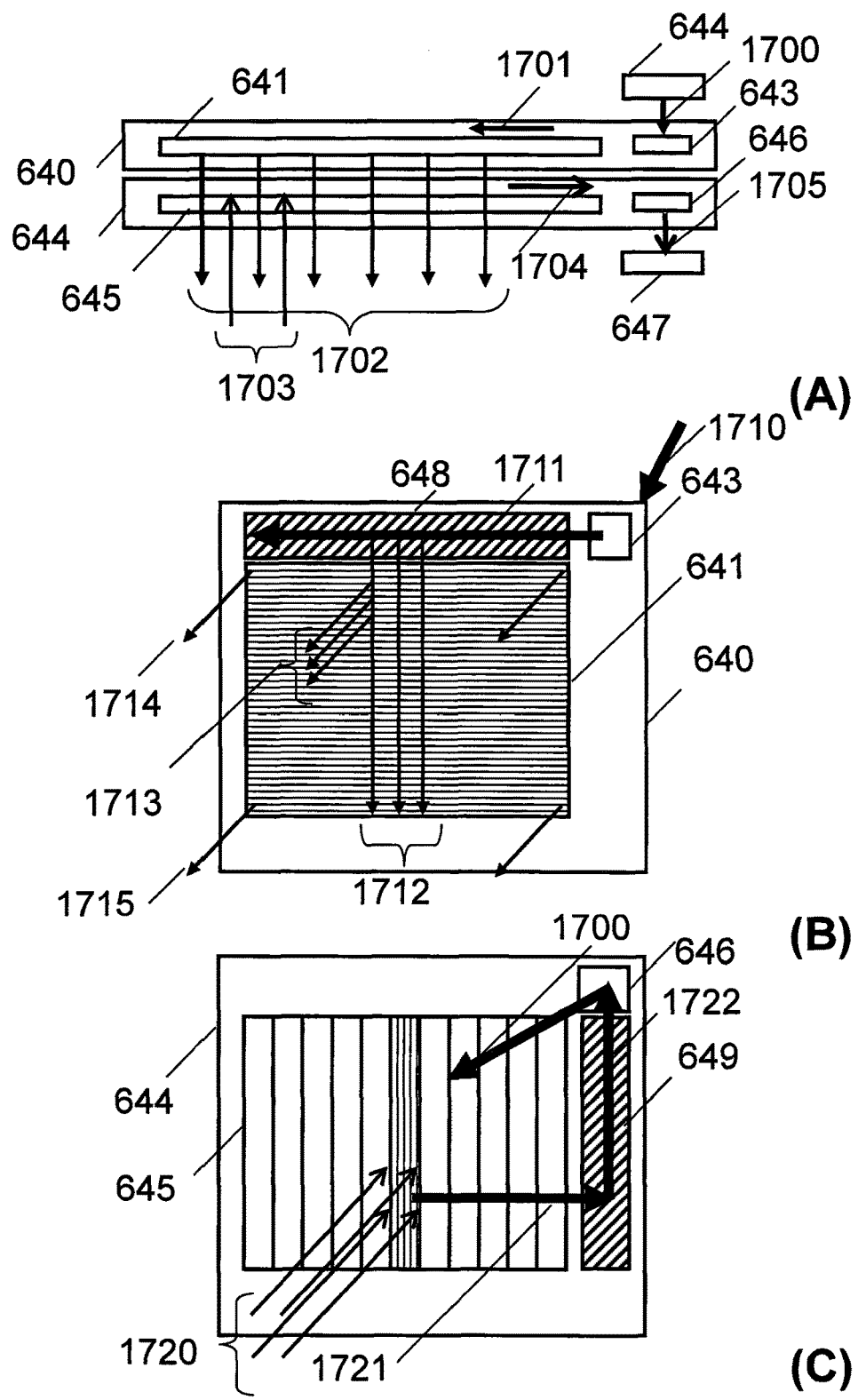
FIG. 51A is a schematic cross section view of an object tracker in one embodiment.
FIG. 51B is a schematic plan view of the illumination waveguide used in the embodiment of FIG. 51A.
FIG. 51C s is a schematic plan view of the detector waveguide used in the embodiment of FIG. 51A.

In the embodiment of FIG. 51 an object tracker comprises an illumination waveguide 640 overlaying a detection waveguide 644. Referring to the plan view of FIG. 51A the illumination waveguide contains a beam expansion grating 641 for extracting light, generally indicated by 1702, out of the waveguide towards the eye box and an input coupling grating 643 for in-coupling light 1700 from the illumination 644. The detection waveguide contains a SBG column array 645 for in-coupling reflected light 1703 from the eye into a TIR path in the waveguide and an output grating 646 for out-coupling light 1705 from the waveguide to a detector 647. The TIR propagation directions in the illumination and detection waveguides are indicated by the arrows 1701, 1704. FIG. 51A is a front elevation view of the illumination waveguide showing the input coupling grating 643 for coupling in light 1710 (out of the plane of the drawing) from the source and the extraction grating 641. A further grating configured as a fold grating 640 expands the in-coupled beam 1711 and deflects it in an orthogonal direction to fill the horizontal dimension of the out-coupling grating. This light then proceeds to propagate down the extraction grating as indicated by the TIR beam directions 1712 providing uniform extraction along the path out of the waveguide towards the eye box as indicated by the rays 1713. Extraction takes place over the entire area of the output coupling grating as indicated by the rays 1714,1715. FIG. 51C is a front elevation view of the detection waveguide 644 showing the array of column gratings 645 coupled to a fold grating 649 which couples the wave guided reflected light from the eye towards the output coupling grating 646. At any time, one SBG column such as the one labelled 650 is in its diffracting state. The active column in-couples light reflected from the eye 1720 into the TIR path 1721. The fold grating then steers the beam into the orthogonal path 1722. The output coupling grating out-couples the light into the direction 1723 (out of the plane of the drawing towards the detector. Note that the input and output gratings may be replaced by prisms if desired.

Figure 52:
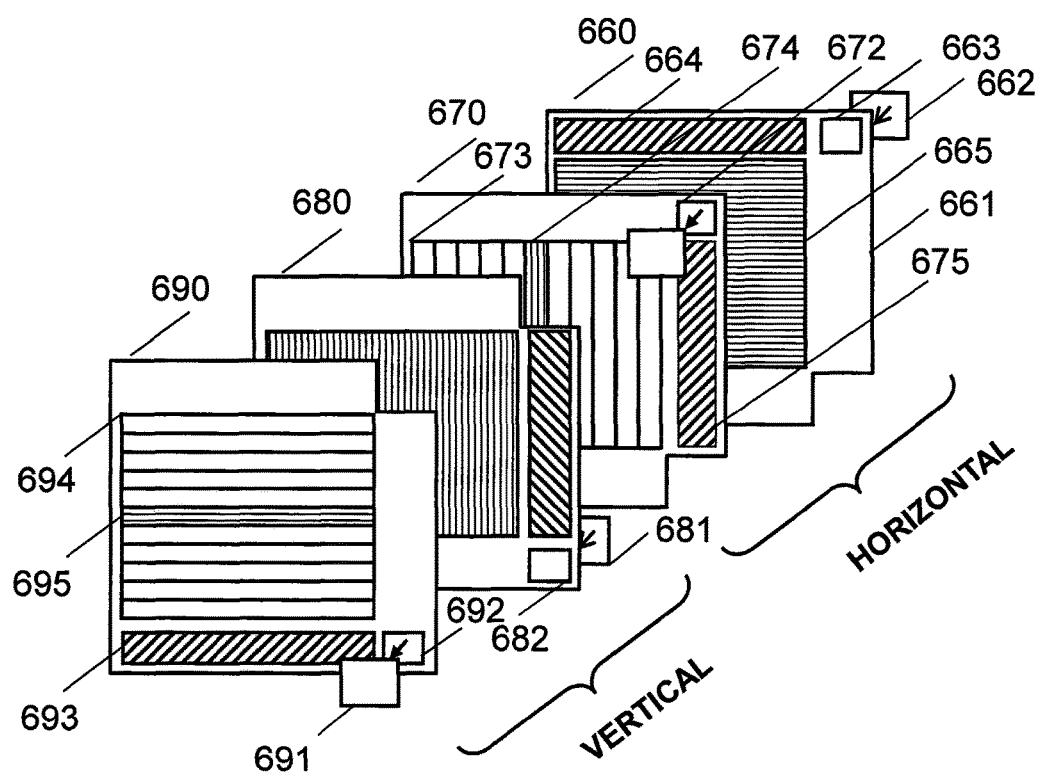
FIG. 52 is an exploded view of an object tracker in one embodiment.

In the embodiment of FIG. 52 an object tracker comprises two identical waveguides based on the embodiment of FIG. 51. The waveguides are rotated at ninety degrees to each other to allow tracking in the vertical and horizontal directions (or any other orthogonal directions). The illumination waveguide 660 and the detection waveguide 670 provide horizontal tracking while the illumination waveguide 680 and the detection waveguide 690 provide vertical tracking. The illumination waveguide 660 comprises an input coupling grating 662 for coupling light from the source 661, a fold grating 664 and a beam extraction grating 663. The detection waveguide 670 comprises the SBG column array 673 one element of which, such as 674 is active at any time, a fold grating 675, and an out-coupling grating 672 for coupling the eye reflection to the detector 673. The illumination waveguide 680 comprises an input coupling grating 682 for coupling light from the source 681, a fold grating 684 and beam extraction grating 683. The detection waveguide 690 comprises the SBG column array 694, a fold grating 693, and an out-coupling grating 692 for coupling the eye reflection to the detector 691. One element of the column array, such as 695, is active at any time Note that the switching column arrays used in the detection waveguides are the only switching gratings; the fold gratings and input/ output coupler gratings in the illumination and detection waveguides are all passive. The source can be edge-coupled or directly bonded to waveguide. The detection waveguide typically contains between three to five columns. Potentially eight or more columns may be used. More columns allow more perspective views for better gaze direction discrimination with larger FOVs. Potential signal ambiguities and vertical/horizontal cross talk are overcome by several measures including: driving the vertical and horizontal switching layers in anti phase; polarization control (eye appears to preserve polarization in practice); and algorithmic methods.

As discussed above, in some embodiments the detector comprises a single element infrared photodetector directly bonded to the waveguide above the output grating. In some embodiments the detector may be coupled to the waveguides by means of prisms overlaying the output gratings. In some embodiments a detector lens prescription is recorded into the output coupling gratings. The signal from the detector is used to track the peak intensity of the eye signature as the eye rotates. The recorded peak intensities are then compared with a Look-Up-Table (LUT) of values of the peak intensity for different gaze directions. Single element infrared detectors have a significant speed advantage over array technology. Detection frequencies of 300 Hz and even 500 Hz, typically required in eye tracking, are well within the dynamic range of these devices. By operating the detector in unbiased (photovoltaic) mode dark current may be eliminated, allowing very high sensitivity and high SNR.

In one embodiment the tracker operates around the infrared wavelength 1550 nm. This is highly desirable from the eye safety perspective since light above 1400 nm is absorbed by the cornea and eye lens. The reflected signal from the cornea is just as strong as at lower IR wavelengths. To emphasise the safety advantage, the allowable eye-safe laser power at 1500 nm is around 50 times higher than at 800 nm.

Figure 53:
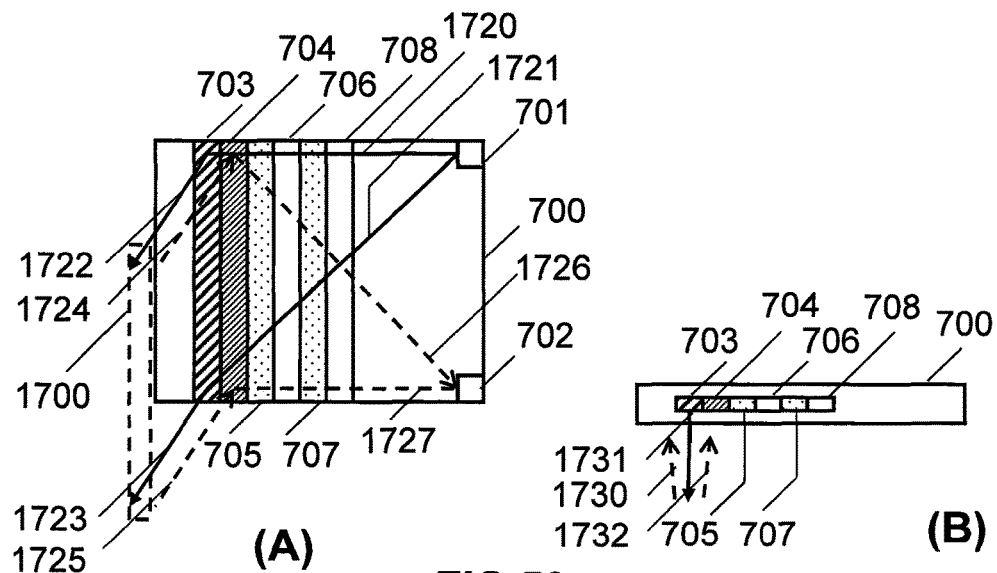
FIG. 53A is schematic plan view of an object tracker in one embodiment.
FIG. 53B is a schematic cross section of a detail of an object tracker in one embodiment.

In the embodiment of FIG. 53 an object tracker has receive and transmit channels recorded in a single layer. The apparatus comprises the waveguide 700 which contains a column array for extracting illumination from the waveguide towards the eye and intersperse columns for coupling reflection from the eye into the waveguide. For example the columns 703,705,707 are used for illumination and columns 704,706,708 are used for detection. In FIG. 53A illumination column 703 and detection column 704 are both in their diffracting state. The columns have optical power such that a divergent beam 1720,1721 from the source 701 is out coupled by the column 703 into the collimated beam 1722, 1723 which illuminates the eyebox strip 1725. The reflected light 1724,1725 is coupled into the waveguide by the column 704 which forms the light into the convergent beam 1726,1727 focused onto the detector 702. FIG. 53B shows a cross section of the waveguide.

Figure 54:
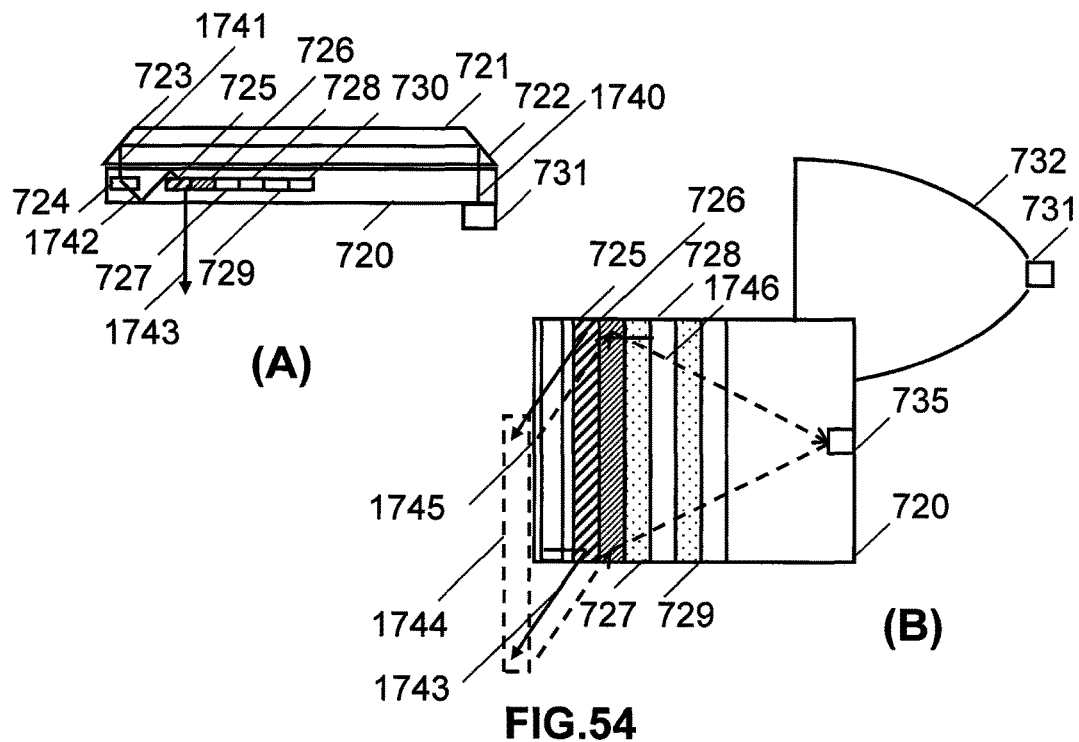
FIG. 54A is schematic plan view of an object tracker in one embodiment.
FIG. 54B is a schematic cross section of a detail of an object tracker in one embodiment.

In the embodiment of FIG. 54 a waveguide 720 similar to the one of FIG. 55 uses an overlaying light guide 721 to expand and collimated light from a source 731. In the waveguide 720 the columns 723,725,727 are used for illumination and columns 724,726,728 are used for detection. As shown in FIG. 54A the light contains tilted surfaces 722, 723 for steering light from the source to the illumination and detection waveguide. The light guide is shown unfolded 732 in FIG. 54B. The detection columns have optical power such that the reflected light 1745 is coupled into the waveguide by the column 726 which forms the light into the convergent beam 1746 focused onto the detector 735.

In the embodiment of FIG. 55 a waveguide 740 uses an overlaying light guide 742 to expand and collimated light from a source 741. The light guide is shown unfolded in FIG. 55B. As shown in FIG. 55A the light contains tilted surfaces 743, 744 for steering light from the source to the illumination and detection waveguide. The light guide is shown unfolded 759 in FIG. 55B. The illumination and detection waveguide contains alternating gratings of two different prescriptions. The first prescription used in the illumination columns 752,754,756 provides passive lossy gratings. The second prescription, which is used in the detection columns 751,752,755, provides optical power for converging the detected light onto the detector element 757

In the embodiment of FIG. 56 an illumination and detection waveguide 770 similar to the one of FIG. 55 contains alternating gratings of two different prescriptions. The first prescription used in the illumination columns 776,778,780 provides passive lossy gratings. The second prescription used in the detection columns 775,777,779 provides optical power for converting the detected light onto the detector element 772. This embodiment differs from FIG. 55 in the illumination is provided by an illuminator 771 coupled to a switching fold grating array 773 each element of which address a unique illumination column. As shown in FIG. 56 an active element 774 of the fold grating array couples the illumination beam 1770 in the illumination column 776 which extracts the light from the waveguide as the collimated beam 1772 forming the illumination strip 1773. Reflected light 1774 is coupled into the waveguide by the active detection column 777 which converges the light 1775 onto the detector.

Figure 57:
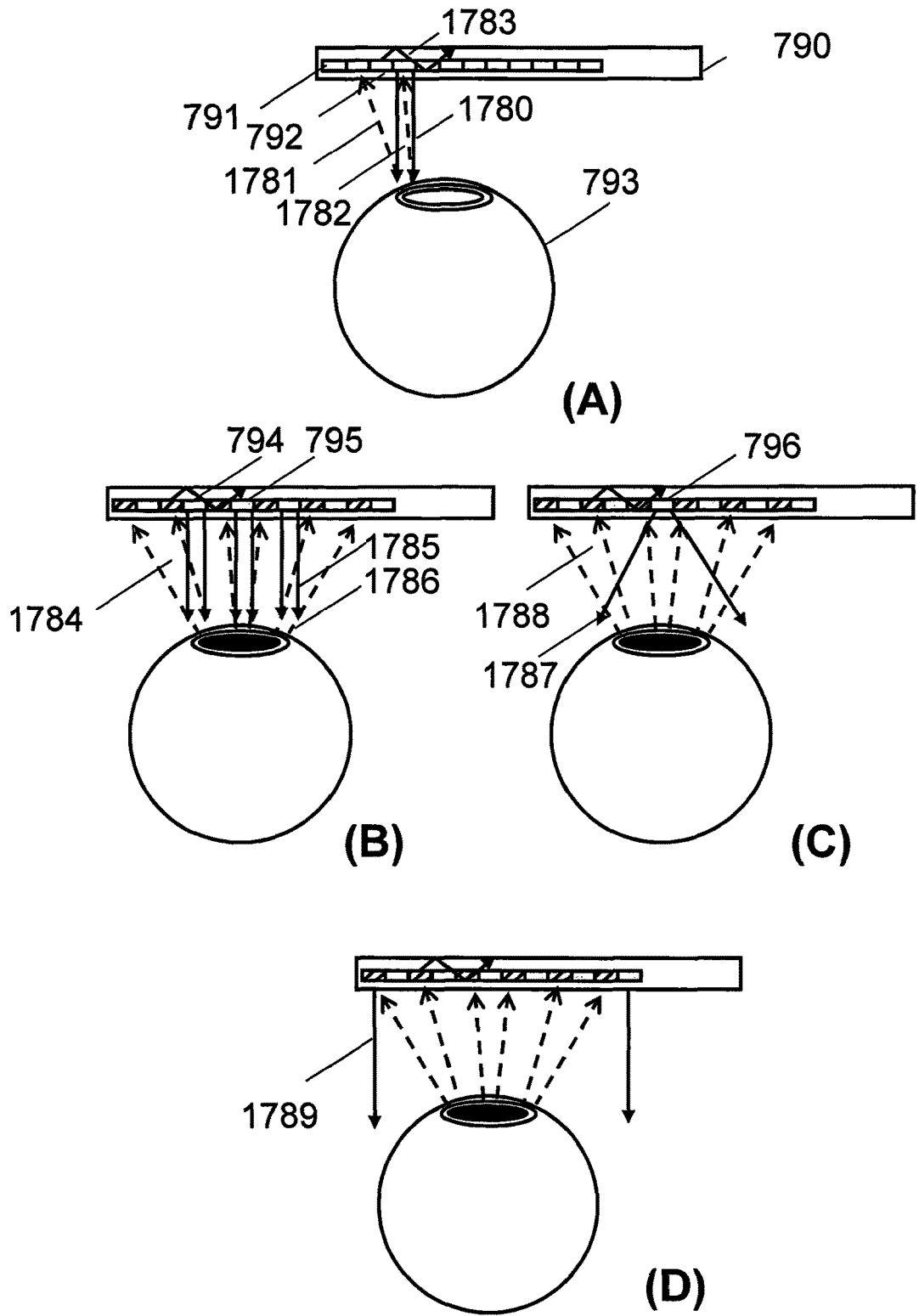
FIG. 57A is a cross section view of an eye tracker showing illumination and reflected signal paths in one embodiment.
FIG. 57B is a cross section view of an eye tracker showing illumination and reflected signal paths in one embodiment.
FIG. 57C is a cross section view of an eye tracker showing illumination and reflected signal paths in one embodiment.
FIG. 57D is a cross section view of an eye tracker showing illumination and reflected signal paths in one embodiment.

As shown in FIG. 57 which refers to and illumination and detection waveguide 790 containing illumination columns and detection columns as discussed above the above embodiments may be configured in several different ways for efficient illumination and detection of the object to be tracked. For example in the embodiment of FIG. 57A an illumination column 792 provides collimated illumination 1780 which is scattered in a divergent beam from a surface of the eye. In the embodiment of FIG. 57B multiple illumination columns such as 1785 are activated simultaneously. The reflected light from each illumination beams has different angular characteristic as indicated by 1784, 1786. In the embodiment of FIG. 57C the illumination columns provide divergent light. In the embodiment of FIG. 57 all of the illumination columns are active simultaneously providing a broad wash of collimated light.

Figure 58:
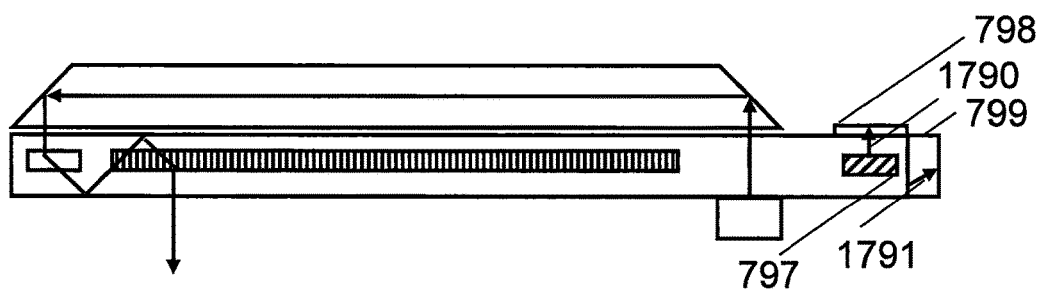
FIG. 58 is a schematic cross section of an object tracker in one embodiment.

In one embodiment shown in FIG. 58 an object tracker waveguide contains a grating 797 for deflecting stray light 1790 towards a light trap 798. The waveguide further comprises a light trap 799 abutting the edge of the waveguide for trapping light such as 1791.

Figure 59:
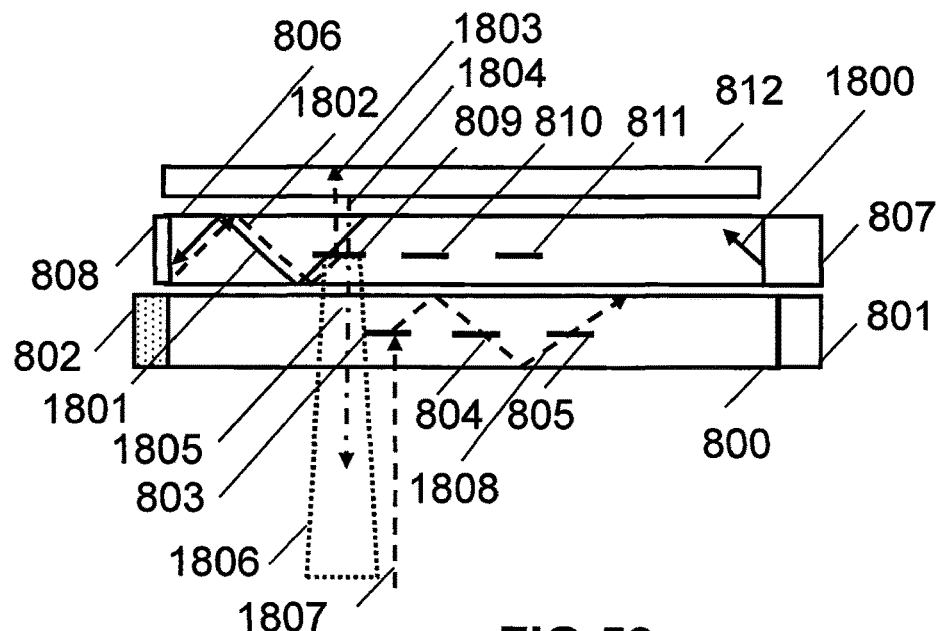
FIG. 59 is a schematic cross section of an object tracker in one embodiment.
Figure 60:
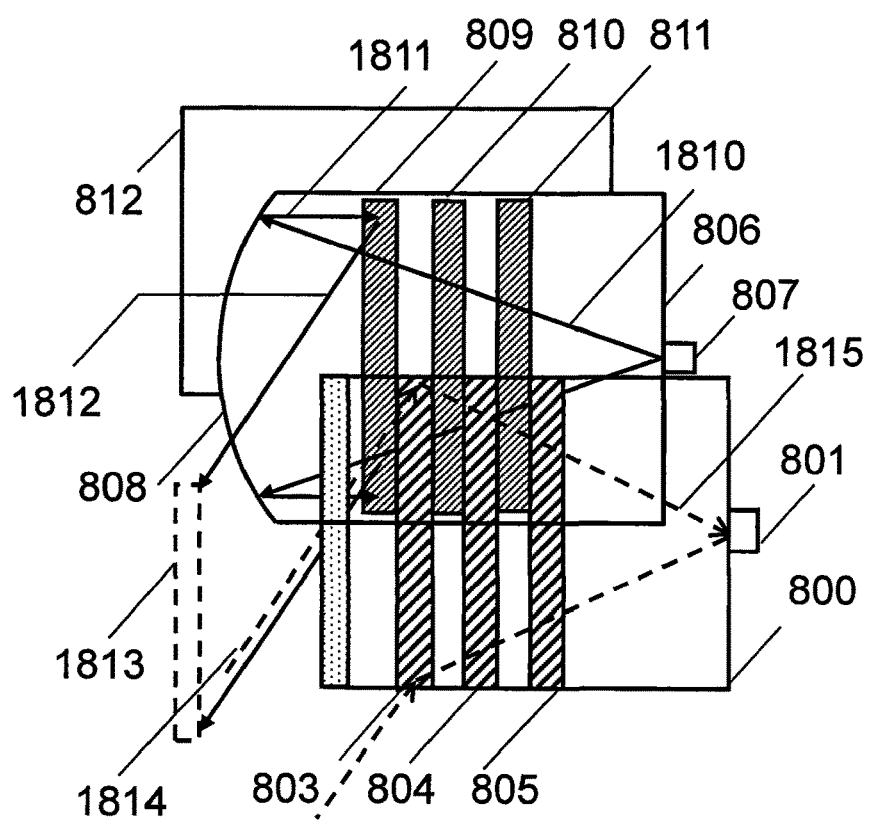
FIG. 60 is a schematic plan vies showing surfaces of an object tracker in one embodiment.

In one embodiment illustrated in cross section in FIG. 59 and in plan view in FIG. 60 there is provided an object tracker comprising a first waveguide containing spaced passive grating columns. A second waveguide containing switching columns interspersed with the columns of the first waveguide overlays the first waveguide. A detector is coupled to one edge of the second waveguide. A source is coupled to one edge of the first waveguide and a curved mirror is formed on the opposing edge. In one embodiment the second waveguide further comprises a light trap. In one embodiment a mirror overlays the first waveguide. In one embodiment the mirror further comprises a quarter waveplate.

Figure 61:
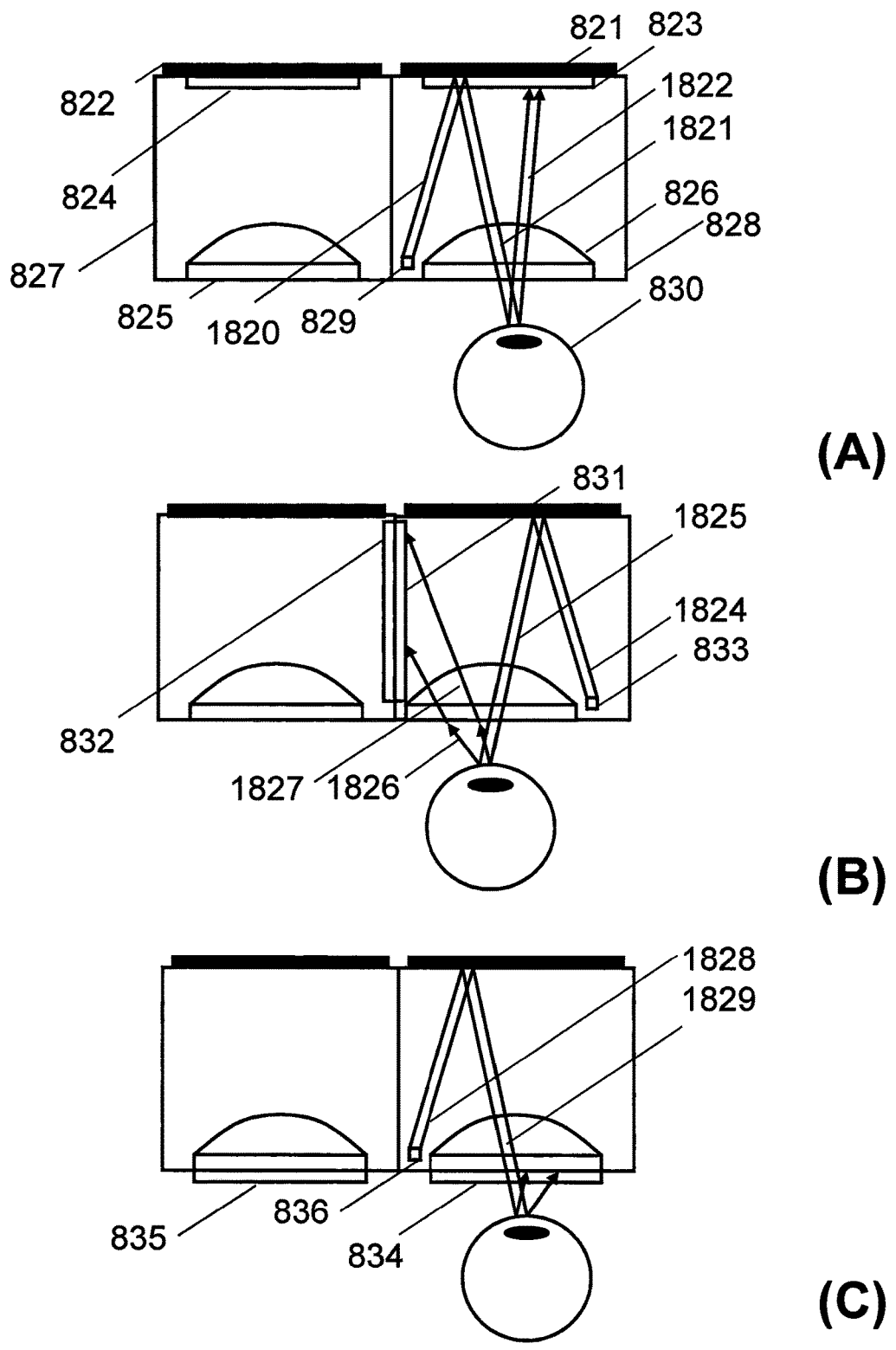
FIG. 61A is a schematic plan view of an eye tracker integrated in a VR headset in one embodiment.
FIG. 61B is a schematic plan view of an eye tracker integrated in a VR headset in one embodiment.
FIG. 61C a schematic plan view of an eye tracker integrated in a VR headset in one embodiment.

In one embodiment illustrated in FIG. 61 there is provided an eye tracked head mounted display. This embodiment does not require a dedicated illumination waveguide. The input image display panel is used to reflect illumination light onto the eye. The illumination is introduced from an out of line-of-sight source, passing through the detector waveguide at an angle that avoids diffraction by the detector gratings. Since the eye tracker is thin and transparent there are several design options to explore. In one embodiment shown in FIG. 61A the eye tracker detector waveguides is mounted directly above the display panel. In one embodiment shown in FIG. 61B the detector waveguide is mounted in a plane at ninety degrees to the display panel The backscattered light from the eye bounces off the display panel and back onto the side wall mounted sensors. In embodiments operating in the 1550 nm band, the light can easily go through paint coatings such that the sensors could be painted black as they are not in the line of sight. Finally, in the embodiment of FIG. 61C the detector waveguide is mounted between the display lens and the eye.

Figure 62:
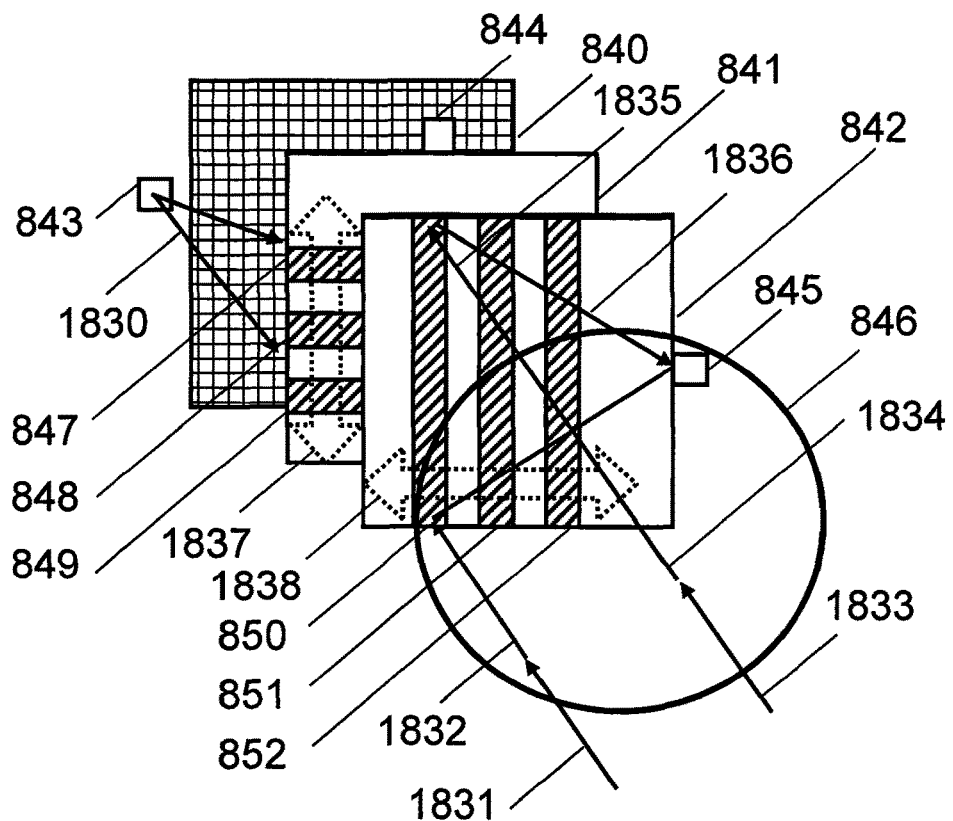
FIG. 62 is an exploded plan view of an object tracker in one embodiment.
Figure 63:
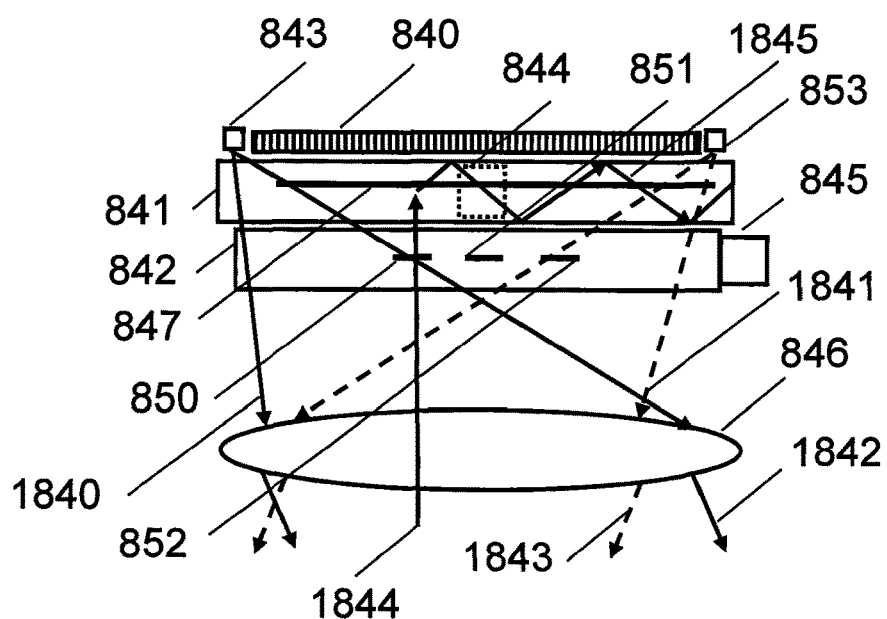
FIG. 63 is a cross section view of the object tracker of FIG. 62.

In one embodiment shown in in exploded view in FIG. 62 and in side view in FIG. 63 the detector has two layers each containing SBG columns the columns of the two waveguides being aligned orthogonally. The waveguides are displayed between the display panel and the display lens. The grating prescriptions of each column contain optical power such that the reflection from the cornea, after being coupled into the waveguide, is focused onto a photodetector element. Since the lens and tracker operate at different conjugates the waveguide gratings must also encode optical power, that is, they perform the dual functions of lensing and beam steering the scattered light from eye to the detector.

Figure 64:
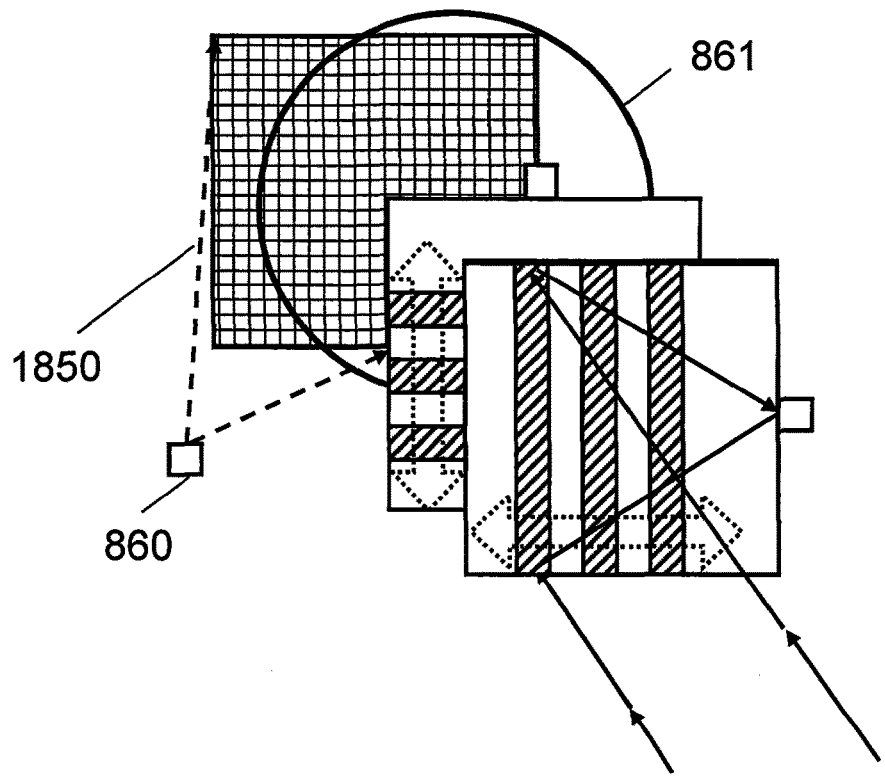
FIG. 64 is an exploded plan view of an object tracker in one embodiment.
Figure 65:
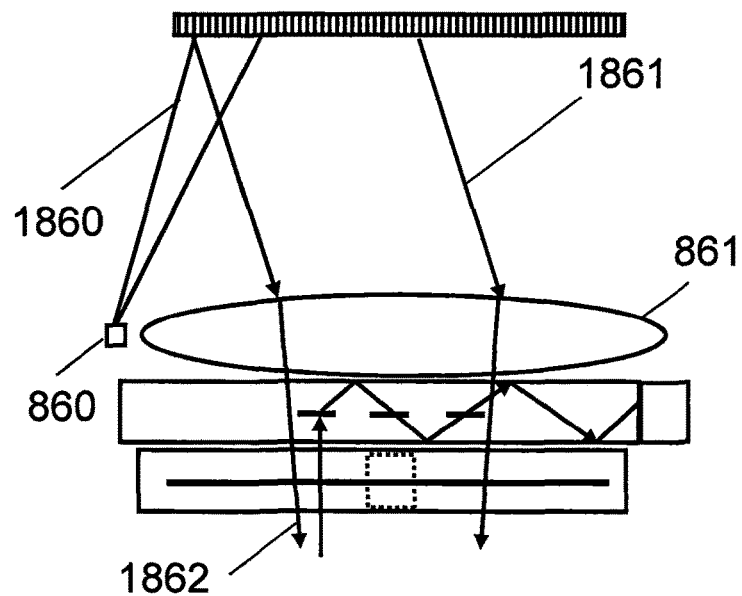
FIG. 65 is a cross section view of the object tracker of FIG. 64.

In one embodiment shown in in exploded view in FIG. 64 and in side view in FIG. 65 the detector has two layers each containing SBG columns the columns of the two waveguides being aligned orthogonally. The waveguides are displayed between the display lens and the eye box. The grating prescriptions of each column contain optical power such that the reflection from the cornea, after being coupled into the waveguide, is focused onto a photodetector element. Since the lens and tracker operate at different conjugates the waveguide gratings must also encode optical power, that is, they perform the dual functions of lensing and beam steering the scattered light from eye to the detector.

Figure 66:
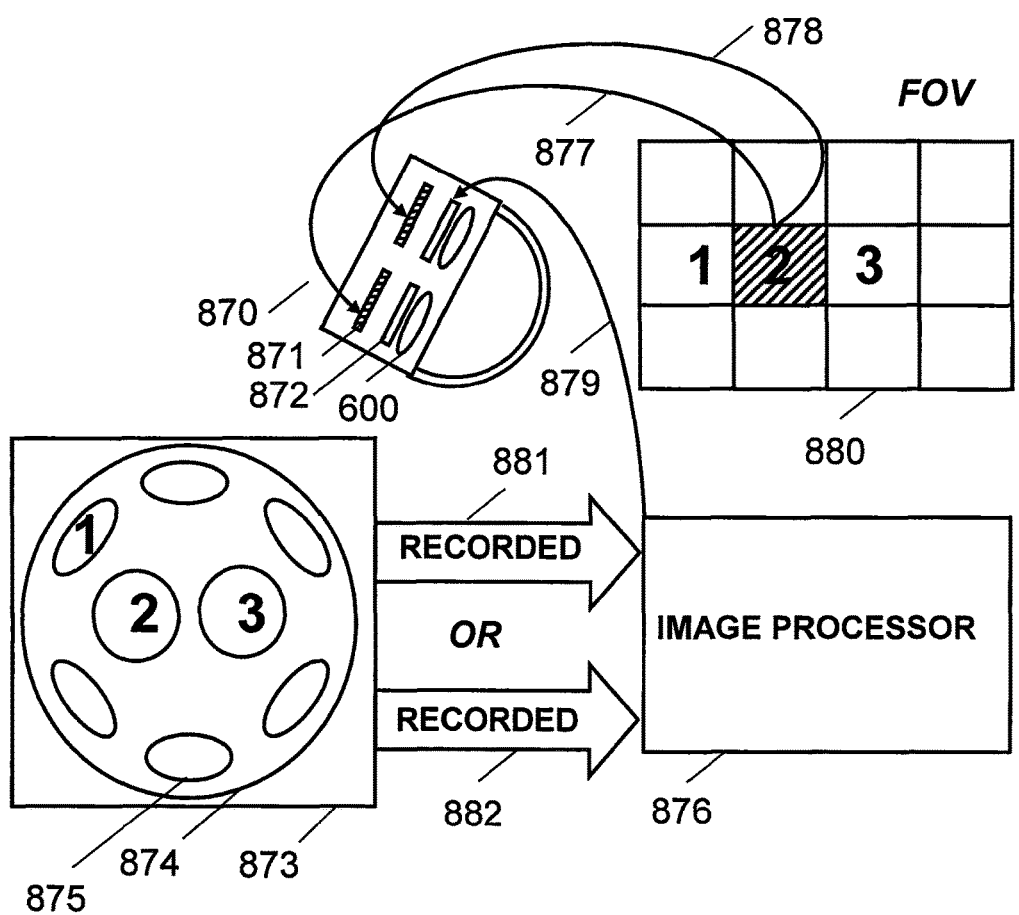
FIG. 66 is schematic illustration of a VR display in one embodiment.

In one embodiment shown in FIG. 66 there is provided a VR display for displaying imagery captured by an omni directional sensor 873 comprising a spherical assembly containing multiple cameras having apertures 875 distributed around the sphere surface. The imagery is fed into a VR headset 870 containing left and right eye display panel 871, an eye tracker waveguide that may be based on any of the above embodiments 872 and a display lens 873. The head set has a data link to an image processor which controls the display of portions of the field of view such as 1-3 in response to the tracked gaze direction.

Figure 67:
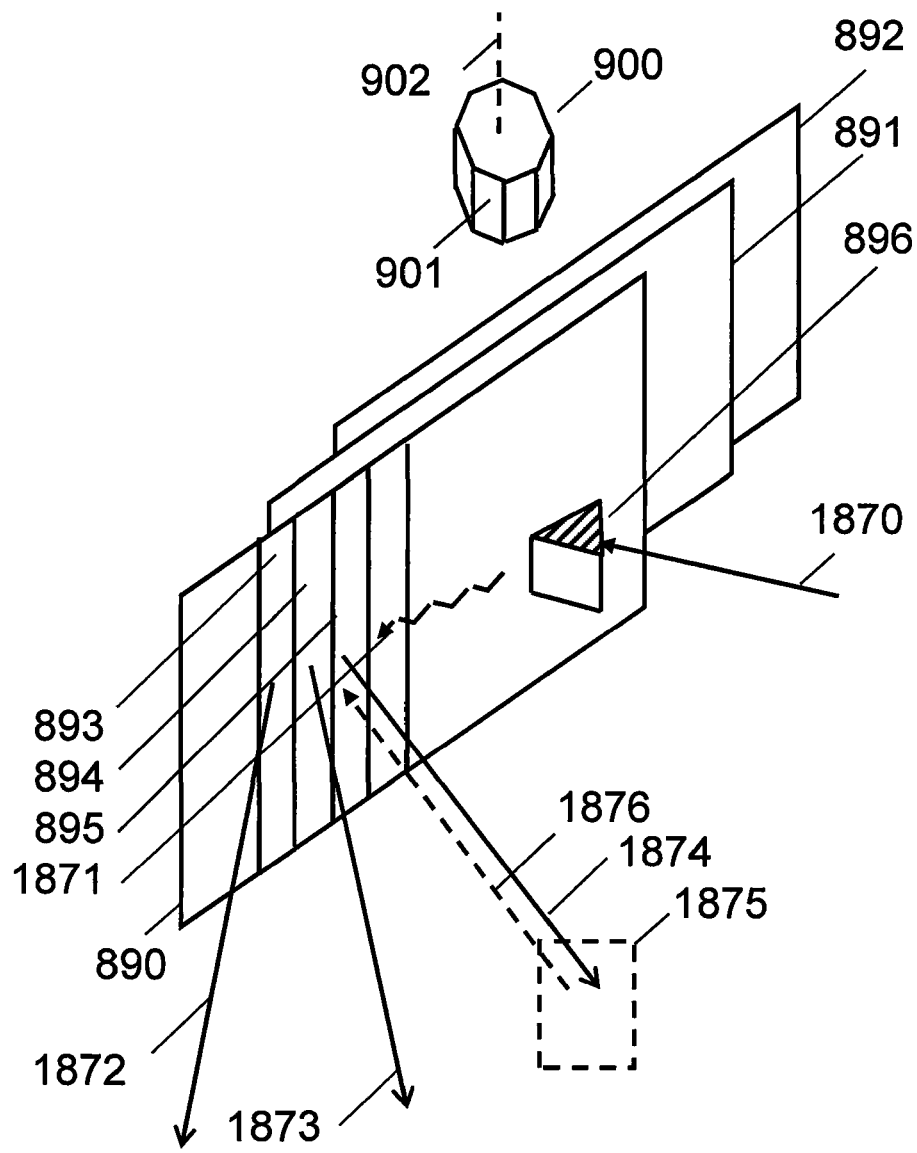
FIG. 67 is a schematic illustration of a LIDAR system in one embodiment.

In one embodiment shown in FIG. 67 there is provided a LIDAR system comprising a stack of waveguides 890-892 each containing SBG columns 893-895. Laser illumination is coupled into the waveguides via a prism 896 and is deflected out of the waveguide by each active SBG column. Each SBG has a prescription corresponding to a unique output direction. Return light is coupled into the waveguide by an active column and relayed to a detector. In one embodiment illumination light is coupled into the waveguide using a scanning prism 900 having facets 901 and an axis of rotation 902. In some embodiments the illumination light is coupled into the waveguide by a grating or prism.

An eye tracker according to the principles of the invention can be used to enable the full range of benefits of augmented reality (AR) displays, namely: a compact and lightweight form factor for encumbrance-free, see-through, mobile and extended use; wide field of view to allow meaningful connections between real world and computer generated images; and the capability of providing robust depth and occlusion cues. The latter are often one of the strongest depth cues. Although recent advances in displays have collectively spanned these requirements no one display technology possesses all of these characteristics.

An eye-slaved waveguide display in which left and right eye trackers according to the principles of the invention triangulate the left and right eye gaze intersections to provide depth cues. The waveguide display overcome vergence-accommodation conflict by providing focal surfaces at different image depths with the display refocusing dynamically according to the depth data provided by the eye tracker. The display also includes a dynamic occlusion mask based on a spatial light modulator.

In one embodiment left and right eye trackers according to the principles of the invention are used in a light field display. Light field displays provide imagery a multiple focal planes thereby supporting continuous accommodation of the eye throughout a finite depth of field. In a binocular configuration a light field display provide a means to address the accommodation-convergence conflict that occurs in existing stereoscopic displays. The left and right eye trackers triangulate the left and right eye gaze intersections to determine the depth of the feature being observed. In an exemplary embodiment shown in FIG. 68 the light field display is a waveguide display device that provides four focal surfaces. However the basic principle of the display can be extended to any number of focal surface. The apparatus comprises input image generators 910,911 each providing images to be displayed at two focal surfaces. Typically the image generators may each comprise a microdisplay panel and associated drive electronics. The images are collimated and the source which is not illustrated may be a laser or LED monochrome or color. An input image node labelled IIN in the drawing couples the image light into the waveguide 913 which contains an output grating 914 and a set of input gratings 915A-915D. The input gratings have optical power. The output gratings will typically be a planar grating; however in some embodiments it may be advantageous to add optical power to this the output grating for the purposes of aberration correction. As will be explained below each input grating forms a second a separate image surface, that is the gratings 915A-915D provide focal surfaces 1886A-1886D. The focal surface correspond to the image depths seen from the eye box indicated at 1885. The first function of the input gratings is to couple the collimated light from the IIN in TIR paths within the waveguide. The second function of the input gratings is to apply a slightly decollimation of the beams such that the form an image surface outside the waveguide. Input light 1880A,1880B from the image generators is coupled into an input image node (IIN) labelled by 912 providing collimated light indicated by 1881A-1881D. The IIN directs light 1880A from the image generator 910 into the light paths 1881A, 1181B (for projection at the focal surfaces 1886A,1186B) into the waveguide. Light in the paths 1881A,1881B is diffracted into a TIR path by the input gratings 915A,915B. The gratings are switched in sequence with the image update of the microdisplay panels. Only one grating is active at any time. The grating 915A is in its active state when the image generator 910 displays information to be projected at focal surface 1886A. The grating 915B is in its active state when the image generator 910 displays information to be projected at focal surface 1886B. The TIR paths of the wave guided light are indicated by the ray path 1182A-1184A in the case of the light imaged onto the focal surface 1886A and the ray path 1182B-1184B in the case of the light imaged onto the focal surface 1886B, where the rays 1884A,1884B correspond to portions of the image light diffracted at one interaction of each ray path with the output grating. The formation of the focal surfaces 1886C,1886D proceeds in a similar fashion with the grating 915C being switched into its active state when the image generator 911 is updated with information to be projected at focal surface 1886C and the grating 915D being switched into its active state when the image generator 911 is updated with information to be projected at focal surface 1886D. The number of switching input gratings may be reduced to three by making one of the input gratings passive and providing a nominal fixed focal surface. The other three focal surfaces are then provide by adding the passive grating focal length to that of each of the switching gratings in turn. In one embodiment the input gratings have at least one of the characteristics of spatially varying thickness, spatially-varying diffraction efficiency, or spatially-varying k-vector directions. In one embodiment the input gratings have a spatially varying thickness. Since diffraction efficiency is proportional to the grating thickness while angular bandwidth is inversely propagation to grating thickness allowing the uniformity of the diffracted light to be controlled. In one embodiment the input gratings have spatially-varying k-vector directions for controlling the efficiency, uniformity and angular range of the grating. In one embodiment input gratings have spatially-varying diffraction efficiency. The application of multiplexing, and spatial varying thickness, k-vector directions and diffraction efficiency in the present invention may be based on the embodiments, drawings and teachings provided in U.S. patent application Ser. No. 13/506,389 entitled COMPACT EDGE ILLUMINATED DIFFRACTIVE DISPLAY; U.S. Pat. No. 8,233,204 entitled OPTICAL DISPLAYS, PCT Application No.: US2006/043938, entitled METHOD AND APPARATUS FOR PROVIDING A TRANSPARENT DISPLAY; PCT Application No.: GB2012/000677 entitled WEARABLE DATA DISPLAY; U.S. patent application Ser. No. 13/317,468 entitled COMPACT EDGE ILLUMINATED EYEGLASS DISPLAY; U.S. patent application Ser. No. 13/869,866 entitled HOLOGRAPHIC WIDE ANGLE DISPLAY; and U.S. patent application Ser. No. 13/844,456 entitled TRANSPARENT WAVEGUIDE DISPLAY. In one embodiment the output grating is designed according to the embodiments and teachings of the above references. In one embodiment the waveguide contains at least one of an exit pupil expanders, fold gratings or beamsplitter layers according to the embodiments and teachings of the above references.

Figure 68:
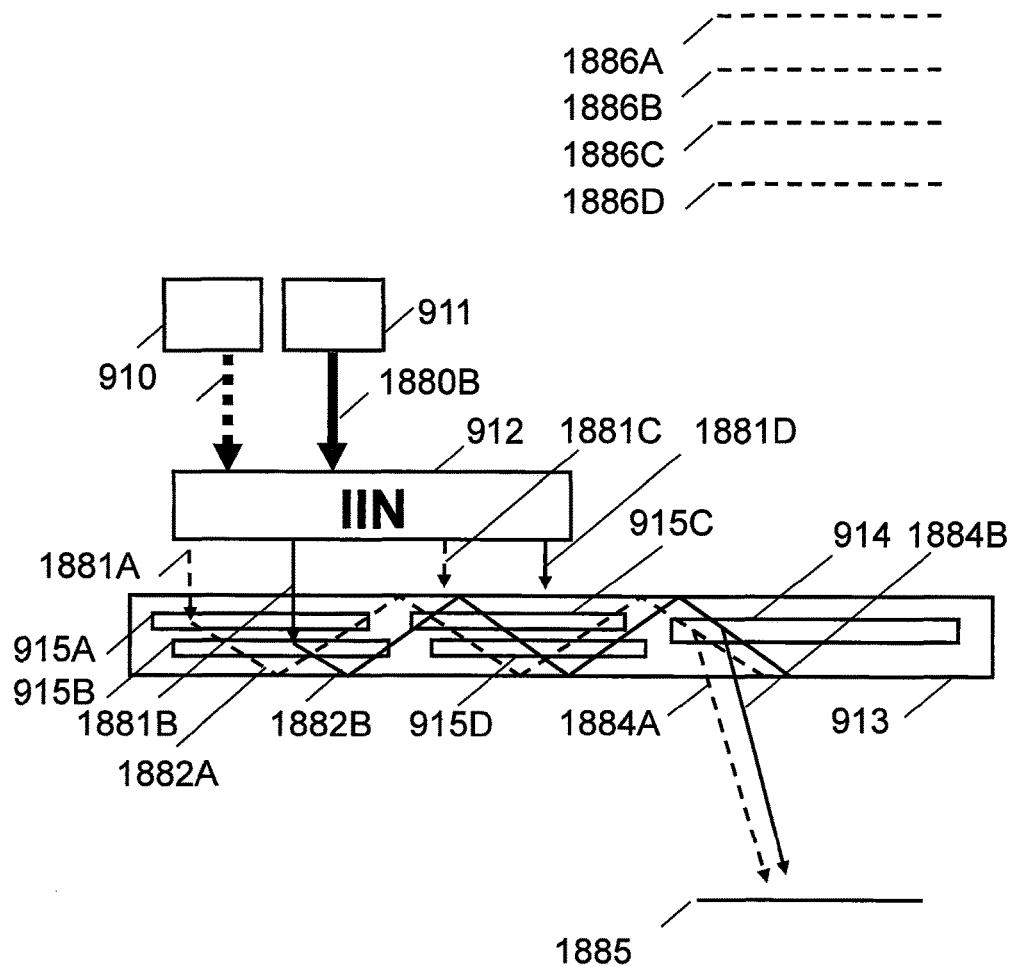
FIG. 68 is a schematic side elevation view of an eye-slaved waveguide display for providing multiple focal surfaces in one embodiment.

Note that FIG. 68 illustrates a monochromatic version of the display. A color display could use multiple stacked red, green, blue waveguides or multiplexed gratings as described in the above references. Not also that although the embodiments are directed at providing four focal surfaces, many more surfaces may be provided by increasing the number of image generators and waveguides as should be apparent from the consideration of the description and drawings. It should further be noted that since the angular image content correspond to each focal surface is more or less the same, in a monochrmaltic display (or in monochromatic layer of a color displays) a common output grating may be used for each of the four focal surface ray paths.

Figure 69:
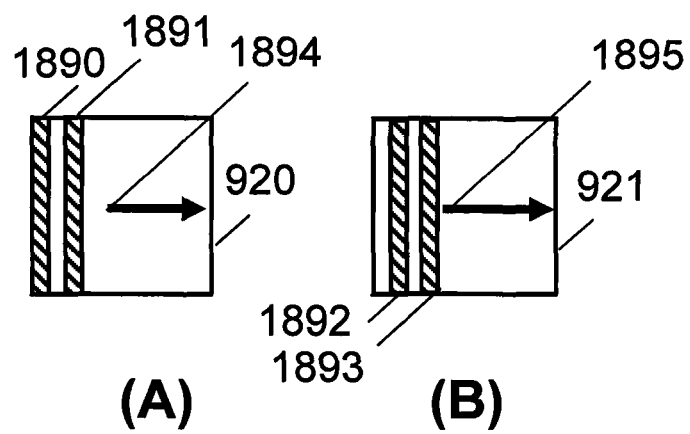
FIG. 69A is a schematic front view of a first input image for an eye-slaved waveguide display for providing multiple focal surfaces in one embodiment.
FIG. 69B is a schematic front view of a second input image for an eye-slaved waveguide display for providing multiple focal surfaces in one embodiment.
FIG. 69C is a schematic front view of a first input grating used in an eye-slaved waveguide display for providing multiple focal surfaces in one embodiment.
FIG. 69D is a schematic front view of a second input grating used in an eye-slaved waveguide display for providing multiple focal surfaces in one embodiment.
Figure 69:
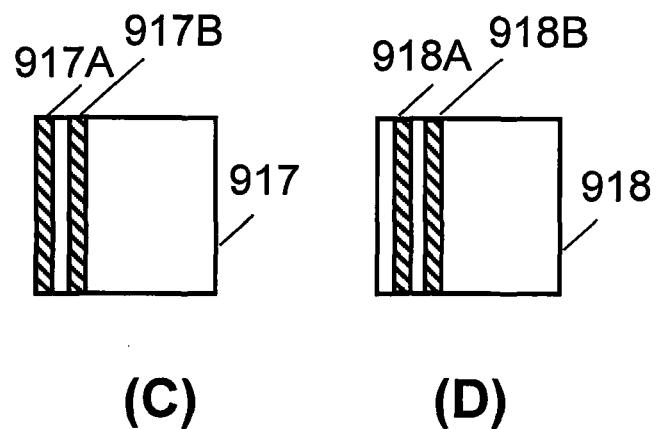

In the embodiment of FIG. 68 the images to be displayed at the four focal surfaces are displayed sequential one entire image field at a time as discussed. In another embodiment the input image generator divides each input image into columns and the input gratings are likewise divided into columns the grating columns being switched into their diffracting states simultaneously with the updating of the corresponding columns of the image generator. In one embodiment shown in FIG. 69 two image generators 920, 921 as shown in FIG. 69A,69B displaying spaced columns 1890,1891 (FIG. 69A) and 1892,1893 (FIG. 69B) that are interlaced in the final projected image. The columns are updated in a scrolling fashion as indicated by the arrow 1894,1895. In one embodiment the entire array of columns in each image generator may be switched simultaneously with the output from each image generator delivered to the IIN sequentially. The input gratings are shown in FIG. 69C-69D. The grating 917 is used to couple and focus light from the image generator 920. The grating 918 is used to couple and focus light from the image generator 921. Grating columns 917A,917B in grating 917 and 918A,918B in grating 918 are indicated. The gratings may correspond to the grating pairs 915A,915C or 915B,9150 of FIG. 68. In some embodiments the gratings may correspond to the stacked gratings 915A,915B or 915C,915D of FIG. 68. In embodiments based on input image scrolling the gratings switching may follow a scrolling scheme synchronized with the scrolling of the input images. It should be apparent from consideration of FIG. 69 that various switching schemes may be devised by combining different image generator column patterning and grating column switching schemes, subject to the space required to implement the required beam-routing optics inside the IIN.

Figure 70:
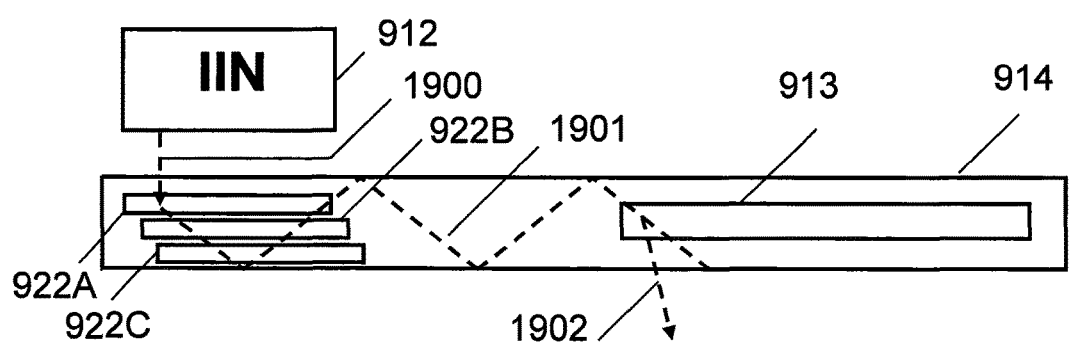
FIG. 70 is a schematic side elevation view of an eye-slaved waveguide display for providing multiple focal surfaces in one embodiment.

FIG. 70 illustrates one embodiment which is similar to that of FIG. 68 except that the input gratings are stacked. FIG. 70 shows part of the display comprising the IIN 912 which now includes the image generator, light source and collimation optics, the waveguide 914, the output grating 913 and stacked input gratings 922A-922C for providing three focal surfaces. A typical ray path from the IIN to the output surface of the waveguide is illustrated by rays 1900-1902.

Figure 71:
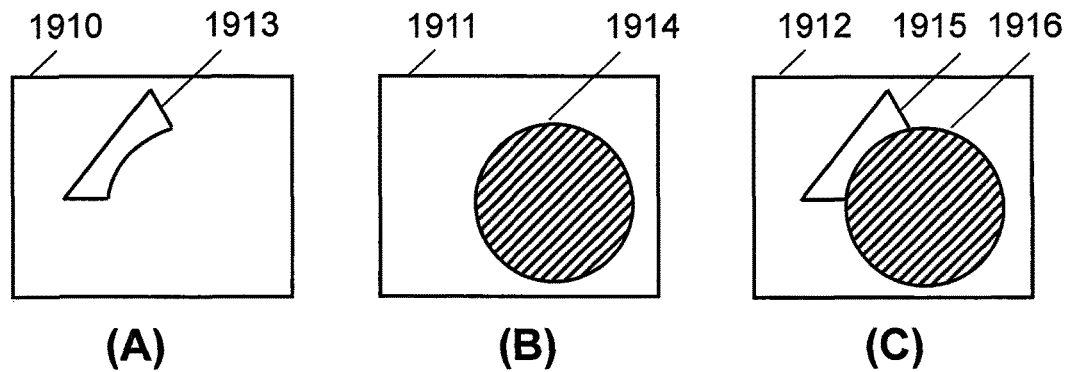
FIG. 71A is a front view of an occluded input image in one embodiment.
FIG. 71B is a front view of an occluding input image in one embodiment.
FIG. 71C is a front view of a composite image showing occlusion.

In one embodiment directed at the display of occluding images the image generators used in the embodiments shown in FIGS. 68-70 provide image components that are masked such that correctly occluded images maybe observed when the image components are displayed on their respective focal surfaces. In the example shown in FIG. 71 a first image 1910 is displayed on a first image generator (FIG. 71A) and as second image 1911 displayed on a second image generator (FIG. 71B). The first image comprises a portion 1913 of a triangle that is partially occluded by the circle 1914 displayed in the second image. The combined image 1912 comprising the occluded triangle 1915 and the circle 1916 as observed from the eye box is shown in FIG. 71C.

Figure 72:
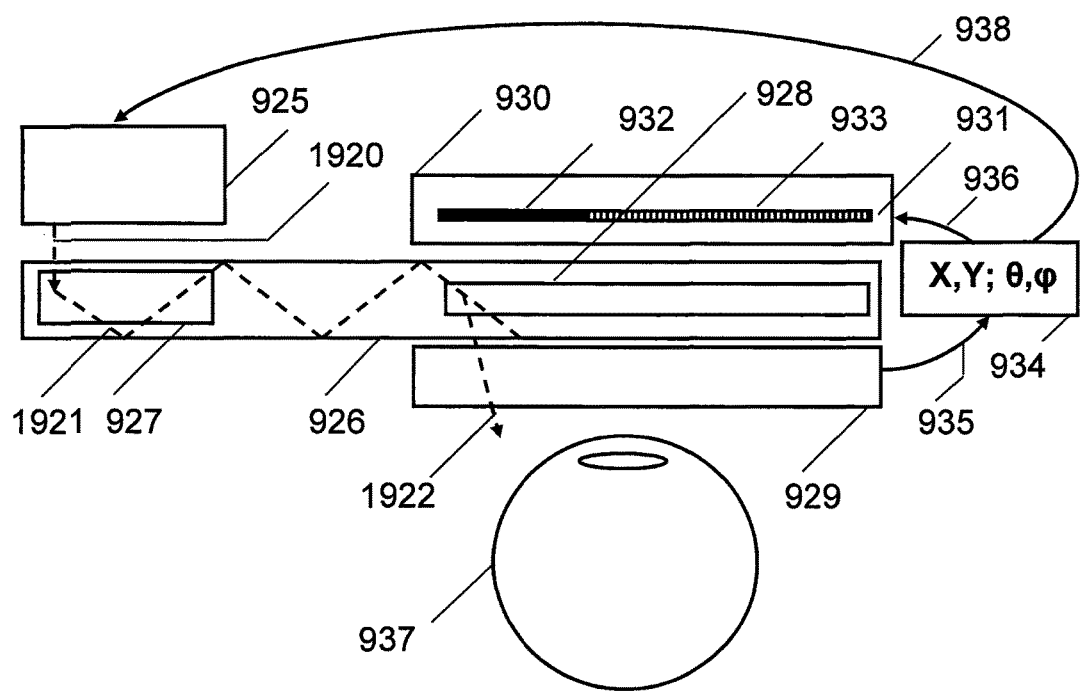
FIG. 72 is a schematic side elevation view of an eye-slaved waveguide display for providing depth and occlusion visual cues in one embodiment.

In one embodiment shown in FIG. 72 there is provided an eye-slaved waveguide display which uses an eye tracker and a dynamic occlusion mask to provide depth and occlusion cues. The apparatus comprises an image generator and TIN module 925 and a waveguide display 926 contain input gratings 927 based on any of the above embodiments and an output grating 928. A ray path through the waveguide up to the eye is indicated by the rays 1920-1922. The apparatus further comprises an eye tracker 929 according to any of the above embodiments and a dynamic occlusion mask 930 which further comprises a two-dimensional spatial light modulator 931 which can be programmed to provide opaque regions 932 and transmitting regions 933. The switching of the spatial light modulator elements is controlled by the output from the eye tracker comprising the X,Y coordinates of the pupil centroid and the angular components of the gaze vector $(\theta, \varphi)$. Data links from the eye tracker to the processor 934 and from the processor to the input image generator and the dynamic occlusion mask are indicated by 935,936,938. FIG. 72 illustrates a single eye piece of a wearable display. In one embodiment the intersection of the left and right eye gaze vectors is computed to determine the focal surface at which data is to be projected, thereby overcoming vergence-accommodation conflicts.

Figure 73:
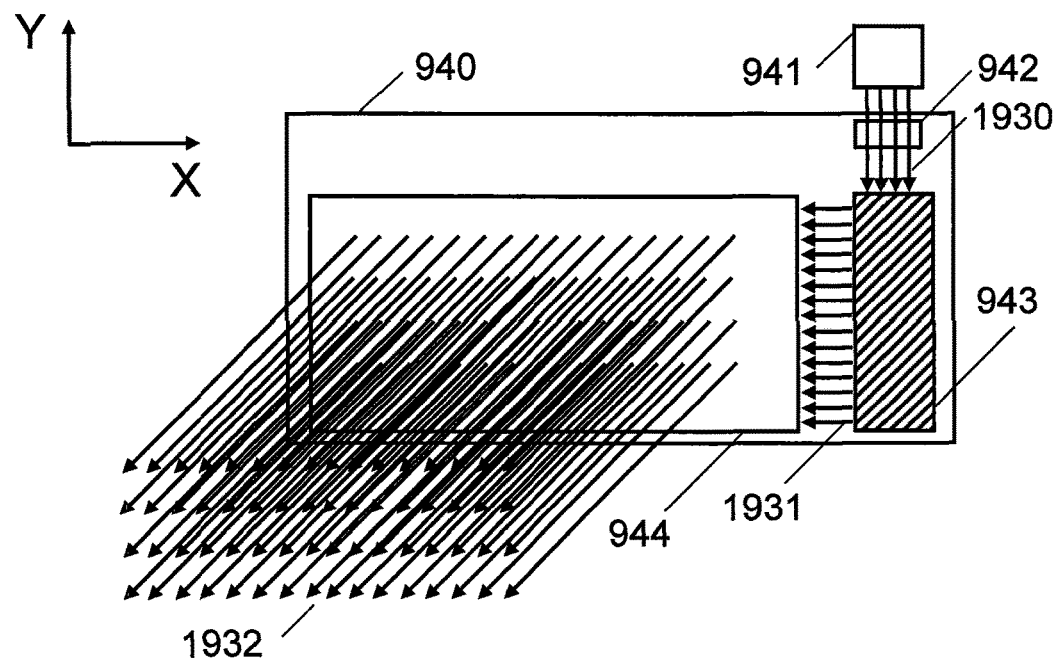
FIG. 73 is a front elevation vie of an eye tracker showing the illumination waveguide in one embodiment.
Figure 74:
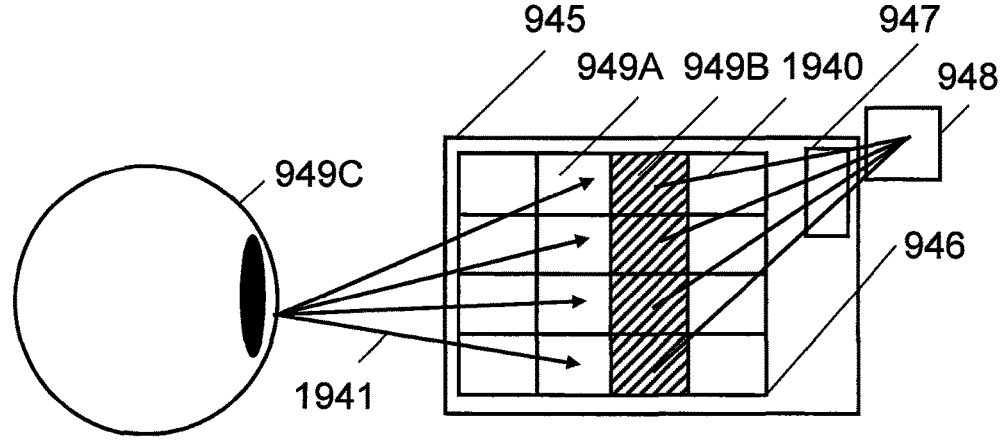
FIG. 74 is a front elevation view of an eye tracker showing the detector waveguide in one embodiment.

In one embodiment illustrated in FIGS. 73-74 an eye tracker comprises an illumination waveguide overlaying a detector waveguide. The illumination waveguide which is shown in FIG. 73 comprises a waveguide 940 a source 941 which couples light into the waveguide by means of a coupler 942 comprising either a prism or grating. A fold grating 943 expanse and redirects the illumination in the waveguide as indicated by the rays 1930,1931. Typically the fold grating will be clocked at 45 degrees where the clock angle is defined as the angle of the grating K-vector projected into the waveguide plane with respect to a principal optical axis of the waveguide. In this case the principal axes would be either the X or Y axis of the Cartesian reference frame shown in FIG. 73. A passive output grating 944 extracts light across the waveguide to flood-illuminated the eye as indicated by the rectangular ray bundle 1932. Turning next to FIG. 74 we see that the detector waveguide 945 contains a two dimensional array 946 of switchable grating elements 949A. The waveguide is optically coupled to the detector 945 using an out coupler 947 comprising a grating or prism. Typically the detector is a single element infrared detector. The grating elements are activated one column, such as the one labelled 949B, at a time. The signal from the eye as represented by the ray bundle 1941 is coupled into a TIR path in the waveguide by the active grating elements of the column 949B. Each grating element diffracts light towards the detector via the output coupler 947. In one embodiment the output coupler is clocked at an angle designed to maximize the effective aperture of the detector. This will also serve to improve the effective angular bandwidth of the eye tracker. In one embodiment the output coupler may comprise more than one coupling element each element having a unique clock angle. In one embodiment more than one detector and more than one coupler may be used. In one embodiment all of grating elements in a column may be switched into their diffracting states simultaneously. In one embodiment the grating elements are switched into their diffracting schemes using an X-Y addressing scheme. In one embodiment the detector is a single element device for recording the peak signal from each grating element. In one embodiment the signals recorded using a single element detector are stored in a computer memory as look-up tables. The eye gaze direction is estimated by comparing the relative amplitudes of the recorded signals. In many cases only very basic processing of the signal is required to measure eye gaze to within one degree resolution and accuracy. The invention dos not assume any particular data processing method. Relevant prior art is to be found in the literature of optical tracking and image processing. In one embodiment the grating elements have optical power for focusing the signal from the eye onto the output coupler.

Figure 75:
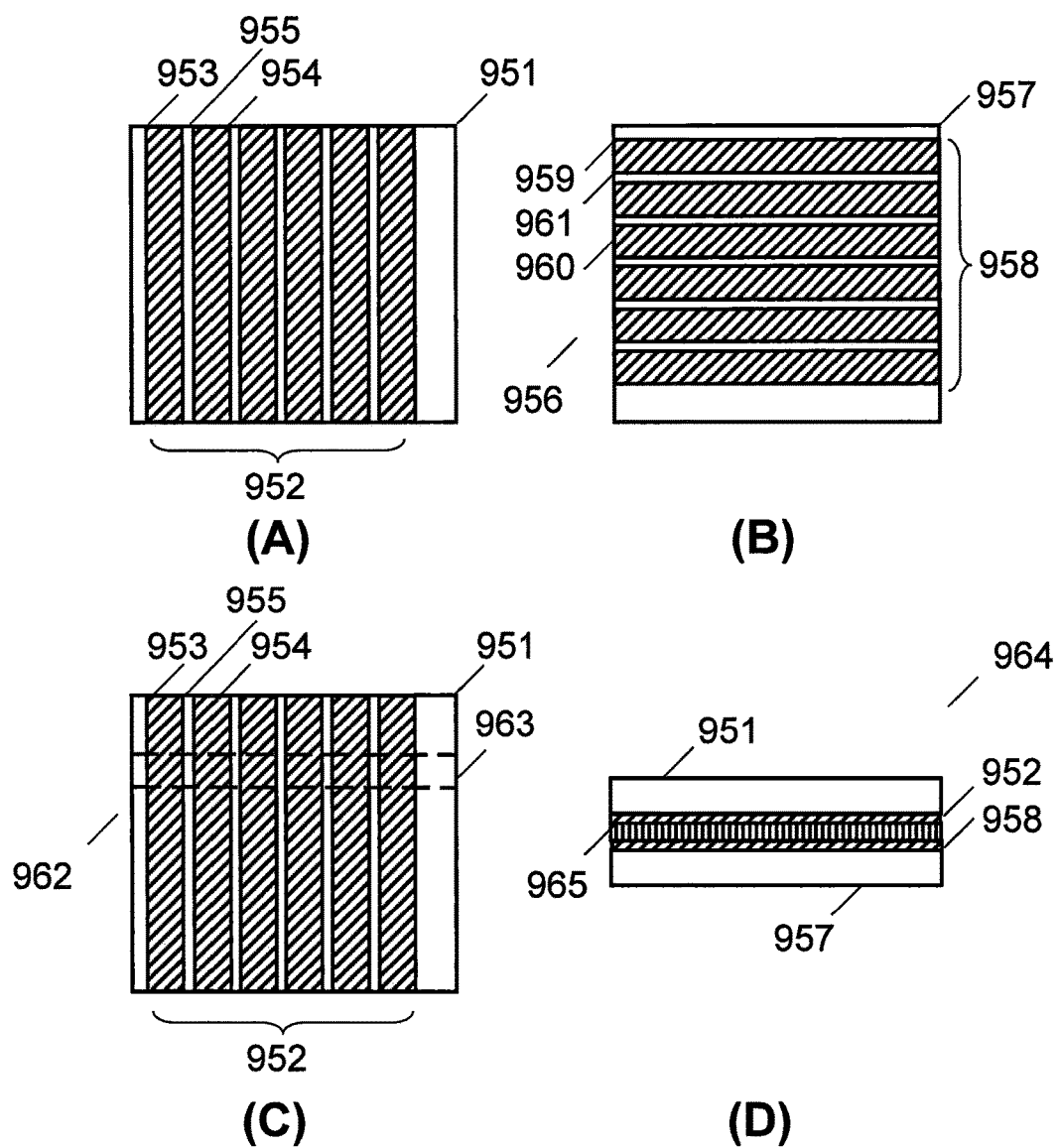
FIG. 75A is a plan view of a first substrate with electrodes as used in a detector waveguide in one embodiment.
FIG. 75B is a plan view of a second substrate with electrodes as used in a detector waveguide in one embodiment.
FIG. 75C is a plan view of the first substrate of FIG. 75A with an active electrode of the second substrate of FIG. 75B overlaid in one embodiment.
FIG. 75D is a cross sectional view of the detector waveguide formed by sandwiching a holographic grating array with the first and second substrates of FIGS. 75A-75B.

In one embodiment the detector waveguide contains an array of switchable gratings that are address using the crossed parallel electrodes illustrated in FIG. 75. The electrodes are applied to first and second substrates sandwiching a grating layer FIG. 75A shows the first substrate 951 to which the column-shaped electrodes 952 including 953,954 have being applied on one surface with small gaps 955. The second substrate 957 shown in FIG. 75B has horizontal electrode bars 958 including the elements 959, 960 applied to a surface of the substrate with small gaps 961. FIG. 75C shows on state of the waveguide in which the electrodes 963 of the second substrate and all of the electrodes of the first substrate are connected to a voltage source. Grating regions overlapped by the electrode 963 are switched in this case. In one embodiment the apparatus of FIG. 75 is configured such that one electrode in each substrates is connected to a voltage source at any time to allow X,Y-addressing of the grating array. FIG. 75D is a cross section vies showing the grating layer sandwiched by the first and second substrates 951,957 and electrode layers 952,958. In one embodiment the grating layer may have a uniform prosecution with individual switchable elements being defined by the cross electrodes. In one embodiment the grating provides optical power. In one embodiment the optical power may vary with X,Y coordinate of the grating array.

Figure 76:
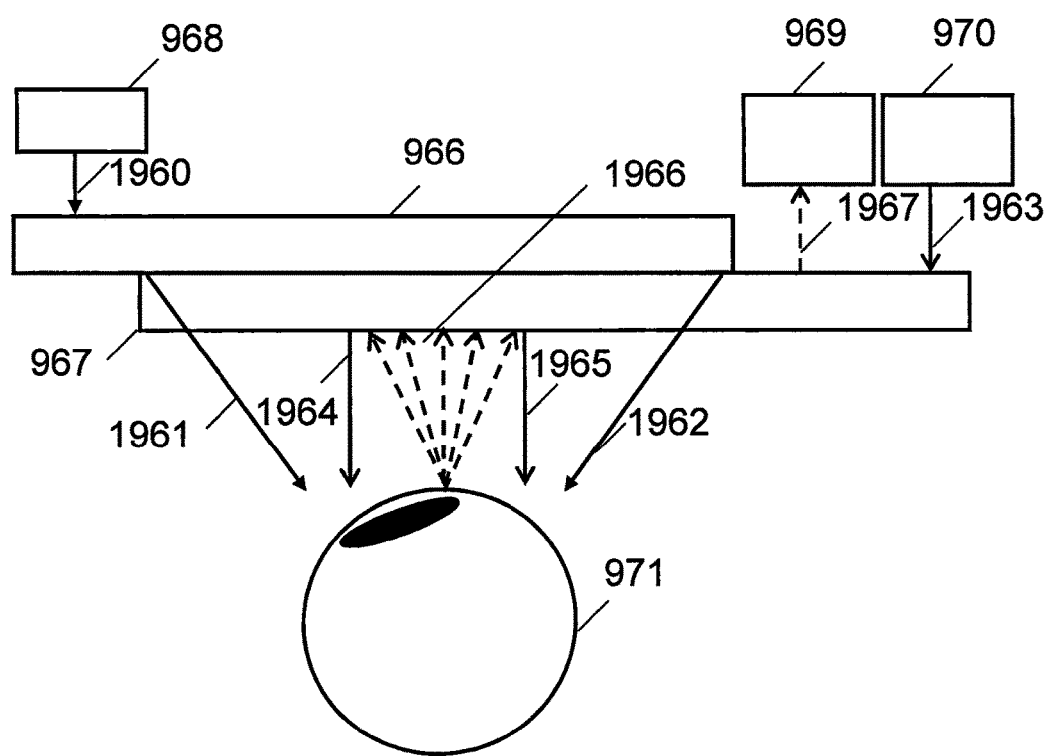
FIG. 76 is a schematic cross section view of an eye-slaved display comprising an eye tracker waveguide and a display waveguide in one embodiment.

In one embodiment illustrated in FIG. 76 there is provide an eye-slaved waveguide display. The eye tracker is a waveguide device based on any of the above embodiments. The eye tracker comprises the waveguide 967 which may include separate illumination and detector waveguides, an infrared detector 969 and infrared source 970. The optical path from the source to the eye is indicated by the rays 1961-1965 the backscattered signal from the eye is indicated by the rays 1966-1967. The display comprises a waveguide 966 and an input image node 968. The optical path from the input image node is indicated by the rays 1960-1962. The waveguide display may be based on any other embodiments disclosed in U.S. patent application Ser. No. 13/506,389 entitled COMPACT EDGE ILLUMINATED DIFFRACTIVE DISPLAY; U.S. Pat. No. 8,233,204 entitled OPTICAL DISPLAYS, PCT Application No.: US2006/043938, entitled METHOD AND APPARATUS FOR PROVIDING A TRANSPARENT DISPLAY; PCT Application No.: GB2012/000677 entitled WEARABLE DATA DISPLAY; U.S. patent application Ser. No. 13/317,468 entitled COMPACT EDGE ILLUMINATED EYEGLASS DISPLAY; U.S. patent application Ser. No. 13/869,866 entitled HOLOGRAPHIC WIDE ANGLE DISPLAY; and U.S. patent application Ser. No. 13/844,456 entitled TRANSPARENT WAVEGUIDE DISPLAY.

Although the description of the invention has addressed the problem of tracking single objects, any of the above embodiments may be applied to tracking multiple objects. The processing will be more complicated requiring algorithms for matching multiple recorded signatures to different moving objects and determining the object trajectories. The invention does not assume any particular algorithms to be used for these purposes. Suitable algorithms will be known to those skilled in the art of image processing. Relevant prior art exists in the literature of radar systems, robotics and other fields.

Although we have discussed the embodiments in relation to the problem of tracking a moving object relative to the waveguide tracking apparatus (eg eye rotation relative to an eye piece) it should be appreciated that the invention is equally applicable to cases where the tracking apparatus is attached to a moving object such as a head, hands, or a moving vehicle and the reflected signature is provided by other moving objects in the locality or by fixed objects. The invention may also be used to detect the position in 3D space of static objects. Such a requirement may arise in robot vehicles.

Any of the above described embodiments of the object tracker may be used to provide a LIDAR. LIDAR is a remote-sensing technology that creates a 3D map of an environment by illuminating a target with a pulsed angularly-scanned laser and analyzing the reflected "point cloud". Currently, there is growing interest in LIDAR systems for a range of platforms including: cars (for applications such as collision avoidance and cruise control systems), robot vehicle, UAVs and wearable displays for night vision. The increasing use of key-hole procedures in surgery is also stimulating medical applications. In LIDAR applications the sources would typically comprise a scanned infrared laser. The detection system would be include electronics for timing the arrival of return laser pulses. The LIDAR would be used for mapping moving objects and/or a surrounding environment.

It should be emphasized that the drawings are exemplary and that the dimensions have been exaggerated. For example thicknesses of the SBG layers have been greatly exaggerated.

In any of the above embodiments the waveguides may be curved or formed from a mosaic of planar or curved facets.

The gratings used in any of the above embodiments may be recorded in a uniform modulation HPDLC material. Exemplary uniform modulation liquid crystal-polymer material systems are disclosed in United State Patent Application Publication No.: US2007/0019152 by Caputo et al and PCT Application No.: PCT/EP2005/006950 by Stumpe et al. both of which are incorporated herein by reference in their entireties. Uniform modulation gratings are characterized by high refractive index modulation (and hence high diffraction efficiency) and low scatter. In one embodiment the input gratings are based on a grating recorded in a reverse mode HPDLC material. Reverse mode HPDLC differs from conventional HPDLC in that the grating is passive when no electric field is applied and becomes diffractive in the presence of an electric field. The reverse mode HPDLC may be based on any of the recipes and processes disclosed in PCT Application No.: PCT/GB2012/000680, entitled IMPROVEMENTS TO HOLOGRAPHIC POLYMER DISPERSED LIQUID CRYSTAL MATERIALS AND DEVICES. The grating may be recorded in any of the above material systems but used in a passive (non-switching) mode. The fabrication process is identical to that used for switched but with the electrode coating stage being omitted. LC polymer material systems are highly desirable in view of their high index modulation.

Waveguides used in any of the above-described embodiments may be implemented using plastic substrates using the materials and processes disclosed in PCT Application No.: PCT/GB2012/000680, entitled IMPROVEMENTS TO HOLOGRAPHIC POLYMER DISPERSED LIQUID CRYSTAL MATERIALS AND DEVICES. Advantageously, the SBGs are recorded in a reverse mode HPDLC material in which the diffracting state of SBG occurs when an electric field is applied across the electrodes. An eye tracker based on any of the above-described embodiments may be implemented using reverse mode materials and processes disclosed in the above PCT application.

While the invention may be applied with gratings of any type including switching or non-switching gratings based on Bragg (volume) holograms, or surface-relief gratings the preferred grating technology is a SBG, which offers the advantages of fast switching, high optical efficiency and transparency and high index modulation.

With regard to the use of grating arrays it should be appreciated the number of elements used in an array need not be very large, depending on the FOV over which gaze is to be tracked.

It should also be noted that the gratings used in the above embodiments are not necessarily all switching gratings. Switching gratings may be used in combination with passive grating technologies. As has been indicated by the description and drawings more than one grating layer (lamina) may be used. The grating layers discussed above are SBGs disposed between internal waveguide surfaces (or in other words sandwiched between transparent substrates that combine to form the waveguide. However in equivalent embodiments some of the gratings layers could be applied to external waveguide surfaces. This would apply in the case of surface relief gratings.

Using sufficiently thin substrates the waveguides used in the invention could in the case of an eye tracker be implemented as a long clear strip appliqué running from the nasal to ear ends of a HMD with a small illumination module continuing laser dies, light guides and display drive chip tucked into the sidewall of the eyeglass. A standard index matched glue would be used to fix the display to the surfaces of the HMD.

The method of fabricating the SBG pixel elements and the ITO electrodes used in any of the above-described embodiments of the invention may be based on the process disclosed in the PCT Application No. US2006/043938, entitled METHOD AND APPARATUS FOR PROVIDING A TRANSPARENT DISPLAY.

The invention does not rely on any particular methods for introducing light from a laser source into a holographic waveguide and directing light scattered from the eye onto a detector. In the preferred embodiments of the invention gratings are used to perform the above functions. The gratings may be non switchable gratings. The gratings may be holographic optical elements. The gratings may be switchable gratings. Alternatively, prismatic elements may be used.

It should be understood by those skilled in the art that while the present invention has been described with reference to exemplary embodiments, it is to be understood that the invention is not limited to the disclosed exemplary embodiments. Various modifications, combinations, subcombinations and alterations may occur depending on design requirements and other factors insofar as they are within the scope of the appended claims or the equivalents thereof.

The invention claimed is:

1. An object tracker for tracking at least one object using structured light, comprising:
  a waveguide;
  a source of illumination light optically coupled to said waveguide;
  a set of one or more grating lamina elements formed within said waveguide,
    wherein said waveguide is configured to direct said illumination light along a first optical path from said source to an object via said set of grating lamina elements, and
    wherein said set of grating lamina elements are configured to modify and diffract said illumination light such that said illumination light is modified by said set of grating lamina elements into structured light having a first signal pattern that is characterized by a first speckle pattern diffracted towards said object; and
  a detector optically coupled to detect image light reflected from said object, wherein said image light is a reflection of at least a portion said illumination light directed at said object, wherein said image light is structured light having a second signal pattern that is characterized by a second speckle pattern and is a reflected derivative of said first signal pattern, wherein said detector is configured to detect said object by detecting the reflected image light and recording said second signal pattern when said waveguide and said detector are in relative motion with said object.

2. The object tracker of claim 1 wherein said first optical path includes a first waveguide path, wherein said reflected image light travels a second optical path that includes a second waveguide path, wherein said set of grating lamina elements is configured to couple said illumination light out of said first waveguide path towards said object, and wherein said set of grating lamina elements is further configured to couple said reflected image light into said second waveguide path towards said detector.

3. The object tracker of claim 2 wherein said set of grating lamina elements includes a first switchable grating element having a diffracting state and a non diffracting state, wherein said first switchable grating element in said diffracting state couples said illumination light in said first waveguide path out of said waveguide towards said object and said first switchable grating element further couples said reflected image light into said second waveguide path towards said detector.

4. The object tracker of claim 2 wherein said set of grating lamina elements includes a first and a second switchable grating element, each having a diffracting state and a non-diffracting state, wherein said first switchable grating element in said diffracting state couples said illumination light in said first waveguide path out of said first waveguide towards said object, and wherein said second switchable grating element in said diffracting state couples said reflected image light into said second waveguide path towards said detector.

5. The object tracker of claim 1 wherein said set of grating lamina elements includes a first switchable grating element having a diffracting state and a non diffracting state.

6. The object tracker of claim 1 wherein said set of grating lamina elements includes at least one grating lamina element selected from the group consisting of: a switchable Bragg grating, a switchable grating recorded in a reverse mode holographic polymer dispersed liquid crystal, a switchable grating recorded in a reverse mode holographic polymer dispersed liquid crystal, a surface relief grating and a non switching Bragg grating.

7. The object tracker of claim 1 wherein said set of grating lamina elements includes at least one pair of grating lamina elements, wherein each orating lamina element of said pair of grating lamina elements is configured to diffract said illumination light into output paths in accordance with a k-vector such the illumination light diffracted by said pair of grating lamina elements each converge towards a center of rotation of said object.

8. The object tracker of claim 1 wherein said set of grating lamina elements includes at least two grating lamina elements, and wherein each grating lamina element of said set of grating lamina elements is configured to diffract said illumination light into parallel output paths.

9. The object tracker of claim 1 wherein said detector is connected to an image processing apparatus for determining at least one spatio-temporal characteristic of an object movement.

10. The object tracker of claim 1 further comprising an image processing system which includes at least one of an edge finding algorithm, a centroid detection algorithm or a neural network.

11. The object tracker of claim 1 wherein the waveguide and detector are implemented in a device selected from the group consisting of: an eye tracker, a LIDAR, an eye-slaved display, a display implementing foveated rendering, and a display using gaze vector data to adjust a displayed image to provide vergence accommodation related depth cues.

12. The object tracker of claim 1 wherein said set of grating lamina elements is configured to diffract said illumination light into multiple illumination perspectives such that reflected high signal to noise ratio throughout the field of view.

13. The object tracker of claim 1 wherein said detector is a fast low resolution detector.

14. The object tracker of claim 1 wherein signal of said first and said second signal pattern is further characterized by at least one of: beam intensity profile, phase distribution, or beam direction.

15. The object tracker of claim 1 further comprising a lens that focuses said image light onto said detector.

16. The object tracker of claim 1 wherein said detector is configured to detect said object when said object is fixed in a three dimensional space and said waveguide or said detector are in motion relative to said object.

17. The object tracker of claim 1 wherein said detector is configured to detect said object when said waveguide or said detector move along a curvilinear path in three dimensional space.

18. The object tracker of claim 1 wherein said set of grating lamina elements include a first and a second grating lamina element, wherein said first grating lamina element is configured to diverge said illumination light into a first beam divergence width, and wherein said second grating lamina element is configured to diverge said illumination light into a second beam divergence width, and wherein said first and said second beam divergence widths are different.

19. The object tracker of claim 1 wherein said set of grating lamina elements include a first and a second grating lamina element, wherein said first grating lamina element is configured to modify said illumination light into a first speckle contrast, and wherein said second grating lamina element is configured to modify said illumination light into a second speckle contrast, wherein said first and said second speckle contrasts are different, and wherein said first speckle pattern is characterized by at least said first and said second speckle contrasts.

20. The object tracker of claim 1 wherein said set of grating lamina elements include a first and a second grating lamina element, wherein said orating lamina first element is configured to modify said illumination light into a first speckle grain size, and wherein said second grating lamina element is configured to modify said illumination light into a second speckle grain size, wherein said first and said second speckle grain sizes are different, and wherein said first speckle pattern is characterized by at least said first and said second speckle grain sizes.

21. The object tracker of claim 1 wherein a first speckle pattern is formed in part by varying size or shape of the two-dimensional area of a number of grating lamina elements within the set of grating laminas.

* * * * *